US011254672B2

(12) United States Patent
Norcross et al.

(10) Patent No.: US 11,254,672 B2
(45) Date of Patent: Feb. 22, 2022

(54) DIHYDROBENZIMIDAZOLONES FOR MEDICAL TREATMENT

(71) Applicant: C4 Therapeutics, Inc., Watertown, MA (US)

(72) Inventors: Roger Norcross, Basel (CH); Annick Goergler, Basel (CH); Fabian Dey, Basel (CH); Eric Andre Kusznir, Basel (CH)

(73) Assignee: C4 Therapeutics, Inc., Watertown, MA (US)

( * ) Notice: Subject to any disclaimer, the term of this patent is extended or adjusted under 35 U.S.C. 154(b) by 0 days.

(21) Appl. No.: 16/809,325

(22) Filed: Mar. 4, 2020

(65) Prior Publication Data

US 2020/0207764 A1    Jul. 2, 2020

Related U.S. Application Data

(63) Continuation of application No. PCT/EP2018/073584, filed on Sep. 3, 2018.

(30) Foreign Application Priority Data

Sep. 4, 2017   (EP) ..................................... 17189228

(51) Int. Cl.
| | | |
|---|---|---|
| *C07D 471/04* | (2006.01) | |
| *C07D 235/26* | (2006.01) | |
| *C07D 401/14* | (2006.01) | |
| *C07D 403/10* | (2006.01) | |
| *C07D 401/10* | (2006.01) | |
| *C07D 417/10* | (2006.01) | |
| *C07D 405/12* | (2006.01) | |
| *C07D 487/08* | (2006.01) | |
| *C07D 405/14* | (2006.01) | |
| *C07D 403/14* | (2006.01) | |

(52) U.S. Cl.
CPC ......... *C07D 471/04* (2013.01); *C07D 235/26* (2013.01); *C07D 401/10* (2013.01); *C07D 401/14* (2013.01); *C07D 403/10* (2013.01); *C07D 403/14* (2013.01); *C07D 405/12* (2013.01); *C07D 405/14* (2013.01); *C07D 417/10* (2013.01); *C07D 487/08* (2013.01)

(58) Field of Classification Search
CPC .. C07D 471/04; C07D 235/26; C07D 401/10; C07D 401/14; C07D 403/10; C07D 403/14; C07D 405/12; C07D 405/14; C07D 417/10; C07D 487/08
USPC .................................................. 514/254.06
See application file for complete search history.

(56) References Cited

U.S. PATENT DOCUMENTS

| | | |
|---|---|---|
| 5,635,517 A | 6/1997 | Muller et al. |
| 6,306,663 B1 | 10/2001 | Kenten et al. |
| 7,041,298 B2 | 5/2006 | Deshaies et al. |
| 7,208,157 B2 | 4/2007 | Deshaies et al. |
| 9,125,915 B2 | 9/2015 | Miyoshi et al. |
| 9,249,161 B2 | 2/2016 | Albrecht et al. |
| 2003/0092749 A1 | 5/2003 | Dombroski et al. |
| 2013/0190340 A1 | 7/2013 | Hedstrom et al. |
| 2014/0302523 A1 | 10/2014 | Crews et al. |
| 2014/0356322 A1 | 12/2014 | Crews et al. |
| 2015/0119435 A1 | 4/2015 | Crews et al. |
| 2015/0274738 A1 | 10/2015 | Gray et al. |
| 2015/0291562 A1 | 10/2015 | Crew et al. |
| 2016/0008356 A1 | 1/2016 | Hege |
| 2016/0016966 A1 | 1/2016 | Amans et al. |
| 2016/0022642 A1 | 1/2016 | Crews et al. |
| 2016/0045607 A1 | 2/2016 | Crew et al. |
| 2016/0046661 A1 | 2/2016 | Gray et al. |
| 2016/0058872 A1 | 3/2016 | Crew et al. |
| 2016/0176916 A1 | 6/2016 | Bradner et al. |
| 2016/0214972 A1 | 7/2016 | Jin et al. |
| 2016/0027263 A1 | 9/2016 | Crew et al. |
| 2017/0008904 A1 | 1/2017 | Crew et al. |
| 2017/0037004 A1 | 2/2017 | Crew et al. |
| 2017/0065719 A1 | 3/2017 | Qian et al. |
| 2018/0015087 A1 | 1/2018 | Liu et al. |
| 2018/0085465 A1 | 3/2018 | Bradner et al. |

FOREIGN PATENT DOCUMENTS

| | | |
|---|---|---|
| BR | PI1100318 A2 | 5/2013 |
| CN | 103421061 A | 12/2013 |
| EP | 385850 A2 | 3/1993 |
| EP | 1256578 A1 | 1/2009 |
| WO | WO 1998/011111 A1 | 3/1998 |
| WO | WO 2001/092239 A1 | 12/2001 |
| WO | WO 2002/059106 A1 | 8/2002 |
| WO | WO 2002/072576 A1 | 9/2002 |
| WO | WO 2004/108133 A2 | 12/2004 |

(Continued)

OTHER PUBLICATIONS

Agafonov Roman et al., Poster Presentation titled "Quantitative and high throughput method for measuring complex formation between target proteins and E3 ubiquitin ligase", EMBO, Sep. 16, 2017.
Bartlett et al., "The Evolution of Thalidomide and its Imid Derivatives as Anticancer Agents", Nat. Rev. Cancer, 2004, 4, 314-322.
Berndsen et al., "New insights into ubiquitin E3 ligase mechanism", Nat. Struct. Mol. Biol., 2014, 21, 301-307.
Bondeson et al., "Catalytic in Vivo Protein Knockdown by Small-Molecule Protacs", Nat. Chem. Biol., 2015, 11, 611-617.
Buckley et al., "Targeting the Von Hippel-Lindau E3 Ubiquitin Ligase Using Small Molecules to Disrupt the Vhl/Hif-1alpha Interaction", J. Am. Chem. Soc., 2012, 134, 4465-4468.

(Continued)

*Primary Examiner* — Kristin A Vajda
(74) *Attorney, Agent, or Firm* — Knowles Intellectual Property Strategies, LLC

(57) ABSTRACT

The present invention provides selected dihydrobenzimidazolones which bind to the ubiquitously expressed E3 ligase protein cereblon (CRBN) and alter the substrate specificity of the CRBN E3 ubiquitin ligase complex, resulting in breakdown of intrinsic downstream proteins. The disclosed compounds are useful for the treatment of cancer.

22 Claims, No Drawings

(56) References Cited

FOREIGN PATENT DOCUMENTS

| WO | WO 2005/060967 A1 | 7/2005 |
| WO | WO 2005/113489 A1 | 12/2005 |
| WO | WO 2006/058338 A2 | 6/2006 |
| WO | WO 2006/102557 A2 | 9/2006 |
| WO | WO 2007/041598 A1 | 4/2007 |
| WO | WO 2007/065518 A1 | 6/2007 |
| WO | WO 2008/027542 A2 | 3/2008 |
| WO | WO 2008/033567 A1 | 3/2008 |
| WO | WO 2008/039489 A2 | 4/2008 |
| WO | WO 2008/115516 A2 | 9/2008 |
| WO | WO 2008/122038 A1 | 10/2008 |
| WO | WO 2009/042177 A1 | 4/2009 |
| WO | WO 2009/050232 A1 | 4/2009 |
| WO | WO 2009/135651 A1 | 11/2009 |
| WO | WO 2009/139880 A1 | 11/2009 |
| WO | WO 2009/145899 A1 | 12/2009 |
| WO | WO 2010/023161 A1 | 3/2010 |
| WO | WO 2010/053732 A1 | 5/2010 |
| WO | WO 2010/085684 A1 | 7/2010 |
| WO | WO 2010/107485 A1 | 9/2010 |
| WO | WO 2010/108187 A2 | 9/2010 |
| WO | WO 2010/130794 A1 | 11/2010 |
| WO | WO 2011/035124 A1 | 3/2011 |
| WO | WO 2011/097218 A1 | 8/2011 |
| WO | WO 2011/130628 A1 | 10/2011 |
| WO | WO 2011/143669 A2 | 11/2011 |
| WO | WO 2011/156245 A2 | 12/2011 |
| WO | WO 2012/021382 A1 | 2/2012 |
| WO | WO 2012/061708 A1 | 5/2012 |
| WO | WO 2012/079022 A1 | 6/2012 |
| WO | WO 2012/174199 A1 | 6/2012 |
| WO | WO 2012/178208 A2 | 12/2012 |
| WO | WO 2013/020557 A1 | 2/2013 |
| WO | WO 2013/059215 A1 | 4/2013 |
| WO | WO 2013/063560 A2 | 5/2013 |
| WO | WO 2013/106643 A2 | 7/2013 |
| WO | WO 2013/106646 A2 | 7/2013 |
| WO | WO 2013/170147 A1 | 11/2013 |
| WO | WO 2014/134240 A1 | 9/2014 |
| WO | WO 2014/145887 A1 | 9/2014 |
| WO | WO 2016/011906 A1 | 1/2016 |
| WO | WO 2016/040508 A1 | 3/2016 |
| WO | WO 2016/065139 A1 | 4/2016 |
| WO | WO 2016/105518 A1 | 6/2016 |
| WO | WO 2016/146985 A1 | 9/2016 |
| WO | WO 2016/169989 A1 | 10/2016 |
| WO | WO 2016/176449 A1 | 11/2016 |
| WO | WO 2016/176460 A1 | 11/2016 |
| WO | WO 2016/191178 A1 | 12/2016 |
| WO | WO 2016/197032 A1 | 12/2016 |
| WO | WO 2016/197114 A1 | 12/2016 |
| WO | WO 2017/007612 A1 | 1/2017 |
| WO | WO 2017/024317 A2 | 2/2017 |
| WO | WO 2017/024318 A1 | 2/2017 |
| WO | WO 2017/024319 A1 | 2/2017 |
| WO | WO 2017/046318 A1 | 3/2017 |
| WO | WO 2017/117473 A1 | 7/2017 |
| WO | WO 2017/161119 A1 | 9/2017 |
| WO | WO 2017/176708 A1 | 10/2017 |
| WO | WO 2017/176957 A1 | 10/2017 |
| WO | WO 2017/176958 A1 | 10/2017 |
| WO | WO 2017/180417 A1 | 10/2017 |
| WO | WO 2017/197240 A1 | 11/2017 |
| WO | WO 2017/201069 A1 | 11/2017 |
| WO | WO 2017/201449 A1 | 11/2017 |
| WO | WO 2018/023029 A1 | 2/2018 |
| WO | WO 2018/051107 A1 | 3/2018 |
| WO | WO 2018/052945 A1 | 3/2018 |
| WO | WO 2018/052949 A1 | 3/2018 |
| WO | WO 2018/053354 A1 | 3/2018 |
| WO | WO 2018/071606 A1 | 4/2018 |
| WO | WO 2018/085247 A1 | 5/2018 |
| WO | WO 2018/102067 A2 | 6/2018 |
| WO | WO 2018/102725 A1 | 6/2018 |
| WO | WO 2018/118598 A1 | 6/2018 |
| WO | WO 2018/118947 A1 | 6/2018 |
| WO | WO 2018/119357 A1 | 6/2018 |
| WO | WO 2018/119441 A1 | 6/2018 |
| WO | WO 2018/119448 A1 | 6/2018 |
| WO | WO 2018/140809 A1 | 8/2018 |
| WO | WO 2018/144649 A1 | 8/2018 |
| WO | WO 2018/169777 A1 | 9/2018 |
| WO | WO 2018/183411 A1 | 10/2018 |
| WO | WO 2018/189554 A1 | 10/2018 |
| WO | WO 2018/191199 A1 | 10/2018 |

OTHER PUBLICATIONS

Buckley et al. "HaloPROTACS: Use of Small Molecule PROTACS to Induce Degradation of HaloTag Fusion Proteins" ACS Chemical Biology 2015, 10:1831-1837.

Buckley et al. "Small-Molecule Control of Intracellular Protein Levels through Modulation of the Ubiquitin Proteasome System" Angewandte Reviews, 2014, 53:2312-2330.

Burkhard et al. "Synthesis and Stability of Oxetane Analogs of Thalidomide and Lenalidomide" Organic Letters 2013, 15(7):4312-4315,.

Chamberlain et al. "Structure of the human cereblon-DDB1-lenalidomide complex reveals basis for responsiveness to thalidomide analogs" Nature Structural and Molecule Biology, 2014, 21(9):803-809.

Chang, X. and Stewart, K. A. "What is the functional role of the thalidomide binding protein cereblon?" Int J Biochem Mol Bio. 2011, 2(3):287-294.

Collins et al., "Chemical approaches to targeted protein degradation through modulation of the ubiquitin-protease pathway", Biochem. J. 2017, 474(7), 1127-1147.

Contino-Pepin, et al., "Preliminary biological evaluations of new thalidomide analogues for multiple sclerosis application", Bioorganic & Medicinal Chemistry Letters, 2009, 19, 878-881.

Corson et al. "Design and applications of bifunctional small molecules: Why two heads are better than one" ACS Chemical Biology 2008, 3(11): 677-692.

Crew, C. M. "Targeting the undruggable proteome: the small molecules of my dreams" Chemistry and Biology 2010, 17(6):551-555.

Deshaies et al., "RING domain E3 ubiquitin ligases.", Ann. Rev. Biochem., 2009, 78, 399-434.

Elam W.A., et al., Poster Presentation titled "Application of Biophysical Techniques to the Targeted Protein Degradation Therapeutic Strategy", Sep. 24, 2017.

Faden et al. "Generic tools for conditionally altering protein abundance and phenotypes on demain" Biol. Chem. 2014, 395(7-8):737-762.

Fisher et al., "Targeted protein degradation and the enzymology of degraders", Current Opinion of Chemical Biology, 2018, 44, 47-55.

Fischer et al. "Structure of the DDB1-CRBN E3 ubiquitin ligase in complex with thalidomide" Nature 2014, 512:49-53.

Fischer et al. "The Molecular Basis of CRL4DDB2/CSA Ubiquitin Ligase Architecture, Targeting, and Activation," Cell 2011, 147:1024-1039.

Gang Lu et al., "The Myeloma Drug Lenalidomide Promotes the Cereblon-Dependent Destruction of Ikaros Proteins", Science, 343, 305-309 (2014).

Gosink et al., "Redirecting the Specificity of Ubiquitination by Modifying Ubiquitin-Conjugating Enzymes", Proc. Natl. Acad. Sci. USA, 1995, 92, 9117-9121.

Gustafson et al., "Small-Molecule-Mediated Degradation of the Androgen Receptor through Hydrophobic Tagging", Angewandte Chemie, International Edition in English, 2015, 54, 9659-9662.

Hines et al. "Posttranslational protein knockdown couple to receptor tyrosine kinase activation with phosphoPROTACs" PNAS 2013, 110(22):8942-8947.

Hyeju Choi et al., "The impact of an indeno[1,2-b]thiophene spacer on dye-sensitized solar cell performances of cyclic thiourea functionalized organic sensitizers", Journal of Materials Chemistry, 2014, 2, 12931-12939; XP002778297.

(56) References Cited

OTHER PUBLICATIONS

International search report and Written Opinion for PCT/EP2018/073584 dated Jan. 28, 2019.
Invitation to pay additional fees for PCT/EP2018/073584 dated Dec. 5, 2018.
Ito et al., "Identification of a Primary Target of Thalidomide Teratogenicity", Science 2010, 327, 1345-1350.
Itoh et al. "Protein knockdown using methyl bestatin-ligand hybrid molecules: design and synthesis of inducers of ubiquitination-mediated degradation of cellular retinoic acid-binding proteins" Journal of the American Chemical Society 2010, 132(16), 5820-5826.
Jacques et al. "Differentiation of anti-inflammatory and antitumorigenic properties of stabilized enantiomers of thalidomide analogs" PNAS 2015, 112:E1471-E1479.
Jun Yon Choi et al., "Structure guided development of novel thymidine minetics targeting pseudomonas aeruginosa thymidylate kinase: From hit to lead generation", Journal of Medicinal Chemistry, 2012, 55(13), 852-870; XP002778247.
Kronke et al., "Lenalidomide Causes Selective Degradation of IKZF1 and IKZF3 in Multiple Myeloma Cells", Science, 2014, 343, 301-305.
Kronke et al. "Lenalidomide induces ubiquitination and degradation of CDK1 [alpha] in del(5q) MDS" Nature 2015, 523(7559): 183-188.
Lai et al., "Modular Protac Design for the Degradation of Oncogenic Bcr-Abl", Angewandte Chemie, International Edition in English, 2016, 55, 807-810.
Lee et al. "Targeted Degradation of the Aryl Hydrocarbon Receptor by the PROTAC Approach: A Useful Chemical Genetic Tool" ChemBioChem 2007, 8:2058-2062.
Li et al., "Genome-wide and functional annotation of human E3 ubiquitin ligases identifies MULAN, a mitochondrial E3 that regulates the organelle's dynamics and signaling", PLOS One, 2008, 3, 1487.
Liu et al. "Design and biological characterization of hybrid compounds of curcumin and thalidomide for multiple myeloma" Organic and Biomolecular Chemistry 2013, 11:4757.
Lu et al., "Hijacking the E3 Ubiquitin Ligase Cereblon to Efficiently Target Brd4", Chem. Biol., 2015, 22, 755-763.
Lu et al. "The myeloma drug lenalidomide promotes the cereblon-dependent destruction of Ikaros proteins" Science 2014, 343:305-309.
Mitsuaki et al., "Novel 5-hydroxytryptamine (5-HT3) Receptor antagonists. IV. Synthesis and pharmacological evaluation of the oxidation products of (−)-(R)-5-[(1-methyl-1-1H-indol-3-yl)-4,5,6,7-tetrahydro-1H-benzimidazole hydrochloride (YM060: Ramosetron)", Chem. Pharm. Bull. 1996, 44(9), 1717-22.
Nasveschuk C., Presentation titled "Advances in the Medicinal Chemistry of Targeted Protein Degradation", Aug. 7, 2018.
Nawaz et al., "Proteasome-Dependent Degradation of the Human Estrogen Receptor", Proc. Natl. Acad. Sci. U. S. A., 1999, 96, 1858-1862.
Neklesa et al. "Small-molecule hydrophobic tagging-induced degradation of HaloTag fusion proteins." Nat Chem Biol 2011, 7(8):538-543.
Patel, J., Poster Presentation titled "Diverse Utility of Targeted Protein Degradation at C4 Therapeutics", Sep. 17, 2017.
Phillips A., Presentation titled "Targeted Protein Degradation", Applied Pharmaceutical Chemistry, Cambridge, MA, Apr. 5, 2018.
Raina et al. "Chemical Inducers of Targeted Protein Degradation" Journal of Biological Chemistry 2010, 285:11057-11060.
Rodriguez-Gonzalez et al. "Targeting steroid hormone receptors for ubiquitination and degradation in breast and prostate cancer" Oncogene 2008, 27:7201-7211.
Ruchelman et al. "Isosteric analogs of lenalidomide and pomalidomide: Synthesis and biological activity" Bioorganic and Medicinal Chemistry Letters 2012, 23:360-365.
Sakamoto et al., "Development of Protacs to Target Cancer-Promoting Proteins for Ubiquitination and Degradation", Mol. Cell. Proteomics, 2003, 2, 1350-1358.
Sakamoto et al., "Protacs: Chimeric Molecules That Target Proteins to the Skp1-Cullin-F Box Complex for Ubiquitination and Degradation", Proc. Natl. Acad. Sci. USA, 2001, 98, 8554-8559.
Schneekloth et al., "Targeted Intracellular Protein Degradation Induced by a Small Molecule: En Route to Chemical Proteomics", Bioorg. Med. Chem. Lett., 2008, 18, 5904-5908.
Schneekloth et al., "Chemical Approaches to Controlling Intracellular Protein Degradation", Chem. Bio. Chem., 2005, 6, 40-46.
Schneekloth et al., "Chemical Genetic Control of Protein Levels: Selective in Vivo Targeted Degradation", J. Am. Chem. Soc., 2004, 126, 3748-3754.
Shoji, et al., "Modified DNA Aptamer That Binds the (R)-Isomer of a Thalidomide Derivative with High Enantioselectivity", J. Am. Chem. Soc., 2007, 129, 1456-1464.
Smith et al. "Targeted Intracellular Protein Degradation Induced by a Small Molecule: En Route to Chemical Proteomics" Bioorg. Med. Chem. Lett. 2008, 18(22):5904-5908.
Smolyar et al., "Synthesis of 1,2-dialkyl-5-(hetaryl-1-yl)-1,3-dihydrobenzimidazol-2-ones", Russian Journal of Organic Chemistry, 2011, 47(8), 119-3.
Spratt et al., "RBR E3 ubiquitin ligases: new structures, new insights, new questions", Biochem, 2014, 458, 421-437.
Terefenko et al., "SAR studies of 6-aryl-1,3-dihydrogenzimidazole-2-ones as progesterone receptor antagonists'" Bioorganic & Med Chem Lett., 2005, 15(15), 3600-03.
Toure et al., "Small-Molecule Protacs: New Approaches to Protein Degradation", Angew. Chem. Int. Ed., 2016, 55, 1966-1973.
Vassilev et al., "In Vivo Activation of the P53 Pathway by Small-Molecule Antagonists of MDM2", Science, 2004, 303, 844-848.
Vieux Ellen et al., Poster Presentation titled "Measuring Small Molecule Induced Ubiquitination of Proteins", EMBO, Sep. 18, 2017.
Vincent et al., "HZSM-5 catalyzed regiospecific benzoylation of activated aromatic compounds", Tetrahedron Lett. 1994, 3 5(16), 2601-2.
Wang et al., "Roles of F-box proteins in cancer", Nat. Rev. Cancer., 2014, 14, 233-347.
Winter et al., "Drug Development. Phthalimide Conjugation as a Strategy for in Vivo Target Protein Degradation", Science, 2015, 348, 1376-1381.
Yu et al., "Synthesis and properties of aroyl derivatives of 2-imidazolone and 2-benzimidazolone", Chemistry of Heterocyclic Compounds, 1968, 4(4), 698-701.
Zengerle et al. "Selective Small Molecule Induced Degradation of the BET Bromodomain Protein BRD4" ACS Chem. Biol. 2015, 10:1770-1777.
Zhou et al., "Harnessing the Ubiquitination Machinery to Target the Degradation of Specific Cellular Proteins", Mol. Cell, 2000, 6, 751-756.
Zeid Rhamy Presentation titled "Targeted protein degradation as a novel therapeutic approach", Gordon Research Conference, Jun. 26, 2017.

DIHYDROBENZIMIDAZOLONES FOR MEDICAL TREATMENT

CROSS-REFERENCE TO RELATED APPLICATIONS

This application is a continuation of International Application No. PCT/EP2018/073584, filed Sep. 3, 2018, which claims the benefit of priority to European Patent Application No. 17189228.4, filed Sep. 4, 2017. The entirety of these applications is hereby incorporated by reference herein for all purposes.

FIELD OF THE INVENTION

The present invention provides dihydrobenzimazolone compounds which bind to the ubiquitously expressed E3 ligase protein cereblon (CRBN) and alter the substrate specificity of the CRBN E3 ubiquitin ligase complex, resulting in breakdown of intrinsic downstream proteins. The disclosed compounds are useful for the treatment of cancer.

BACKGROUND OF THE INVENTION

The field of targeted protein degradation promoted by small molecules has been intensively studied over the last years[1].

Protein degradation plays a role in various cellular functions, i.e. the concentrations of regulatory proteins are adjusted through degradation into small peptides to maintain health and productivity of the cells.

Cereblon is a protein that forms an E3 ubiquitin ligase complex, which ubiquinates various other proteins. Cereblon is known as primary target for anticancer thalidomide analogs. A higher expression of cereblon has been linked to the efficiency of thalidomide analogs in cancer therapy.

In recent years, a few bifunctional compounds have been described as useful modulators of targeted ubiquitination, e.g. WO2013020557[2], WO2013063560[3], WO2013066643[4], WO2015160845[5], WO2016011906[6], WO2016105518[7], WO2017007612[8], WO2017024318[9] and WO2017117473[10].

WO2011035124[11], WO02072576[12], WO2010085684[13], WO2014134240[14], WO2011130628[15], WO2007065518[16], WO2016176460[17], WO2009135651[18], WO2011156245[19], WO2017046318[20], WO2010130794[21], WO2012021382[22], WO2005060967[23], WO2012174199[24], EP385850[25], WO2016176449[26], WO2016040508[27], WO0020358[28], EP1256578[29], WO2006058338[30], WO2004108133[31], WO2010108187[32], WO2005113489[33], WO2012061708[34], WO2010023161[35], WO2007041598[36], WO2009050232[37], Terefenko et al.[38], Smolyar et al.[39], Jun Yon Choi et al.[40], Hyeju Choi et al.[41], Mitsuaki et al.[42], Yu et al.[43], Vincent et al.[44] describe structurally related compounds.

However, there is still an ongoing need for effective treatment of cancers.

SUMMARY OF THE INVENTION

The present invention provides dihydrobenzimidazolones of formula I, or a pharmaceutically acceptable salt thereof,

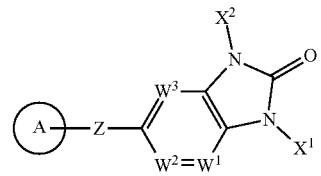

I wherein the substituents and variables are as described below and in the claims, or a pharmaceutically acceptable salt thereof.

The present compounds are useful for the therapeutic and/or prophylactic treatment of cancer.

The compounds of present invention can further be used as part of bifunctional compounds that comprise the compounds of present invention as E3 Ubiquitin Ligase moiety that is linked to a moiety that binds to a target protein where the target protein is proximate to the ubiquitin ligase to effect degradation of said protein.

DETAILED DESCRIPTION OF THE INVENTION

The present invention provides a compound of formula I and their pharmaceutically acceptable salts thereof, the preparation of the above-mentioned compounds, medicaments containing them and their manufacture as well as the use of the above-mentioned compounds in the therapeutic and/or prophylactic treatment of cancer.

The following definitions of the general terms used in the present description apply irrespectively of whether the terms in question appear alone or in combination with other groups.

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

The term "$C_{1-6}$-alkyl", alone or in combination with other groups, stands for a hydrocarbon radical which may be linear or branched, with single or multiple branching, wherein the alkyl group in general comprises 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl (2-methyl-propyl), 1,2-dimethyl-propyl and the like. A specific group is methyl.

The term "halogen-$C_{1-6}$-alkyl", alone or in combination with other groups, refers to $C_{1-6}$-alkyl as defined herein, which is substituted by one or multiple halogen, particularly 1-5 halogen, more particularly 1-3 halogen. Particular halogen is fluoro. Particular "halogen-$C_{1-6}$-alkyl" is fluoro-$C_{1-6}$-alkyl and a particular "halogen-$C_{1-3}$-alkyl" is fluoro-$C_{1-3}$-alkyl. Examples are trifluoromethyl, difluoromethyl, fluoromethyl and the like.

The term "hydroxy-$C_{1-6}$-alkyl", alone or in combination with other groups, refers to $C_{1-6}$-alkyl as defined herein, which is substituted by one or multiple hydroxy, particularly by 1 hydroxy. Examples are —$CH_2OH$, —$CH_2CH_2OH$ and the like.

The term "cycloalkyl" denotes a monovalent saturated monocyclic or bicyclic hydrocarbon group of 3 to 10 ring carbon atoms, particularly a monovalent saturated monocyclic hydrocarbon group of 3 to 8 ring carbon atoms. Bicyclic means consisting of two carbocycles having one or more carbon atoms in common, while one carbocycle is saturated, the other one may be aromatic. Particular cycloalkyl groups are monocyclic. Examples for monocyclic cycloalkyl are "$C_{3-7}$cycloalkyl" such as cyclopropyl, cyclobutanyl, cyclopentyl, cyclohexyl or cycloheptyl. Examples for saturated bicyclic cycloalkyl are bicyclo[2.2.1]heptanyl, or bicyclo[2.2.2]octanyl. Examples for bicyclic cycloalkyl wherein one ring is aromatic are 1H-indenyl or 1,2,3,4-tetrahydronaphthalenyl.

The term "hydroxy", alone or in combination with other groups, refers to OH.

The term "Bz" stands for benzyl.

The term "halogen", alone or in combination with other groups, denotes chloro (Cl), iodo (I), fluoro (F) and bromo (Br). A specific group is F.

The term "heteroaryl" denotes a monovalent heterocyclic mono- or bicyclic ring system of 5 to 12 ring atoms, comprising 1, 2, 3 or 4 heteroatoms selected from N, O and S, the remaining ring atoms being carbon and in which at least one ring is aromatic. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolinyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl. Specific examples include benzimidazolyl, pyridinyl, thiazolyl, indolinyl, 1,2,3,4-tetrahydroquinolinyl, 3,4-dihydroquinolinyl, benzofuranyl, furanyl, imidazolyl, isoindolyl, and quinolinyl.

The term "heterocycloalkyl" denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Examples for monocyclic saturated heterocycloalkyl are azetidinyl, pyrrolidinyl, tetrahydrofuranyl, tetrahydrothienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl. Specific examples include piperazinyl, piperidinyl, pyrrolidinyl and 3,8-diazabicyclo[3.2.1]octanyl.

The term "$C_{1-6}$-alkoxy", alone or in combination with other groups, stands for an —O—$C_{1-6}$-alkyl radical which may be linear or branched, with single or multiple branching, wherein the alkyl group in general comprises 1 to 6 carbon atoms, for example, methoxy (OMe, MeO), ethoxy (OEt), propoxy, isopropoxy (i-propoxy), n-butoxy, i-butoxy (iso-butoxy), 2-butoxy (sec-butoxy), t-butoxy (tert-butoxy), isopentyloxy (i-pentyloxy) and the like. Particular "$C_{1-6}$-alkoxy" are groups with 1 to 4 carbon atoms. A specific group is methoxy.

The term "aryl" denotes a monovalent aromatic carbocyclic mono- or bicyclic ring system comprising 6 to 10 carbon ring atoms. Examples of aryl moieties include phenyl (Ph), Benzyl (Bz) and naphthyl. Specific "aryl" is phenyl.

Terms like "a-b-x substituted by R" means that the "x" portion of the moiety is substituted by R.

The compound of formula I with Z=—NH—C(=O)— is a compound of formula I-1

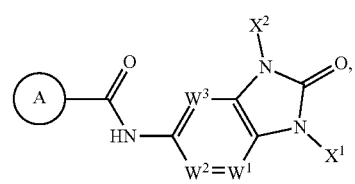

and the compound of formula I with Z=—C(=O)—NH— is a compound of formula I-2

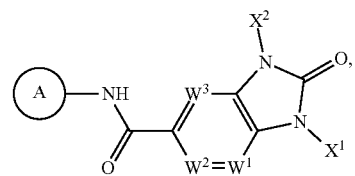

and the like.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The term "a pharmaceutically acceptable salt" refers to a salt that is suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid (sulphuric acid), tartaric acid, trifluoroacetic acid and the like. Particular acids are formic acid, trifluoroacetic acid and hydrochloric acid. Specific acids are hydrochloric acid, trifluoroacetic acid and fumaric acid.

The terms "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Particularly it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as particularly, more particularly and most particularly definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "aromatic" denotes the conventional idea of aromaticity as defined in the literature, in particular in IUPAC—Compendium of Chemical Terminology, 2$^{nd}$ Edition, A. D. McNaught & A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

Whenever a chiral carbon is present in a chemical structure, it is intended that all stereoisomers associated with that chiral carbon are encompassed by the structure as pure stereoisomers as well as mixtures thereof.

The invention also provides pharmaceutical compositions, methods of using, and methods of preparing the aforementioned compounds.

All separate embodiments may be combined.

E1: One embodiment of the invention provides a compound of formula I, or a pharmaceutically acceptable salt thereof

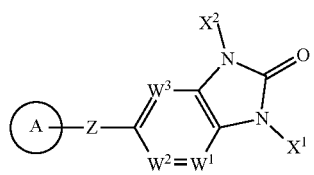

wherein
$X^1$ is H or —$C_{1-6}$alkyl,
$X^2$ is H or —$C_{1-6}$alkyl,
$W^1$ is CH or N,
$W^2$ is CH or N,
$W^3$ is CH or N,
and if one of $W^1$, $W^2$ or $W^3$ is N, then the other two are CH,
Z is absent or selected from the group consisting of
i) —$(CH_2)_{0-2}$—$NR^1$—$(CH_2)_{0-2}$—,
ii) —$(NR^1)_{0-1}$—C(=O)—$(NR^1)_{0-1}$,
iii) —$(NR^1)_{0-1}$—C(=O)—$(CH_2)_{1-3}$—,
iv) —$(CH_2)_{1-3}$—,
v) —$(CH_2)_{0-2}$—O—$(CH_2)_{0-2}$, and
vi) —$(NR^1)_{0-1}$—$SO_{0,2}$—$(NR^1)_{0-1}$—,
$R^1$ is each independently selected from H and $C_{1-6}$alkyl, A is selected from the group consisting of
i) aryl substituted with one or two $R^2$,
ii) aryl,
iii) heteroaryl substituted with one or two $R^3$
iv) heteroaryl,
v) heterocycloalkyl substituted with one or two $R^4$,
vi) heterocycloalkyl,
vii) —NH—C(=O)—$C_{1-6}$alkyl, and
viii) cycloalkyl;
$R^2$ is independently selected from the group consisting of
i) —$(CH_2)_{0-1}$—$(C_{3-7}$cycloalkyl)-aryl substituted by $R^{10}$,
ii) —$(CH_2)_{0-1}$—$(C_{3-7}$cycloalkyl)-aryl,
iii) —$(CH_2)_{0-1}$-aryl substituted by $R^{10}$,
iv) —$(CH_2)_{0-1}$-aryl,
v) —$(CH_2)_{0-1}$—$C_{3-7}$cycloalkyl substituted by $R^{10}$,
vi) —$(CH_2)_{0-1}$—$C_{3-7}$cycloalkyl,
vii) —$(CH_2)_{0-1}$-heteroaryl substituted by $R^9$,
viii) —$(CH_2)_{0-1}$-heteroaryl,
ix) —C(=O)$C_{1-6}$alkyl,
x) —C(=O)—N($R^7$,$R^8$),
xi) —C(=O)O$C_{1-6}$alkyl,
xii) —$C_{1-6}$alkoxy,
xiii) —$C_{1-6}$alkyl,
xiv) —$CH_2$—O—$(CH_2)_{0-1}$-aryl substituted by $R^{10}$,
xv) —$CH_2$—O—$(CH_2)_{0-1}$-aryl,
xvi) —O—$(CH_2)_{0-1}$-aryl,
xvii) -halogen,
xviii) -halogen-$C_{1-6}$alkyl,
xix) -hydroxy-$C_{1-6}$alkyl,
xx) —N($R^5$,$R^6$),
xxi) —$NO_2$,
xxii) —NH—C(=O)$C_{1-6}$alkyl, and
xxiii) —$SO_2$—N($R^5$,$R^6$);
$R^3$ is independently selected from the group consisting of
i) —$(CH_2)_{0-1}$—$(C_{3-7}$cycloalkyl)-aryl substituted by $R^{10}$,
ii) —$(CH_2)_{0-1}$—$(C_{3-7}$cycloalkyl)-aryl,
iii) —$(CH_2)_{0-1}$-aryl substituted by $R^{10}$,
iv) —$(CH_2)_{0-1}$-aryl,
v) —$(CH_2)_{0-1}$—$C_{3-7}$cycloalkyl substituted by $R^{10}$,
vi) —$(CH_2)_{0-1}$—$C_{3-7}$cycloalkyl,
vii) —$(CH_2)_{0-1}$-heteroaryl substituted by $R^9$,
viii) —$(CH_2)_{0-1}$-heteroaryl,
ix) —$(CH_2)_{0-1}$-heterocycloalkyl,
x) —C(=O)$C_{1-6}$alkyl
xi) —$(CH_2)_{0-2}$—C(=O)—N($R^7$,$R^8$),
xii) —C(=O)O$C_{1-6}$alkyl,
xiii) —$C_{1-6}$alkoxy,
xiv) —$C_{1-6}$alkyl,
xv) —$C_{1-6}$alkyl-N($R^{11}$)—C(=O)—$R^{12}$,
xvi) —$CH_2$—O—$(CH_2)_{0-1}$-aryl substituted by $R^{10}$,
xvii) —$CH_2$—O—$(CH_2)_{0-1}$-aryl,
xviii) —O—$(CH_2)_{0-1}$-aryl,
xix) -halogen,
xx) -halogen-$C_{1-6}$alkyl,
xxi) -hydroxy-$C_{1-6}$alkyl
xxii) -hydroxy-$C_{1-6}$alkyl-aryl,
xxiii) —N($R^5$,$R^6$),
xxiv) —NH—C(=O)$C_{1-6}$alkyl,
xxv) —NH—C(=O)O$C_{1-6}$alkyl, and
xxvi) =O;
$R^4$ is independently selected from the group consisting of
i) —$(CH_2)_{0-1}$—$(C_{3-7}$cycloalkyl)-aryl substituted by $R^{10}$,
ii) —$(CH_2)_{0-1}$—$(C_{3-7}$cycloalkyl)-aryl,
iii) —$(CH_2)_{0-1}$-aryl substituted by $R^{10}$, iv) —(CH$_2$)$_{0-1}$-aryl,
v) —(CH$_2$)$_{0-1}$—C$_{3-7}$cycloalkyl substituted by R$^{10}$,
vi) —(CH$_2$)$_{0-1}$—C$_{3-7}$cycloalkyl,
vii) —(CH$_2$)$_{0-1}$-heteroaryl substituted by R$^9$,
viii) —(CH$_2$)$_{0-1}$-heteroaryl,
ix) =O,
x) —C(=O)C$_{1-6}$alkyl
xi) —C(=O)—N(R$^7$,R$^8$),
xii) —C(=O)OC$_{1-6}$alkyl,
xiii) —C$_{1-6}$alkoxy,
xiv) —C$_{1-6}$alkyl,
xv) —CH$_2$—O—(CH$_2$)$_{0-1}$-aryl substituted by R$^{10}$,
xvi) —CH$_2$—O—(CH$_2$)$_{0-1}$-aryl,
xvii) -halogen,
xviii) -halogen-C$_{1-6}$alkyl,
xix) -hydroxy-C$_{1-6}$alkyl,
xx) —N(R$^5$,R$^6$), and
xxi) —NH—C(=O)C$_{1-6}$alkyl,
R$^5$ is each independently selected from H, C$_{1-6}$alkyl and phenyl,
R$^6$ is each independently selected from H and C$_{1-6}$alkyl,
R$^7$ is each independently selected from H and C$_{1-6}$alkyl,
R$^8$ is each independently selected from H and C$_{1-6}$alkyl,
or R$^7$ and R$^8$ form together with the nitrogen they are attached to a heterocycloalkyl,
R$^9$ is each independently selected from the group consisting of
  i) C$_{1-6}$alkoxy,
  ii) C$_{1-6}$alkyl
  iii) halogen,
  iv) halogen-C$_{1-6}$alkyl,
  v) heteroaryl, and
  vi) heteroaryl substituted by C$_{1-6}$alkyl or C$_{1-6}$alkoxy,
R$^{10}$ is each independently selected from the group consisting of
  i) C$_{1-6}$alkoxy,
  ii) C$_{1-6}$alkyl
  iii) C$_{1-6}$alkyl-C$_{1-6}$alkoxy,
  iv) halogen, and
  v) halogen-C$_{1-6}$alkyl;
R$^{11}$ is each independently selected from H and C$_{1-6}$alkyl,
R$^{12}$ is each independently selected from C$_{1-6}$alkyl and C$_{3-7}$cycloalkyl,
for use as therapeutically active substance.

E2: A certain embodiment of the invention relates to the compound of formula I, or pharmaceutically acceptable salts thereof, for use as therapeutically active substance, wherein
X$^1$ is H or —C$_{1-6}$alkyl,
X$^2$ is H or —C$_{1-6}$alkyl,
W$^1$ is CH or N,
W$^2$ is CH or N,
W$^3$ is CH or N,
and if one of W$^1$, W$^2$ or W$^3$ is N, then the other two are CH,
Z is absent or selected from the group consisting of
  i) —(CH$_2$)$_{0-2}$—NR$^1$—(CH$_2$)$_{0-2}$—,
  ii) —(NR$^1$)$_{0-1}$—C(=O)—(NR$^1$)$_{0-1}$,
  iii) —(CH$_2$)$_{1-3}$—,
  iv) —(CH$_2$)$_{0-2}$—O—(CH$_2$)$_{0-2}$—, and
  v) —(NR$^1$)$_{0-1}$—SO$_{0,2}$—(NR$^1$)$_{0-1}$—,
R$^1$ is each independently selected from H and C$_{1-6}$alkyl,
A is selected from the group consisting of
  i) aryl substituted with one or two R$^2$,
  ii) aryl,
  iii) heteroaryl substituted with one or two R$^3$,
  iv) heteroaryl,
  v) heterocycloalkyl substituted with one or two R$^4$, and
  vi) heterocycloalkyl, R$^2$ is independently selected from the group consisting of
  i) —(CH$_2$)$_{0-1}$—(C$_{3-7}$cycloalkyl)-aryl substituted by R$^{10}$,
  ii) —(CH$_2$)$_{0-1}$—(C$_{3-7}$cycloalkyl)-aryl,
  iii) —(CH$_2$)$_{0-1}$-aryl substituted by R$^{10}$,
  iv) —(CH$_2$)$_{0-1}$-aryl,
  v) —(CH$_2$)$_{0-1}$—C$_{3-7}$cycloalkyl substituted by R$^{10}$,
  vi) —(CH$_2$)$_{0-1}$—C$_{3-7}$cycloalkyl,
  vii) —(CH$_2$)$_{0-1}$-heteroaryl substituted by R$^9$,
  viii) —(CH$_2$)$_{0-1}$-heteroaryl,
  ix) —C(=O)C$_{1-6}$alkyl,
  x) —C(=O)—N(R$^7$,R$^8$),
  xi) —C(=O)OC$_{1-6}$alkyl,
  xii) —C$_{1-6}$alkoxy,
  xiii) —C$_{1-6}$alkyl,
  xiv) —CH$_2$—O—(CH$_2$)$_{0-1}$-aryl substituted by R$^{10}$,
  xv) —CH$_2$—O—(CH$_2$)$_{0-1}$-aryl,
  xvi) -halogen,
  xvii) -halogen-C$_{1-6}$alkyl,
  xviii) -hydroxy-C$_{1-6}$alkyl,
  xix) —N(R$^5$,R$^6$), and
  xx) —NH—C(=O)C$_{1-6}$alkyl,
R$^3$ is independently selected from the group consisting of
  i) —(CH$_2$)$_{0-1}$—(C$_{3-7}$cycloalkyl)-aryl substituted by R$^{10}$,
  ii) —(CH$_2$)$_{0-1}$—(C$_{3-7}$cycloalkyl)-aryl,
  iii) —(CH$_2$)$_{0-1}$-aryl substituted by R$^{10}$,
  iv) —(CH$_2$)$_{0-1}$-aryl,
  v) —(CH$_2$)$_{0-1}$—C$_{3-7}$cycloalkyl substituted by R$^{10}$,
  vi) —(CH$_2$)$_{0-1}$—C$_{3-7}$cycloalkyl,
  vii) —(CH$_2$)$_{0-1}$-heteroaryl substituted by R$^9$,
  viii) —(CH$_2$)$_{0-1}$-heteroaryl,
  ix) —(CH$_2$)$_{0-1}$-heterocycloalkyl,
  x) —C(=O)C$_{1-6}$alkyl
  xi) —C(=O)—N(R$^7$,R$^8$),
  xii) —C(=O)OC$_{1-6}$alkyl,
  xiii) —C$_{1-6}$alkoxy,
  xiv) —C$_{1-6}$alkyl,
  xv) —C$_{1-6}$alkyl-N(R$^{11}$)—C(=O)—R$^{12}$,
  xvi) —CH$_2$—O—(CH$_2$)$_{0-1}$-aryl substituted by R$^{10}$,
  xvii) —CH$_2$—O—(CH$_2$)$_{0-1}$-aryl,
  xviii) -halogen,
  xix) -halogen-C$_{1-6}$alkyl,
  xx) -hydroxy-C$_{1-6}$alkyl,
  xxi) —N(R$^5$,R$^6$), and
  xxii) —NH—C(=O)C$_{1-6}$alkyl,
R$^4$ is independently selected from the group consisting of
  i) —(CH$_2$)$_{0-1}$—(C$_{3-7}$cycloalkyl)-aryl substituted by R$^{10}$,
  ii) —(CH$_2$)$_{0-1}$—(C$_{3-7}$cycloalkyl)-aryl,
  iii) —(CH$_2$)$_{0-1}$-aryl substituted by R$^{10}$,
  iv) —(CH$_2$)$_{0-1}$-aryl,
  v) —(CH$_2$)$_{0-1}$—C$_{3-7}$cycloalkyl substituted by R$^{10}$,
  vi) —(CH$_2$)$_{0-1}$—C$_{3-7}$cycloalkyl,
  vii) —(CH$_2$)$_{0-1}$-heteroaryl substituted by R$^9$,
  viii) —(CH$_2$)$_{0-1}$-heteroaryl,
  ix) =O,
  x) —C(=O)C$_{1-6}$alkyl
  xi) —C(=O)—N(R$^7$,R$^8$),
  xii) —C(=O)OC$_{1-6}$alkyl,
  xiii) —C$_{1-6}$alkoxy,
  xiv) —C$_{1-6}$alkyl,
  xv) —CH$_2$—O—(CH$_2$)$_{0-1}$-aryl substituted by R$^{10}$,
  xvi) —CH$_2$—O—(CH$_2$)$_{0-1}$-aryl,
  xvii) -halogen,
  xviii) -halogen-C$_{1-6}$alkyl, xix) -hydroxy-$C_{1-6}$alkyl,
xx) —N($R^5$,$R^6$), and
xxi) —NH—C(=O)$C_{1-6}$alkyl, $R^5$ is each independently selected from H and $C_{1-6}$alkyl,
$R^6$ is each independently selected from H and $C_{1-6}$alkyl,
$R^7$ is each independently selected from H and $C_{1-6}$alkyl,
$R^8$ is each independently selected from H and $C_{1-6}$alkyl,
or $R^7$ and $R^8$ form together with the nitrogen they are attached to a heterocycloalkyl,
$R^9$ is each independently selected from the group consisting of
  i) $C_{1-6}$alkoxy,
  ii) $C_{1-6}$alkyl
  iii) halogen,
  iv) halogen-$C_{1-6}$alkyl,
  v) heteroaryl, and
  vi) heteroaryl substituted by $C_{1-6}$alkyl,
$R^{10}$ is each independently selected from the group consisting of
  i) $C_{1-6}$alkoxy,
  ii) $C_{1-6}$alkyl,
  iii) halogen, and
  iv) halogen-$C_{1-6}$alkyl;
$R^{11}$ is each independently selected from H and $C_{1-6}$alkyl,
$R^{12}$ is each independently selected from $C_{1-6}$alkyl and $C_{3-7}$cycloalkyl,
for use as therapeutically active substance.

E3: A certain embodiment of the invention relates to the compound of formula I, or pharmaceutically acceptable salts thereof, for use as therapeutically active substance, wherein (R)—N-(2-oxo-2,3-dihydro-1H-benzo[d]imidazol-5-yl)-1,2,3,4-tetrahydronaphthalene-1-carboxamide,
(S)—N-(2-oxo-2,3-dihydro-1H-benzo[d]imidazol-5-yl)-1,2,3,4-tetrahydronaphthalene-1-carboxamide,
1-(1,3-dimethyl-2-oxo-benzimidazol-5-yl)-N-methyl-2-[2-(3-methylimidazol-4-yl)-4-quinolyl]benzimidazole-5-carboxamide,
1-(2-oxo-2,3-dihydro-1H-benzo[d]imidazol-5-yl)-3-(4-(phenylamino)phenyl)urea,
1-(2-oxo-2,3-dihydro-1H-benzo[d]imidazol-5-yl)-3-phenylurea,
1-(3-fluorophenyl)-3-(2-oxo-2,3-dihydro-1H-benzo[d]imidazol-5-yl)urea,
1',3'-dimethyl-2-(2-(1-methyl-1H-imidazol-5-yl)quinolin-4-yl)-1',3'-dihydro-2'H-[1,5'-bibenzo[d]imidazol]-2'-one,
1,3-dimethyl-5-((2-nitrophenyl)amino)-1,3-dihydro-2H-benzo[d]imidazol-2-one,
1-acetyl-N-(2-oxo-2,3-dihydro-1H-benzo[d]imidazol-5-yl)indoline-4-carboxamide,
1-acetyl-N-(2-oxo-2,3-dihydro-1H-benzo[d]imidazol-5-yl)piperidine-4-carboxamide,
1-benzyl-3-(2-oxo-2,3-dihydro-1H-benzo[d]imidazol-5-yl)urea,
1-methyl-2-oxo-N-phenyl-3H-imidazo[4,5-b]pyridine-6-carboxamide,
1-methyl-5-phenyl-3H-imidazo[4,5-b]pyridin-2-one,
2-(1-(4-methoxyphenyl)cyclopropyl)-N-methyl-2'-oxo-2',3'-dihydro-1'H-[1,5'-bibenzo[d]imidazole]-5-carboxamide,
2-(1H-imidazol-5-yl)-N-methyl-1-(2-oxo-1,3-dihydrobenzimidazol-5-yl)benzimidazole-5-carboxamide,
2-(2-(1-methyl-1H-imidazol-5-yl)quinolin-4-yl)-2'-oxo-2',3'-dihydro-1'H-[1,5'-bibenzo[d]imidazole]-5-carboxamide,
2-(2-methoxybenzyl)-N-methyl-2'-oxo-2',3'-dihydro-1'H-[1,5'-bibenzo[d]imidazole]-5-carboxamide,
2-(2-methoxypyridin-4-yl)-N-methyl-2'-oxo-2',3'-dihydro-1'H-[1,5'-bibenzo[d]imidazole]-5-carboxamide,
2-(3-(methoxymethyl)phenyl)-N-methyl-2'-oxo-2',3'-dihydro-1'H-[1,5'-bibenzo[d]imidazole]-5-carboxamide,
2-(3-methoxybenzyl)-N-methyl-2'-oxo-2',3'-dihydro-1'H-[1,5'-bibenzo[d]imidazole]-5-carboxamide,
2-(3-methoxyphenyl)-N-(2-oxo-2,3-dihydro-1H-benzo[d]imidazol-5-yl)nicotinamide,
2-(4-(N-methylsulfamoyl)phenyl)-N-(2-oxo-2,3-dihydro-1H-benzo[d]imidazol-5-yl)acetamide,
2-(4-acetamidophenyl)-N-(2-oxo-2,3-dihydro-1H-benzo[d]imidazol-5-yl)acetamide,
2-(4-aminophenyl)-N-(2-oxo-2,3-dihydro-1H-benzo[d]imidazol-5-yl)acetamide,
2-(4-methoxycyclohexyl)-N-methyl-2'-oxo-2',3'-dihydro-1'H-[1,5'-bibenzo[d]imidazole]-5-carboxamide,
2-(tert-butyl)-N-methyl-2'-oxo-2',3'-dihydro-1'H-[1,5'-bibenzo[d]imidazole]-5-carboxamide,
2-benzyl-N-(2-oxo-2,3-dihydro-1H-benzo[d]imidazol-5-yl)benzamide,
2-ethyl-N-methyl-1-(2-oxo-1,3-dihydrobenzimidazol-5-yl)benzimidazole-5-carboxamide,
2-isopropyl-1'-methyl-1',3'-dihydro-2'H-[1,5'-bibenzo[d]imidazole]-2'-one,
2-isopropyl-3'-methyl-1',3'-dihydro-2'H-[1,5'-bibenzo[d]imidazol]-2'-one,
2-isopropyl-5-methoxy-1',3'-dihydro-2'H-[1,5'-bibenzo[d]imidazol]-2'-one,
2-isopropyl-N-methyl-1-(2-oxo-1,3-dihydrobenzimidazol-5-yl)benzimidazole-5-carboxamide,
2-isopropyl-N-methyl-1-(2-oxo-1,3-dihydroimidazo[4,5-b]pyridin-6-yl)benzimidazole-5-carboxamide,
2-isopropyl-N-methyl-2'-oxo-2',3'-dihydro-1'H-[1,5'-bibenzo[d]imidazole]-6-carboxamide,
2-isopropyl-N-methyl-2'-oxo-2',3'-dihydro-1'H-[1,5'-bibenzo[d]imidazole]-4-carboxamide,
2'-methyl-N-(2-oxo-2,3-dihydro-1H-benzo[d]imidazol-5-yl)-[1,1'-biphenyl]-2-carboxamide,
2-oxo-N-(4-piperidyl)-1,3-dihydrobenzimidazole-5-carboxamide,
2-oxo-N-phenyl-2,3-dihydro-1H-benzo[d]imidazole-5-carboxamide,
2-oxo-N-phenyl-2,3-dihydro-1H-imidazo[4,5-b]pyridine-6-carboxamide,
3-acetamido-N-(2-oxo-2,3-dihydro-1H-benzo[d]imidazol-5-yl)benzamide,
3-acetamido-N-(2-oxo-2,3-dihydro-1H-benzo[d]imidazol-5-yl)propanamide,
3-amino-N-methyl-4-[(2-oxo-1,3-dihydrobenzimidazol-5-yl)amino]benzamide,
3-methoxy-N-(2-oxo-2,3-dihydro-1H-benzo[d]imidazol-5-yl)isonicotinamide,
4-(2-methoxyphenyl)-N-(2-oxo-2,3-dihydro-1H-benzo[d]imidazol-5-yl)piperazine-1-carboxamide,
4-(4-chlorobenzyl)-N-(2-oxo-2,3-dihydro-1H-benzo[d]imidazol-5-yl)piperazine-1-carboxamide,
4-acetamido-N-(2-oxo-2,3-dihydro-1H-benzo[d]imidazol-5-yl)benzamide,
5-((1-benzylpiperidin-4-yl)amino)-1,3-dihydro-2H-benzo[d]imidazol-2-one,
5-((2-aminophenyl)amino)-1,3-dimethyl-1,3-dihydro-2H-benzo[d]imidazol-2-one,
5-((2-aminophenyl)amino)-1-methyl-1,3-dihydro-2H-benzo[d]imidazol-2-one,
5-((5-aminoindolin-1-yl)methyl)-1,3-dihydro-2H-benzo[d]imidazol-2-one, 5-(1,2,3,4-tetrahydroquinoline-1-carbonyl)-1,3-dihydro-2H-benzo[d]imidazol-2-one,
5-(2,4-difluoro-phenyl)-1,3-dihydro-benzoimidazol-2-one,
5-(2,5-difluoro-phenyl)-1,3-dihydro-benzoimidazol-2-one,
5-(2-aminoanilino)-1,3-dihydrobenzimidazol-2-one,
5-(2-chloro-4-pyridyl)-1,3-dihydrobenzimidazol-2-one,
5-(2-isopropyl-1H-imidazol-1-yl)-1,3-dihydro-2H-benzo[d]imidazol-2-one,
5-(2-methylthiazol-5-yl)-1,3-dihydrobenzimidazol-2-one,
5-(2-oxopyrrolidin-1-yl)-1,3-dihydro-2H-benzo[d]imidazol-2-one,
5-(3-phenyl-propyl)-1,3-dihydro-imidazo[4,5-b]pyridin-2-one,
5-(3-pyridyl)-1,3-dihydrobenzimidazol-2-one,
5-(4-acetylpiperazin-1-yl)-1,3-dihydro-2H-benzo[d]imidazol-2-one,
5-(4-acetylpiperazine-1-carbonyl)-1,3-dihydrobenzimidazol-2-one,
5-(4-pyrrol-1-yl-phenyl)-1,3-dihydro-benzoimidazol-2-one,
5-(5-aminoindolin-1-yl)-1,3-dihydro-2H-benzo[d]imidazol-2-one,
5-(5-bromo-1-oxo-isoindolin-2-yl)-1,3-dihydrobenzimidazol-2-one,
5-(benzimidazol-1-yl)-1,3-dihydrobenzimidazol-2-one,
5-(benzyloxy)-1,3-dihydro-2H-benzo[d]imidazol-2-one,
5-(benzyloxy)-2-isopropyl-1',3'-dihydro-2'H-[1,5'-bibenzo[d]imidazol]-2'-one,
5-(indolin-1-ylsulfonyl)-1,3-dihydro-2H-benzo[d]imidazol-2-one,
5-(indoline-1-carbonyl)-1,3-dihydrobenzimidazol-2-one,
5-(piperazin-1-yl)-1,3-dihydro-2H-benzo[d]imidazol-2-one,
5-[(1S,5R)-3,8-diazabicyclo[3.2.1]octan-3-yl]-1,3-dihydrobenzimidazol-2-one,
5-[(1S,5R)-8-acetyl-3,8-diazabicyclo[3.2.1]octan-3-yl]-1,3-dihydrobenzimidazol-2-one,
5-[(4-methoxyphenyl)methyl]-1,3-dihydrobenzimidazol-2-one,
5-[2-(1-hydroxyethyl)benzimidazol-1-yl]-1,3-dihydrobenzimidazol-2-one,
5-[2-(4-quinolyl)benzimidazol-1-yl]-1,3-dihydrobenzimidazol-2-one,
5-[2-(4-quinolyl)imidazol-1-yl]-1,3-dihydrobenzimidazol-2-one,
5-[2-(hydroxymethyl)benzimidazol-1-yl]-1,3-dihydrobenzimidazol-2-one,
5-[2-(piperidine-1-carbonyl)benzimidazol-1-yl]-1,3-dihydrobenzimidazol-2-one,
5-[2-[2-(3-methylimidazol-4-yl)-4-quinolyl]benzimidazol-1-yl]-1,3-dihydrobenzimidazol-2-one,
5-[2-[hydroxy(phenyl)methyl]benzimidazol-1-yl]-1,3-dihydrobenzimidazol-2-one,
5-[4-(2-pyridyl)piperazin-1-yl]-1,3-dihydroimidazo[4,5-b]pyridin-2-one,
5-amino-N-(2-oxo-2,3-dihydro-1H-benzo[d]imidazol-5-yl)indoline-1-carboxamide hydrochloride,
5-quinolin-5-yl-1,3-dihydro-benzoimidazol-2-one,
6-((2-aminophenyl)amino)-1-methyl-1,3-dihydro-2H-benzo[d]imidazol-2-one,
6-(1,2,3,4-tetrahydroquinoline-1-carbonyl)-1,3-dihydro-2H-imidazo[4,5-b]pyridin-2-one,
6-(2-(benzyloxy)phenyl)-1,3-dihydro-2H-imidazo[4,5-b]pyridin-2-one,
6-(4-fluorophenyl)-1,3-dihydroimidazo[4,5-c]pyridin-2-one,
6-(indoline-1-carbonyl)-1,3-dihydro-2H-imidazo[4,5-b]pyridin-2-one,
6-chloro-N-(2-oxo-2,3-dihydro-1H-benzo[d]imidazol-5-yl)indoline-1-carboxamide,
ethyl 1-oxo-2-(2-oxo-1,3-dihydrobenzimidazol-5-yl)isoindoline-5-carboxylate,
ethyl 4-((2-oxo-2,3-dihydro-1H-benzo[d]imidazole)-5-sulfonamido)benzoate,
ethyl 4-(3-(2-oxo-2,3-dihydro-1H-benzo[d]imidazol-5-yl)ureido)benzoate,
methyl 1-((2-oxo-2,3-dihydro-1H-benzo[d]imidazol-5-yl)carbamoyl)-1,2,3,4-tetrahydroquinoline-5-carboxylate,
methyl 1-((2-oxo-2,3-dihydro-1H-benzo[d]imidazol-5-yl)carbamoyl)indoline-4-carboxylate,
methyl 1-((2-oxo-2,3-dihydro-1H-benzo[d]imidazol-5-yl)carbamoyl)indoline-5-carboxylate,
methyl 1-(2-oxo-1,3-dihydrobenzimidazol-5-yl)benzimidazole-2-carboxylate,
methyl 1-(2-oxo-2,3-dihydro-1H-benzo[d]imidazole-5-carbonyl)indoline-4-carboxylate,
methyl 1-oxo-2-(2-oxo-1,3-dihydrobenzimidazol-5-yl)isoindoline-5-carboxylate,
methyl 2-((2-oxo-2,3-dihydro-1H-benzo[d]imidazol-5-yl)carbamoyl)benzoate,
methyl 2-((2-oxo-2,3-dihydro-1H-benzo[d]imidazol-5-yl)methyl)isoindoline-5-carboxylate,
methyl 2-(2-(1-methyl-1H-imidazol-5-yl)quinolin-4-yl)-2'-oxo-2',3'-dihydro-1'H-[1,5'-bibenzo[d]imidazole]-5-carboxylate,
methyl 2-isopropyl-2'-oxo-2',3'-dihydro-1'H-[1,5'-bibenzo[d]imidazole]-4-carboxylate,
methyl 2-isopropyl-2'-oxo-2',3'-dihydro-1'H-[1,5'-bibenzo[d]imidazole]-6-carboxylate,
methyl 3-amino-4-[(2-oxo-1,3-dihydrobenzimidazol-5-yl)amino]benzoate,
methyl 4-(N-(2-oxo-2,3-dihydro-1H-benzo[d]imidazol-5-yl)sulfamoyl)benzoate,
methyl 6-((2-oxo-2,3-dihydro-1H-benzo[d]imidazol-5-yl)amino)nicotinate,
N-(1-((2-oxo-2,3-dihydro-1H-benzo[d]imidazol-5-yl)methyl)indolin-5-yl)acetamide,
N-(1-(2-oxo-2,3-dihydro-1H-benzo[d]imidazol-5-yl)indolin-5-yl)acetamide,
N-(1-(2-oxo-2,3-dihydro-1H-benzo[d]imidazole-5-carbonyl)piperidin-4-yl)acetamide,
N-(1,3-dimethyl-2-oxo-benzimidazol-5-yl)furan-2-carboxamide,
N-(1-acetyl-4-piperidyl)-2-oxo-1,3-dihydrobenzimidazole-5-carboxamide,
N-(1-acetylpiperidin-4-yl)-2-oxo-2,3-dihydro-1H-benzo[d]imidazole-5-sulfonamide,
N-(1-acetylpiperidin-4-yl)-2-oxo-2,3-dihydro-1H-imidazo[4,5-b]pyridine-6-carboxamide,
N-(1-acetylpiperidin-4-yl)-N-methyl-2-oxo-2,3-dihydro-1H-benzo[d]imidazole-5-carboxamide,
N-(1-benzylpiperidin-4-yl)-2-oxo-2,3-dihydro-1H-benzo[d]imidazole-5-carboxamide,
N-(2-(methylcarbamoyl)phenyl)-2-oxo-2,3-dihydro-1H-benzo[d]imidazole-5-carboxamide,
N-(2-oxo-2,3-dihydro-1H-benzo[d]imidazol-5-yl)-2-(4-sulfamoylphenyl)acetamide,
N-(2-oxo-2,3-dihydro-1H-benzo[d]imidazol-5-yl)-2-(pyridin-4-yl)benzamide,
N-(2-oxo-2,3-dihydro-1H-benzo[d]imidazol-5-yl)-2,3-dihydro-1H-indene-1-carboxamide,
N-(2-oxo-2,3-dihydro-1H-benzo[d]imidazol-5-yl)-4-sulfamoylbenzamide,
N-(2-oxo-2,3-dihydro-1H-benzo[d]imidazol-5-yl)benzamide, N-(2-oxo-2,3-dihydro-1H-benzo[d]imidazol-5-yl)benzofuran-3-carboxamide,
N-(2-oxo-2,3-dihydro-1H-benzo[d]imidazol-5-yl)benzofuran-3-sulfonamide,
N-(2-oxo-2,3-dihydro-1H-benzo[d]imidazol-5-yl)indoline-1-carboxamide,
N-(2-oxo-2,3-dihydro-1H-benzo[d]imidazol-5-yl)indoline-4-carboxamide,
N-(2-oxo-2,3-dihydro-1H-benzo[d]imidazol-5-yl)piperidine-4-sulfonamide,
N-(3-(1-methyl-1H-pyrazol-3-yl)phenyl)-2-oxo-2,3-dihydro-1H-benzo[d]imidazole-5-carboxamide,
N-(3-(oxazol-5-yl)phenyl)-2-oxo-2,3-dihydro-1H-benzo[d]imidazole-5-carboxamide,
N-(4-(((2-oxo-2,3-dihydro-1H-benzo[d]imidazol-5-yl)methyl)amino)phenyl)acetamide,
N-(4-(3-(2-oxo-2,3-dihydro-1H-benzo[d]imidazol-5-yl)ureido)phenyl)acetamide,
N,2-dimethyl-1-(2-oxo-1,3-dihydrobenzimidazol-5-yl)benzimidazole-5-carboxamide,
N,N-dimethyl-2-[2-(3-methylimidazol-4-yl)-4-quinolyl]-1-(2-oxo-1,3-dihydrobenzimidazol-5-yl)benzimidazole-5-carboxamide,
N-[2-[1-(2-oxo-1,3-dihydrobenzimidazol-5-yl)benzimidazol-2-yl]ethyl]acetamide,
N2-methyl-N5-(2-oxo-2,3-dihydro-1H-benzo[d]imidazol-5-yl)pyridine-2,5-dicarboxamide,
N4-methyl-N1-(2-oxo-2,3-dihydro-1H-benzo[d]imidazol-5-yl)indoline-1,4-dicarboxamide,
N5-methyl-N1-(2-oxo-2,3-dihydro-1H-benzo[d]imidazol-5-yl)-3,4-dihydroquinoline-1,5(2H)-dicarboxamide,
N-methyl-1-(2-oxo-1,3-dihydrobenzimidazol-5-yl)-2-(4-pyridyl)benzimidazole-5-carboxamide,
N-methyl-1-(2-oxo-1,3-dihydrobenzimidazol-5-yl)-2-(4-quinolyl)benzimidazole-5-carboxamide,
N-methyl-1-(2-oxo-1,3-dihydrobenzimidazol-5-yl)-2-(trifluoromethyl)benzimidazole-5-carboxamide,
N-methyl-1-(2-oxo-1,3-dihydrobenzimidazol-5-yl)-2-phenyl-benzimidazole-5-carboxamide,
N-methyl-1-(2-oxo-1,3-dihydrobenzimidazol-5-yl)-2-propyl-benzimidazole-5-carboxamide,
N-methyl-1-(2-oxo-1,3-dihydrobenzimidazol-5-yl)benzimidazole-2-carboxamide,
N-methyl-2-(1-methyl-1H-imidazol-4-yl)-2'-oxo-2',3'-dihydro-1'H-[1,5'-bibenzo[d]imidazole]-5-carboxamide,
N-methyl-2-[2-(3-methylimidazol-4-yl)-4-quinolyl]-1-(2-oxo-1,3-dihydrobenzimidazol-5-yl)benzimidazole-5-carboxamide,
N-methyl-2'-oxo-2-(1H-pyrrol-3-yl)-2',3'-dihydro-1'H-[1,5'-bibenzo[d]imidazole]-5-carboxamide,
N-methyl-2'-oxo-2-(1-phenylcyclopropyl)-2',3'-dihydro-1'H-[1,5'-bibenzo[d]imidazole]-5-carboxamide,
N-methyl-2'-oxo-2-(tetrahydro-2H-pyran-4-yl)-2',3'-dihydro-1'H-[1,5'-bibenzo[d]imidazole]-5-carboxamide,
N-methyl-2-oxo-N-phenyl-2,3-dihydro-1H-benzo[d]imidazole-5-carboxamide,
N-methyl-2-oxo-N-phenyl-2,3-dihydro-1H-imidazo[4,5-b]pyridine-6-carboxamide,
N-methyl-3-[1-(2-oxo-1,3-dihydrobenzimidazol-5-yl)benzimidazol-2-yl]propanamide,
N-methyl-4-((2-oxo-2,3-dihydro-1H-benzo[d]imidazol-5-yl)oxy)benzamide,
tert-butyl (1-((2-oxo-2,3-dihydro-1H-benzo[d]imidazol-5-yl)carbamoyl)indolin-5-yl)carbamate,
tert-butyl (1-((2-oxo-2,3-dihydro-1H-benzo[d]imidazol-5-yl)methyl)indolin-5-yl)carbamate,
tert-butyl 4-((2-oxo-2,3-dihydro-1H-benzo[d]imidazol-5-yl)carbamoyl)indoline-1-carboxylate, and
tert-butyl 4-(N-(2-oxo-2,3-dihydro-1H-benzo[d]imidazol-5-yl)sulfamoyl)piperidine-1-carboxylate.

E4: A certain embodiment of the invention relates to the compound of formula I, or pharmaceutically acceptable salts thereof, for use as therapeutically active substance, selected from the group consisting of
1-(1,3-dimethyl-2-oxo-benzimidazol-5-yl)-N-methyl-2-[2-(3-methylimidazol-4-yl)-4-quinolyl]benzimidazole-5-carboxamide,
1',3'-dimethyl-2-(2-(1-methyl-1H-imidazol-5-yl)quinolin-4-yl)-1',3'-dihydro-2'H-[1,5'-bibenzo[d]imidazol]-2'-one,
1-methyl-2-oxo-N-phenyl-3H-imidazo[4,5-b]pyridine-6-carboxamide,
2-(1H-imidazol-5-yl)-N-methyl-1-(2-oxo-1,3-dihydrobenzimidazol-5-yl)benzimidazole-5-carboxamide,
2-(3-methoxybenzyl)-N-methyl-2'-oxo-2',3'-dihydro-1'H-[1,5'-bibenzo[d]imidazole]-5-carboxamide,
2-ethyl-N-methyl-1-(2-oxo-1,3-dihydrobenzimidazol-5-yl)benzimidazole-5-carboxamide,
2-isopropyl-1'-methyl-1',3'-dihydro-2'H-[1,5'-bibenzo[d]imidazol]-2'-one,
2-isopropyl-3'-methyl-1',3'-dihydro-2'H-[1,5'-bibenzo[d]imidazol]-2'-one,
2-isopropyl-N-methyl-1-(2-oxo-1,3-dihydrobenzimidazol-5-yl)benzimidazole-5-carboxamide,
2-isopropyl-N-methyl-2'-oxo-2',3'-dihydro-1'H-[1,5'-bibenzo[d]imidazole]-6-carboxamide,
3-amino-N-methyl-4-[(2-oxo-1,3-dihydrobenzimidazol-5-yl)amino]benzamide,
5-(2-aminoanilino)-1,3-dihydrobenzimidazol-2-one,
5-(2-chloro-4-pyridyl)-1,3-dihydrobenzimidazol-2-one,
5-(2-isopropyl-1H-imidazol-1-yl)-1,3-dihydro-2H-benzo[d]imidazol-2-one,
5-(2-methylthiazol-5-yl)-1,3-dihydrobenzimidazol-2-one,
5-(2-oxopyrrolidin-1-yl)-1,3-dihydro-2H-benzo[d]imidazol-2-one,
5-(3-phenyl-propyl)-1,3-dihydro-imidazo[4,5-b]pyridin-2-one,
5-(3-pyridyl)-1,3-dihydrobenzimidazol-2-one,
5-(4-acetylpiperazine-1-carbonyl)-1,3-dihydrobenzimidazol-2-one,
5-(indoline-1-carbonyl)-1,3-dihydrobenzimidazol-2-one,
5-[2-(4-quinolyl)benzimidazol-1-yl]-1,3-dihydrobenzimidazol-2-one,
5-[2-(4-quinolyl)imidazol-1-yl]-1,3-dihydrobenzimidazol-2-one,
5-[2-[2-(3-methylimidazol-4-yl)-4-quinolyl]benzimidazol-1-yl]-1,3-dihydrobenzimidazol-2-one,
6-(4-fluorophenyl)-1,3-dihydroimidazo[4,5-c]pyridin-2-one,
methyl 3-amino-4-[(2-oxo-1,3-dihydrobenzimidazol-5-yl)amino]benzoate,
N-(1-(2-oxo-2,3-dihydro-1H-benzo[d]imidazole-5-carbonyl)piperidin-4-yl)acetamide,
N-(1,3-dimethyl-2-oxo-benzimidazol-5-yl)furan-2-carboxamide,
N-(1-acetyl-4-piperidyl)-2-oxo-1,3-dihydrobenzimidazole-5-carboxamide,
N,2-dimethyl-1-(2-oxo-1,3-dihydrobenzimidazol-5-yl)benzimidazole-5-carboxamide,
N,N-dimethyl-2-[2-(3-methylimidazol-4-yl)-4-quinolyl]-1-(2-oxo-1,3-dihydrobenzimidazol-5-yl)benzimidazole-5-carboxamide,
N-methyl-1-(2-oxo-1,3-dihydrobenzimidazol-5-yl)-2-(4-pyridyl)benzimidazole-5-carboxamide, N-methyl-1-(2-oxo-1,3-dihydrobenzimidazol-5-yl)-2-(4-quinolyl)benzimidazole-5-carboxamide,
N-methyl-1-(2-oxo-1,3-dihydrobenzimidazol-5-yl)-2-(trifluoromethyl)benzimidazole-5-carboxamide,
N-methyl-1-(2-oxo-1,3-dihydrobenzimidazol-5-yl)-2-phenyl-benzimidazole-5-carboxamide,
N-methyl-1-(2-oxo-1,3-dihydrobenzimidazol-5-yl)-2-propyl-benzimidazole-5-carboxamide, and
N-methyl-2-[2-(3-methylimidazol-4-yl)-4-quinolyl]-1-(2-oxo-1,3-dihydrobenzimidazol-5-yl)benzimidazole-5-carboxamide.

E5: A certain embodiment of the invention relates to a compound of formula I, or a pharmaceutically acceptable salt thereof, for use as therapeutically active substance, wherein Z is absent.

E6: A certain embodiment of the invention relates to a compound of formula I, or a pharmaceutically acceptable salt thereof,

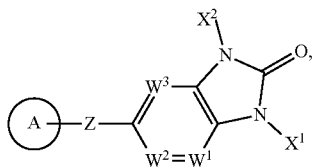

I wherein
$X^1$ is H or —$C_{1-6}$alkyl,
$X^2$ is H or —$C_{1-6}$alkyl,
$W^1$ is CH or N,
$W^2$ is CH or N,
$W^3$ is CH or N,
and if one of $W^1$, $W^2$ or $W^3$ is N, then the other two are CH,
Z is absent or selected from the group consisting of
   i) —$(CH_2)_{0-2}$—$NR^1$—$(CH_2)_{0-2}$—,
   ii) —$(NR^1)_{0-1}$—C(=O)—$(NR^1)_{0-1}$,
   iii) —$(CH_2)_{1-3}$—,
   iv) —$(CH_2)_{0-2}$—O—$(CH_2)_{0-2}$, and
   v) —$(NR^1)_{0-1}$—$SO_{0,2}$—$(NR^1)_{0-1}$—,
$R^1$ is each independently selected from H and $C_{1-6}$alkyl,
A is selected from the group consisting of
   i) aryl substituted with one or two $R^2$,
   ii) aryl,
   iii) heteroaryl substituted with one or two $R^3$
   iv) heteroaryl,
   v) heterocycloalkyl substituted with one or two $R^4$, and
   vi) heterocycloalkyl,
$R^2$ is independently selected from the group consisting of
   i) —$(CH_2)_{0-1}$—$(C_{3-7}$cycloalkyl)-aryl substituted by $R^{10}$,
   ii) —$(CH_2)_{0-1}$—$(C_{3-7}$cycloalkyl)-aryl,
   iii) —$(CH_2)_{0-1}$-aryl substituted by $R^{10}$,
   iv) —$(CH_2)_{0-1}$-aryl,
   v) —$(CH_2)_{0-1}$—$C_{3-7}$cycloalkyl substituted by $R^{10}$,
   vi) —$(CH_2)_{0-1}$—$C_{3-7}$cycloalkyl,
   vii) —$(CH_2)_{0-1}$-heteroaryl substituted by $R^9$,
   viii) —$(CH_2)_{0-1}$-heteroaryl,
   ix) —C(=O)$C_{1-6}$alkyl,
   x) —C(=O)—N($R^7,R^8$),
   xi) —C(=O)O$C_{1-6}$alkyl,
   xii) —$C_{1-6}$alkoxy,
   xiii) —$C_{1-6}$alkyl,
   xiv) —$CH_2$—O—$(CH_2)_{0-1}$-aryl substituted by $R^{10}$,
   xv) —$CH_2$—O—$(CH_2)_{0-1}$-aryl,
   xvi) -halogen,
   xvii) -halogen-$C_{1-6}$alkyl,
   xviii) -hydroxy-$C_{1-6}$alkyl,
   xix) —N($R^5,R^6$), and
   xx) —NH—C(=O)$C_{1-6}$alkyl,
$R^3$ is independently selected from the group consisting of
   i) —$(CH_2)_{0-1}$—$(C_{3-7}$cycloalkyl)-aryl substituted by $R^{10}$,
   ii) —$(CH_2)_{0-1}$—$(C_{3-7}$cycloalkyl)-aryl,
   iii) —$(CH_2)_{0-1}$-aryl substituted by $R^{10}$,
   iv) —$(CH_2)_{0-1}$-aryl,
   v) —$(CH_2)_{0-1}$—$C_{3-7}$cycloalkyl substituted by $R^{10}$,
   vi) —$(CH_2)_{0-1}$—$C_{3-7}$cycloalkyl,
   vii) —$(CH_2)_{0-1}$-heteroaryl substituted by $R^9$,
   viii) —$(CH_2)_{0-1}$-heteroaryl,
   ix) —$(CH_2)_{0-1}$-heterocycloalkyl,
   x) —C(=O)$C_{1-6}$alkyl
   xi) —C(=O)—N($R^7,R^8$),
   xii) —C(=O)O$C_{1-6}$alkyl,
   xiii) —$C_{1-6}$alkoxy,
   xiv) —$C_{1-6}$alkyl,
   xv) —$C_{1-6}$alkyl-N($R^{11}$)—C(=O)—$R^{12}$,
   xvi) —$CH_2$—O—$(CH_2)_{0-1}$-aryl substituted by $R^{10}$,
   xvii) —$CH_2$—O—$(CH_2)_{0-1}$-aryl,
   xviii) -halogen,
   xix) -halogen-$C_{1-6}$alkyl,
   xx) -hydroxy-$C_{1-6}$alkyl,
   xxi) —N($R^5,R^6$), and
   xxii) —NH—C(=O)$C_{1-6}$alkyl,
$R^4$ is independently selected from the group consisting of
   i) —$(CH_2)_{0-1}$—$(C_{3-7}$cycloalkyl)-aryl substituted by $R^{10}$,
   ii) —$(CH_2)_{0-1}$—$(C_{3-7}$cycloalkyl)-aryl,
   iii) —$(CH_2)_{0-1}$-aryl substituted by $R^{10}$,
   iv) —$(CH_2)_{0-1}$-aryl,
   v) —$(CH_2)_{0-1}$—$C_{3-7}$cycloalkyl substituted by $R^{10}$,
   vi) —$(CH_2)_{0-1}$—$C_{3-7}$cycloalkyl,
   vii) —$(CH_2)_{0-1}$-heteroaryl substituted by $R^9$,
   viii) —$(CH_2)_{0-1}$-heteroaryl,
   ix) =O,
   x) —C(=O)$C_{1-6}$alkyl
   xi) —C(=O)—N($R^7,R^8$),
   xii) —C(=O)O$C_{1-6}$alkyl,
   xiii) —$C_{1-6}$alkoxy,
   xiv) —$C_{1-6}$alkyl,
   xv) —$CH_2$—O—$(CH_2)_{0-1}$-aryl substituted by $R^{10}$,
   xvi) —$CH_2$—O—$(CH_2)_{0-1}$-aryl,
   xvii) -halogen,
   xviii) -halogen-$C_{1-6}$alkyl,
   xix) -hydroxy-$C_{1-6}$alkyl,
   xx) —N($R^5,R^6$), and
   xxi) —NH—C(=O)$C_{1-6}$alkyl,
$R^5$ is each independently selected from H and $C_{1-6}$alkyl,
$R^6$ is each independently selected from H and $C_{1-6}$alkyl,
$R^7$ is each independently selected from H and $C_{1-6}$alkyl,
$R^8$ is each independently selected from H and $C_{1-6}$alkyl,
or $R^7$ and $R^8$ form together with the nitrogen they are attached to a heterocycloalkyl,
$R^9$ is each independently selected from the group consisting of
   i) $C_{1-6}$alkoxy,
   ii) $C_{1-6}$alkyl
   iii) halogen,
   iv) halogen-$C_{1-6}$alkyl,
   v) heteroaryl, and
   vi) heteroaryl substituted by $C_{1-6}$alkyl, $R^{10}$ is each independently selected from the group consisting of
  i) $C_{1-6}$alkoxy,
  ii) $C_{1-6}$alkyl,
  iii) halogen, and
  iv) halogen-$C_{1-6}$alkyl;
$R^{11}$ is each independently selected from H and $C_{1-6}$alkyl, and
$R^{12}$ is each independently selected from $C_{1-6}$alkyl and $C_{3-7}$cycloalkyl,
with the proviso that 5-(2-aminoanilino)-1,3-dihydrobenzimidazol-2-one and 5-(2-amino-N-methyl-anilino)-1,3-dihydrobenzimidazol-2-one are excluded.

E7: The compound of any one of the embodiments, wherein $X^1$ and $X^2$ are each H.

E8: The compound of any one of the embodiments, wherein $X^1$ is H.

E9: The compound of any one of the embodiments, wherein $X^2$ is H.

E10: The compound of any one of the embodiments, wherein $W^1$, $W^2$ and $W^3$ are each CH.

E11: The compound of any one of the embodiments, wherein $W^1$ is CH.

E12: The compound of any one of the embodiments, wherein $W^2$ is CH.

E13: The compound of any one of the embodiments, wherein $W^3$ is CH.

E14: The compound of any one of the embodiments, wherein Z is —$NR^1$— and $R^1$ is H or $C_{1-6}$alkyl.

E15: The compound of any one of the embodiments, wherein Z is —NH—.

E16: The compound of any one of the embodiments, wherein A is phenyl substituted by —N($R^5$,$R^6$), wherein $R^5$ and $R^6$ is each independently selected from H and $C_{1-6}$alkyl, and optionally further substituted by one $R^2$ selected from the group consisting of
  i) —(CH$_2$)$_{0-1}$—(C$_{3-7}$cycloalkyl)-aryl substituted by $R^{10}$,
  ii) —(CH$_2$)$_{0-1}$—(C$_{3-7}$cycloalkyl)-aryl,
  iii) —(CH$_2$)$_{0-1}$-aryl substituted by $R^{10}$,
  iv) —(CH$_2$)$_{0-1}$-aryl,
  v) —(CH$_2$)$_{0-1}$—C$_{3-7}$cycloalkyl substituted by $R^{10}$,
  vi) —(CH$_2$)$_{0-1}$—C$_{3-7}$cycloalkyl,
  vii) —(CH$_2$)$_{0-1}$-heteroaryl substituted by $R^9$,
  viii) —(CH$_2$)$_{0-1}$-heteroaryl,
  ix) —C(=O)C$_{1-6}$alkyl,
  x) —C(=O)—N($R^7$,$R^8$),
  xi) —C(=O)OC$_{1-6}$alkyl,
  xii) —C$_{1-6}$alkoxy,
  xiii) —C$_{1-6}$alkyl,
  xiv) —CH$_2$—O—(CH$_2$)$_{0-1}$-aryl substituted by $R^{10}$,
  xv) —CH$_2$—O—(CH$_2$)$_{0-1}$-aryl,
  xvi) -halogen,
  xvii) -halogen-C$_{1-6}$alkyl,
  xviii) -hydroxy-C$_{1-6}$alkyl, and
  xix) —NH—C(=O)C$_{1-6}$alkyl,
wherein $R^7$, $R^8$, $R^9$ and $R^{10}$ are defined as in any of the embodiments.

E17: The compound of any one of the embodiments, wherein $R^2$ is —C(=O)—N($R^7$,$R^8$) or —C(=O)OC$_{1-6}$alkyl, wherein $R^7$ and $R^8$ is each independently selected from H and $C_{1-6}$alkyl.

E18: The compound of any one of the embodiments, wherein A is selected from the group consisting of
  i) phenyl substituted with one or two $R^2$,
  ii) phenyl,
  iii) benzimidazolyl, pyridyl, thiazolyl, indolinyl, furan or imidazolyl, each individually substituted with one or two $R^3$
  iv) benzimidazolyl, pyridyl, thiazolyl, indolinyl, furan or imidazolyl,
  v) piperazinyl, piperidyl or pyrrolidinyl, each individually substituted with one or two $R^4$, and
  vi) piperazinyl, piperidyl or pyrrolidinyl.
wherein $R^2$, $R^3$ and $R^4$ are defined as in any of the embodiments.

E19: The compound of any one of the embodiments, wherein $R^2$ is selected from the group consisting of acetyl, halogen, N($R^5$,$R^6$), CON($R^7$,$R^8$), COOC$_{1-6}$alkyl and NC(O)$R^{10}$, wherein $R^5$, $R^6$, $R^7$, $R^8$ and $R^{10}$ are defined as in any of the embodiments.

E20: The compound of any one of the embodiments, wherein $R^2$ is selected from the group consisting of acetyl, Cl, NC(O)Me, NH$_2$, CON(H,Me) and COOMe.

E21: The compound of any one of the embodiments, wherein $R^3$ is selected from the group consisting of aryl, CON($R^7$,$R^8$), $C_{1-6}$alkyl, —CH$_2$-aryl, halogen-C$_{1-6}$alkyl and heteroaryl.

E22: The compound of any one of the embodiments, wherein $R^3$ is selected from the group consisting of 1H-imidazolyl, CON(H,Me), Bz, CF$_3$, Et, isopropyl, Me, Ph, propyl, pyridinyl, quinolyl, CON(H,Et) and thiazolyl.

E23: The compound of any one of the embodiments, wherein $R^4$ is selected from the group consisting of acetyl and oxo.

E24: The compound of any one of the embodiments, wherein $R^5$ is H.

E25: The compound of any one of the embodiments, wherein $R^6$ is H.

E26: The compound of any one of the embodiments, wherein $R^7$ is H.

E27: The compound of any one of the embodiments, wherein $R^8$ is $C_{1-6}$alkyl.

E28: The compound of any one of the embodiments, wherein $R^8$ is Me or Et.

E29: The compound of any one of the embodiments, wherein $R^9$ is halogen, $C_{1-6}$alkyl or heteroaryl substituted by $C_{1-6}$alkyl.

E30: The compound of any one of the embodiments, wherein $R^9$ is F, Cl, Me, isopropyl or methylimidazolyl.

E31: The compound of any one of the embodiments, wherein Z is —(CH$_2$)$_3$—, —C(=O)—, —C(=O)—$NR^1$—, $NR^1$, —$NR^1$—C(=O)—, wherein $R^1$ is defined as in any of the embodiments, in particular wherein $R^1$ is H.

E32: The compound of any one of the embodiments, or pharmaceutically acceptable salts thereof, any one of the embodiments, selected from the group consisting of
3-amino-N-methyl-4-[(2-oxo-1,3-dihydrobenzimidazol-5-yl)amino]benzamide,
N-methyl-2-[2-(3-methylimidazol-4-yl)-4-quinolyl]-1-(2-oxo-1,3-dihydrobenzimidazol-5-yl)benzimidazole-5-carboxamide,
N-methyl-1-(2-oxo-1,3-dihydrobenzimidazol-5-yl)-2-(4-quinolyl)benzimidazole-5-carboxamide,
2-ethyl-N-methyl-1-(2-oxo-1,3-dihydrobenzimidazol-5-yl)benzimidazole-5-carboxamide,
N,2-dimethyl-1-(2-oxo-1,3-dihydrobenzimidazol-5-yl)benzimidazole-5-carboxamide,
5-(2-aminoanilino)-1,3-dihydrobenzimidazol-2-one,
5-[2-(4-quinolyl)benzimidazol-1-yl]-1,3-dihydrobenzimidazol-2-one,
5-[2-[2-(3-methylimidazol-4-yl)-4-quinolyl]benzimidazol-1-yl]-1,3-dihydrobenzimidazol-2-one, methyl 3-amino-4-[(2-oxo-1,3-dihydrobenzimidazol-5-yl)amino]benzoate,
N-methyl-1-(2-oxo-1,3-dihydrobenzimidazol-5-yl)-2-phenyl-benzimidazole-5-carboxamide,
N-methyl-1-(2-oxo-1,3-dihydrobenzimidazol-5-yl)-2-(4-pyridyl)benzimidazole-5-carboxamide,
5-[2-(4-quinolyl)imidazol-1-yl]-1,3-dihydrobenzimidazol-2-one,
N-methyl-1-(2-oxo-1,3-dihydrobenzimidazol-5-yl)-2-(trifluoromethyl)benzimidazole-5-carboxamide,
N-methyl-1-(2-oxo-1,3-dihydrobenzimidazol-5-yl)-2-propyl-benzimidazole-5-carboxamide,
2-(1H-imidazol-5-yl)-N-methyl-1-(2-oxo-1,3-dihydrobenzimidazol-5-yl)benzimidazole-5-carboxamide,
2-isopropyl-N-methyl-1-(2-oxo-1,3-dihydrobenzimidazol-5-yl)benzimidazole-5-carboxamide,
1-(1,3-dimethyl-2-oxo-benzimidazol-5-yl)-N-methyl-2-[2-(3-methylimidazol-4-yl)-4-quinolyl]benzimidazole-5-carboxamide,
N,N-dimethyl-2-[2-(3-methylimidazol-4-yl)-4-quinolyl]-1-(2-oxo-1,3-dihydrobenzimidazol-5-yl)benzimidazole-5-carboxamide,
5-(3-pyridyl)-1,3-dihydrobenzimidazol-2-one,
5-(2-chloro-4-pyridyl)-1,3-dihydrobenzimidazol-2-one,
5-(2-methylthiazol-5-yl)-1,3-dihydrobenzimidazol-2-one,
5-(4-acetylpiperazine-1-carbonyl)-1,3-dihydrobenzimidazol-2-one,
N-(1-acetyl-4-piperidyl)-2-oxo-1,3-dihydrobenzimidazole-5-carboxamide,
5-(indoline-1-carbonyl)-1,3-dihydrobenzimidazol-2-one,
N-(1,3-dimethyl-2-oxo-benzimidazol-5-yl)furan-2-carboxamide,
5-(3-phenyl-propyl)-1,3-dihydro-imidazo[4,5-b]pyridin-2-one,
1-methyl-2-oxo-N-phenyl-3H-imidazo[4,5-b]pyridine-6-carboxamide,
2-(3-methoxybenzyl)-N-methyl-2'-oxo-2',3'-dihydro-1'H-[1,5'-bibenzo[d]imidazole]-5-carboxamide,
N-(1-(2-oxo-2,3-dihydro-1H-benzo[d]imidazole-5-carbonyl)piperidin-4-yl)acetamide,
2-isopropyl-N-methyl-2'-oxo-2',3'-dihydro-1'H-[1,5'-bibenzo[d]imidazole]-6-carboxamide,
1',3'-dimethyl-2-(2-(1-methyl-1H-imidazol-5-yl)quinolin-4-yl)-1',3'-dihydro-2'H-[1,5'-bibenzo[d]imidazol]-2'-one,
5-(2-isopropyl-1H-imidazol-1-yl)-1,3-dihydro-2H-benzo[d]imidazol-2-one,
5-(2-oxopyrrolidin-1-yl)-1,3-dihydro-2H-benzo[d]imidazol-2-one,
2-isopropyl-1'-methyl-1',3'-dihydro-2'H-[1,5'-bibenzo[d]imidazol]-2'-one,
2-isopropyl-3'-methyl-1',3'-dihydro-2'H-[1,5'-bibenzo[d]imidazol]-2'-one,
6-(4-fluorophenyl)-1,3-dihydroimidazo[4,5-c]pyridin-2-one,
5-(2,5-difluoro-phenyl)-1,3-dihydro-benzoimidazol-2-one,
5-(2,4-difluoro-phenyl)-1,3-dihydro-benzoimidazol-2-one,
5-[(4-methoxyphenyl)methyl]-1,3-dihydrobenzimidazol-2-one,
5-[4-(2-pyridyl)piperazin-1-yl]-1,3-dihydroimidazo[4,5-b]pyridin-2-one,
5-(4-pyrrol-1-yl-phenyl)-1,3-dihydro-benzoimidazol-2-one,
5-quinolin-5-yl-1,3-dihydro-benzoimidazol-2-one,
ethyl 4-((2-oxo-2,3-dihydro-1H-benzo[d]imidazole)-5-sulfonamido)benzoate,
1-methyl-5-phenyl-3H-imidazo[4,5-b]pyridin-2-one,
2-(2-methoxybenzyl)-N-methyl-2'-oxo-2',3'-dihydro-1'H-[1,5'-bibenzo[d]imidazole]-5-carboxamide,
2-(tert-butyl)-N-methyl-2'-oxo-2',3'-dihydro-1'H-[1,5'-bibenzo[d]imidazole]-5-carboxamide,
methyl 2-isopropyl-2'-oxo-2',3'-dihydro-1'H-[1,5'-bibenzo[d]imidazole]-4-carboxylate,
methyl 2-isopropyl-2'-oxo-2',3'-dihydro-1'H-[1,5'-bibenzo[d]imidazole]-6-carboxylate,
1,3-dimethyl-5-((2-nitrophenyl)amino)-1,3-dihydro-2H-benzo[d]imidazol-2-one,
5-((2-aminophenyl)amino)-1,3-dimethyl-1,3-dihydro-2H-benzo[d]imidazol-2-one,
2-oxo-N-(4-piperidyl)-1,3-dihydrobenzimidazole-5-carboxamide,
6-((2-aminophenyl)amino)-1-methyl-1,3-dihydro-2H-benzo[d]imidazol-2-one,
5-((2-aminophenyl)amino)-1-methyl-1,3-dihydro-2H-benzo[d]imidazol-2-one,
methyl 1-(2-oxo-2,3-dihydro-1H-benzo[d]imidazole-5-carbonyl)indoline-4-carboxylate,
6-(indoline-1-carbonyl)-1,3-dihydro-2H-imidazo[4,5-b]pyridin-2-one,
N-(1-acetylpiperidin-4-yl)-2-oxo-2,3-dihydro-1H-imidazo[4,5-b]pyridine-6-carboxamide,
2-(3-(methoxymethyl)phenyl)-N-methyl-2'-oxo-2',3'-dihydro-1'H-[1,5'-bibenzo[d]imidazole]-5-carboxamide,
5-(piperazin-1-yl)-1,3-dihydro-2H-benzo[d]imidazol-2-one,
5-[(1S,5R)-3,8-diazabicyclo[3.2.1]octan-3-yl]-1,3-dihydrobenzimidazol-2-one,
2-isopropyl-N-methyl-2'-oxo-2',3'-dihydro-1'H-[1,5'-bibenzo[d]imidazole]-4-carboxamide,
5-[2-(hydroxymethyl)benzimidazol-1-yl]-1,3-dihydrobenzimidazol-2-one,
5-(4-acetylpiperazin-1-yl)-1,3-dihydro-2H-benzo[d]imidazol-2-one,
5-[(1S,5R)-8-acetyl-3,8-diazabicyclo[3.2.1]octan-3-yl]-1,3-dihydrobenzimidazol-2-one,
N-methyl-2'-oxo-2-(tetrahydro-2H-pyran-4-yl)-2',3'-dihydro-1'H-[1,5'-bibenzo[d]imidazole]-5-carboxamide,
N-methyl-2-(1-methyl-1H-imidazol-4-yl)-2'-oxo-2',3'-dihydro-1'H-[1,5'-bibenzo[d]imidazole]-5-carboxamide,
N-methyl-2'-oxo-2-(1H-pyrrol-3-yl)-2',3'-dihydro-1'H-[1,5'-bibenzo[d]imidazole]-5-carboxamide,
2-oxo-N-phenyl-2,3-dihydro-1H-imidazo[4,5-b]pyridine-6-carboxamide,
N-(2-oxo-2,3-dihydro-1H-benzo[d]imidazol-5-yl)benzofuran-3-carboxamide,
2-(4-aminophenyl)-N-(2-oxo-2,3-dihydro-1H-benzo[d]imidazol-5-yl)acetamide,
N-(2-oxo-2,3-dihydro-1H-benzo[d]imidazol-5-yl)benzamide,
4-acetamido-N-(2-oxo-2,3-dihydro-1H-benzo[d]imidazol-5-yl)benzamide,
3-acetamido-N-(2-oxo-2,3-dihydro-1H-benzo[d]imidazol-5-yl)benzamide,
N-methyl-2-oxo-N-phenyl-2,3-dihydro-1H-imidazo[4,5-b]pyridine-6-carboxamide,
2-oxo-N-phenyl-2,3-dihydro-1H-benzo[d]imidazole-5-carboxamide,
2-isopropyl-N-methyl-1-(2-oxo-1,3-dihydroimidazo[4,5-b]pyridin-6-yl)benzimidazole-5-carboxamide,
N-[2-[1-(2-oxo-1,3-dihydrobenzimidazol-5-yl)benzimidazol-2-yl]ethyl]acetamide,
N-methyl-3-[1-(2-oxo-1,3-dihydrobenzimidazol-5-yl)benzimidazol-2-yl]propanamide,
methyl 1-(2-oxo-1,3-dihydrobenzimidazol-5-yl)benzimidazole-2-carboxylate,
5-(benzimidazol-1-yl)-1,3-dihydrobenzimidazol-2-one, 5-[2-(1-hydroxyethyl)benzimidazol-1-yl]-1,3-dihydrobenzimidazol-2-one,
5-[2-[hydroxy(phenyl)methyl]benzimidazol-1-yl]-1,3-dihydrobenzimidazol-2-one,
N-(1-acetylpiperidin-4-yl)-N-methyl-2-oxo-2,3-dihydro-1H-benzo[d]imidazole-5-carboxamide,
1-(2-oxo-2,3-dihydro-1H-benzo[d]imidazol-5-yl)-3-(4-(phenylamino)phenyl)urea,
1-(2-oxo-2,3-dihydro-1H-benzo[d]imidazol-5-yl)-3-phenylurea,
methyl 1-((2-oxo-2,3-dihydro-1H-benzo[d]imidazol-5-yl)carbamoyl)indoline-4-carboxylate,
1-acetyl-N-(2-oxo-2,3-dihydro-1H-benzo[d]imidazol-5-yl)piperidine-4-carboxamide,
methyl 1-((2-oxo-2,3-dihydro-1H-benzo[d]imidazol-5-yl)carbamoyl)indoline-5-carboxylate,
N4-methyl-N1-(2-oxo-2,3-dihydro-1H-benzo[d]imidazol-5-yl)indoline-1,4-dicarboxamide,
1-benzyl-3-(2-oxo-2,3-dihydro-1H-benzo[d]imidazol-5-yl)urea,
6-(1,2,3,4-tetrahydroquinoline-1-carbonyl)-1,3-dihydro-2H-imidazo[4,5-b]pyridin-2-one,
N-methyl-2-oxo-N-phenyl-2,3-dihydro-1H-benzo[d]imidazole-5-carboxamide,
5-(1,2,3,4-tetrahydroquinoline-1-carbonyl)-1,3-dihydro-2H-benzo[d]imidazol-2-one,
methyl 1-((2-oxo-2,3-dihydro-1H-benzo[d]imidazol-5-yl)carbamoyl)-1,2,3,4-tetrahydroquinoline-5-carboxylate,
N-(2-oxo-2,3-dihydro-1H-benzo[d]imidazol-5-yl)-4-sulfamoylbenzamide,
N-(4-(3-(2-oxo-2,3-dihydro-1H-benzo[d]imidazol-5-yl)ureido)phenyl)acetamide,
N-methyl-1-(2-oxo-1,3-dihydrobenzimidazol-5-yl)benzimidazole-2-carboxamide,
5-[2-(piperidine-1-carbonyl)benzimidazol-1-yl]-1,3-dihydrobenzimidazol-2-one,
6-(2-(benzyloxy)phenyl)-1,3-dihydro-2H-imidazo[4,5-b]pyridin-2-one,
N-(2-oxo-2,3-dihydro-1H-benzo[d]imidazol-5-yl)indoline-1-carboxamide,
methyl 2-(2-(1-methyl-1H-imidazol-5-yl)quinolin-4-yl)-2'-oxo-2',3'-dihydro-1'H-[1,5'-bibenzo[d]imidazole]-5-carboxylate,
2-(2-methoxypyridin-4-yl)-N-methyl-2'-oxo-2',3'-dihydro-1'H-[1,5'-bibenzo[d]imidazole]-5-carboxamide,
N5-methyl-N1-(2-oxo-2,3-dihydro-1H-benzo[d]imidazol-5-yl)-3,4-dihydroquinoline-1,5(2H)-dicarboxamide,
5-(5-bromo-1-oxo-isoindolin-2-yl)-1,3-dihydrobenzimidazol-2-one,
ethyl 1-oxo-2-(2-oxo-1,3-dihydrobenzimidazol-5-yl)isoindoline-5-carboxylate,
methyl 1-oxo-2-(2-oxo-1,3-dihydrobenzimidazol-5-yl)isoindoline-5-carboxylate,
2-(2-(1-methyl-1H-imidazol-5-yl)quinolin-4-yl)-2'-oxo-2',3'-dihydro-1'H-[1,5'-bibenzo[d]imidazole]-5-carboxamide,
N-methyl-2'-oxo-2-(1-phenylcyclopropyl)-2',3'-dihydro-1'H-[1,5'-bibenzo[d]imidazole]-5-carboxamide,
2-(1-(4-methoxyphenyl)cyclopropyl)-N-methyl-2'-oxo-2',3'-dihydro-1'H-[1,5'-bibenzo[d]imidazole]-5-carboxamide,
5-(indolin-1-ylsulfonyl)-1,3-dihydro-2H-benzo[d]imidazol-2-one,
N-(1-acetylpiperidin-4-yl)-2-oxo-2,3-dihydro-1H-benzo[d]imidazole-5-sulfonamide,
methyl 4-(N-(2-oxo-2,3-dihydro-1H-benzo[d]imidazol-5-yl)sulfamoyl)benzoate,
tert-butyl (1-((2-oxo-2,3-dihydro-1H-benzo[d]imidazol-5-yl)carbamoyl)indolin-5-yl)carbamate,
5-(benzyloxy)-2-isopropyl-1',3'-dihydro-2'H-[1,5'-bibenzo[d]imidazol]-2'-one,
5-amino-N-(2-oxo-2,3-dihydro-1H-benzo[d]imidazol-5-yl)indoline-1-carboxamide hydrochloride,
2'-methyl-N-(2-oxo-2,3-dihydro-1H-benzo[d]imidazol-5-yl)-[1,1'-biphenyl]-2-carboxamide,
2-benzyl-N-(2-oxo-2,3-dihydro-1H-benzo[d]imidazol-5-yl)benzamide,
2-isopropyl-5-methoxy-1',3'-dihydro-2'H-[1,5'-bibenzo[d]imidazol]-2'-one,
tert-butyl 4-(N-(2-oxo-2,3-dihydro-1H-benzo[d]imidazol-5-yl)sulfamoyl)piperidine-1-carboxylate,
ethyl 4-(3-(2-oxo-2,3-dihydro-1H-benzo[d]imidazol-5-yl)ureido)benzoate,
1-(3-fluorophenyl)-3-(2-oxo-2,3-dihydro-1H-benzo[d]imidazol-5-yl)urea,
4-(2-methoxyphenyl)-N-(2-oxo-2,3-dihydro-1H-benzo[d]imidazol-5-yl)piperazine-1-carboxamide,
6-chloro-N-(2-oxo-2,3-dihydro-1H-benzo[d]imidazol-5-yl)indoline-1-carboxamide,
N-(3-(1-methyl-1H-pyrazol-3-yl)phenyl)-2-oxo-2,3-dihydro-1H-benzo[d]imidazole-5-carboxamide,
2-(4-methoxycyclohexyl)-N-methyl-2'-oxo-2',3'-dihydro-1'H-[1,5'-bibenzo[d]imidazole]-5-carboxamide,
3-methoxy-N-(2-oxo-2,3-dihydro-1H-benzo[d]imidazol-5-yl)isonicotinamide,
N2-methyl-N5-(2-oxo-2,3-dihydro-1H-benzo[d]imidazol-5-yl)pyridine-2,5-dicarboxamide,
N-(2-oxo-2,3-dihydro-1H-benzo[d]imidazol-5-yl)piperidine-4-sulfonamide,
4-(4-chlorobenzyl)-N-(2-oxo-2,3-dihydro-1H-benzo[d]imidazol-5-yl)piperazine-1-carboxamide,
N-(2-oxo-2,3-dihydro-1H-benzo[d]imidazol-5-yl)-2-(pyridin-4-yl)benzamide,
N-(2-oxo-2,3-dihydro-1H-benzo[d]imidazol-5-yl)benzofuran-3-sulfonamide,
2-(3-methoxyphenyl)-N-(2-oxo-2,3-dihydro-1H-benzo[d]imidazol-5-yl)nicotinamide,
N-(1-benzylpiperidin-4-yl)-2-oxo-2,3-dihydro-1H-benzo[d]imidazole-5-carboxamide,
5-(5-aminoindolin-1-yl)-1,3-dihydro-2H-benzo[d]imidazol-2-one,
N-(1-(2-oxo-2,3-dihydro-1H-benzo[d]imidazol-5-yl)indolin-5-yl)acetamide,
N-(3-(oxazol-5-yl)phenyl)-2-oxo-2,3-dihydro-1H-benzo[d]imidazole-5-carboxamide,
tert-butyl 4-((2-oxo-2,3-dihydro-1H-benzo[d]imidazol-5-yl)carbamoyl)indoline-1-carboxylate,
N-(2-oxo-2,3-dihydro-1H-benzo[d]imidazol-5-yl)indoline-4-carboxamide,
1-acetyl-N-(2-oxo-2,3-dihydro-1H-benzo[d]imidazol-5-yl)indoline-4-carboxamide,
N-(4-(((2-oxo-2,3-dihydro-1H-benzo[d]imidazol-5-yl)methyl)amino)phenyl)acetamide,
N-(2-(methylcarbamoyl)phenyl)-2-oxo-2,3-dihydro-1H-benzo[d]imidazole-5-carboxamide,
tert-butyl (1-((2-oxo-2,3-dihydro-1H-benzo[d]imidazol-5-yl)methyl)indolin-5-yl)carbamate,
5-((5-aminoindolin-1-yl)methyl)-1,3-dihydro-2H-benzo[d]imidazol-2-one,
N-(1-((2-oxo-2,3-dihydro-1H-benzo[d]imidazol-5-yl)methyl)indolin-5-yl)acetamide,
methyl 2-((2-oxo-2,3-dihydro-1H-benzo[d]imidazol-5-yl)carbamoyl)benzoate, 5-((1-benzylpiperidin-4-yl)amino)-1,3-dihydro-2H-benzo[d]imidazol-2-one,
methyl 6-((2-oxo-2,3-dihydro-1H-benzo[d]imidazol-5-yl)amino)nicotinate,
5-(benzyloxy)-1,3-dihydro-2H-benzo[d]imidazol-2-one,
methyl 2-((2-oxo-2,3-dihydro-1H-benzo[d]imidazol-5-yl)methyl)isoindoline-5-carboxylate, and
N-methyl-4-((2-oxo-2,3-dihydro-1H-benzo[d]imidazol-5-yl)oxy)benzamide, E33: The compound of any one of the embodiments, or pharmaceutically acceptable salts thereof, any one of the embodiments, selected from the group consisting of
3-amino-N-methyl-4-[(2-oxo-1,3-dihydrobenzimidazol-5-yl)amino]benzamide,
N-methyl-2-[2-(3-methylimidazol-4-yl)-4-quinolyl]-1-(2-oxo-1,3-dihydrobenzimidazol-5-yl)benzimidazole-5-carboxamide,
N-methyl-1-(2-oxo-1,3-dihydrobenzimidazol-5-yl)-2-(4-quinolyl)benzimidazole-5-carboxamide,
2-ethyl-N-methyl-1-(2-oxo-1,3-dihydrobenzimidazol-5-yl)benzimidazole-5-carboxamide,
N,2-dimethyl-1-(2-oxo-1,3-dihydrobenzimidazol-5-yl)benzimidazole-5-carboxamide,
5-[2-(4-quinolyl)benzimidazol-1-yl]-1,3-dihydrobenzimidazol-2-one,
5-[2-[2-(3-methylimidazol-4-yl)-4-quinolyl]benzimidazol-1-yl]-1,3-dihydrobenzimidazol-2-one,
methyl 3-amino-4-[(2-oxo-1,3-dihydrobenzimidazol-5-yl)amino]benzoate,
N-methyl-1-(2-oxo-1,3-dihydrobenzimidazol-5-yl)-2-phenyl-benzimidazole-5-carboxamide,
N-methyl-1-(2-oxo-1,3-dihydrobenzimidazol-5-yl)-2-(4-pyridyl)benzimidazole-5-carboxamide,
N-methyl-1-(2-oxo-1,3-dihydrobenzimidazol-5-yl)-2-(trifluoromethyl)benzimidazole-5-carboxamide,
N-methyl-1-(2-oxo-1,3-dihydrobenzimidazol-5-yl)-2-propyl-benzimidazole-5-carboxamide,
2-(1H-imidazol-5-yl)-N-methyl-1-(2-oxo-1,3-dihydrobenzimidazol-5-yl)benzimidazole-5-carboxamide,
2-isopropyl-N-methyl-1-(2-oxo-1,3-dihydrobenzimidazol-5-yl)benzimidazole-5-carboxamide,
1-(1,3-dimethyl-2-oxo-benzimidazol-5-yl)-N-methyl-2-[2-(3-methylimidazol-4-yl)-4-quinolyl]benzimidazole-5-carboxamide,
N,N-dimethyl-2-[2-(3-methylimidazol-4-yl)-4-quinolyl]-1-(2-oxo-1,3-dihydrobenzimidazol-5-yl)benzimidazole-5-carboxamide,
2-(3-methoxybenzyl)-N-methyl-2'-oxo-2',3'-dihydro-1'H-[1,5'-bibenzo[d]imidazole]-5-carboxamide, and
2-isopropyl-N-methyl-2'-oxo-2',3'-dihydro-1'H-[1,5'-bibenzo[d]imidazole]-6-carboxamide.

E34: A compound, or pharmaceutically acceptable salts thereof, having a chemical structure comprising:

P-L-C wherein
L is a linker group;
C is a compound of formula I according to any one of the embodiments, wherein L is chemically linked to C; and
P is a protein target moiety that binds to a target protein or a target polypeptide, wherein L is chemically linked to P.

E35: The compound according to any one of the embodiments, wherein L is selected from the group consisting of:
i) —NHCH$_2$—(CH$_2$)$_{1-30}$—CH$_2$NH—, and
ii) —NH—(CH$_2$CH$_2$O)$_{1-25}$—CH$_2$CH$_2$—NH—.

E36: The compound according to any one of the embodiments, wherein L is selected from the group consisting of:
i) —NHCH$_2$—(CH$_2$)$_{1-10}$—CH$_2$NH—, and
ii) —NH—(CH$_2$CH$_2$O)$_{1-5}$—CH$_2$CH$_2$—NH—.

E37: The compound according to any one of the embodiments, wherein P is a BRD4 inhibitor, in particular wherein P is

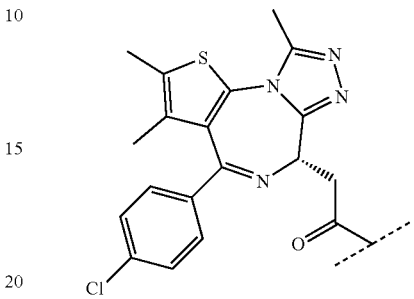

E38: The compound according to any one of the embodiments, selected from the group consisting of
N-[5-[[2-[(9S)-7-(4-chlorophenyl)-4,5,13-trimethyl-3-thia-1,8,11,12-tetrazatricyclo[8.3.0.02,6]trideca-2(6),4,7,10,12-pentaen-9-yl]acetyl]amino]pentyl]-2-ethyl-1-(2-oxo-1,3-dihydrobenzimidazol-5-yl)benzimidazole-5-carboxamide,
N-[2-[2-[2-[[2-[(9S)-7-(4-chlorophenyl)-4,5,13-trimethyl-3-thia-1,8,11,12-tetrazatricyclo[8.3.0.02,6]trideca-2(6),4,7,10,12-pentaen-9-yl]acetyl]amino]ethoxy]ethoxy]ethyl]-2-ethyl-1-(2-oxo-1,3-dihydrobenzimidazol-5-yl)benzimidazole-5-carboxamide, and
N-[2-[2-[2-[[2-[(9S)-7-(4-chlorophenyl)-4,5,13-trimethyl-3-thia-1,8,11,12-tetrazatricyclo[8.3.0.02,6]trideca-2(6),4,7,10,12-pentaen-9-yl]acetyl]amino]ethoxy]ethoxy]ethyl]-1-(2-oxo-1,3-dihydrobenzimidazol-5-yl)-2-(4-quinolyl)benzimidazole-5-carboxamide.

E39: A certain embodiment of the invention relates to the compound of formula I as described herein, or a pharmaceutically acceptable salt thereof, for use as therapeutically active substance.

E40: A certain embodiment of the invention relates to the compound of formula I as described herein, or a pharmaceutically acceptable salt thereof, for the use in the therapeutic and/or prophylactic treatment of cancer.

E41: A certain embodiment of the invention relates to the compound of formula I as described herein, or a pharmaceutically acceptable salt thereof, for the manufacture of a medicament for the therapeutic and/or prophylactic treatment of cancer.

E42: A certain embodiment of the invention relates to a pharmaceutical composition comprising the compound of formula I as described herein, or a pharmaceutically acceptable salt thereof, and a pharmaceutically acceptable auxiliary substance.

E43: A certain embodiment of the invention relates to a method for the therapeutic and/or prophylactic treatment of cancer, by administering the compound of formula I as described herein, or a pharmaceutically acceptable salt thereof, to a patient.

E44: A certain embodiment of the invention relates to the compound of P-L-C as described herein, or a pharmaceutically acceptable salt thereof, for use as therapeutically active substance.

E45: A certain embodiment of the invention relates to the compound of P-L-C as described herein, or a pharmaceutically acceptable salt thereof, for the use in the therapeutic and/or prophylactic treatment of cancer.

E46: A certain embodiment of the invention relates to the compound of P-L-C as described herein, or a pharmaceutically acceptable salt thereof, for the manufacture of a medicament for the therapeutic and/or prophylactic treatment of cancer.

E47: A certain embodiment of the invention relates to a pharmaceutical composition comprising the compound of P-L-C as described herein, or a pharmaceutically acceptable salt thereof, and a pharmaceutically acceptable auxiliary substance, in particular an inert carrier.

E48: A certain embodiment of the invention relates to a method for the therapeutic and/or prophylactic treatment of cancer, by administering the compound of P-L-C as described herein, or a pharmaceutically acceptable salt thereof, to a patient.

Furthermore, the invention includes all optical isomers, i.e. diastereoisomers, diastereomeric mixtures, racemic mixtures, all their corresponding enantiomers and/or tautomers as well as their solvates of the compounds of formula I.

The compounds of formula I or formula P-L-C may contain one or more asymmetric centers and can therefore occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

In the embodiments, where optically pure enantiomers are provided, optically pure enantiomer means that the compound contains >90% of the desired isomer by weight, particularly >95% of the desired isomer by weight, or more particularly >99% of the desired isomer by weight, said weight percent based upon the total weight of the isomer(s) of the compound. Chirally pure or chirally enriched compounds may be prepared by chirally selective synthesis or by separation of enantiomers. The separation of enantiomers may be carried out on the final product or alternatively on a suitable intermediate.

The compounds of formula I or formula P-L-C may be prepared in accordance with the schemes described in the examples. The starting material is commercially available or may be prepared in accordance with known methods.

The preparation of compounds of formula I or formula P-L-C is further described in more detail in the schemes below.

The preparation of compounds of formula I of the present invention may be carried out in sequential or convergent synthetic routes. Syntheses of the compounds of the invention are shown in the following schemes 1-14 and in the description of 160 specific examples. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in schemes 1-14, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

Scheme 1

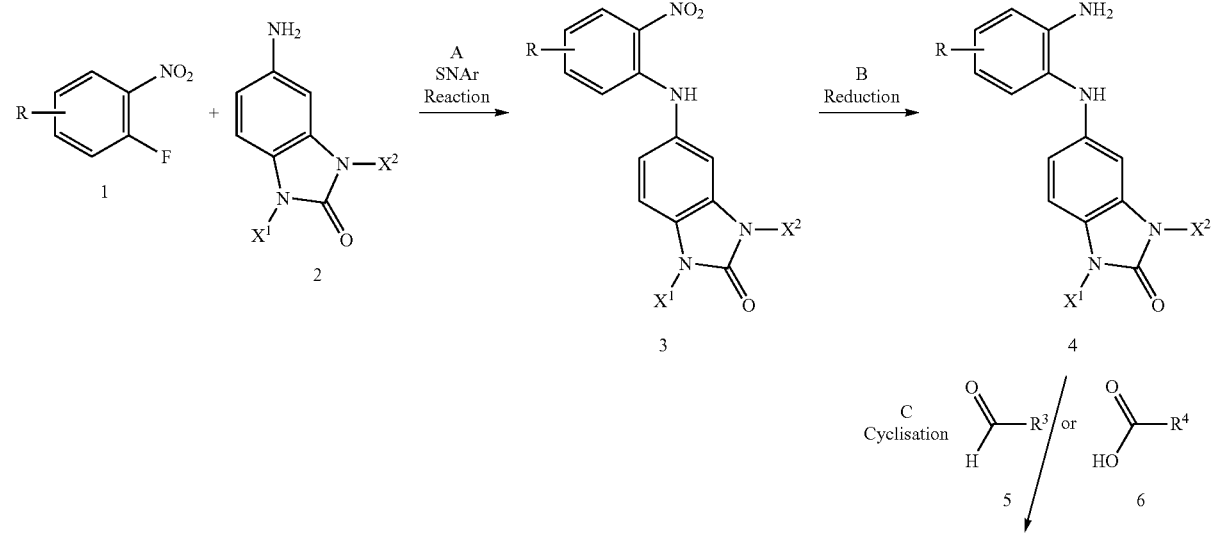

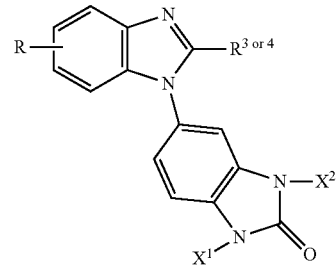

R = H, —C(O)NHMe, —C(O)OMe
X1, X2 = as defined herein
R3, R4 = as defined herein Step A:

Nitro-amino-arene compound 3 can be obtained by an aromatic nucleophilic substitution ($S_NAr$) reaction between a 1,2-fluoro-nitro-arene 1 and an aromatic amine compound 2.

Examples of suitable 1,2-fluoro-nitro-arenes 1 include, but are not limited to, 1-fluoro-2-nitrobenzene[45], 4-fluoro-N-methyl-3-nitrobenzamide[46], 3-fluoro-N-methyl-4-nitrobenzamide[47], methyl 4-fluoro-3-nitrobenzoate[48], methyl 3-fluoro-4-nitrobenzoate[49].

Examples of suitable aromatic amine compounds 2 include, but are not limited to, 5-amino-1H-benzo[d]imidazol-2(3H)-one[50], 5-amino-1-methyl-1,3-dihydro-2H-benzo[d]imidazol-2-one[51], 6-amino-1-methyl-1,3-dihydro-2H-benzo[d]imidazol-2-one[52], 5-amino-1,3-dimethyl-1H-benzo[d]imidazol-2(3H)-one[53].

The $S_NAr$ reaction is carried out in the presence of an organic base such as N,N-diisopropylethylamine, triethylamine or N-methylmorpholine in a polar aprotic organic solvent such as N-methyl-2-pyrrolidinone or N,N-dimethylformamide at elevated temperatures. Preferred conditions are N,N-diisopropylethylamine in N-methyl-2-pyrrolidinone at 120° C. overnight.

Step B:

Reduction of nitro-amino-arene compound 3 to diamino-arene 4 can be effected by hydrogenation with hydrogen under normal or elevated pressure in the presence of a catalyst such as $PtO_2$, Pd—C or Raney nickel in polar solvents such as MeOH, EtOH, dioxane, THF, or mixtures thereof.

Preferred conditions are 1 atm of hydrogen in the presence of 10% palladium on charcoal in a mixture of methanol and THF at room temperature overnight.

Step C:

Benzimidazole 7 can be obtained by cyclisation of diamino-arene 4 with an aldehyde 5 in the presence of sodium metabisulfite. The cyclisation reaction is carried out in a polar aprotic organic solvent such as N-methyl-2-pyrrolidinone or N,N-dimethylformamide at elevated temperatures. Preferred conditions are N-methyl-2-pyrrolidinone at 120° C. for 3-18 hours.

Benzimidazole 7 can also be obtained by cyclisation of diamino-arene 4 with a carboxylic acid 6 in the presence of another acid. The cyclisation reaction is carried out in an aqueous solution of a strong acid such as HCl or $H_2SO_4$. Preferred conditions are 6 M aq. HCl at 120° C. for 12-48 hours.

Scheme 2

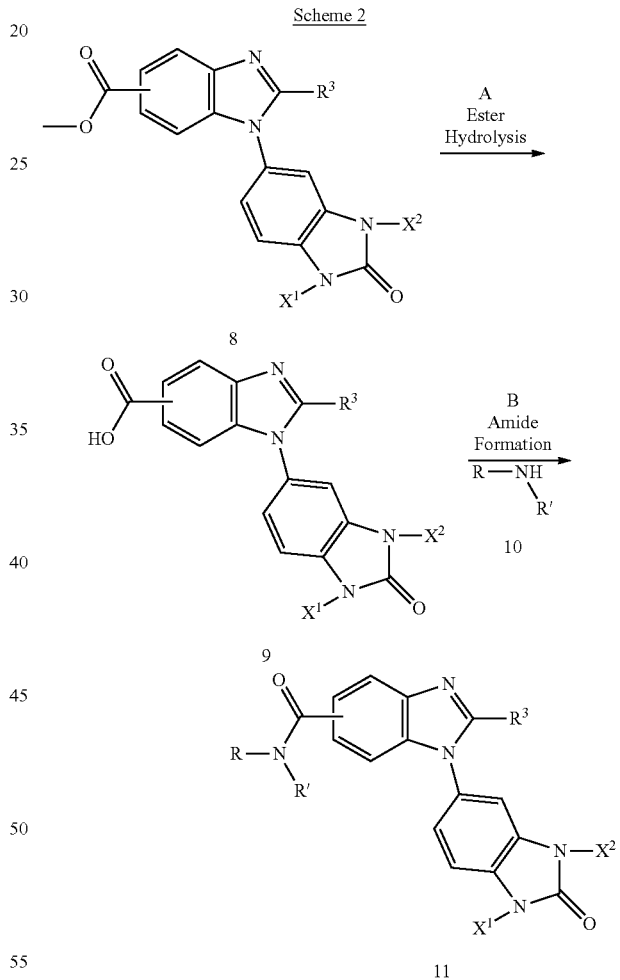

R, R' = H, Me independently of one another
X1, X2 = as defined herein
R3 = as defined herein Step A:

Ester compound 8 can be hydrolysed to carboxylic acid 9 by treatment with an aqueous base such as lithium hydroxide, sodium hydroxide or potassium hydroxide. The hydrolysis reaction is carried out in a mixture of water and a polar ethereal solvent such as dioxane, THF, DME or TBME at room temperature or at elevated temperatures for 2-18 hours.

Preferred conditions are 1 M aq. LiOH solution in 1,4-dioxane at room temperature for 3 h.

Step B:

Amide bond formation can be accomplished by a coupling reaction between carboxylic acid 9 and a primary or secondary amine 10 in the presence of a coupling reagent such as DMTMM, DCC, EDC, TBTU or HATU in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF, DME or TBME or polar non-protic organic solvent such as N,N-dimethylformamide at room temperature or at elevated temperatures for 2-18 hours.

Preferred conditions are HATU with N,N-diisopropylethylamine in a mixture of THF and N,N-dimethylformamide at room temperature for 3 hours.

Scheme 3

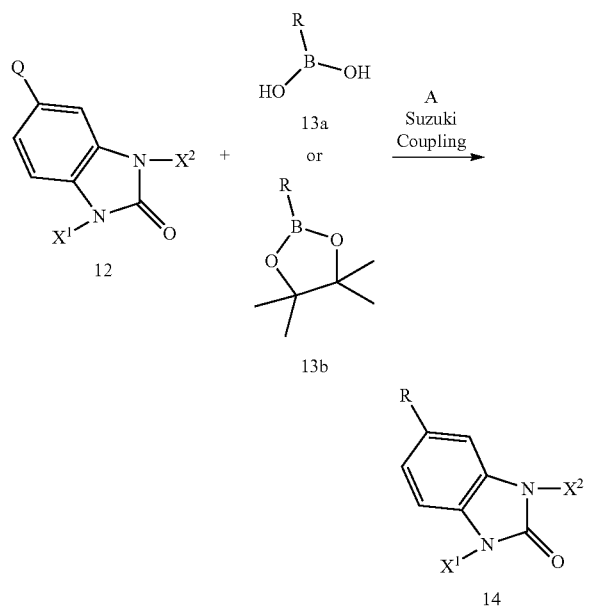

Q = Br, I
R = aryl, heteroaryl, as defined herein
X1, X2 = as defined herein

Step A:

Suzuki-Miyaura coupling between a suitable aryl bromide or aryl iodide 12 and an aryl or heteroaryl boronic acid 13a, or the corresponding aryl or heteroaryl boronate 13b, can be accomplished by treatment with a palladium catalyst, a phosphine ligand, and a base such as $K_2CO_3$, $Na_2CO_3$, $Cs_2CO_3$, $K_2HPO_4$, $KO^tBu$, in solvents such as DMF, acetonitrile, DMSO, THF, DME, toluene, 1,4-dioxane, $H_2O$ or mixtures thereof, at room temperature to elevated temperatures.

Examples of suitable aryl halide compounds 12 include, but are not limited to, 5-bromo-1H-benzo[d]imidazol-2(3H)-one[54] or 5-iodo-1H-benzo[d]imidazol-2(3H)-one[55].

Preferred conditions are catalytic [1,1-bis(diphenyl-phosphino)ferrocene]dichloropalladium(II) and aq. sodium carbonate in dioxane at 100° C. for 18 hours.

Scheme 4

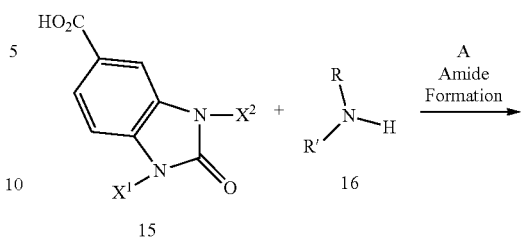

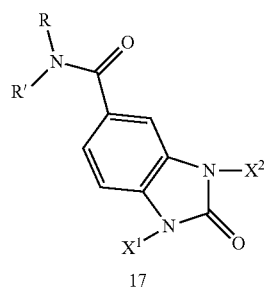

R, R' = H, heterocycloalkyl, heteroaryl or form together with the nitrogen they are attached to a heterocycloalkyl or a heteroaryl, as defined herein
$X^1$, $X^2$ = as decribed herein Step A:

Amide bond formation can be accomplished by a coupling reaction between a suitable carboxylic acid 15 and a primary or secondary amine 16 in the presence of a coupling reagent such as DCC, EDC, TBTU or HATU in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF, DME or TBME or polar non-protic organic solvent such as N,N-dimethylformamide at room temperature or at elevated temperatures for 2-18 hours.

Examples of suitable carboxylic acids 15 include, but are not limited to, 2-oxo-2,3-dihydro-1H-benzo[d]imidazole-5-carboxylic acid[56].

Preferred conditions are HATU with N,N-diisopropylethylamine in N,N-dimethylformamide at room temperature for 4 hours.

Scheme 5

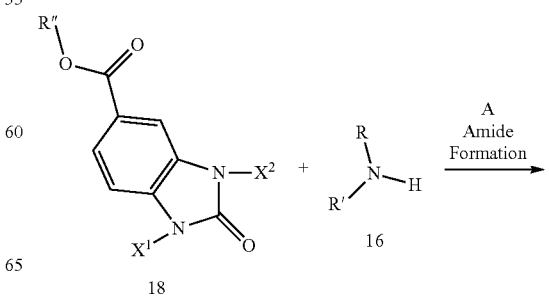

-continued

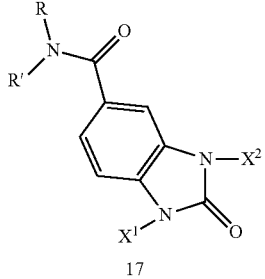

17

R, R' = H, heterocycloalkyl, heteroaryl or form together with the nitrogen they are attached to a heterocycloalkyl or a heteroaryl, as defined herein
$X^1, X^2$ = as decribed herein
R'' = methyl, ethyl Step A:

Amide bond formation can alternatively be accomplished by a coupling reaction between a suitable carboxylic acid ester 18 and a primary or secondary amine 16 in the presence of trimethylaluminium in nonpolar aprotic solvents such as benzene, xylene or toluene at elevated temperatures for 1-3 hours.

Examples of suitable carboxylic acid esters 18 include, but are not limited to, methyl 2-oxo-2,3-dihydro-1H-benzo[d]imidazole-5-carboxylate[57] and ethyl 2-oxo-2,3-dihydro-1H-benzo[d]imidazole-5-carboxylate[58].

Preferred conditions are trimethylaluminium in toluene at 110° C. for 2 hours.

Scheme 6

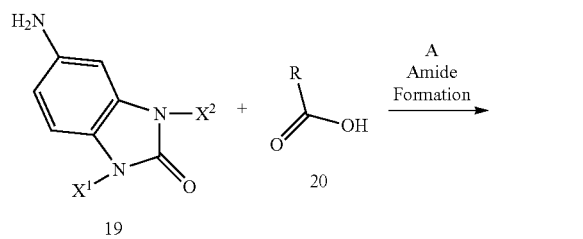

R = as defined herein
$X^1, X^2$ = as decribed herein

Step A:

Amide bond formation can be accomplished by a coupling reaction between a suitable amine 19 and a carboxylic acid 20 in the presence of a coupling reagent such as DCC, EDC, TBTU or HATU in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF, DME or TBME or polar non-protic organic solvent such as N,N-dimethylformamide at room temperature or at elevated temperatures for 2-18 hours.

Examples of suitable amines 19 include, but are not limited to, 5-amino-1,3-dihydro-2H-benzo[d]imidazol-2-one[50].

Preferred conditions are HATU with N,N-diisopropylethylamine in N,N-dimethylformamide at room temperature for 2 hours.

Scheme 7

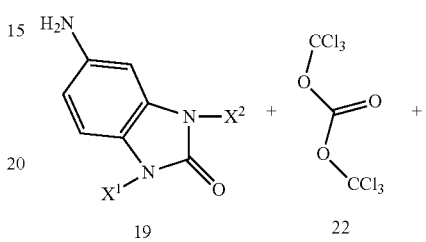

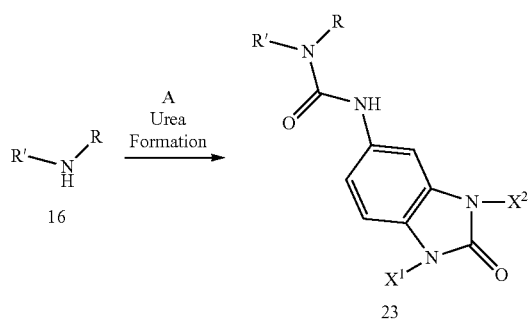

R, R' = as defined herein
X1, X2 = as decribed herein

Step A:

Urea formation can be accomplished by a coupling reaction between a suitable aromatic amine 19 and a primary or secondary amine 16 mediated by triphosgene 22. The reaction involves sequential treatment of the aromatic amine 19 with triphosgene 22 to form the corresponding aryl-isocyanate intermediate which is then reacted in situ with the primary or secondary amine 16 to afford urea 23. The reaction is carried out in halogenated solvents such as dichloromethane or 1,2-dichloroethane or ethereal solvents such as diethyl ether, dioxane, THF, DME or TBME, optionally in the presence of a base such as triethylamine or N,N-diisopropylethylamine.

Examples of suitable amines 19 include, but are not limited to, 5-amino-1,3-dihydro-2H-benzo[d]imidazol-2-one[50].

Preferred conditions are triethylamine in THF at room temperature for 1 hours for the first step (formation of aryl-isocyanate intermediate from aromatic amine 19), and at room temperature for 3 hours for the second step (reaction of aryl-isocyanate intermediate with primary or secondary amine 16 to form urea 23).

Scheme 8

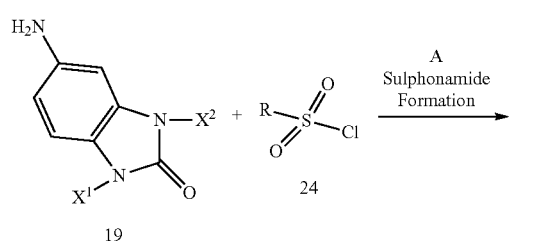

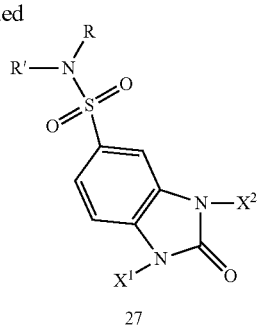

R, R' = H, heterocycloalkyl, heteroaryl or form together with the nitrogen they are attached to a heterocycloalkyl or a heteroaryl, as defined herein
X1, X2 = as decribed herein Step A:

Sulphonamide formation can be accomplished by a coupling reaction between a suitable sulphonyl chloride 26 and a primary or secondary amine 16. The reaction is carried out in the presence of an organic base such as pyridine, triethylamine, N,N-diisopropylethylamine or N-methylmorpholine in halogenated solvents such as dichloromethane or 1,2-dichloroethane or ethereal solvents such as diethyl ether, dioxane, THF, DME or TBME or polar non-protic organic solvent such as N,N-dimethylformamide, or aromatic solvents such as pyridine or toluene at room temperature or at elevated temperatures for 2-18 hours.

Examples of suitable sulphonyl chloride 26 include, but are not limited to, 2-oxo-2,3-dihydro-1H-benzo[d]imidazole-5-sulfonyl chloride[59].

Preferred conditions are pyridine (as base and solvent) at room temperature for 1 hour.

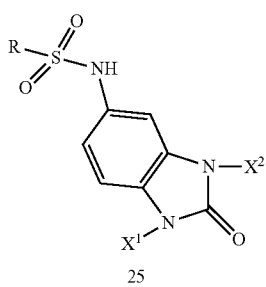

R = as defined herein
X1, X2 = as decribed herein

Step A:

Sulphonamide formation can be accomplished by a coupling reaction between a suitable aromatic amine 19 and a sulphonyl chloride 24. The reaction is carried out in the presence of an organic base such as pyridine, triethylamine, N,N-diisopropylethylamine or N-methylmorpholine in halogenated solvents such as dichloromethane or 1,2-dichloroethane or ethereal solvents such as diethyl ether, dioxane, THF, DME or TBME or polar non-protic organic solvent such as N,N-dimethylformamide, or aromatic solvents such as pyridine or toluene at room temperature or at elevated temperatures for 2-18 hours.

Examples of suitable amines 19 include, but are not limited to, 5-amino-1,3-dihydro-2H-benzo[d]imidazol-2-one[50].

Preferred conditions are pyridine (as base and solvent) at room temperature for 1 hour.

Scheme 10

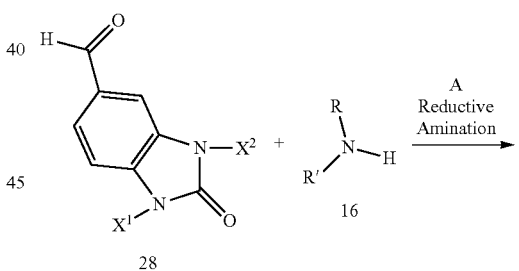

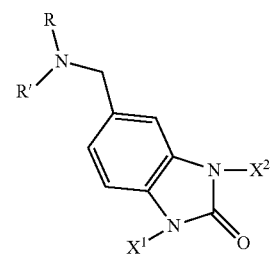

R, R' = H, heterocycloalkyl, heteroaryl or form together with the nitrogen they are attached to a heterocycloalkyl or a heteroaryl, as defined herein
X1, X2 = as decribed herein Step A:

Amine 29 can be prepared by a reduction amination reaction involving treatment of a suitable aromatic aldehyde 28 with a primary or secondary amine 16 in the presence of

Scheme 9

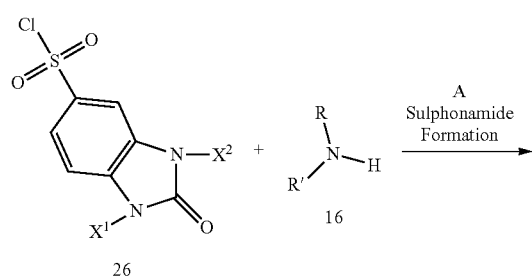

a Bronsted acid or Lewis acid so as to form the corresponding imine compound, with in situ treatment with a reducing agent such as sodium triacetoxyborohydride or sodium cyanoborohydride. The reaction is carried out in alcoholic solvents such as methanol, ethanol, or isopropanol.

Examples of suitable aromatic aldehydes 28 include, but are not limited to, 2-oxo-2,3-dihydro-1H-benzo[d]imidazole-5-carbaldehyde[60].

Preferred conditions are zinc chloride and sodium cyanoborohydride in methanol at 60° C. for 3 h.

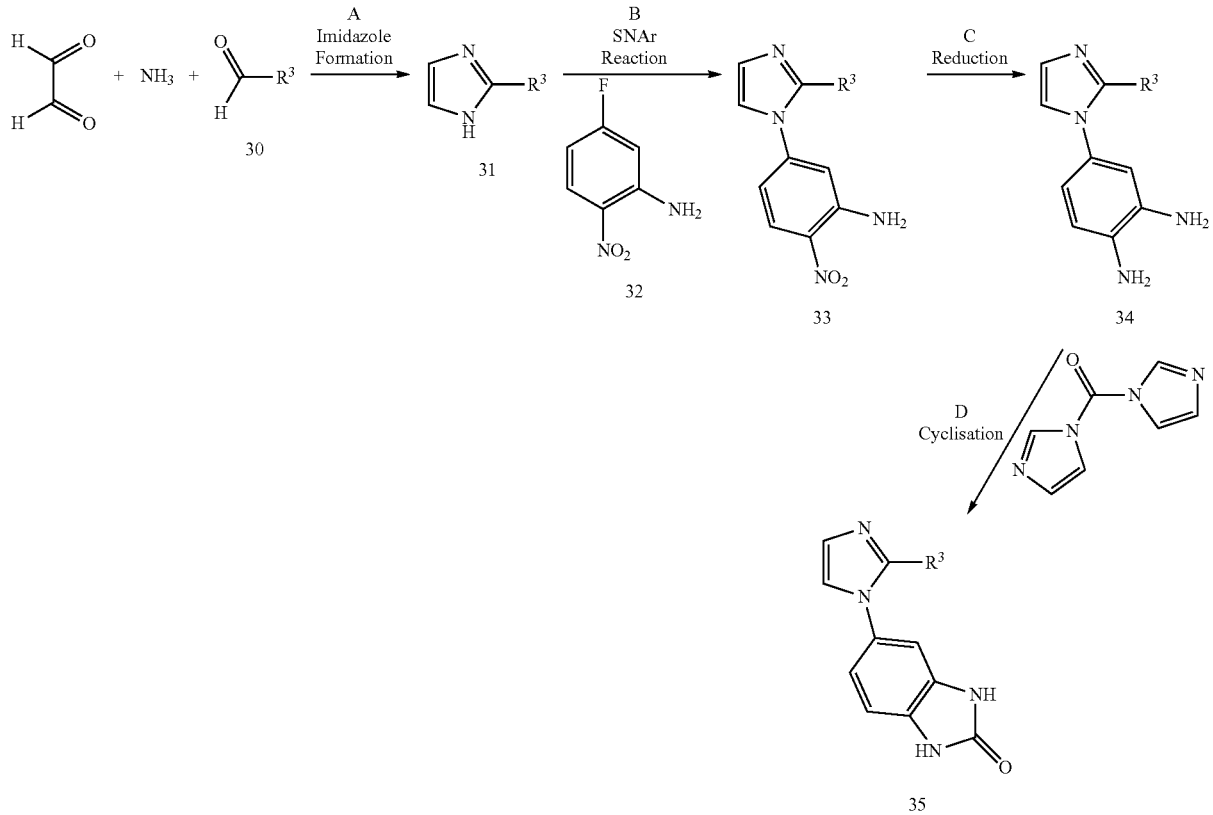

R3 = as defined herein

Step A:

Imidazole 31 can be obtained by reaction of a suitable aldehyde 30 with aqueous ammonia in a polar solvent such as methanol, ethanol, water or a mixture thereof followed by treatment with oxalaldehyde. Preferred conditions are aqueous methanol at room temperature for 72 hours.

Step B:

Nitro-amino-arene compound 33 can be obtained by an aromatic nucleophilic substitution ($S_NAr$) reaction between 5-fluoro-2-nitroaniline[61] 32 and imidazole compound 31.

The $S_NAr$ reaction is carried out in the presence of a strong non-nucleophilic base such as sodium hydride or potassium hydride in a polar non-protic organic solvent such as N,N-dimethylformamide at elevated temperatures. Preferred conditions are deprotonation of imidazole compound 31 with sodium hydride in N,N-dimethylformamide at room temperature followed by reaction with 5-fluoro-2-nitroaniline at 60° C. overnight.

Step C:

Reduction of nitro-amino-arene compound 33 to diamino-arene 34 can be effected by hydrogenation with hydrogen under normal or elevated pressure in the presence of a catalyst such as $PtO_2$, Pd—C or Raney nickel in polar solvents such as MeOH, EtOH, dioxane, THF, or mixtures thereof.

Preferred conditions are 1 atm of hydrogen in the presence of 10% palladium on charcoal in a mixture of methanol and THF at room temperature for 1 hour.

Step D:

Dihydrobenzimidazolone 35 can be obtained by cyclisation of diamino-arene 34 with di(1H-imidazol-1-yl)methanone. The cyclisation reaction is carried out in a polar organic ethereal solvents such as diethyl ether, dioxane, THF, DME or TBME at elevated temperatures. Preferred conditions are THF at room temperature for 18 hours.

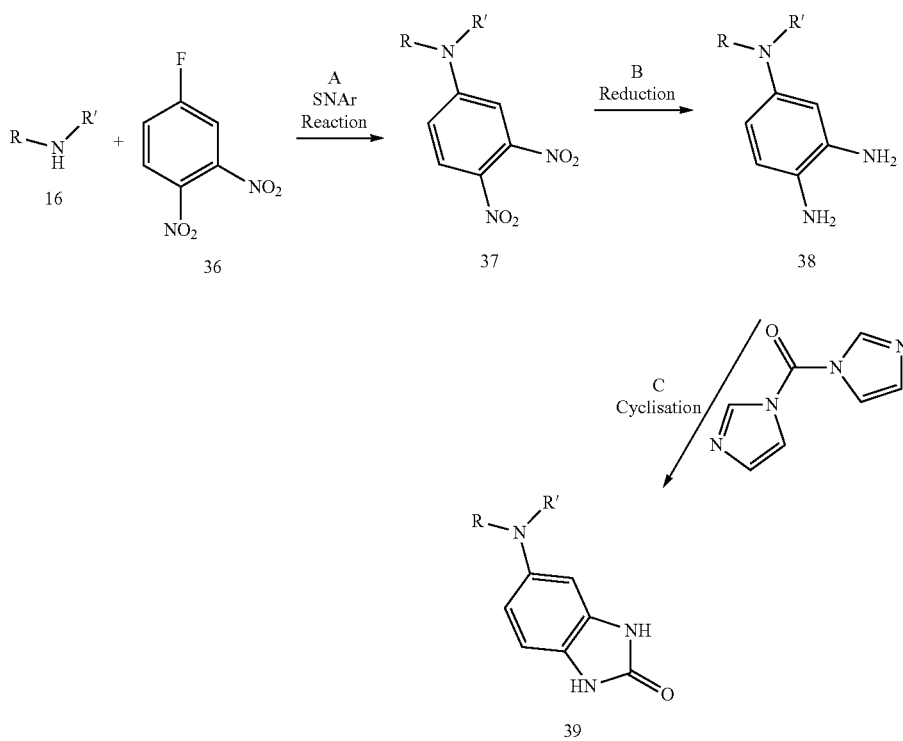

R, R' = as defined herein

Step A:

Di-nitro-arene compound 37 can be obtained by an aromatic nucleophilic substitution ($S_NAr$) reaction between 4-fluoro-1,2-dinitrobenzene[62] 36 and a primary or secondary amine 16. The $S_NAr$ reaction is carried out in the presence of an organic base such as triethylamine, N,N-diisopropylethylamine or N-methylmorpholine in a polar non-protic organic solvent such as N,N-dimethylformamide or acetonitrile.

Preferred conditions are N,N-diisopropylethylamine in acetonitrile at room temperature overnight.

Step B:

Reduction of Di-nitro-arene compound 37 to diamino-arene 38 can be effected by hydrogenation with hydrogen under normal or elevated pressure in the presence of a catalyst such as $PtO_2$, Pd—C or Raney nickel in polar solvents such as MeOH, EtOH, dioxane, THF, or mixtures thereof.

Preferred conditions are 1 atm of hydrogen in the presence of 10% palladium on charcoal in a mixture of ethanol and THF at room temperature overnight.

Step C:

Dihydrobenzimidazolone 39 can be obtained by cyclisation of diamino-arene 38 with di(1H-imidazol-1-yl)methanone. The cyclisation reaction is carried out in a polar organic ethereal solvents such as diethyl ether, dioxane, THF, DME or TBME at elevated temperatures. Preferred conditions are THF at room temperature for 1 hour.

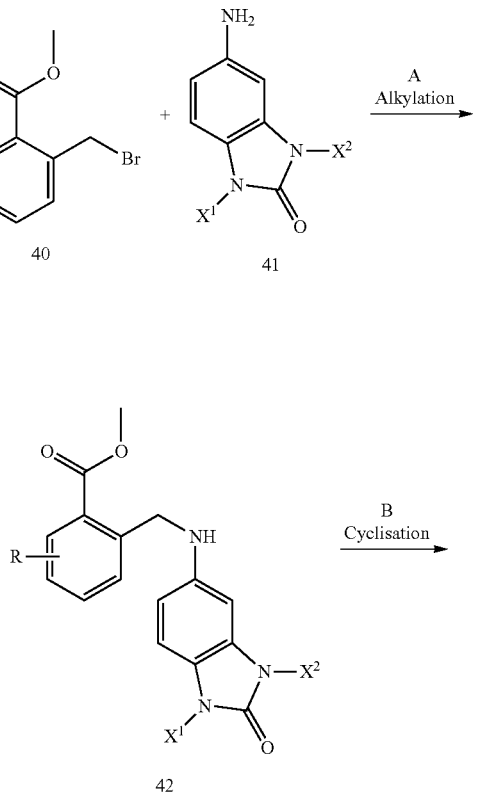

39

-continued

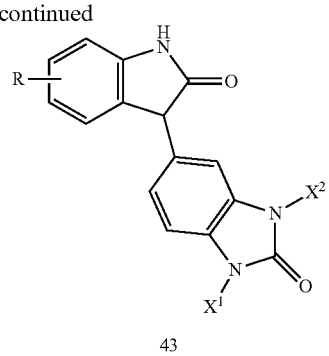

R = Br, —C(O)OMe
X1, X2 = as defined herein

Step A:
Amine-ester 42 can be obtained by an alkylation reaction between a benzyl bromide 40 and an aromatic amine compound 41 in the presence of a base such as triethylamine or potassium carbonate in solvents such as acetonitrile, methanol, DME, DMF and DMSO at room temperature to elevated temperatures.

Examples of suitable benzyl bromides 40 include, but are not limited to, dimethyl 2-(bromomethyl)benzene-1,4-dicarboxylate[63] and methyl 4-bromo-2-(bromomethyl)benzoate[160].

Examples of suitable aromatic amine compounds 41 include, but are not limited to, 5-amino-1,3-dihydro-2H-benzimidazol-2-one[50].

Preferred conditions are triethylamine in methanol at 25° C. for 12 hours.

Step B:
Cyclisation can be performed by heating amine-ester 42 at elevated temperature in presence of a base such as sodium methanolate or potassium carbonate in solvents such as methanol or ethanol.

Preferred conditions are potassium carbonate in methanol at 80° C. for 2 hours.

Scheme 14

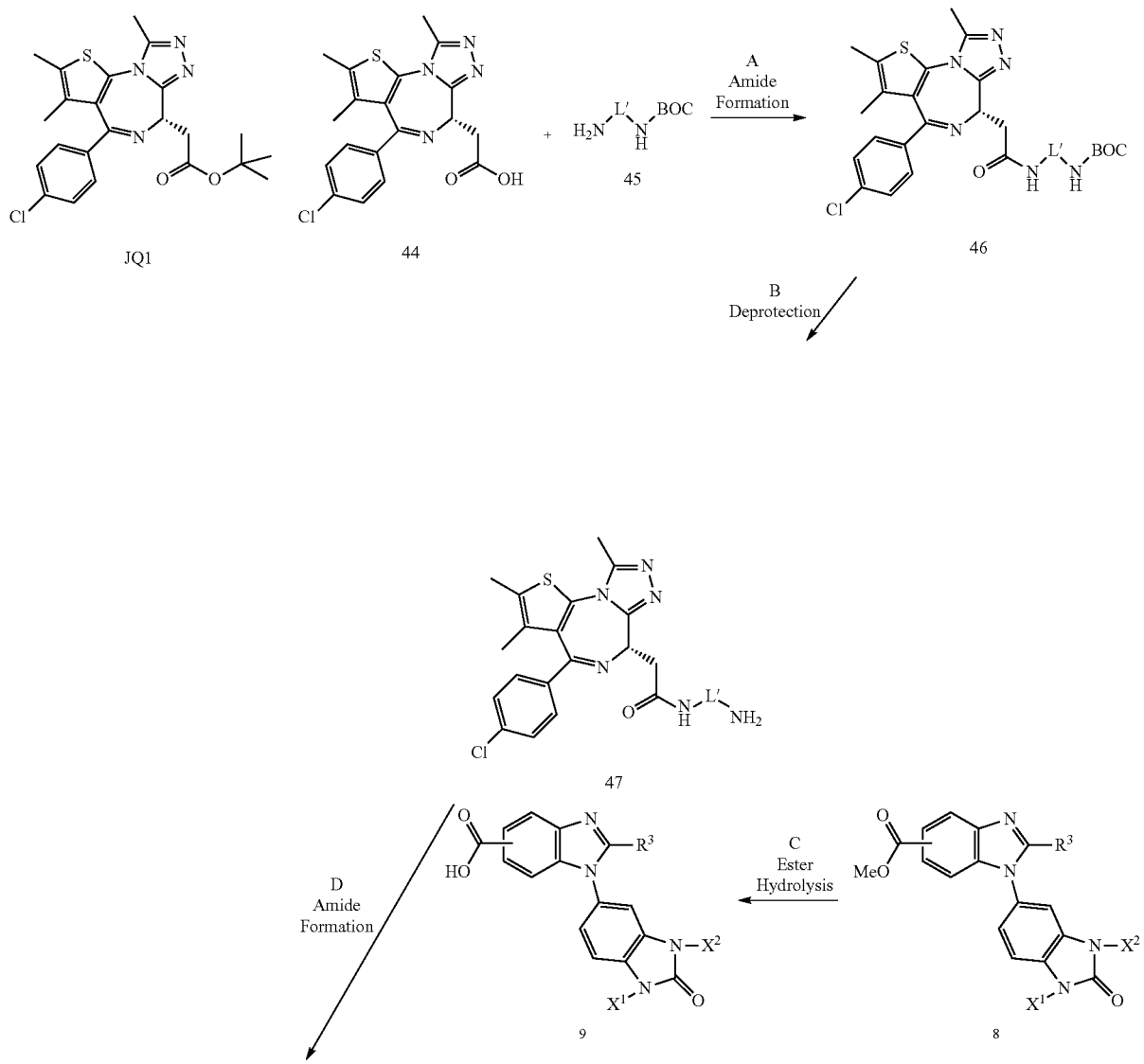

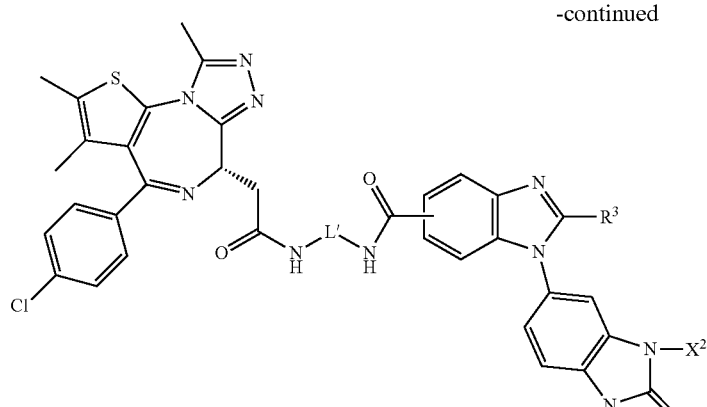

48

L = ——(CH₂)1-32   or   ——(CH2CH2O)1-5—CH2CH2
X1, X2 = as defined herein
R3 = as defined herein As an illustrative example, degrader compounds targeting the BET bromodomain BRD4 can be prepared based on the known BRD4 ligand JQ1[64,65]. The synthesis starts from the corresponding carboxylic acid derivative 44[66].

Step A:

Amide bond formation can be accomplished by a coupling reaction between carboxylic acid 44 and a linker-containing compound 45 bearing a terminal amine functionality and a terminal BOC-protected amine functionality. The reaction is carried out in the presence of a coupling reagent such as DCC, EDC, TBTU or HATU in the presence of an organic base such as triethylamine, N,N-diisopropylethylamine, N-methylmorpholine or 4-(N,N-dimethylamino)pyridine in halogenated solvents such as dichloromethane or 1,2-dichloroethane or ethereal solvents such as diethyl ether, dioxane, THF, DME or TBME or polar non-protic organic solvent such as N,N-dimethylformamide at room temperature or at elevated temperatures for 2-18 hours.

Preferred conditions are 1-ethyl-3-(3-dimethylaminopropyl)carbodiimide (EDC) with 4-(N,N-dimethylamino)pyridine (4-DMAP) in dichloromethane at room temperature for 48 hours.

Step B:

Removal of the Boc N-protecting group of 46 can be effected with mineral acids such as HCl, H₂SO₄ or H₃PO₄ or organic acids such as CF₃COOH, CHCl₂COOH, HOAc or p-toluenesulfonic acid in solvents such as CH₂Cl₂, CHCl₃, THF, Dioxane, MeOH, EtOH or H₂O at 0° C. to reflux temperature.

Preferred conditions are 4 M HCl in dioxane at room temperature for 1 hour.

Step C:

Ester compound 8 (Scheme 2) can be hydrolysed to carboxylic acid 9 by treatment with an aqueous base such as lithium hydroxide, sodium hydroxide or potassium hydroxide. The hydrolysis reaction is carried out in a mixture of water and an alcohol solvent such as methanol, ethanol, isopropanol or n-butanol, or a polar ethereal solvent such as dioxane, THF, DME or TBME, or a mixture therefore, at room temperature or at elevated temperatures for 2-18 hours.

Preferred conditions are 1 M aq. LiOH solution in MeOH and THF at room temperature for 48 h.

Step D:

Amide bond formation can be accomplished by a coupling reaction between carboxylic acid 9 and amine 47 in the presence of a coupling reagent such as DCC, EDC, TBTU or HATU in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF, DME or TBME or polar non-protic organic solvent such as N,N-dimethylformamide at room temperature or at elevated temperatures for 2-18 hours.

Preferred conditions are HATU with N,N-diisopropylethylamine in N,N-dimethylformamide at room temperature for 4 hours.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC. Racemic mixtures of chiral synthetic intermediates may also be separated using chiral HPLC.

In cases where the compounds of formula I or formula P-L-C are basic they may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

Insofar as their preparation is not described in the examples, the compounds of formula I or formula P-L-C as well as all intermediate products can be prepared according to analogous methods or according to the methods set forth herein. Starting materials are commercially available, known in the art or can be prepared by methods known in the art or in analogy thereto.

It will be appreciated that the compounds of general formula I or formula P-L-C in this invention may be derivatised at functional groups to provide derivatives which are capable of conversion back to the parent compound in vivo.

Pharmacological Tests

The compounds of formula I or formula P-L-C and their pharmaceutically acceptable salts possess valuable pharmacological properties. The compounds were investigated in accordance with the test given hereinafter.

Dual Fluorescent Reporter Assay

In order to measure BRD4 protein abundance in a mammalian cell system at medium throughput, a dual fluorescent reporter system was developed based on a principle described in[1]. Transient expression vectors were designed that contain the BRD4 coding sequence (NM_058243.2) fused to a fluorescent tag. Vectors were synthesized at ATUM (Newark, Calif., USA) using the pD2610 CMV backbone and were built up as follows: c-terminal version BRD4_eGFP-IRES-FresnoRFP_NLS, n-terminal version eGFP_BRD4-IRES-FresnoRFP_NLS, empty vector control eGFP-IRES-FresnoRFP_NLS. The c-terminal version was used for the reporter assays, as it presented with the best assay window. HEK293A cells (Invitrogen, Cat. No. R705-07) were cultured in Dulbecco's Modified Eagle Medium (DMEM), 10% fetal calf serum, 2 mM L-Glutamine, 1% Penicillin/Streptomycin. Transfections of the plasmids were performed with Lipofectamine 2000 according to the manufacturer's protocol (Invitrogen, Carlsbad, Calif., USA). 40 hours after transfection, cells were seeded at a density of 40'000/100 ul/96 well flat-bottom and 8 hours later treated with compounds (stocks 10 mM in DMSO) at a 10-point dilution ranging from 0-25 µM. After 16 hours of treatment, cells were washed with PBS, resuspended in Accumax solution[67] and analyzed by flow-cytometry (CytoFlex S, BeckmanCoulter). Single cells were gated based on their forward and side-scatter profiles and pulse-width was used to exclude doublets. A minimum of 20'000 cells was acquired per sample. Analysis was performed with the program Flow Jo V10.1 on BRD4-eGFP low/medium cells (<$10^6$ FL1-A Mean Fluorescence Intensity (MFI)). A factor was derived to normalize BRD4-eGFP values to the RFP protein abundance control (20×FL1A-GFP/FL11A-RFP), then Median and Mode values were calculated and used for comparisons between treatment conditions.

Capillary-Based Immunoassays to Measure Endogenous BRD4 Levels

The biological activity of selected compounds (cut-off>20% reduction in BRD4-eGFP levels) was confirmed in an additional assay which allowed the quantification of endogenous BRD4 levels. To this end, HEK293A cells (origin and culture conditions see above) were seeded at 400'000/300 ul/48 well and were treated 6 hours later with compound concentrations as indicated for. 16 hours after the treatment, the cells were washed with PBS and lysed in 50 ul of UREA lysis buffer (10 mM Tris-HCl pH 8, 2% CHAPS, 7M UREA, 0.4% DTT), supplemented with 1× protease inhibitor cocktail (Complete Mini, Roche) and 1× phosphatase inhibitor cocktail (PhosSTOP, Sigma-Aldrich). Samples were then analyzed by Peggy Sue or WES capillary-based immunoassay systems according to the manufacturer's protocol (Protein Simple/Bio-Techne, San Jose, Calif., 95134 USA). Antibodies used were anti-BRD4 (Cell signaling, CST 13440 1:50) and anti-Vinculin (Sigma, V9131, 1:4000). To quantify BRD4 protein levels, the peak signal areas were normalized to the vinculin loading control and to the DMSO condition.

Further, please see Yen et al.[68].

Fluorescence Direct Binding Protocol

Principle

Determination of the affinities of compounds to protein containing one or more tryptophan is measurable by monitoring the fluorescence emission in direct mode. The measurements depending on the protein available amounts are performed either manually in a cuvette on ISS-PC1 photon counting spectrofluorometer or automatically in well plates on a fluorescence plate reader device. Fluorescence titrations are performed at 20° C. in the chosen binding assay buffer by using a defined constant protein concentration against ligand concentration variations. Small aliquots of known ligand concentration solubilized in DMSO were added and the fluorescence, excited at 280 nm, was recorded at 340 nm. The fluorescence intensity was corrected for protein dilution and for the filter effect (Birdsall et al.[69]). The corrected fluorescence intensity was plotted against the ligand concentration and fitted using a four-parameter sigmoidal function, from which the equilibrium dissociation constant Kd was computed using the law of mass action assuming a 1:1 protein-ligand complex (Eftink, 1997[70]).

Process

1) Optimization of measurement parameters to minimize protein consumption and to minimize the dilution effect and the DMSO content 2) Titration measurements of the protein against ligand by at least 12 titration steps to obtain a good s-curve fit 3) Repeat the same titration measurements with the ligand alone to enable correction 4) Check the stability of the protein once by titration against DMSO alone 5) Determination of the molar extinction coefficients of the ligand at 280 and 340 nm with help of an UV-spectrophotometer 6) Use Excel template for the correction of the measured raw data 7) Use GraphPad Prism software for the quadratic binding fit and the KD evaluation.

Experimental Details

TABLE 1

Protein - buffers, Reference compound: thalidomide, Contergan, Softenon

| | |
|---|---|
| Protein Batch # | Cereblon_17_13 |
| Construct name | hCereblon(M1-L442)_hDDB1(M1-H1140) |
| Concentration | 2.54 mg/ml |
| MW | 180180 Da |
| Molar extinction coefficient | $\varepsilon_{280}$ = 165045 $M^{-1} \cdot cm^{-1}$ |
| Storage buffer | 20 mM MES pH 6.5 200 mM NaCl 1 mM TCEP |
| Assay buffer | 50 mM Hepes 7.4 200 mM NaCl |

TABLE 2

| Settings | |
|---|---|
| Device | ISS-PC1 |
| Excitation wavelength [nm] | 280 |
| Emission wavelength [nm] | 340 |
| Cuvette | Hellma 115F-QS |
| Volume [μL] | 500 |

Protein Preparation:

TABLE 3

| Protein preparation | | |
|---|---|---|
| Volume Protein [μL] | Volume buffer [μL] | Protein concentration [M] |
| 1.8 @ 2.54 mg/ml | 498.2 | 5.0 E-8 |

TABLE 4

| Titration steps | | | | |
|---|---|---|---|---|
| C Lig [M] | C Aliquot [M] | V Aliquot [μL] | C Prot [M] | Dilution factor |
| 1E-10 | 1.0E-07 | 0.5 | 4.995E-08 | 1.001 |
| 1.1E-09 | 1.0E-06 | 0.5 | 4.990E-08 | 1.002 |
| 3.1E-09 | 1.0E-06 | 1 | 4.980E-08 | 1.004 |
| 5.1E-09 | 1.0E-06 | 1 | 4.970E-08 | 1.006 |
| 1.51E-08 | 1.0E-05 | 0.5 | 4.965E-08 | 1.007 |
| 2.51E-08 | 1.0E-05 | 0.5 | 4.960E-08 | 1.008 |
| 4.51E-08 | 1.0E-05 | 1 | 4.950E-08 | 1.01 |
| 6.51E-08 | 1.0E-05 | 1 | 4.941E-08 | 1.012 |
| 1.651E-07 | 1.0E-04 | 0.5 | 4.936E-08 | 1.013 |
| 3.651E-07 | 1.0E-04 | 1 | 4.926E-08 | 1.015 |
| 5.651E-07 | 1.0E-04 | 1 | 4.916E-08 | 1.017 |
| 7.651E-07 | 1.0E-04 | 1 | 4.907E-08 | 1.019 |
| 9.651E-07 | 1.0E-04 | 1 | 4.897E-08 | 1.021 |
| 1.9651E-06 | 1.0E-03 | 0.5 | 4.892E-08 | 1.022 |
| 2.9651E-06 | 1.0E-03 | 0.5 | 4.888E-08 | 1.023 |
| 1.29651E-05 | 1.0E-02 | 0.5 | 4.883E-08 | 1.024 |
| 2.29651E-05 | 1.0E-02 | 0.5 | 4.878E-08 | 1.025 |
| 4.29651E-05 | 1.0E-02 | 1 | 4.869E-08 | 1.027 |
| 6.29651E-05 | 1.0E-02 | 1 | 4.859E-08 | 1.029 |
| 8.29651E-05 | 1.0E-02 | 1 | 4.850E-08 | 1.031 |

TABLE 5 affinities of examples to protein

| Example | Name | Fluorescence h-Cereblon_DDB1 Mean $K_d\_EQ$ (μm) |
|---|---|---|
| 1 | 3-amino-N-methyl-4-[(2-oxo-1,3-dihydrobenzimidazol-5-yl)amino]benzamide | 0.587 |
| 2 | N-methyl-2-[2-(3-methylimidazol-4-yl)-4-quinolyl]-1-(2-oxo-1,3-dihydrobenzimidazol-5-yl)benzimidazole-5-carboxamide | 0.028 |
| 3 | N-methyl-1-(2-oxo-1,3-dihydrobenzimidazol-5-yl)-2-(4-quinolyl)benzimidazole-5-carboxamide | 0.039 |
| 4 | 2-ethyl-N-methyl-1-(2-oxo-1,3-dihydrobenzimidazol-5-yl)benzimidazole-5-carboxamide | 0.036 |
| 5 | N,2-dimethyl-1-(2-oxo-1,3-dihydrobenzimidazol-5-yl)benzimidazole-5-carboxamide | 0.180 |
| 6 | 5-(2-aminoanilino)-1,3-dihydrobenzimidazol-2-one | 0.054 |
| 7 | 5-[2-(4-quinolyl)benzimidazol-1-yl]-1,3-dihydrobenzimidazol-2-one | 0.027 |
| 8 | 5-[2-[2-(3-methylimidazol-4-yl)-4-quinolyl]benzimidazol-1-yl]-1,3-dihydrobenzimidazol-2-one | 0.006 |
| 9 | methyl 3-amino-4-[(2-oxo-1,3-dihydrobenzimidazol-5-yl)amino]benzoate | 0.029 |
| 10 | N-methyl-1-(2-oxo-1,3-dihydrobenzimidazol-5-yl)-2-phenyl-benzimidazole-5-carboxamide | 0.088 |
| 11 | N-methyl-1-(2-oxo-1,3-dihydrobenzimidazol-5-yl)-2-(4-pyridyl)benzimidazole-5-carboxamide | 0.008 |
| 12 | 5-[2-(4-quinolyl)imidazol-1-yl]-1,3-dihydrobenzimidazol-2-one | 0.001 |
| 13 | N-methyl-1-(2-oxo-1,3-dihydrobenzimidazol-5-yl)-2-(trifluoromethyl)benzimidazole-5-carboxamide | 0.007 |
| 14 | N-methyl-1-(2-oxo-1,3-dihydrobenzimidazol-5-yl)-2-propyl-benzimidazole-5-carboxamide | 0.321 |
| 15 | 2-(1H-imidazol-5-yl)-N-methyl-1-(2-oxo-1,3-dihydrobenzimidazol-5-yl)benzimidazole-5-carboxamide | 0.049 |
| 16 | 2-isopropyl-N-methyl-1-(2-oxo-1,3-dihydrobenzimidazol-5-yl)benzimidazole-5-carboxamide | 0.011 |
| 17 | 1-(1,3-dimethyl-2-oxo-benzimidazol-5-yl)-N-methyl-2-[2-(3-methylimidazol-4-yl)-4-quinolyl]benzimidazole-5-carboxamide | 0.042 |
| 18 | N,N-dimethyl-2-[2-(3-methylimidazol-4-yl)-4-quinolyl]-1-(2-oxo-1,3-dihydrobenzimidazol-5-yl)benzimidazole-5-carboxamide | 0.016 |
| 19 | 5-(3-pyridyl)-1,3-dihydrobenzimidazol-2-one | 0.007 |
| 20 | 5-(2-chloro-4-pyridyl)-1,3-dihydrobenzimidazol-2-one | 0.068 |
| 21 | 5-(2-methylthiazol-5-yl)-1,3-dihydrobenzimidazol-2-one | 0.005 |

TABLE 5-continued affinities of examples to protein

| Example | Name | Fluorescence h-Cereblon_DDB1 Mean $K_d$_EQ (μm) |
|---|---|---|
| 22 | 5-(4-acetylpiperazine-1-carbonyl)-1,3-dihydrobenzimidazol-2-one | 0.103 |
| 23 | N-(1-acetyl-4-piperidyl)-2-oxo-1,3-dihydrobenzimidazole-5-carboxamide | 0.003 |
| 24 | 5-(indoline-1-carbonyl)-1,3-dihydrobenzimidazol-2-one | 0.001 |
| 25 | N-(1,3-dimethyl-2-oxo-benzimidazol-5-yl)furan-2-carboxamide | 0.111 |
| 26 | 5-(3-phenyl-propyl)-1,3-dihydro-imidazo[4,5-b]pyridin-2-one | 0.041 |
| 27 | 1-methyl-2-oxo-N-phenyl-3H-imidazo[4,5-b]pyridine-6-carboxamide | 0.001 |
| 28 | 2-(3-methoxybenzyl)-N-methyl-2'-oxo-2',3'-dihydro-1'H-[1,5'-bibenzo[d]imidazole]-5-carboxamide | 0.012 |
| 29 | N-(1-(2-oxo-2,3-dihydro-1H-benzo[d]imidazole-5-carbonyl)piperidin-4-yl)acetamide | 0.020 |
| 30 | 2-isopropyl-N-methyl-2'-oxo-2',3'-dihydro-1'H-[1,5'-bibenzo[d]imidazole]-6-carboxamide | 0.001 |
| 31 | 1',3'-dimethyl-2-(2-(1-methyl-1H-imidazol-5-yl)quinolin-4-yl)-1',3'-dihydro-2'H-[1,5'-bibenzo[d]imidazol]-2'-one | 0.007 |
| 32 | 5-(2-isopropyl-1H-imidazol-1-yl)-1,3-dihydro-2H-benzo[d]imidazol-2-one | 0.006 |
| 33 | 5-(2-oxopyrrolidin-1-yl)-1,3-dihydro-2H-benzo[d]imidazol-2-one | 0.024 |
| 34 | 2-isopropyl-1'-methyl-1',3'-dihydro-2'H-[1,5'-bibenzo[d]imidazol]-2'-one | 0.019 |
| 35 | 2-isopropyl-3'-methyl-1',3'-dihydro-2'H-[1,5'-bibenzo[d]imidazol]-2'-one | 0.024 |
| 36 | 6-(4-fluorophenyl)-1,3-dihydroimidazo[4,5-c]pyridin-2-one | 0.077 |
| 37 | 5-(2,5-difluoro-phenyl)-1,3-dihydro-benzoimidazol-2-one | 0.010 |
| 38 | 5-(2,4-difluoro-phenyl)-1,3-dihydro-benzoimidazol-2-one | 0.082 |
| 39 | 5-[(4-methoxyphenyl)methyl]-1,3-dihydrobenzimidazol-2-one | 0.006 |
| 40 | 5-[4-(2-pyridyl)piperazin-1-yl]-1,3-dihydroimidazo[4,5-b]pyridin-2-one | 0.007 |
| 41 | 5-(4-pyrrol-1-yl-phenyl-1,3-dihydro-benzoimidazol-2-one | 0.018 |
| 42 | 5-quinolin-5-yl-1,3-dihydro-benzoimidazol-2-one | 0.336 |
| 43 | ethyl 4-((2-oxo-2,3-dihydro-1H-benzo[d]imidazole)-5-sulfonamido)benzoate | 0.100 |
| 44 | 1-methyl-5-phenyl-3H-imidazo[4,5-b]pyridin-2-one | <0.001 |
| 45 | 2-(2-methoxybenzyl)-N-methyl-2'-oxo-2',3'-dihydro-1'H-[1,5'-bibenzo[d]imidazole]-5-carboxamide | 0.022 |
| 46 | 2-(tert-butyl)-N-methyl-2'-oxo-2',3'-dihydro-1'H-[1,5'-bibenzo[d]imidazole]-5-carboxamide | 0.010 |
| 47 | methyl 2-isopropyl-2'-oxo-2',3'-dihydro-1'H-[1,5'-bibenzo[d]imidazole]-4-carboxylate | 0.020 |
| 48 | methyl 2-isopropyl-2'-oxo-2',3'-dihyrdro-1'H-[1,5'-bibenzo[d]imidazole]-6-carboxylate | 0.011 |
| 49 | 1,3-dimethyl-5-((2-nitrophenyl)amino)-1,3-dihydro-2H-benzo[d]imidazol-2-one | 0.023 |
| 50 | 5-((2-aminophenyl)amino)-1,3-dimethyl-1,3-dihydro-2H-benzo[d]imidazol-2-one | 0.011 |
| 51 | 2-oxo-N-(4-piperidyl)-1,3-dihydrobenzimidazole-5-carboxamide | 0.138 |
| 52 | 6-((2-aminophenyl)amino)-1-methyl-1,3-dihydro-2H-benzo[d]imidazol-2-one | 0.006 |
| 53 | 5-((2-aminophenyl)amino)-1-methyl-1,3-dihydro-2H-benzo[d]imidazol-2-one | 0.049 |
| 54 | methyl 1-(2-oxo-2,3-dihydro-1H-benzo[d]imidazole-5-carbonyl)indoline-4-carboxylate | 0.025 |
| 55 | 6-(indoline-1-carbonyl)-1,3-dihydro-2H-imidazo[4,5-b]pyridin-2-one | <0.001 |
| 56 | N-(1-acetylpiperidin-4-yl)-2-oxo-2,3-dihydro-1H-imidazo[4,5-b]pyridine-6-carboxamide | 0.002 |
| 57 | 2-(3-(methoxymethyl)phenyl)-N-methyl-2'-oxo-2',3'-dihydro-1'H-[1,5'-bibenzo[d]imidazole]-5-carboxamide | 0.007 |
| 58 | 5-(piperazin-1-yl)-1,3-dihydro-2H-benzo[d]imidazol-2-one | 0.012 |
| 59 | 5-[rac-(1S,5R)-3,8-diazabicyclo[3.2.1]octan-3-yl]-1,3-dihydrobenzimidazol-2-one | 0.006 |
| 60 | 2-isopropyl-N-methyl-2'-oxo-2',3'-dihydro-1'H-[1,5'-bibenzo[d]imidazole]-4-carboxamide | 0.047 |

TABLE 5-continued affinities of examples to protein

| Example | Name | Fluorescence h-Cereblon_DDB1 Mean $K_d$_EQ (μm) |
|---|---|---|
| 61 | 5-[2-(hydroxymethyl)benzimidazol-1-yl]-1,3-dihydrobenzimidazol-2-one | 0.029 |
| 62 | 5-(4-acetylpiperazin-1-yl)-1,3-dihydro-2H-benzo[d]imidazol-2-one | <0.001 |
| 63 | 5-[rac-(1S,5R)-8-acetyl-3,8-diazabicyclo[3.2.1]octan-3-yl]-1,3-dihydrobenzimidazol-2-one | 0.079 |
| 64 | N-methyl-2'-oxo-2-(tetrahydro-2H-pyran-4-yl)-2',3'-dihydro-1'H-[1,5'-bibenzo[d]imidazole]-5-carboxamide | 0.045 |
| 65 | N-methyl-2-(1-methyl-1H-imidazol-4-yl)-2'-oxo-2',3'-dihydro-1'H-[1,5''-bibenzo[d]imidazole]-5-carboxamide | 0.009 |
| 66 | N-methyl-2'-oxo-2-(1H-pyrrol-3-yl)-2',3'-dihydro-1'H-[1,5'-bibenzo[d]imidazole]-5-carboxamide | 0.051 |
| 67 | 2-oxo-N-phenyl-2,3-dihydro-1H-imidazo[4,5-b]pyridine-6-carboxamide | 0.005 |
| 68 | N-(2-oxo-2,3-dihydro-1H-benzo[d]imidazol-5-yl)benzofuran-3-carboxamide | 0.009 |
| 69 | N-(2-oxo-2,3-dihydro-1H-benzo[d]imidazol-5-yl)-2,3-dihydro-1H-indene-1-carboxamide | 0.029 |
| 70 | 2-(4-aminophenyl)-N-(2-oxo-2,3-dihydro-1H-benzo[d]imidazol-5-yl)acetamide | 0.001 |
| 71 | (S)-N-(2-oxo-2,3-dihydro-1H-benzo[d]imidazol-5-yl)-1,2,3,4-tetrahydronaphthalene-1-carboxamide | 0.016 |
| 72 | (R)-N-(2-oxo-2,3-dihydro-1H-benzo[d]imidazol-5-yl)-1,2,3,4-tetrahydronaphthalene-1-carboxamide | 0.014 |
| 73 | N-(2-oxo-2,3-dihydro-1H-benzo[d]imidazol-5-yl)benzamide | 0.011 |
| 74 | 4-acetamido-N-(2-oxo-2,3-dihydro-1H-benzo[d]imidazol-5-yl)benzamide | 0.002 |
| 75 | 3-acetamido-N-(2-oxo-2,3-dihydro-1H-benzo[d]imidazol-5-yl)benzamide | 0.007 |
| 76 | N-methyl-2-oxo-N-phenyl-2,3-dihydro-1H-imidazo[4,5-b]pyridine-6-carboxamide | 0.041 |
| 77 | 2-oxo-N-phenyl-2,3-dihydro-1H-benzo[d]imidazole-5-carboxamide | 0.042 |
| 78 | 2-(4-acetamidophenyl)-N-(2-oxo-2,3-dihydro-1H-benzo[d]imidazol-5-yl)acetamide | 0.023 |
| 79 | 2-isopropyl-N-methyl-1-(2-oxo-1,3-dihydroimidazo[4,5-b]pyridin-6-yl)benzimidazole-5-carboxamide | 0.004 |
| 80 | N-[2-[1-(2-oxo-1,3-dihydrobenzimidazol-5-yl)benzimidazol-2-yl]ethyl]acetamide | 0.015 |
| 81 | N-methyl-3-[1-(2-oxo-1,3-dihydrobenzimidazol-5-yl)benzimidazol-2-yl]propanamide | 0.004 |
| 82 | methyl 1-(2-oxo-1,3-dihydrobenzimidazol-5-yl)benzimidazole-2-carboxylate | 0.003 |
| 83 | 5-(benzimidazol-1-yl)-1,3-dihydrobenzimidazol-2-one | 0.003 |
| 84 | 5-[2-(1-hydroxyethyl)benzimidazol-1-yl]-1,3-dihydrobenzimidazol-2-one | 0.003 |
| 85 | 5-[2-[hydroxy(phenyl)methyl]benzimidazol-1-yl]-1,3-dihydrobenzimidazol-2-one | 0.003 |
| 86 | N-(1-acetylpiperidin-4-yl)-N-methyl-2-oxo-2,3-dihydro-1H-benzo[d]imidazole-5-carboxamide | 0.004 |
| 87 | 1-(2-oxo-2,3-dihydro-1H-benzo[d]imidazol-5-yl)-3-(4-(phenylamino)phenyl)urea | 0.027 |
| 88 | 1-(2-oxo-2,3-dihydro-1H-benzo[d]imidazol-5-yl)-3-phenylurea | 0.017 |
| 89 | methyl 1-((2-oxo-2,3-dihydro-1H-benzo[d]imidazol-5-yl)carbamoyl)indoline-4-carboxylate | 0.025 |
| 90 | 3-acetamido-N-(2-oxo-2,3-dihydro-1H-benzo[d]imidazol-5-yl)propanamide | 0.019 |
| 91 | 1-acetyl-N-(2-oxo-2,3-dihydro-1H-benzo[d]imidazol-5-yl)piperidine-4-carboxamide | 0.005 |
| 92 | methyl 1-((2-oxo-2,3-dihydro-1H-benzo[d]imidazol-5-yl)carbamoyl)indoline-5-carboxylate | 0.033 |
| 93 | N4-methyl-N1-(2-oxo-2,3-dihydro-1H-benzo[d]imidazol-5-yl)indoline-1,4-dicarboxamide | 0.010 |
| 94 | 1-benzyl-3-(2-oxo-2,3-dihydro-1H-benzo[d]imidazol-5-yl)urea | <0.001 |
| 95 | 6-(1,2,3,4-tetrahydroquinoline-1-carbonyl)-1,3-dihydro-2H-imidazo[4,5-b]pyridin-2-one | 0.020 |
| 96 | N-methyl-2-oxo-N-phenyl-2,3-dihydro-1H-benzo[d]imidazole-5-carboxamide | 0.009 |
| 97 | 5-(1,2,3,4-tetrahydroquinoline-1-carbonyl)-1,3-dihydro-2H-benzo[d]imidazol-2-one | 0.009 |

TABLE 5-continued affinities of examples to protein

| Example | Name | Fluorescence h-Cereblon_DDB1 Mean $K_d$_EQ (μm) |
|---|---|---|
| 98 | methyl 1-((2-oxo-2,3-dihydro-1H-benzo[d]imidazol-5-yl)carbamoyl)-1,2,3,4-tetrahydroquinoline-5-carboxylate | 0.086 |
| 99 | N-(2-oxo-2,3-dihydro-1H-benzo[d]imidazol-5-yl)-2-(4-sulfamoylphenyl)acetamide | 0.046 |
| 100 | N-(2-oxo-2,3-dihydro-1H-benzo[d]imidazol-5-yl)-4-sulfamoylbenzamide | 0.029 |
| 101 | N-(4-(3-(2-oxo-2,3-dihydro-1H-benzo[d]imidazol-5-yl)ureido)phenyl)acetamide | 0.014 |
| 102 | N-methyl-1-(2-oxo-1,3-dihydrobenzimidazol-5-yl)benzimidazole-2-carboxamide | 0.130 |
| 103 | 5-[2-(piperidine-1-carbonyl)benzimidazol-1-yl]-1,3-dihydrobenzimidazol-2-one | 0.035 |
| 104 | 6-(2-(benzyloxy)phenyl)-1,3-dihydro-2H-imidazo[4,5-b]pyridin-2-one | 0.014 |
| 105 | N-(2-oxo-2,3-dihydro-1H-benzo[d]imidazol-5-yl)indoline-1-carboxamide | 0.004 |
| 106 | 2-(4-(N-methylsulfamoyl)phenyl)-N-(2-oxo-2,3-dihydro-1H-benzo[d]imidazol-5-yl)acetamide | 0.001 |
| 107 | methyl 2-(2-(1-methyl-1H-imidazol-5-yl)quinolin-4-yl)-2'-oxo-2',3'-dihydro-1'H-[1,5-bibenzo[d]imidazole]-5-carboxylate | 0.831 |
| 108 | 2-(2-methoxy pyridin-4-yl)-N-methyl-2'-oxo-2',3'-dihydro-1'H-[1,5'-bibenzo[d]imidazole]-5-carboxamide | 0.107 |
| 109 | N5-methyl-N1-(2-oxo-2,3-dihydro-1H-benzo[d]imidazol-5-yl)-3,4-dihydroquinoline-1,5(2H)-dicarboxamide | 0.039 |
| 110 | 5-(5-bromo-1-oxo-isoindolin-2-yl)-1,3-dihydrobenzimidazol-2-one | 0.029 |
| 111 | ethyl 1-oxo-2-(2-oxo-1,3-dihydrobenzimidazol-5-yl)isoindoline-5-carboxylate | 0.018 |
| 112 | methyl 1-oxo-2-(2-oxo-1,3-dihydrobenzimidazol-5-yl)isoindoline-5-carboxylate | 0.057 |
| 113 | 2-(2-(1-methyl-1H-imidazol-5-yl)quinolin-4-yl)-2'-oxo-2',3'-dihydro-1'H-[1,5'-bibenzo[d]imidazole]-5-carboxamide | 0.899 |
| 114 | N-methyl-2'-oxo-2-(1-phenylcyclopropyl)-2',3'-dihydro-1'H-[1,5'-bibenzo[d]imidazole]-5-carboxamide | 0.008 |
| 115 | 2-(1-(4-methoxyphenyl)cyclopropyl)-N-methyl-2'-oxo-2',3'-dihydro-1'H-[1,5'-bibenzo[d]imidazole]-5-carboxamide | 0.096 |
| 116 | 5-(indolin-1-ylsulfonyl)-1,3-dihydro-2H-benzo[d]imidazol-2-one | 0.048 |
| 117 | N-(1-acetylpiperidin-4-yl)-2-oxo-2,3-dihydro-1H-benzo[d]imidazole-5-sulfonamide | 0.008 |
| 118 | methyl 4-(N-(2-oxo-2,3-dihydro-1H-benzo[d]imidazol-5-yl)sulfamoyl)benzoate | 0.082 |
| 119 | tert-butyl (1-((2-oxo-2,3-dihydro-1H-benzo[d]imidazol-5-yl)carbamoyl)indolin-5-yl)carbamate | 0.113 |
| 120 | 5-(benzyloxy)-2-isopropyl-1',3'-dihydro-2'H-[1,5'-bibenzo[d]imidazol]-2'-one | 0.194 |
| 121 | 5-amino-N-(2-oxo-2,3-dihydro-1H-benzo[d]imidazol-5-yl)indoline-1-carboxamide hydrochloride | 0.065 |
| 122 | 2'-methyl-N-(2-oxo-2,3-dihydro-1H-benzo[d]imidazol-5-yl)-[1,1'-biphenyl]-2-carboxamide | 0.730 |
| 123 | 2-benzyl-N-(2-oxo-2,3-dihydro-1H-benzo[d]imidazol-5-yl)benzamide | 0.022 |
| 124 | 2-isopropyl-5-methoxy-1',3'-dihydro-2'H-[1,5'-bibenzo[d]imidazol]-2'-one | 0.013 |
| 125 | tert-butyl 4-(N-(2-oxo-2,3-dihydro-1H-benzo[d]imidazol-5-yl)sulfamoyl)piperidine-1-carboxylate | 0.020 |
| 126 | ethyl 4-(3-(2-oxo-2,3-dihydro-1H-benzo[d]imidazol-5-yl)ureido)benzoate | 0.009 |
| 127 | 1-(3-fluorophenyl)-3-(2-oxo-2,3-dihydro-1H-benzo[d]imidazol-5-yl)urea | 0.026 |
| 128 | 4-(2-methoxyphenyl)-N-(2-oxo-2,3-dihydro-1H-benzo[d]imidazol-5-yl)piperazine-1-carboxamide | 0.014 |
| 129 | 6-chloro-N-(2-oxo-2,3-dihydro-1H-benzo[d]imidazol-5-yl)indoline-1-carboxamide | 0.188 |
| 130 | N-(3-(1-methyl-1H-pyrazol-3-yl)phenyl)-2-oxo-2,3-dihydro-1H-benzo[d]imidazole-5-carboxamide | 0.781 |
| 131 | 2-(4-methoxycyclohexyl)-N-methyl-2'-oxo-2',3'-dihydro-1'H-[1,5'-bibenzo[d]imidazole]-5-carboxamide | 0.010 |
| 132 | 3-methoxy-N-(2-oxo-2,3-dihydro-1H-benzo[d]imidazol-5-yl)isonicotinamide | <0.001 |

TABLE 5-continued affinities of examples to protein

| Example | Name | Fluorescence h-Cereblon_DDB1 Mean $K_d$_EQ (μm) |
|---|---|---|
| 133 | N2-methyl-N5-(2-oxo-2,3-dihydro-1H-benzo[d]imidazol-5-yl)pyridine-2,5-dicarboxamide | 0.121 |
| 134 | N-(2-oxo-2,3-dihydro-1H-benzo[d]imidazol-5-yl)piperidine-4-sulfonamide | 0.007 |
| 135 | 4-(4-chlorobenzyl)-N-(2-oxo-2,3-dihydro-1H-benzo[d]imidazol-5-yl)piperazine-1-carboxamide | 0.007 |
| 136 | N-(2-oxo-2,3-dihydro-1H-benzo[d]imidazol-5-yl)-2-(pyridin-4-yl)benzamide | 0.079 |
| 137 | N-(2-oxo-2,3-dihydro-1H-benzo[d]imidazol-5-yl)benzofuran-3-sulfonamide | 0.022 |
| 138 | 2-(3-methoxyphenyl)-N-(2-oxo-2,3-dihydro-1H-benzo[d]imidazol-5-yl)nicotinamide | 0.109 |
| 139 | N-(1-benzylpiperidin-4-yl)-2-oxo-2,3-dihydro-1H-benzo[d]imidazole-5-carboxamide | 0.004 |
| 140 | 5-(5-aminoindolin-yl)-1,3-dihydro-2H-benzo[d]imidazol-2-one | 0.168 |
| 141 | N-(1-(2-oxo-2,3-dihydro-1H-benzo[d]imidazol-5-yl)indolin-5-yl)acetamide | 0.053 |
| 142 | N-(3-(oxazol-5-yl)phenyl)-2-oxo-2,3-dihydro-1H-benzo[d]imidazole-5-carboxamide | 0.011 |
| 143 | tert-butyl 4-((oxo-2,3-dihydro-1H-benzo[d]imidazol-5-yl)carbamoyl)indoline-1-carboxylate | 0.159 |
| 144 | N-(2-oxo-2,3-dihydro-1H-benzo[d]imidazol-5-yl)indoline-4-carboxamide | 0.029 |
| 145 | 1-acetyl-N-(2-oxo-2,3-dihydro-1H-benzo[d]imidazol-5-yl)indoline-4-carboxamide | 0.084 |
| 146 | N-(4-(((2-oxo-2,3-dihydro-1H-benzo[d]imidazol-5-yl)methyl)amino)phenyl)acetamide | 0.018 |
| 147 | N-(2-(methylcarbamoyl)phenyl)-2-oxo-2,3-dihydro-1H-benzo[d]imidazole-5-carboxamide | 0.338 |
| 148 | tert-butyl (1-((2-oxo-2,3-dihydro-1H-benzo[d]imidazol-5-yl)methyl)indolin-5-yl)carbamate | 0.019 |
| 149 | 5-((5-aminoindolin-1-yl)methyl)-1,3-dihydro-2H-benzo[d]imidazol-2-one | 0.017 |
| 150 | N-(1-((2-oxo-2,3-dihydro-1H-benzo[d]imidazol-5-yl)methyl)indolin-5-yl)acetamide | 0.003 |
| 151 | methyl 2-((2-oxo-2,3-dihydro-1H-benzo[d]imidazol-5-yl)carbamoyl)benzoate | 0.052 |
| 152 | 5-((1-benzylpiperidin-4-yl)amino)-1,3-dihydro-2H-benzo[d]imidazol-2-one | 0.021 |
| 153 | methyl 6-((2-oxo-2,3-dihydro-1H-benzo[d]imidazol-5-yl)amino)nicotinate | 0.016 |
| 154 | 5-(benzyloxy)-1,3-dihydro-2H-benzo[d]imidazol-2-one | 0.017 |
| 155 | methyl 2-((2-oxo-2,3-dihydro-1H-benzo[d]imidazol-5-yl)methyl)isoindoline-5-carboxylate | 0.029 |
| 156 | N-methyl-4-((2-oxo-2,3-dihydro-1H-benzo[d]imidazol-5-yl)oxy)benzamide | 0.022 |
| A | N-[5-[[2-[(9S)-7-(4-chlorophenyl)-4,5,13-trimethyl-3-thia-1,8,11,12-tetrazatricyclo[8.3.0.02,6]trideca-2(6),4,7,10,12-pentaen-9-yl]acetyl]amino]pentyl]-2-ethyl-1-(2-oxo-1,3-dihydrobenzimidazol-5-yl)benzimidazole-5-carboxamide | 0.055 |
| B | N-[2-[2-[2-[[2-[(9S)-7-(4-chlorophenyl)-4,5,13-trimethyl-3-thia-1,8,11,12-tetrazatricyclo[8.3.0.02,6]trideca-2(6),4,7,10,12-pentaen-9-yl]acetyl]amino]ethoxy]ethoxy]ethyl]-2-ethyl-1-(2-oxo-1,3-dihydrobenzimidazol-5-yl)benzimidazole-5-carboxamide | 0.051 |
| C | N-[2-[2-[2-[[2-[(9S)-7-(4-chlorophenyl)-4,5,13-trimethyl-3-thia-1,8,11,12-tetrazatricyclo[8.3.0.02,6]trideca-2(6),4,7,10,12-pentaen-9-yl]acetyl]amino]ethoxy]ethoxy]ethyl]-1-(2-oxo-1,3-dihydrobenzimidazol-5-yl)-2-(4-quinolyl)benzimidazole-5-carboxamide | 0.019 |
| D | N4-[5-[[2-[(9S)-7-(4-chlorophenyl)-4,5,13-trimethyl-3-thia-1,8,11,12-tetrazatricyclo[8.3.0.02,6]trideca-2(6),4,7,10,12-pentaen-9-yl]acetyl]amino]pentyl]-N1-(2-oxo-1,3-dihydrobenzimidazol-5-yl)indoline-1,4-dicarboxamide | 0.007 |

Pharmaceutical Compositions

The compounds of formula I or formula P-L-C and the pharmaceutically acceptable salts can be used as therapeutically active substances, e.g. in the form of pharmaceutical preparations. The pharmaceutical preparations can be administered orally, e.g. in the form of tablets, coated tablets, dragees, hard and soft gelatin capsules, solutions, emulsions or suspensions. The administration can, however, also be effected rectally, e.g. in the form of suppositories, or parenterally, e.g. in the form of injection solutions.

The compounds of formula I or formula P-L-C and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or formula P-L-C or a pharmaceutically acceptable salt thereof and a therapeutically inert carrier are also provided by the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, particularly 1-100 mg, of a compound of formula I or formula P-L-C. Examples of compositions according to the invention are:

Example A

Tablets of the following composition are manufactured in the usual manner:

TABLE 6 possible tablet composition

| ingredient | mg/tablet | | | |
|---|---|---|---|---|
| | 5 | 25 | 100 | 500 |
| Compound of formula I or formula P-L-C | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure

1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 7 possible capsule ingredient composition

| ingredient | mg/capsule | | | |
|---|---|---|---|---|
| | 5 | 25 | 100 | 500 |
| Compound of formula I or formula P-L-C | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

The compound of formula I or formula P-L-C, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Example B-2

Soft Gelatin Capsules of the following composition are manufactured:

TABLE 8

| possible soft gelatin capsule ingredient composition | |
| --- | --- |
| ingredient | mg/capsule |
| Compound of formula I or formula P-L-C | 5 |
| Yellow wax | 8 |
| Hydrogenated Soya bean oil | 8 |
| Partially hydrogenated plant oils | 34 |
| Soya bean oil | 110 |
| Total | 165 |

TABLE 9

| possible soft gelatin capsule composition | |
| --- | --- |
| ingredient | mg/capsule |
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I or formula P-L-C is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 10

| possible suppository composition | |
| --- | --- |
| ingredient | mg/supp. |
| Compound of formula I or formula P-L-C | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I or formula P-L-C is added thereto and stirred until it has dispersed completely. The mixture is poured into suppository moulds of suitable size, left to cool; the suppositories are then removed from the moulds and packed individually in wax paper or metal foil.

Example D

Injection solutions of the following composition are manufactured:

TABLE 11

| possible injection solution composition | |
| --- | --- |
| ingredient | mg/injection solution. |
| Compound of formula I or formula P-L-C | 3 |
| Polyethylene Glycol 400 | 150 |
| acetic acid | q.s. ad pH 5.0 |
| water for injection solutions | ad 1.0 ml |

Manufacturing Procedure

The compound of formula I or formula P-L-C is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 12

| possible sachet composition | |
| --- | --- |
| ingredient | mg/sachet |
| Compound of formula I or formula P-L-C | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I or formula P-L-C is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

EXPERIMENTAL PART

The following examples are provided for illustration of the invention. They should not be considered as limiting the scope of the invention, but merely as being representative thereof.

Example 1

3-Amino-N-methyl-4-[(2-oxo-1,3-dihydrobenzimidazol-5-yl)amino]benzamide

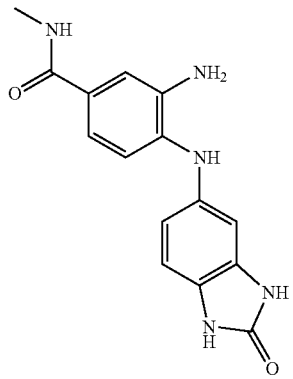 [SMILES: CNC(=O)c1ccc(Nc2ccc3[nH]c(=O)[nH]c3c2)c(N)c1]

a) N-Methyl-3-nitro-4-((2-oxo-2,3-dihydro-1H-benzo[d]imidazol-5-yl)amino)benzamide A stirred solution of 4-fluoro-N-methyl-3-nitrobenzamide[46] (200 mg), 5-amino-1H-benzo[d]imidazol-2(3H)-one[50] (151 mg) and N,N-diisopropylethylamine (264 μl) in N-methyl-2-pyrrolidinone (1 ml) was heated at 120° C. overnight. The reaction mixture was then cooled to room temperature and the crude product was collected by filtration, washed with water, and then dried in vacuo at 40° C. to afford N-methyl-3-nitro-4-((2-oxo-2,3-dihydro-1H-benzo[d]imidazol-5-yl)amino)benzamide (296 mg, 90%) as a red solid which was used in the next step without further purification. MS (ISP): 328.0 ([M+H]$^+$).

b) 3-Amino-N-methyl-4-[(2-oxo-1,3-dihydrobenzimidazol-5-yl)amino]benzamide

To a stirred suspension of N-methyl-3-nitro-4-((2-oxo-2,3-dihydro-1H-benzo[d]imidazol-5-yl)amino)benzamide (295 mg) in methanol (158 ml) and THF (158 ml) was added 10% palladium on charcoal (48 mg). The reaction mixture was stirred overnight at room temperature under an atmosphere of hydrogen. The catalyst was collected by filtration, washing with methanol. The filtrate was then concentrated in vacuo to afford 3-amino-N-methyl-4-[(2-oxo-1,3-dihydrobenzimidazol-5-yl)amino]benzamide (265 mg, 99%) as a brown solid. MS (ISP): 298.0 ([M+H]$^+$).

Example 2

N-Methyl-2-(2-(1-methyl-1H-imidazol-5-yl)quinolin-4-yl)-2'-oxo-2',3'-dihydro-1'H-[1,5'-bibenzo[d]imidazole]-5-carboxamide

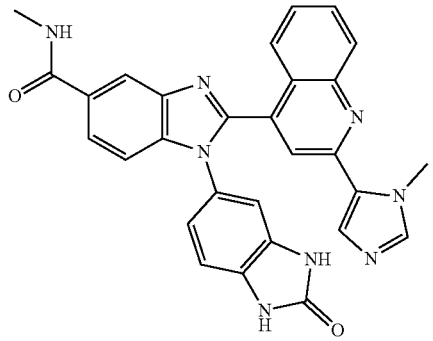 [SMILES: CNC(=O)c1ccc2c(c1)nc(-c1cc(-c3cncn3C)nc3ccccc13)n2-c1ccc2[nH]c(=O)[nH]c2c1]

To a stirred solution of 3-amino-N-methyl-4-[(2-oxo-1,3-dihydrobenzimidazol-5-yl)amino]benzamide (50 mg, example 1) and 2-(3-methylimidazol-4-yl)quinoline-4-carbaldehyde[71] (39.9 mg) in N,N-dimethylformamide (1.5 ml) was added sodium metabisulfite (128 mg) at room temperature. The reaction mixture was then heated at 120° C. overnight. Subsequent TLC and LC-MS analysis showed the reaction was complete. The reaction mixture was then cooled to room temperature and poured into EtOAc/THF (30 ml, 1:1 mixture). The resulting mixture was washed sequentially with water and with saturated brine. The organic phase was then separated, dried over MgSO$_4$, filtered, and concentrated in vacuo. The crude material was purified by preparative reversed phase HPLC to afford after lyophilisation N-methyl-2-(2-(1-methyl-1H-imidazol-5-yl)quinolin-4-yl)-2'-oxo-2',3'-dihydro-1'H-[1,5'-bibenzo[d]imidazole]-5-carboxamide (21 mg, 24%) as a white solid. 515.2 ([M+H]$^+$).

Example 3

N-Methyl-2'-oxo-2-(quinolin-4-yl)-2',3'-dihydro-1'H-[1,5'-bibenzo[d]imidazole]-5-carboxamide

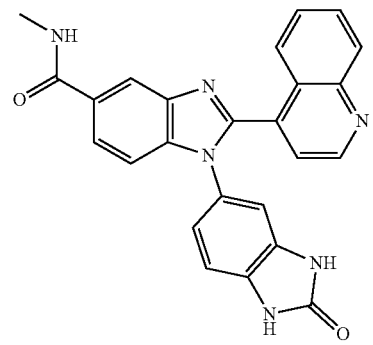 [SMILES: CNC(=O)c1ccc2c(c1)nc(-c1ccnc3ccccc13)n2-c1ccc2[nH]c(=O)[nH]c2c1]

The title compound was obtained in analogy to example 2 using quinoline-4-carbaldehyde[72] in place of 2-(3-methylimidazol-4-yl)quinoline-4-carbaldehyde. White solid. MS (ISP): 435.2 ([M+H]$^+$).

Example 4

2-Ethyl-N-methyl-2'-oxo-2',3'-dihydro-1'H-[1,5'-bibenzo[d]imidazole]-5-carboxamide

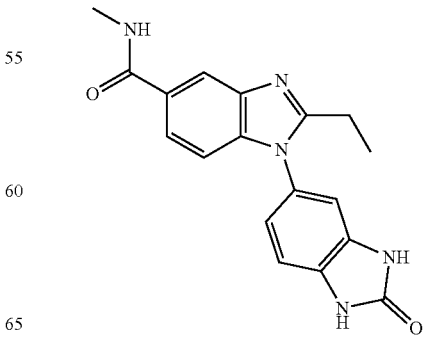

The title compound was obtained in analogy to example 2 using propionaldehyde[73] in place of 2-(3-methylimidazol-4-yl)quinoline-4-carbaldehyde. White solid. MS (ISP): 336.1 ([M+H]+).

Example 5

N,2-Dimethyl-2'-oxo-2',3'-dihydro-1'H-[1,5'-bibenzo[d]imidazole]-5-carboxamide

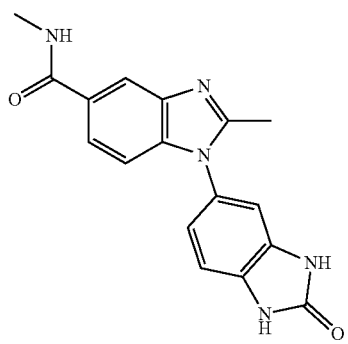 [SMILES: CNC(=O)c1ccc2c(c1)nc(C)n2-c1ccc2[nH]c(=O)[nH]c2c1]

The title compound was obtained in analogy to example 2 using acetaldehyde[74] in place of 2-(3-methylimidazol-4-yl)quinoline-4-carbaldehyde. White solid. MS (ISP): 322.1 ([M+H]+).

Example 6

5-((2-Aminophenyl)amino)-1H-benzo[d]imidazol-2(3H)-one

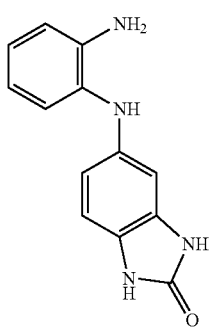 [SMILES: Nc1ccccc1Nc1ccc2[nH]c(=O)[nH]c2c1]

The title compound was obtained in analogy to example 1 using 1-fluoro-2-nitrobenzene[45] in place of 4-fluoro-N-methyl-3-nitrobenzamide in step a. Brown solid. MS (ISP): 240.9 ([M+H]+).

Example 7

2-(Quinolin-4-yl)-1'H-[1,5'-bibenzo[d]imidazol]-2'(3'H)-one

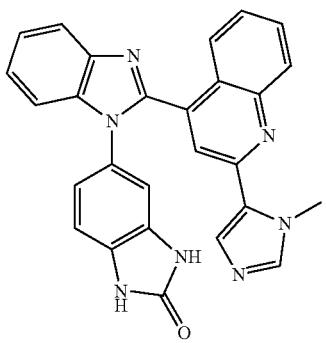 [SMILES: Cn1cncc1-c1cc(-c2nc3ccccc3n2-c2ccc3[nH]c(=O)[nH]c3c2)c2ccccc2n1]

The title compound was obtained in analogy to example 2 using 5-((2-aminophenyl)amino)-1H-benzo[d]imidazol-2(3H)-one (example 6) in place of 3-amino-N-methyl-4-[(2-oxo-1,3-dihydrobenzimidazol-5-yl)amino]benzamide and quinoline-4-carbaldehyde[72] in place of 2-(3-methylimidazol-4-yl)quinoline-4-carbaldehyde. White solid. MS (ISP): 378.1 ([M+H]+).

Example 8

2-(2-(1-Methyl-1H-imidazol-5-yl)quinolin-4-yl)-1'H-[1,5'-bibenzo[d]imidazol]-2'(3'H)-one The title compound was obtained in analogy to example 2 using 5-((2-aminophenyl)amino)-1H-benzo[d]imidazol-2(3H)-one (example 6) in place of 3-amino-N-methyl-4-[(2-oxo-1,3-dihydrobenzimidazol-5-yl)amino]benzamide. White solid. MS (ISP): 458.2 ([M+H]+).

Example 9

Methyl 3-amino-4-((2-oxo-2,3-dihydro-1H-benzo[d]imidazol-5-yl)amino)benzoate

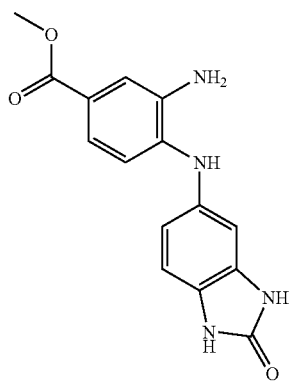 [SMILES: COC(=O)c1ccc(Nc2ccc3[nH]c(=O)[nH]c3c2)c(N)c1]

The title compound was obtained in analogy to example 1 using methyl 4-fluoro-3-nitrobenzoate[48] in place of 4-fluoro-N-methyl-3-nitrobenzamide in step a. Grey solid. MS (ISP): 299.2 ([M+H]$^+$).

Example 10

N-Methyl-2'-oxo-2-phenyl-2',3'-dihydro-1'H-[1,5'-bibenzo[d]imidazole]-5-carboxamide

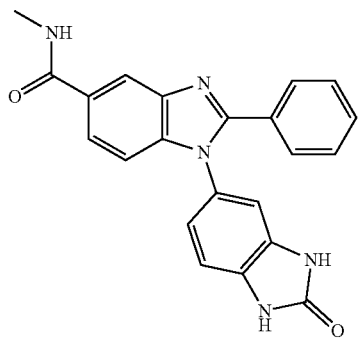 [SMILES: CNC(=O)c1ccc2c(c1)nc(-c1ccccc1)n2-c1ccc2[nH]c(=O)[nH]c2c1]

The title compound was obtained in analogy to example 2 using benzaldehyde[75] in place of 2-(3-methylimidazol-4-yl)quinoline-4-carbaldehyde. White solid. MS (ISP): 384.1 ([M+H]$^+$).

Example 11

N-Methyl-2'-oxo-2-(pyridin-4-yl)-2',3'-dihydro-1'H-[1,5'-bibenzo[d]imidazole]-5-carboxamide

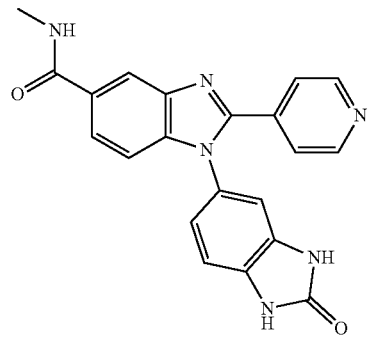 [SMILES: CNC(=O)c1ccc2c(c1)nc(-c1ccncc1)n2-c1ccc2[nH]c(=O)[nH]c2c1]

The title compound was obtained in analogy to example 2 using isonicotinaldehyde[76] in place of 2-(3-methylimidazol-4-yl)quinoline-4-carbaldehyde. White solid. MS (ISP): 385.1 ([M+H]$^+$).

Example 12

5-(2-(Quinolin-4-yl)-1H-imidazol-1-yl)-1H-benzo[d]imidazol-2(3H)-one

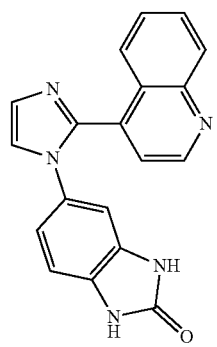 [SMILES: O=c1[nH]c2ccc(-n3ccnc3-c3ccnc4ccccc34)cc2[nH]1]

a) 4-(1H-Imidazol-2-yl)quinoline

To a stirred solution of quinoline-4-carbaldehyde[72] (1 g) in methanol (55 ml) at 0° C. was added 25% aq. ammonium hydroxide solution (4.96 ml) followed by dropwise addition of oxalaldehyde (7.3 ml, 40% solution in water). The reaction mixture was stirred at room temperature for 72 hours. The solvent was then evaporated and the residue was partitioned between ethyl acetate (20 ml) and water (20 ml). The phases were separated and the organic phase was dried over MgSO$_4$, filtered, and concentrated in vacuo. The crude material was purified by flash chromatography (silica gel, eluent: 0 to 10% of methanol in dichloromethane) to afford 4-(1H-imidazol-2-yl)quinoline (320 mg, 26%) as an off-white solid. MS (ISP): 196.4 ([M+H]$^+$).

b) 2-Nitro-5-(2-(quinolin-4-yl)-1H-imidazol-1-yl)aniline

To a stirred solution of 4-(1H-imidazol-2-yl)quinoline (190 mg) in DMF (3 ml) was added sodium hydride (38.9 mg) and the mixture was stirred at room temperature for 15 min (gas evolution). 5-Fluoro-2-nitroaniline[61] (152 mg) was added and the reaction mixture was heated at 60° C. overnight. After cooling, the reaction mixture was diluted with ethyl acetate and washed with 1 M aq. sodium bicarbonate solution. The organic phase was dried over MgSO₄, filtered, and concentrated in vacuo. The crude material was purified by flash chromatography (silica gel, eluent: 0 to 10% of methanol in dichloromethane) to afford 2-nitro-5-(2-(quinolin-4-yl)-1H-imidazol-1-yl)aniline (44 mg, 14%) as a yellow solid. MS (ISP): 332.1 ([M+H]⁺).

c) 4-(2-(Quinolin-4-yl)-1H-imidazol-1-yl)benzene-1,2-diamine

To a stirred solution of 2-nitro-5-(2-(quinolin-4-yl)-1H-imidazol-1-yl)aniline (44 mg) in a mixture of methanol (5 ml) and THF (2 ml) was added 10% palladium on charcoal (14.1 mg). The reaction mixture was hydrogenated under an atmosphere of hydrogen. After stirring vigorously for 1 hour, the catalyst was collected by filtration, washing with methanol. The filtrate was then concentrated in vacuo to afford 4-(2-(quinolin-4-yl)-1H-imidazol-1-yl)benzene-1,2-diamine as a green solid (38 mg, 95%), which was used in the next step without further purification. MS (ISP): 302.2 ([M+H]⁺).

d) 5-(2-(Quinolin-4-yl)-1H-imidazol-1-yl)-1H-benzo[d]imidazol-2(3H)-one

To a stirred solution of 4-(2-(quinolin-4-yl)-1H-imidazol-1-yl)benzene-1,2-diamine (38 mg) in THF (1 ml) was added dropwise a solution of di(1H-imidazol-1-yl)methanone (20.4 mg) in THF (1 ml). The reaction mixture was stirred at room temperature overnight. TLC analysis showed that the reaction was not finished. A solution of di(1H-imidazol-1-yl)methanone (20.4 mg) in tetrahydrofuran (0.5 ml) was added dropwise and the reaction was stirred at room temperature for 2 h. The reaction mixture was then partitioned between ethyl acetate (5 ml) and water (5 ml). The phases were separated and the organic phase was dried over MgSO₄, filtered, and concentrated in vacuo. The crude material was purified by flash chromatography (silica gel, eluent: 0 to 10% of methanol in dichloromethane) to afford 5-(2-(quinolin-4-yl)-1H-imidazol-1-yl)-1H-benzo[d]imidazol-2(3H)-one (10 mg, 24%) as a white solid. MS (ISP): 328.1 ([M+H]⁺).

Example 13

N-Methyl-2'-oxo-2-(trifluoromethyl)-2',3'-dihydro-1'H-[1,5'-bibenzo[d]imidazole]-5-carboxamide

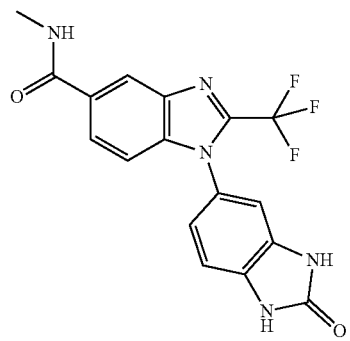 [SMILES: CNC(=O)c1ccc2c(c1)nc(C(F)(F)F)n2-c1ccc2[nH]c(=O)[nH]c2c1]

A stirred solution of 3-amino-N-methyl-4-[(2-oxo-1,3-dihydrobenzimidazol-5-yl)amino]benzamide (39 mg, example 1) in 2,2,2-trifluoroacetic acid (299 mg, 201 µl) was heated at 120° C. overnight in a sealed tube. The reaction mixture was then cooled to room temperature and concentrated in vacuo. The crude product was dissolved in DMSO, and then 25% aq. ammonia was added to adjust the pH to 14. The mixture was poured into THF/EtOAc (2:1) and extracted sequentially with water and with saturated brine. The organic layer was then separated, dried over MgSO₄ and concentrated in vacuo. The product was purified by reversed phase HPLC followed by lyophilisation to afford N-methyl-2'-oxo-2-(trifluoromethyl)-2',3'-dihydro-1'H-[1,5'-bibenzo[d]imidazole]-5-carboxamide (10 mg, 20%) as a white solid. MS (ISP): 376.1 ([M+H]⁺).

Example 14

N-Methyl-2'-oxo-2-propyl-2',3'-dihydro-1'H-[1,5'-bibenzo[d]imidazole]-5-carboxamide The title compound was obtained in analogy to example 2 using butyraldehyde[77] in place of 2-(3-methylimidazol-4-yl)quinoline-4-carbaldehyde. White solid. MS (ISP): 350.2 ([M+H]⁺).

Example 15

2-(1H-Imidazol-4-yl)-N-methyl-2'-oxo-2',3'-dihydro-1'H-[1,5'-bibenzo[d]imidazole]-5-carboxamide The title compound was obtained in analogy to example 2 using 1H-imidazole-4-carbaldehyde[78] in place of 2-(3-methylimidazol-4-yl)quinoline-4-carbaldehyde. White solid. MS (ISP): 374.1 ([M+H]⁺).

Example 16

2-Isopropyl-N-methyl-2'-oxo-2',3'-dihydro-1'H-[1,5'-bibenzo[d]imidazole]-5-carboxamide

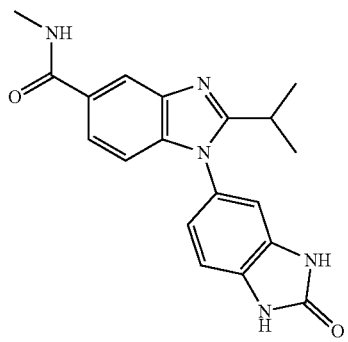 [SMILES: CNC(=O)c1ccc2c(c1)nc(C(C)C)n2-c1ccc2[nH]c(=O)[nH]c2c1]

The title compound was obtained in analogy to example 2 using isobutyraldehyde[79] in place of 2-(3-methylimidazol-4-yl)quinoline-4-carbaldehyde. White solid. MS (ISP): 350.2 ([M+H]$^+$).

Example 17

N,1',3'-Trimethyl-2-(2-(1-methyl-1H-imidazol-5-yl)quinolin-4-yl)-2'-oxo-2',3'-dihydro-1'H-[1,5'-bibenzo[d]imidazole]-5-carboxamide

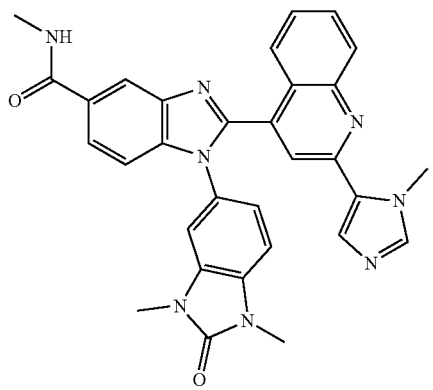

a) 3-Amino-4-[(1,3-dimethyl-2-oxobenzimidazole-5-yl)amino]-N-methylbenzamide

The title compound was obtained in analogy to example 1 using 5-amino-1,3-dimethyl-1H-benzo[d]imidazol-2(3H)-one[53] in place of 5-amino-1H-benzo[d]imidazol-2(3H)-one in step a. Grey solid. MS (ISP): 326.1 ([M+H]$^+$).

b) N,1',3'-trimethyl-2-(2-(1-methyl-1H-imidazol-5-yl)quinolin-4-yl)-2'-oxo-2',3'-dihydro-1'H-[1,5'-bibenzo[d]imidazole]-5-carboxamide The title compound was obtained in analogy to example 2 using 3-amino-4-[(1,3-dimethyl-2-oxobenzimidazole-5-yl)amino]-N-methylbenzamide in place of 3-amino-N-methyl-4-[(2-oxo-1,3-dihydrobenzimidazol-5-yl)amino]benzamide. White solid. MS (ISP): 543.2 ([M+H]$^+$).

Example 18

N,N-Dimethyl-2-(2-(1-methyl-1H-imidazol-5-yl)quinolin-4-yl)-2'-oxo-2',3'-dihydro-1'H-[1,5'-bibenzo[d]imidazole]-5-carboxamide

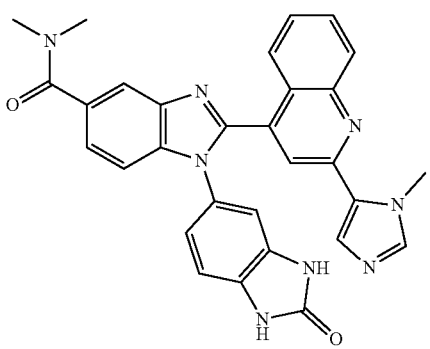

a) Methyl 3-nitro-4-[(2-oxo-1,3-dihydrobenzimidazol-5-yl)amino]benzoate

To a stirred solution of methyl 4-fluoro-3-nitrobenzoate[48] (1.5 g) and 5-amino-1H-benzo[d]imidazol-2(3H)-one[50] (1.12 g) in N-methyl-2-pyrrolidinone (1 ml) was added dropwise N,N-diisopropylethylamine (1.97 ml). The reaction mixture was heated at 120° C. overnight. The reaction mixture was then cooled to room temperature and filtered through sintered glass to afford methyl 3-nitro-4-[(2-oxo-1,3-dihydrobenzimidazol-5-yl)amino]benzoate (2.48 g, quant.) as a red solid. MS (ISP): 329.1 ([M+H]$^+$).

b) Methyl 3-amino-4-[(2-oxo-1,3-dihydrobenzimidazol-5-yl)amino]benzoate

To a stirred suspension of methyl 3-nitro-4-[(2-oxo-1,3-dihydrobenzimidazol-5-yl)amino]benzoate (2.48 g) in methanol (30 ml) and THF (30 ml) was added 10% palladium on charcoal (402 mg). The reaction mixture was stirred at room temperature overnight under an atmosphere of hydrogen. The reaction mixture was filtered through celite, washing with methanol. The filtrate was then concentrated in vacuo to afford methyl 3-amino-4-[(2-oxo-1,3-dihydrobenzimidazol-5-yl)amino]benzoate (2.2 g, 98%) as a grey solid. MS (ISP): 299.2 ([M+H]$^+$).

c) Methyl 2-(2-(1-methyl-1H-imidazol-5-yl)quinolin-4-yl)-2'-oxo-2',3'-dihydro-1'H-[1,5'-bibenzo[d]imidazole]-5-carboxylate To a stirred solution of methyl 3-amino-4-[(2-oxo-1,3-dihydrobenzimidazol-5-yl)amino]benzoate (200 mg) and 2-(1-methyl-1H-imidazol-5-yl)quinoline-4-carbaldehyde[1] (159 mg) in N,N-dimethylformamide (2.2 ml) was added sodium metabisulfite (510 mg) at room temperature. The reaction mixture was then heated at 120° C. for 3 h. LC-MS analysis showed the reaction was complete. The reaction mixture was then cooled to room temperature and partitioned between ethyl acetate/THF (1:1, 50 ml) and 1 M aqueous sodium hydroxide solution (30 ml). The layers were separated and the aqueous layer was extracted twice with ethyl acetate (2×30 ml). The combined organic layers were washed with saturated brine (30 ml), dried over anhydrous Na$_2$SO$_4$, filtered, and concentrated in vacuo. The residue was purified by preparative reverse phase HPLC on a Gemini NX 3u 50×4.6 mm column to afford methyl 2-(2-(1-methyl-1H-imidazol-5-yl)quinolin-4-yl)-2'-oxo-2',3'-dihydro-1'H-[1,5'-bibenzo[d]imidazole]-5-carboxylate (166 mg, 48%) as a light brown solid. MS (ISP): 516.1 ([M+H]$^+$).

d) 2-(2-(1-Methyl-1H-imidazol-5-yl)quinolin-4-yl)-2'-oxo-2',3'-dihydro-1'H-[1,5'-bibenzo[d]imidazole]-5-carboxylic Acid To a stirred solution of methyl 2-(2-(1-methyl-1H-imidazol-5-yl)quinolin-4-yl)-2'-oxo-2',3'-dihydro-1'H-[1,5'-bibenzo[d]imidazole]-5-carboxylate (166 mg) in 1,4-dioxane (4 ml) was added dropwise 1 M aq. LiOH solution (2 ml). The reaction mixture was stirred at room temperature for 3 h. Subsequent LC-MS showed the reaction was complete. The reaction mixture was partitioned between ethyl acetate/THF (1:1, 50 ml) and 1 M aqueous HCl (5 ml). The layers were separated. The aqueous layer was extracted three times with ethyl acetate (3×20 ml). The combined organic layers were dried over anhydrous sodium sulfate and concentrated in vacuo. Most product was detected in aqueous layer. The aqueous layer was concentrated in vacuo and the residue was lyophilised to afford 2-(2-(1-methyl-1H-imidazol-5-yl)quinolin-4-yl)-2'-oxo-2',3'-dihydro-1'H-[1,5'-bibenzo[d]imidazole]-5-carboxylic acid as a yellow solid (451 mg, 100%, 36% purity) which was used in the next step without further purification. MS (ISP): 500.1 ([M−H]$^-$).

e) N,N-Dimethyl-2-(2-(1-methyl-1H-imidazol-5-yl)quinolin-4-yl)-2'-oxo-2',3'-dihydro-1'H-[1,5'-bibenzo[d]imidazole]-5-carboxamide To a solution of 2-(2-(1-methyl-1H-imidazol-5-yl)quinolin-4-yl)-2'-oxo-2',3'-dihydro-1'H-[1,5'-bibenzo[d]imidazole]-5-carboxylic acid (451 mg), N,N-diisopropylethylamine (188 µl) and dimethylamine (202 µl, 2 M solution in THF) in N,N-dimethylformamide (4 ml) was added HATU (226 mg). The reaction mixture was stirred at room temperature for 3 h. The reaction mixture was partitioned between ethyl acetate (50 ml) and water (30 ml). The layers were separated and the organic layer was washed with saturated brine (30 ml), dried over anhydrous sodium sulfate, and concentrated in vacuo. The residue was purified by reversed phase HPLC on a Gemini NX 3u 50×4.6 mm column to afford N,N-dimethyl-2-(2-(1-methyl-1H-imidazol-5-yl)quinolin-4-yl)-2'-oxo-2',3'-dihydro-1'H-[1,5'-bibenzo[d]imidazole]-5-carboxamide as a yellow solid (74 mg, 52%). MS (ISP): 527.1 ([M−H]$^-$).

Example 19

5-(Pyridin-3-yl)-1H-benzo[d]imidazol-2(3H)-one

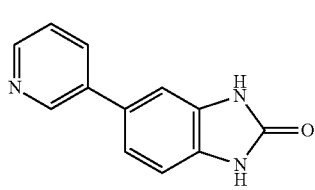

To a solution of 5-bromo-1H-benzo[d]imidazol-2(3H)-one[80] (50 mg) in dioxane (1 ml) were added pyridin-3-ylboronic acid[81] (43.3 mg), [1,1-bis(diphenyl-phosphino)ferrocene]dichloropalladium(II) (17.2 mg) and 2 M aq. sodium carbonate solution (235 µl). The reaction mixture was heated at 100° C. for 18 hours. The reaction mixture was then cooled to room temperature, diluted with water (50 ml). and extracted twice with ethyl acetate (2×30 ml). The combined organic layers were dried over Na$_2$SO$_4$, filtered and concentrated in vacuo. The residue was purified by chromatography (silica gel; 12 g; eluent: dichloromethane/methanol=100/0 to 95/05 in 10 minutes) to afford 5-(pyridin-3-yl)-1H-benzo[d]imidazol-2(3H)-one (12 mg, 23%) as a red solid. MS (ISP): 212.1 ([M+H]$^+$).

Example 20

5-(2-Chloropyridin-4-yl)-1H-benzo[d]imidazol-2(3H)-one

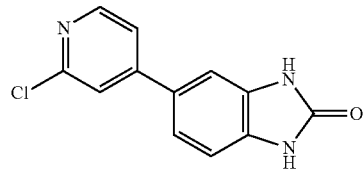 [SMILES: O=c1[nH]c2ccc(-c3ccnc(Cl)c3)cc2[nH]1]

The title compound was obtained in analogy to example 19 using (2-chloropyridin-4-yl)boronic acid[82] in place of pyridin-3-ylboronic acid. Light yellow solid. MS (ISP): 246.1 ($\{^{35}Cl\}$[M+H]$^+$), 248.1 ($\{^{37}Cl\}$[M+H]$^+$).

Example 21

5-(2-Methylthiazol-5-yl)-1H-benzo[d]imidazol-2(3H)-one

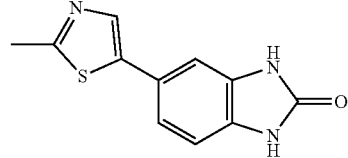 [SMILES: Cc1ncc(-c2ccc3[nH]c(=O)[nH]c3c2)s1]

The title compound was obtained in analogy to example 19 using 2-methyl-5-(4,4,5,5-tetramethyl-1,3,2-dioxaborolan-2-yl)thiazole[83] in place of pyridin-3-ylboronic acid. Light brown solid. MS (ISP): 232.0 ([M+H]$^+$).

Example 22

5-(4-Acetylpiperazine-1-carbonyl)-1H-benzo[d]imidazol-2(3H)-one

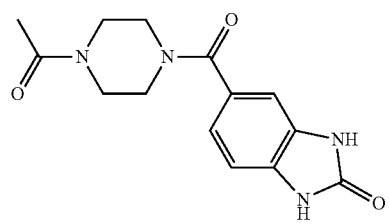 [SMILES: CC(=O)N1CCN(C(=O)c2ccc3[nH]c(=O)[nH]c3c2)CC1]

To a stirred solution of 2-oxo-2,3-dihydro-1H-benzo[d]imidazole-5-carboxylic acid[56] (70 mg), 1-(piperazin-1-yl)ethanone[84] (50.4 mg) and N,N-diisopropylethylamine (206 µl) in DMF (1 ml) was added HATU (224 mg). The reaction mixture was stirred at room temperature for 4 h. The reaction mixture was concentrated in vacuo and the residue was purified by preparative reverse-phase HPLC (Gemini NX C18, 12 nm, 5µ, 100×30 mm, flow rate 40 ml/min, eluant: $CH_3CN/H_2O$ containing formic acid) followed by lyophilisation to afford 5-(4-acetylpiperazine-1-carbonyl)-1H-benzo[d]imidazol-2(3H)-one (50 mg, 44%) as white solid. MS (ISP): 289.1 ([M+H]$^+$).

Example 23

N-(1-Acetylpiperidin-4-yl)-2-oxo-2,3-dihydro-1H-benzo[d]imidazole-5-carboxamide

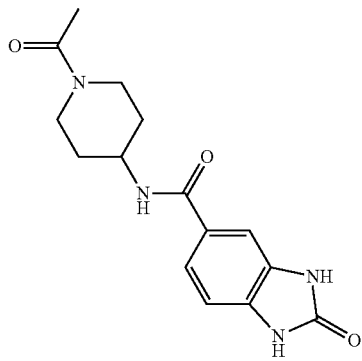 [SMILES: CC(=O)N1CCC(NC(=O)c2ccc3[nH]c(=O)[nH]c3c2)CC1]

The title compound was obtained in analogy to example 22 using 1-(4-aminopiperidin-1-yl)ethanone[85] in place of 1-(piperazin-1-yl)ethanone. Brown solid. MS (ISP): 303.1 ([M+H]$^+$).

Example 24

5-(Indoline-1-carbonyl)-1H-benzo[d]imidazol-2(3H)-one

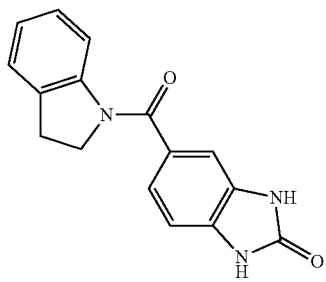 [SMILES: O=C(c1ccc2[nH]c(=O)[nH]c2c1)N1CCc2ccccc21]

The title compound was obtained in analogy to example 22 using indoline[86] in place of 1-(piperazin-1-yl)ethanone. Light yellow solid. MS (ISP): 280.1 ([M+H]$^+$).

Example 25

N-(1,3-Dimethyl-2-oxo-benzimidazol-5-yl)furan-2-carboxamide

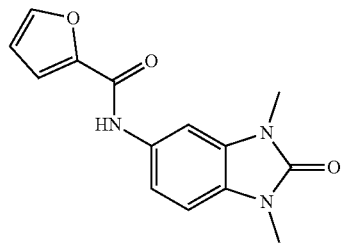 [SMILES: Cn1c(=O)n(C)c2cc(NC(=O)c3ccco3)ccc21]

The title compound[87] can be purchased.

Example 26

5-(3-Phenyl-propyl)-1,3-dihydro-imidazo[4,5-b]pyridin-2-one

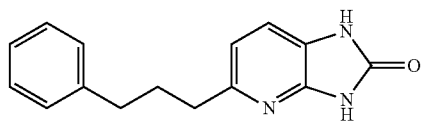 [SMILES: O=c1[nH]c2ccc(CCCc3ccccc3)nc2[nH]1]

a) Benzyl N-[2-(benzyloxycarbonylamino)-6-methyl-3-pyridyl]carbamate

To a stirred solution of 6-methylpyridine-2,3-diamine[88] (1.53 g) in THF (10 ml) were added N,N-diisopropylethylamine (5.13 ml) and benzyl chloroformiate (4.3 ml). The reaction mixture was stirred at room temperature for 24 hours. Water and ethyl acetate were added. The organic layer was washed with brine, dried over $MgSO_4$, filtered, and concentrated in vacuo. The crude material was purified by flash chromatography (silica gel, 20 g, eluent: 50% ethyl acetate in heptane) followed by crystallisation in EtOAc/heptane to afford benzyl N-[2-(benzyloxycarbonylamino)-6-methyl-3-pyridyl]carbamate (3.15 g, 65%) as a yellow oil.

$^1$H NMR (300 MHz, $CDCl_3$) δ 7.30-7.43 (m, 12H), 7.04 (br d, J=8.07 Hz, 1H), 5.21 (s, 2H), 5.19 (s, 2H), 4.70 (d, J=5.85 Hz, 1H), b) Benzyl N-[2-(benzyloxycarbonylamino)-6-(bromomethyl)-3-pyridyl]carbamate To a stirred solution of benzyl N-[2-(benzyloxycarbonylamino)-6-methyl-3-pyridyl]carbamate (3.15 g) in benzene (20 ml) was added N-bromosuccinimide (1.6 g) and 2,2'-azobis(2-methylpropionitrile) (150 mg). The orange reaction mixture was stirred at 80° C. for 6 hours. Water and ethyl acetate were added. The organic layer was washed with brine, dried over $MgSO_4$, filtered, and concentrated in vacuo to afford benzyl N-[2-(benzyloxycarbonylamino)-6-(bromomethyl)-3-pyridyl]carbamate (3.64 g, 96%) as a brown oil which was used in the next step without further purification.

c) [5,6-Bis(benzyloxycarbonylamino)-2-pyridyl]methyl-triphenyl-phosphonium bromide To a stirred solution of benzyl N-[2-(benzyloxycarbonylamino)-6-(bromomethyl)-3-pyridyl]carbamate (3.64 g) in THF (30 ml) was added triphenylphosphine (6 g). The orange reaction mixture was stirred at 50° C. for 18 hours. The by-product was filtered off and the filtrate was concentrated in vacuo. The residue was dissolved in $CH_2Cl_2$ (20 ml) and added dropwise with stirring to TBME (300 ml). The resulting suspension was filtered to afford crude [5,6-bis(benzyloxycarbonylamino)-2-pyridyl]methyl-triphenyl-phosphonium bromide (3.2 g, 56%) as a beige solid which was used in the next step without further purification.

d) Benzyl N-[2-(benzyloxycarbonylamino)-6-[(E)-3-phenylprop-1-enyl]-3-pyridyl]carbamate To a stirred solution of [5,6-bis(benzyloxycarbonylamino)-2-pyridyl]methyl-triphenyl-phosphonium bromide (3.20 g) in dichloromethane (25 ml) was added 1,8-diazabicyclo[5.4.0]undec-7-ene (1 ml) and phenylacetaldehyde[89] (1 ml). The brown reaction mixture was stirred at room temperature for 21 hours. Water and ethyl acetate were added. The pH was adjusted to 5 with 1 M aq. HCl. The organic layer was dried over $MgSO_4$, filtered, and concentrated in vacuo to afford crude benzyl N-[2-(benzyloxycarbonylamino)-6-[(E)-3-phenylprop-1-enyl]-3-pyridyl]carbamate (3.5 g, >100%) as a yellow oil which was used in the next step without further purification.

e) 5-(3-Phenyl-propyl)-1,3-dihydro-imidazo[4,5-b]pyridin-2-one

To a stirred suspension of benzyl N-[2-(benzyloxycarbonylamino)-6-[(E)-3-phenylprop-1-enyl]-3-pyridyl]carbamate (3.5 g) in ethanol (100 ml) were added N,N-diisopropylethylamine (5 ml) and 10% palladium on charcoal (500 mg). The reaction mixture was stirred at room temperature under an atmosphere of hydrogen for 23 h. The reaction mixture was filtered through celite, washing with methanol. The filtrate was then concentrated in vacuo. The crude material was purified by flash chromatography (silica gel, 20 g, eluent: 50% of ethyl acetate in heptane to 20% methanol in ethyl acetate) followed by crystallisation in EtOAc/heptane to afford 5-(3-phenyl-propyl)-1,3-dihydro-imidazo[4,5-b]pyridin-2-one (109 mg, 6%) as a light brown solid. MS (ISP): 254.3 ([M+H]$^+$).

Example 27

1-Methyl-2-oxo-N-phenyl-3H-imidazo[4,5-b]pyridine-6-carboxamide

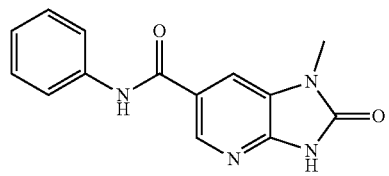

The title compound was obtained in analogy to example 22 using aniline[90] in place of 1-(piperazin-1-yl)ethanone and 1-methyl-2-oxo-3H-imidazo[4,5-b]pyridine-6-carboxylic acid[91] in place of 2-oxo-2,3-dihydro-1H-benzo[d]imidazole-5-carboxylic acid. Off-white solid. MS (ISP): 269.1 ([M+H]$^+$).

Example 28

2-(3-Methoxybenzyl)-N-methyl-2'-oxo-2',3'-dihydro-1'H-[1,5'-bibenzo[d]imidazole]-5-carboxamide

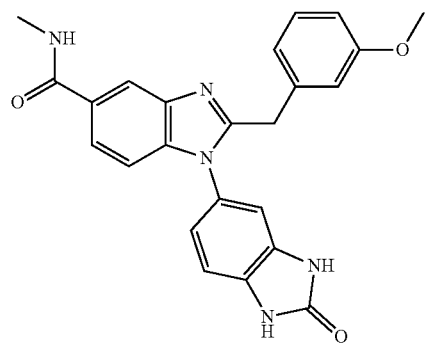 [SMILES: CNC(=O)c1ccc2c(c1)nc(Cc1cccc(OC)c1)n2-c1ccc2[nH]c(=O)[nH]c2c1]

The title compound was obtained in analogy to example 2 using 2-(3-methoxyphenyl)acetaldehyde[92] in place of 2-(1-methyl-1H-imidazol-5-yl)quinoline-4-carbaldehyde. White solid. MS (ISP): 347.2 ([M+H]$^+$).

Example 29

N-(1-(2-Oxo-2,3-dihydro-1H-benzo[d]imidazole-5-carbonyl)piperidin-4-yl)acetamide

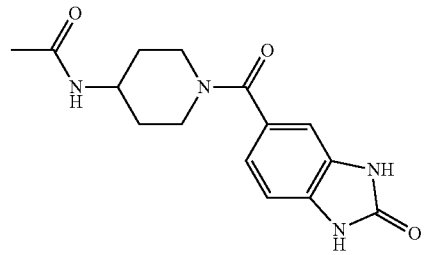 [SMILES: CC(=O)NC1CCN(C(=O)c2ccc3[nH]c(=O)[nH]c3c2)CC1]

The title compound was obtained in analogy to example 22 using N-(piperidin-4-yl)acetamide[93] in place of 1-(piperazin-1-yl)ethanone. White solid. MS (ISP): 303.1 ([M+H]$^+$).

Example 30

2-Isopropyl-N-methyl-2'-oxo-2',3'-dihydro-1'H-[1,5'-bibenzo[d]imidazole]-6-carboxamide

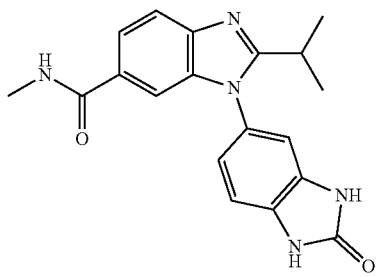 [SMILES: CNC(=O)c1ccc2nc(C(C)C)n(-c3ccc4[nH]c(=O)[nH]c4c3)c2c1]

The title compound was obtained in analogy to example 18 using methyl 3-fluoro-4-nitrobenzoate[49] in place of methyl 4-fluoro-3-nitrobenzoate in step a, isobutyraldehyde[79] in place of 2-(1-methyl-1H-imidazol-5-yl)quinoline-4-carbaldehyde in step c, and methylamine[94] (2 M solution in THF) in place of dimethylamine (2 M solution in THF) in step e. White solid. MS (ISP): 350.2 ([M+H]$^+$).

Example 31

1',3'-Dimethyl-2-(2-(1-methyl-1H-imidazol-5-yl)quinolin-4-yl)-1',3'-dihydro-2'H-[1,5'-bibenzo[d]imidazol]-2'-one a) 5-((2-Aminophenyl)amino)-1,3-dimethyl-1,3-dihydro-2H-benzo[d]imidazol-2-one

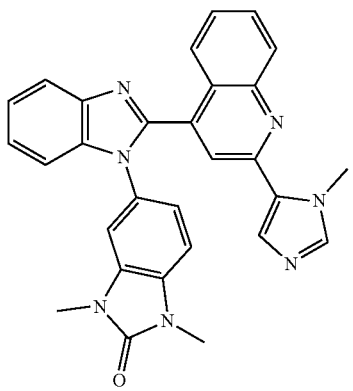 [SMILES: Cn1cncc1-c1cc(-c2nc3ccccc3n2-c2ccc3c(c2)n(C)c(=O)n3C)c2ccccc2n1]

The title compound was obtained in analogy to example 1 using 1-fluoro-2-nitrobenzene[45] in place of 4-fluoro-N-methyl-3-nitrobenzamide and 5-amino-1,3-dimethyl-1H-benzo[d]imidazol-2(3H)-one[53] in place of 5-amino-1H-benzo[d]imidazol-2(3H)-one in step a. Amorphous brown solid. MS (ISP): 269.1 ([M+H]$^+$).

b) 1',3'-Dimethyl-2-(2-(1-methyl-1H-imidazol-5-yl)quinolin-4-yl)-1',3'-dihydro-2'H-[1,5'-bibenzo[d]imidazol]-2'-one The title compound was obtained in analogy to example 2 using 5-((2-aminophenyl)amino)-1,3-dimethyl-1,3-dihydro-2H-benzo[d]imidazol-2-one in place of 3-amino-N-methyl-4-[(2-oxo-1,3-dihydrobenzimidazol-5-yl)amino]benzamide. White solid. MS (ISP): 486.2 ([M+H]$^+$).

Example 32

5-(2-Isopropyl-1H-imidazol-1-yl)-1,3-dihydro-2H-benzo[d]imidazol-2-one

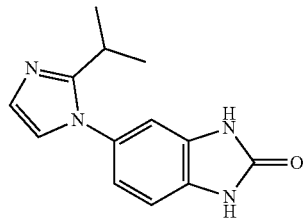 [SMILES: CC(C)c1nccn1-c1ccc2[nH]c(=O)[nH]c2c1]

a) 5-(2-Isopropyl-1H-imidazol-1-yl)-2-nitroaniline

To a solution of 2-isopropyl-1H-imidazole[95] (155 mg) in N,N-dimethylformamide (4 ml), was added NaH (56.4 mg) portionwise. After stirring for 15 min at room temperature, 5-fluoro-2-nitroaniline[61] (200 mg) was added and the reaction mixture was heated at 60° C. for 16 hours. The reaction mixture was diluted with ethyl acetate and washed with aq. sodium bicarbonate. The organic layer was dried over MgSO$_4$, filtered and concentrated in vacuo. The crude material was purified by flash chromatography (silica gel, eluent: 0 to 5% of methanol in dichloromethane) to afford 5-(2-isopropyl-1H-imidazol-1-yl)-2-nitroaniline (85 mg, 27%) as an orange solid. MS (ISP): 247.2 ([M+H]$^+$).

b) 4-(2-Isopropyl-1H-imidazol-1-yl)benzene-1,2-diamine

To a stirred solution of 5-(2-isopropyl-1H-imidazol-1-yl)-2-nitroaniline (85 mg) in methanol (2 ml) was added 10% palladium on charcoal (37 mg). The reaction mixture was hydrogenated under an atmosphere of hydrogen. After stirring vigorously for 1 hour, the catalyst was collected by filtration, washing with methanol. The filtrate was then concentrated in vacuo to afford 4-(2-isopropyl-1H-imidazol-1-yl)benzene-1,2-diamine as a brown solid (61.8 mg, 83%) which was used in the next step without further purification. MS (ISP): 217.1 ([M+H]$^+$).

c) 5-(2-Isopropyl-1H-imidazol-1-yl)-1,3-dihydro-2H-benzo[d]imidazol-2-one

To a solution of 5-(2-isopropyl-1H-imidazol-1-yl)-1,3-dihydro-2H-benzo[d]imidazol-2-one (27.1 mg) in THF (1 ml) was added dropwise a solution of di(1H-imidazol-1-yl)methanone (93 mg) in THF (1 ml). The reaction mixture was stirred at room temperature for 1 hour. The light purple suspension was filtered and the solid was purified by preparative HPLC (Gemini NX, 12 nm, 5 µm, 100×30 mm, acetonitrile/water+0.1% triethylamine) to afford 5-(2-isopropyl-1H-imidazol-1-yl)-1,3-dihydro-2H-benzo[d]imidazol-2-one as a brown solid (27.1 mg, 39%). MS (ISP): 243.3 ([M+H]$^+$).

Example 33

5-(2-Oxopyrrolidin-1-yl)-1,3-dihydro-2H-benzo[d]imidazol-2-one

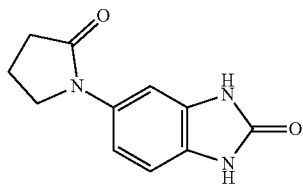 [SMILES: O=C1CCCN1c1ccc2[nH]c(=O)[nH]c2c1]

a) 1-(3-Amino-4-nitro-phenyl)pyrrolidin-2-one

To a solution of 5-bromo-2-nitroaniline (200 mg) in anhydrous dioxane (500 µl) were successively added pyrrolidin-2-one[96] (94.1 mg), potassium carbonate (255 mg), trans-1, 2-cyclohexanediamine (105 mg) and copper (I) iodide (176 mg). The reaction mixture was heated at 110° C. for 16 hours. After cooling to room temperature, the mixture was partitioned between water and ethyl acetate. The aqueous layer was extracted with additional ethyl acetate and the combined extracts were dried over anhydrous sodium sulfate, filtered, and concentrated in vacuo. The crude material was purified by flash chromatography (silica gel, eluent: 50 to 100% of ethyl acetate in heptane) to afford 1-(3-amino-4-nitro-phenyl)pyrrolidin-2-one (40 mg, 20%) as a yellow solid. MS (ISP): 222.2 ([M+H]$^+$).

b) 1-(3,4-Diaminophenyl)pyrrolidin-2-one

To a stirred solution of 1-(3-amino-4-nitro-phenyl)pyrrolidin-2-one (40 mg) in MeOH (2 ml) was added 10% palladium on charcoal (19.2 mg). The reaction mixture was hydrogenated under an atmosphere of hydrogen. After stirring vigorously for 1 hour, the catalyst was collected by filtration, washing with methanol. The filtrate was then concentrated in vacuo to afford 1-(3,4-diaminophenyl)pyrrolidin-2-one as a light yellow solid (34 mg, 98%) which was used in the next step without further purification. MS (ISP): 192.1 ([M+H]$^+$).

c) 5-(2-Oxopyrrolidin-1-yl)-1,3-dihydro-2H-benzo[d]imidazol-2-one

To a solution of 1-(3,4-diaminophenyl)pyrrolidin-2-one (28.1 mg) in THF (548 µl) was added dropwise a solution of di(1H-imidazol-1-yl)methanone (57.7 mg) in THF (548 µl). The reaction mixture was stirred at room temperature for 16 hours. The suspension was filtered, then the solid was washed with THF and dried under high vacuum to afford 5-(2-oxopyrrolidin-1-yl)-1,3-dihydro-2H-benzo[d]imidazol-2-one as a light brown solid (28.1 mg, 73%). MS (ISP): 218.1 ([M+H]$^+$).

Example 34

2-Isopropyl-1'-methyl-1',3'-dihydro-2'H-[1,5'-bibenzo[d]imidazol]-2'-one

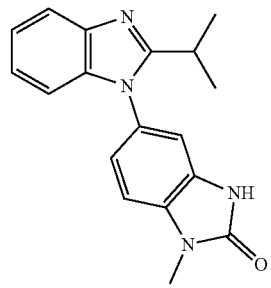 [SMILES: CC(C)c1nc2ccccc2n1-c1ccc2c(c1)[nH]c(=O)n2C]

a) 5-((2-Aminophenyl)amino)-1-methyl-1,3-dihydro-2H-benzo[d]imidazol-2-one

The title compound was obtained in analogy to example 1 using 5-amino-1-methyl-1,3-dihydro-2H-benzo[d]imidazol-2-one[51] in place of 5-amino-1H-benzo[d]imidazol-2(3H)-one and 1-fluoro-2-nitrobenzene[45] in place of 4-fluoro-N-methyl-3-nitrobenzamide in step a. Dark brown solid. MS (ISP): 255.1 ([M+H]$^+$).

b) 2-Isopropyl-3'-methyl-1',3'-dihydro-2'H-[1,5'-bibenzo[d]imidazole]-2'-one The title compound was obtained in analogy to example 2 using isobutyraldehyde[79] in place of 2-(1-methyl-1H-imidazol-5-yl)quinoline-4-carbaldehyde and 5-((2-aminophenyl)amino)-1-methyl-1,3-dihydro-2H-benzo[d]imidazol-2-one instead of 3-amino-N-methyl-4-[(2-oxo-1,3-dihydrobenzimidazol-5-yl)amino]benzamide. Orange foam (59.7 mg, 62%). MS (ISP): 307.1 ([M+H]$^+$).

Example 35

2-Isopropyl-3'-methyl-1',3'-dihydro-2'H-[1,5'-bibenzo[d]imidazol]-2'-one

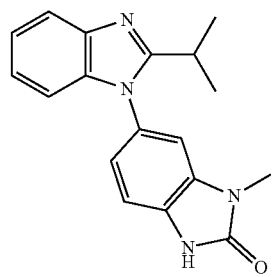 [SMILES: CC(C)c1nc2ccccc2n1-c1ccc2[nH]c(=O)n(C)c2c1]

a) 6-((2-Aminophenyl)amino)-1-methyl-1,3-dihydro-2H-benzo[d]imidazol-2-one

The title compound was obtained in analogy to example 1 using 6-amino-1-methyl-1,3-dihydro-2H-benzo[d]imidazol-2-one hydrochloride[97] in place of 5-amino-1H-benzo[d]

imidazol-2(3H)-one and 1-fluoro-2-nitrobenzene[45] in place of 4-fluoro-N-methyl-3-nitrobenzamide in step a. Dark brown solid. MS (ISP): 255.1 ([M+H]$^+$).

b) 2-Isopropyl-1'-methyl-1',3'-dihydro-2'H-[1,5'-bibenzo[d]imidazol]-2'-one

The title compound was obtained in analogy to example 2 using isobutyraldehyde[79] in place of 2-(1-methyl-1H-imidazol-5-yl)quinoline-4-carbaldehyde and 6-((2-aminophenyl)amino)-1-methyl-1,3-dihydro-2H-benzo[d]imidazol-2-one instead of 3-amino-N-methyl-4-[(2-oxo-1,3-dihydrobenzimidazol-5-yl)amino]benzamide. Orange foam (59.7 mg, 62%). MS (ISP): 307.1 ([M+H]$^+$).

Example 36

6-(4-Fluoro-phenyl)-1,3-dihydro-imidazo[4,5-c]pyridin-2-one

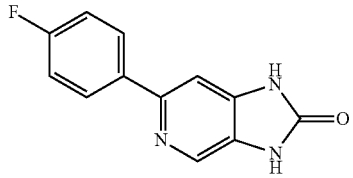 [SMILES: O=c1[nH]c2cnc(-c3ccc(F)cc3)cc2[nH]1]

a) Ethyl 4-azido-6-(4-fluorophenyl)pyridine-3-carboxylate

To a stirred solution of ethyl 4-chloro-6-(4-fluorophenyl)pyridine-3-carboxylate[98] (11.36 g) in DMF (115 ml) was added sodium azide (7.92 g). The reaction mixture was stirred at 70° C. for 2 hours. TLC analysis indicated that the reaction was finished. The reaction mixture was cooled to room temperature and the white solid was removed by filtration, washing with ethyl acetate. The filtrate was evaporated in vacuo and the residue was partitioned between ethyl acetate (100 ml) and water (300 ml). The aqueous phase was extracted twice with ethyl acetate (2×100 ml). The combined organic layers were dried over MgSO$_4$, filtered, and concentrated in vacuo. The crude material was purified by chromatography (silica gel, 300 g, eluent: 33% of ethyl acetate in cyclohexane) to afford ethyl 4-azido-6-(4-fluorophenyl)pyridine-3-carboxylate (10.74 g, 93%) as an orange solid. MS (ISP): 286.1 ([M+H]$^+$).

b) 4-Azido-6-(4-fluorophenyl)pyridine-3-carboxylic Acid

To a stirred solution of ethyl 4-chloro-6-(4-fluorophenyl)pyridine-3-carboxylate (10.37 g) in ethanol (210 ml) at 0° C. was added dropwise a solution of KOH (4.8 g) in water (23 ml). The reaction mixture was allowed to reach room temperature and stirring continued for 1 hour. The solvents were evaporated and the residue was dissolved in water (100 ml) and a solution of 1 M aq. HCl (100 ml) was added. The resulting white solid was collected by filtration, washing with water, and dried under high vacuum to afford 4-azido-6-(4-fluorophenyl)pyridine-3-carboxylic acid (8.82 g, 94%) as a white solid. MS (ISP): 257.1 ([M−H]$^−$).

c) tert-Butyl N-[4-azido-6-(4-fluorophenyl)-3-pyridyl]carbamate

To a stirred solution of 4-azido-6-(4-fluorophenyl)pyridine-3-carboxylic acid (8.80 g) and triethylamine (5.2 ml) in THF (215 ml) at −10° C. was added dropwise a solution of ethyl chloroformate (3.6 ml) in THF (90 ml). After stirring for 30 min, a solution of sodium azide (11 g) in water (80 ml) was added dropwise at −10° C. The reaction mixture was allowed to reach room temperature and stirring continued 2.5 hours. The solvents were evaporated and the residue was suspended in water (200 ml). The yellow solid was collected by filtration, washing with water, and dissolved in a mixture of dichloromethane and THF. The organic solution was washed with sat. brine, dried over MgSO$_4$, filtered, and concentrated in vacuo to afford a yellow solid. This solid was dissolved in 1,2-dichloroethane (190 ml) and tert-butanol (80 ml) and the resulting solution was stirred at reflux for 2 hours. The reaction mixture was concentrated in vacuo and the crude material was purified by chromatography (silica gel, 600 g, eluent: 20% to 33% of ethyl acetate in cyclohexane) to afford tert-butyl N-[4-azido-6-(4-fluorophenyl)-3-pyridyl]carbamate (3.45 g, 31%) as an orange solid. MS (ISP): 330.3 ([M+H]$^+$).

d) tert-Butyl N-[4-amino-6-(4-fluorophenyl)-3-pyridyl]carbamate

To a stirred solution of tert-butyl N-[4-azido-6-(4-fluorophenyl)-3-pyridyl]carbamate (3.4 g) in a mixture of MeOH (200 ml) and THF (60 ml) was added 10% palladium on charcoal (360 mg). The reaction mixture was stirred under a hydrogen atmosphere for 4 hours at room temperature. The catalyst was filtered off and the filter cake was washed with methanol. The filtrate was concentrated in vacuo to afford tert-butyl N-[4-amino-6-(4-fluorophenyl)-3-pyridyl]carbamate as a beige solid (3.28 g) which was used in the next step without further purification. MS (ISP): 304.2 ([M+H]$^+$).

e) 6-(4-Fluoro-phenyl)-1,3-dihydro-imidazo[4,5-c]pyridin-2-one

A stirred solution of tert-butyl N-[4-amino-6-(4-fluorophenyl)-3-pyridyl]carbamate (303 mg) in toluene (4 ml) was refluxed for 48 h. After cooling to room temperature, the resulting solid was collected by filtration, washing with toluene and diethyl ether, to afford 6-(4-fluoro-phenyl)-1,3-dihydro-imidazo[4,5-c]pyridin-2-one (170 mg, 74%) as a yellow solid. MS (ISP): 229.1 ([M+H]$^+$).

Example 37

5-(2,5-Difluoro-phenyl)-1,3-dihydro-benzoimidazol-2-one

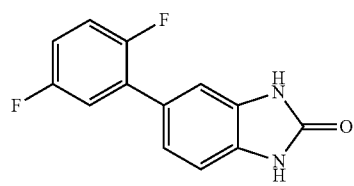 [SMILES: O=c1[nH]c2ccc(-c3cc(F)ccc3F)cc2[nH]1]

The title compound was obtained in analogy to example 36 step e using tert-butyl N-[2-amino-4-(2,5-difluorophenyl)phenyl]carbamate[99] in place of tert-butyl N-[4-amino-6-(4-fluorophenyl)-3-pyridyl]carbamate. Beige solid. MS (ISP): 247.2 ([M+H]+).

Example 38

5-(2,4-Difluoro-phenyl)-1,3-dihydro-benzoimidazol-2-one

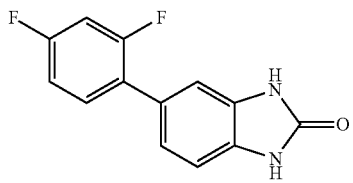 [SMILES: O=c1[nH]c2ccc(-c3ccc(F)cc3F)cc2[nH]1]

The title compound was obtained in analogy to example 36 step e using tert-butyl N-[2-amino-4-(2,4-difluorophenyl)phenyl]carbamate[100] in place of tert-butyl N-[4-amino-6-(4-fluorophenyl)-3-pyridyl]carbamate. Beige solid. MS (ISP): 247.2 ([M+H]+).

Example 39

5-[(4-Methoxyphenyl)methyl]-1,3-dihydrobenzimidazol-2-one

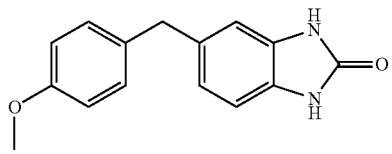 [SMILES: COc1ccc(Cc2ccc3[nH]c(=O)[nH]c3c2)cc1]

The title compound was obtained in analogy to example 19 using p-methoxybenzylboronic acid[101] in place of pyridin-3-ylboronic acid. White solid. MS (ISP): 255.3 ([M+H]+).

Example 40

5-[4-(2-Pyridyl)piperazin-1-yl]-1,3-dihydroimidazo[4,5-b]pyridin-2-one

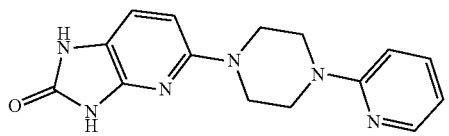 [SMILES: O=c1[nH]c2ccc(N3CCN(c4ccccn4)CC3)nc2[nH]1]

The title compound was obtained in analogy to example 58 step c using 6-[4-(2-pyridyl)piperazin-1-yl]pyridine-2,3-diamine[102] in place of tert-butyl 4-(3,4-diaminophenyl)piperazine-1-carboxylate. White solid. MS (ISP): 297.3 ([M+H]+).

Example 41

5-(4-Pyrrol-1-yl-phenyl)-1,3-dihydro-benzoimidazol-2-one

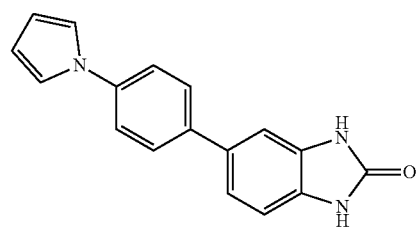 [SMILES: O=c1[nH]c2ccc(-c3ccc(-n4cccc4)cc3)cc2[nH]1]

The title compound was obtained in analogy to example 19 using B-[4-(1H-pyrrol-1-yl)phenyl]boronic acid[103] in place of pyridin-3-ylboronic acid. White solid. MS (ISP): 276.1 ([M+H]+).

Example 42

5-Quinolin-5-yl-1,3-dihydro-benzoimidazol-2-one

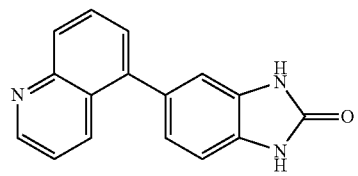 [SMILES: O=c1[nH]c2ccc(-c3cccc4ncccc34)cc2[nH]1]

To a stirred solution of 5-bromo-1H-benzo[d]imidazol-2(3H)-one[104] (930 mg) in a mixture of dioxane (47 ml) and 1 M aqueous sodium carbonate (24 ml) was added 5-quinolylboronic acid[105] (906 mg). The reaction mixture was purged three times with Argon before adding 2-dicyclohexylphosphino-2',6'-dimethoxybiphenyl (0.358 g) and palladium(II) acetate (0.098 g). The reaction mixture was refluxed for 4 hours. Dioxane was removed by evaporation and ethyl acetate was added. The solid obtained was filtered, dissolved in dichloromethane and washed with water. The organic layer was dried over MgSO$_4$, filtered and concentrated in vacuo. The crude material was purified by flash chromatography (silica gel, eluent: 0 to 5% of methanol in dichloromethane) to afford 5-(2-isopropyl-1H-imidazol-1-yl)-2-nitroaniline (85 mg, 27%) as an orange solid. MS (ISP): 247.2 ([M+H]+). The organic layer off and the filter cake was washed with methanol. The filtrate was concentrated in vacuo to 5-quinolin-5-yl-1,3-dihydro-benzoimidazol-2-one as a dark brown solid (949 mg). MS (ISP): 262.2 ([M+H]+).

Example 43

Ethyl 4-((2-oxo-2,3-dihydro-1H-benzo[d]imidazole)-5-sulfonamido)benzoate

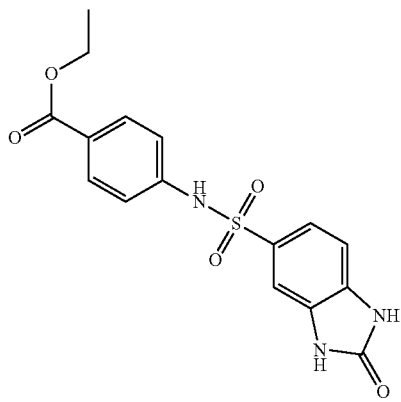 [SMILES: CCOC(=O)c1ccc(NS(=O)(=O)c2ccc3[nH]c(=O)[nH]c3c2)cc1]

To a solution of ethyl 4-aminobenzoate[106] (35.5 mg) in pyridine (0.5 ml) was added 2-oxo-2,3-dihydro-1H-benzo[d]imidazole-5-sulfonyl chloride[59] (50 mg) and the mixture was stirred at room temperature for 2 h. LC-MS analysis indicated that the reaction was finished. The reaction mixture was partitioned between ethyl acetate/THF (1:3, 30 ml) and 2 M aqueous HCl (20 ml). The layers were separated. The aqueous layer was extracted with ethyl acetate/THF (1:1, 20 ml). The combined organic layers were washed with saturated brine (15 ml), dried over anhydrous sodium sulfate, and concentrated in vacuo. The crude material was purified by flash chromatography (SiO$_2$, eluant: dichloromethane/methanol 100:0 to 90:10) to afford ethyl 4-((2-oxo-2,3-dihydro-1H-benzo[d]imidazole)-5-sulfonamido)benzoate as an off-white solid. MS (ISP): 360.1 ([M−H]$^-$).

Example 44

1-Methyl-5-phenyl-3H-imidazo[4,5-b]pyridin-2-one

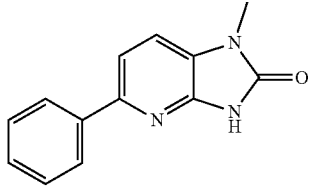 [SMILES: Cn1c(=O)[nH]c2nc(-c3ccccc3)ccc21]

The title compound was obtained in analogy to example 19 using phenylboronic acid[107] in place of pyridin-3-ylboronic acid and 5-chloro-1,3-dihydro-1-methyl-2H-imidazo[4,5-b]pyridin-2-one[108] in place of 5-bromo-1H-benzo[d]imidazol-2(3H)-one. White solid. MS (ISP): 226.2 ([M+H]$^+$).

Example 45

2-(2-Methoxybenzyl)-N-methyl-2'-oxo-2',3'-dihydro-1'H-[1,5'-bibenzo[d]imidazole]-5-carboxamide

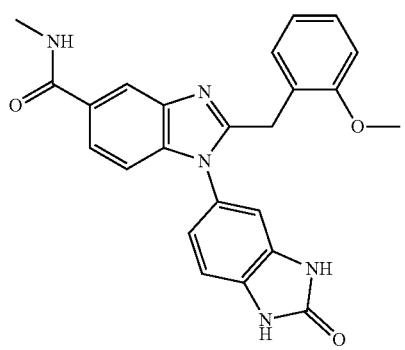 [SMILES: CNC(=O)c1ccc2c(c1)nc(Cc1ccccc1OC)n2-c1ccc2[nH]c(=O)[nH]c2c1]

The title compound was obtained in analogy to example 2 using 2-(2-methoxyphenyl)acetaldehyde[109] in place of 2-(3-methylimidazol-4-yl)quinoline-4-carbaldehyde. Off-white solid. MS (ISP): 428.4 ([M+H]$^+$).

Example 46

2-(tert-Butyl)-N-methyl-2'-oxo-2',3'-dihydro-1'H-[1,5'-bibenzo[d]imidazole]-5-carboxamide

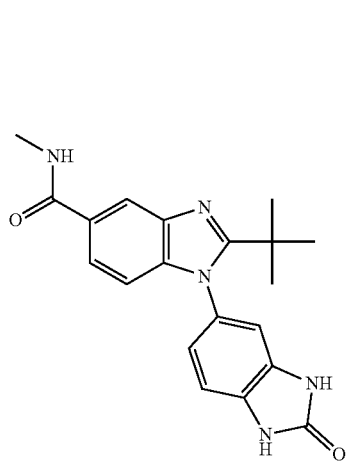 [SMILES: CNC(=O)c1ccc2c(c1)nc(C(C)(C)C)n2-c1ccc2[nH]c(=O)[nH]c2c1]

The title compound was obtained in analogy to example 2 using pivaldehyde[110] in place of 2-(3-methylimidazol-4-yl)quinoline-4-carbaldehyde. White solid. MS (ISP): 364.2 ([M+H]$^+$).

Example 47

Methyl 2-isopropyl-2'-oxo-2',3'-dihydro-1'H-[1,5'-bibenzo[d]imidazole]-4-carboxylate

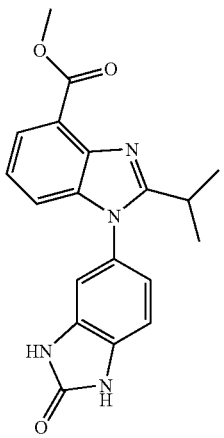 [SMILES: COC(=O)c1cccc2c1nc(C(C)C)n2-c1ccc2[nH]c(=O)[nH]c2c1]

a) Methyl 2-amino-3-((2-oxo-2,3-dihydro-1H-benzo[d]imidazol-5-yl)amino)benzoate The title compound was obtained in analogy to example 1 using methyl 3-fluoro-2-nitrobenzoate[11] in place of 4-fluoro-N-methyl-3-nitrobenzamide in step a. Yellow solid. MS (ISP): 299.1 ([M+H]+).

b) Methyl 2-isopropyl-2'-oxo-2',3'-dihydro-1'H-[1,5'-bibenzo[d]imidazole]-4-carboxylate The title compound was obtained in analogy to example 2 using isobutyraldehyde[79] in place of 2-(3-methylimidazol-4-yl)quinoline-4-carbaldehyde and methyl 2-amino-3-((2-oxo-2,3-dihydro-1H-benzo[d]imidazol-5-yl)amino)benzoate in place of 3-amino-N-methyl-4-[(2-oxo-1,3-dihydrobenzimidazol-5-yl)amino]benzamide. White solid. MS (ISP): 351.1 ([M+H]1).

Example 48

Methyl 2-isopropyl-2'-oxo-2',3'-dihydro-1'H-[1,5'-bibenzo[d]imidazole]-6-carboxylate

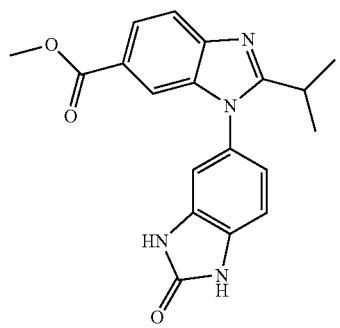 [SMILES: COC(=O)c1ccc2nc(C(C)C)n(-c3ccc4[nH]c(=O)[nH]c4c3)c2c1]

a) Methyl 4-amino-3-((2-oxo-2,3-dihydro-1H-benzo[d]imidazol-5-yl)amino)benzoate The title compound was obtained in analogy to example 1 using methyl 3-fluoro-4-nitrobenzoate[49] in place of 4-fluoro-N-methyl-3-nitrobenzamide in step a. Brown solid. MS (ISP): 299.1 ([M+H]+).

b) Methyl 2-isopropyl-2'-oxo-2',3'-dihydro-1'H-[1,5'-bibenzo[d]imidazole]-6-carboxylate The title compound was obtained in analogy to example 2 using isobutyraldehyde[79] in place of 2-(3-methylimidazol-4-yl)quinoline-4-carbaldehyde and methyl 4-amino-3-((2-oxo-2,3-dihydro-1H-benzo[d]imidazol-5-yl)amino)benzoate in place of 3-amino-N-methyl-4-[(2-oxo-1,3-dihydrobenzimidazol-5-yl)amino]benzamide. White solid. MS (ISP): 351.1 ([M+H]+).

Example 49

1,3-Dimethyl-5-((2-nitrophenyl)amino)-1,3-dihydro-2H-benzo[d]imidazol-2-one

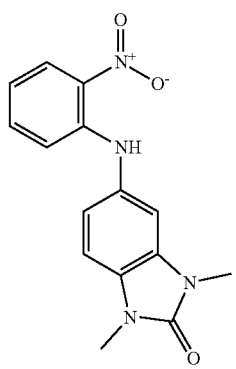 [SMILES: Cn1c(=O)n(C)c2cc(Nc3ccccc3[N+](=O)[O-])ccc21]

The title compound was obtained in analogy to example 1 step a using 1-fluoro-2-nitrobenzene[45] in place of 4-fluoro-N-methyl-3-nitrobenzamide and 5-amino-1,3-dimethyl-1,3-dihydro-2H-benzo[d]imidazol-2-one[53] in place of 5-amino-1H-benzo[d]imidazol-2(3H)-one. Red solid. MS (ISP): 299.1 ([M+H]+).

Example 50

5-((2-Aminophenyl)amino)-1,3-dimethyl-1,3-dihydro-2H-benzo[d]imidazol-2-one

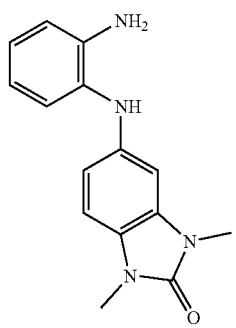 [SMILES: Cn1c(=O)n(C)c2cc(Nc3ccccc3N)ccc21]

The title compound was obtained in analogy to example 1 step b using 1,3-dimethyl-5-((2-nitrophenyl)amino)-1,3-dihydro-2H-benzo[d]imidazol-2-one in place of N-methyl-3-nitro-4-((2-oxo-2,3-dihydro-1H-benzo[d]imidazol-5-yl)amino)benzamide. Amorphous brown solid. MS (ISP): 269.1 ([M+H]$^+$).

Example 51

2-Oxo-N-(4-piperidyl)-1,3-dihydrobenzimidazole-5-carboxamide

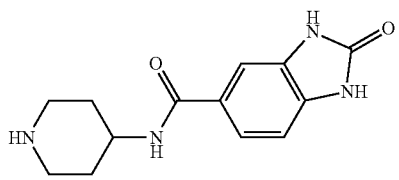 [SMILES: O=C(NC1CCNCC1)c1ccc2[nH]c(=O)[nH]c2c1]

a) tert-Butyl 4-[(2-oxo-1,3-dihydrobenzimidazole-5-carbonyl)amino]piperidine-1-carboxylate The title compound was obtained in analogy to example 22 using tert-butyl 4-aminopiperidine-1-carboxylate[12] in place of 1-(piperazin-1-yl)ethanone. White solid. MS (ISP): 305.1 ([M+H—C$_4$H$_8$]$^+$).

b) 2-Oxo-N-(4-piperidyl)-1,3-dihydrobenzimidazole-5-carboxamide

To a stirred suspension of tert-butyl 4-[(2-oxo-1,3-dihydrobenzimidazole-5-carbonyl)amino]piperidine-1-carboxylate (54 mg) in dichloromethane (2 ml) was added dropwise a solution of 4 M HCl in dioxane (1.1 ml). The reaction mixture was stirred at room temperature overnight. The reaction mixture was then concentrated in vacuo. Diethyl ether was added and the resulting mixture was ultrasonicated. The mixture was then filtered through sintered glass, and the filter cake was dried in vacuo to afford 2-oxo-N-(4-piperidyl)-1,3-dihydrobenzimidazole-5-carboxamide as its hydrochloride salt (39 mg, 88%) as a white solid. MS (ISP): 261.1 ([M+H—C$_4$H$_8$]$^+$).

Example 52

6-((2-Aminophenyl)amino)-1-methyl-1,3-dihydro-2H-benzo[d]imidazol-2-one

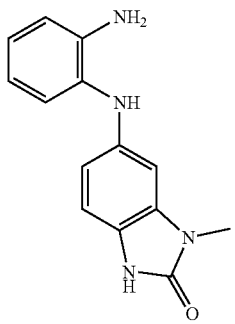 [SMILES: Cn1c(=O)[nH]c2ccc(Nc3ccccc3N)cc21]

The title compound was obtained in analogy to example 1 using 1-fluoro-2-nitrobenzene[45] in place of 4-fluoro-N-methyl-3-nitrobenzamide and 6-amino-1-methyl-1,3-dihydro-2H-benzo[d]imidazol-2-one[97] instead of 5-amino-1H-benzo[d]imidazol-2(3H)-one in step a. Brown solid. MS (ISP): 285.2 ([M+H]$^+$).

Example 53

5-((2-Aminophenyl)amino)-1-methyl-1,3-dihydro-2H-benzo[d]imidazol-2-one

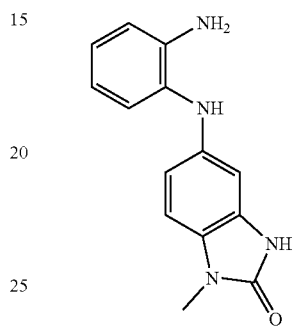

The title compound was obtained in analogy to example 1 using 1-fluoro-2-nitrobenzene[45] in place of 4-fluoro-N-methyl-3-nitrobenzamide and 5-amino-1-methyl-1,3-dihydro-2H-benzo[d]imidazol-2-one hydrochloride[113] instead of 5-amino-1H-benzo[d]imidazol-2(3H)-one in step a. Brown solid. MS (ISP): 255.3 ([M+H]$^+$).

Example 54

Methyl 1-(2-oxo-2,3-dihydro-1H-benzo[d]imidazole-5-carbonyl)indoline-4-carboxylate

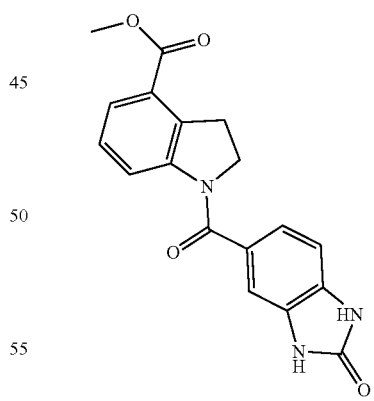

To a stirred solution of 2-oxo-2,3-dihydro-1H-benzo[d]imidazole-5-carboxylic acid[56] (150 mg) and methyl indoline-4-carboxylate[114] (149 mg) in methanol (5 ml) was added 4-(4,6-dimethoxy-1,3,5-triazin-2-yl)-4-methylmorpholin-4-ium chloride[115] (280 mg, DMTMM). The reaction mixture was stirred for 4 h at room temperature. LC/MS analysis indicated that the reaction was complete. The reaction mixture was concentrated in vacuo and the residue was purified by preparative reverse-phase HPLC (Gemini NX C18, 12 nm, 5μ, 100×30 mm, flow rate 40 ml/min, eluant: CH₃CN/H₂O containing formic acid) followed by lyophilisation in vacuo to afford methyl 1-(2-oxo-2,3-dihydro-1H-benzo[d]imidazole-5-carbonyl)indoline-4-carboxylate (60 mg, 21%) as a white solid. MS (ISP): 338.1 ([M+H]⁺).

Example 55

6-(Indoline-1-carbonyl)-1,3-dihydro-2H-imidazo[4,5-b]pyridin-2-one

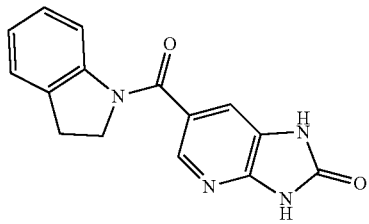 [SMILES: O=C(c1cnc2[nH]c(=O)[nH]c2c1)N1CCc2ccccc21]

The title compound was obtained in analogy to example 22 using indoline[86] in place of 1-(piperazin-1-yl)ethanone and 2-oxo-2,3-dihydro-1H-imidazo[4,5-b]pyridine-6-carboxylic acid[116] in place of 2-oxo-2,3-dihydro-1H-benzo[d]imidazole-5-carboxylic acid. White solid. MS (ISP): 281.1 ([M+H]⁺).

Example 56

N-(1-Acetylpiperidin-4-yl)-2-oxo-2,3-dihydro-1H-imidazo[4,5-b]pyridine-6-carboxamide

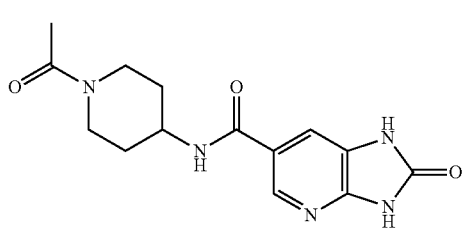 [SMILES: CC(=O)N1CCC(NC(=O)c2cnc3[nH]c(=O)[nH]c3c2)CC1]

The title compound was obtained in analogy to example 22 using 1-(4-aminopiperidin-1-yl)ethan-1-one[85] in place of 1-(piperazin-1-yl)ethanone and 2-oxo-2,3-dihydro-1H-imidazo[4,5-b]pyridine-6-carboxylic acid[116] in place of 2-oxo-2,3-dihydro-1H-benzo[d]imidazole-5-carboxylic acid. White solid. MS (ISP): 304.1 ([M+H]⁺).

Example 57

2-(3-(Methoxymethyl)phenyl)-N-methyl-2'-oxo-2',3'-dihydro-1'H-[1,5'-bibenzo[d]imidazole]-5-carboxamide

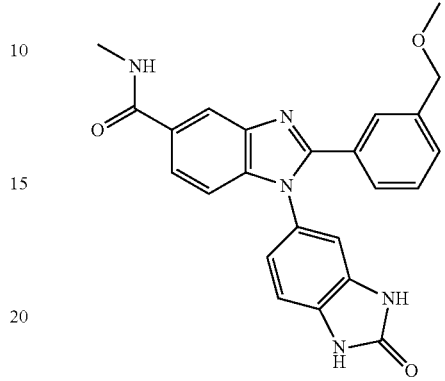

The title compound was obtained in analogy to example 2 using 3-(methoxymethyl)benzaldehyde[117] in place of 2-(3-methylimidazol-4-yl)quinoline-4-carbaldehyde. White solid. MS (ISP): 428.2 ([M+H]⁺).

Example 58

5-(Piperazin-1-yl)-1,3-dihydro-2H-benzo[d]imidazol-2-one

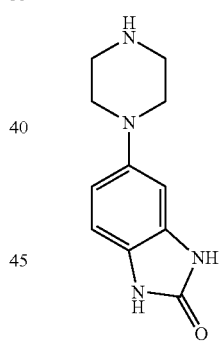

a) tert-Butyl 4-(3,4-dinitrophenyl)piperazine-1-carboxylate

A mixture of 4-fluoro-1,2-dinitrobenzene[62] (250 mg), tert-butyl piperazine-1-carboxylate[118] (275 mg) and N,N-diisopropylethylamine (351 μl) in acetonitrile (2 ml) was stirred at room temperature overnight. Pentane (1 ml) was added and the suspension was filtered. The filter cake was dried in vacuo to afford tert-butyl 4-(3,4-dinitrophenyl)piperazine-1-carboxylate (385 mg, 81%) as a yellow solid. MS (ISP): 353.3 ([M+H]⁺).

b) tert-Butyl 4-(3,4-diaminophenyl)piperazine-1-carboxylate

A mixture of tert-butyl 4-(3,4-dinitrophenyl)piperazine-1-carboxylate (385 mg) and 10% Pd/C (116 mg) in THF (1 ml) and Ethanol (1 ml) was stirred at room temperature overnight under a hydrogen atmosphere. The mixture was then filtered through a membrane filter and the filtrate was concentrated in vacuo to afford tert-butyl 4-(3,4-diaminophenyl)piperazine-1-carboxylate (237 mg, 74%) as an off-white solid. MS (ISP): 293.3 ([M+H]+).

c) tert-Butyl 4-(2-oxo-2,3-dihydro-1H-benzo[d]imidazol-5-yl)piperazine-1-carboxylate To a stirred solution of tert-butyl 4-(3,4-diaminophenyl)piperazine-1-carboxylate (230 mg) in THF (2 ml) was added CDI (140 mg). The reaction mixture was stirred at room temperature for 1 hour. LC-MS analysis indicated that no starting material was left. The reaction mixture was diluted with water (40 ml) and extracted twice with ethyl acetate (2×30 ml). The combined organic layers were dried over Na2SO4, filtered, and concentrated in vacuo. The residue was purified by preparative HPLC to afford tert-butyl 4-(2-oxo-2,3-dihydro-1H-benzo[d]imidazol-5-yl)piperazine-1-carboxylate (57.7 mg, 23%) as an off-white solid. MS (ISP): 319.3 ([M+H]+).

d) 5-(Piperazin-1-yl)-1,3-dihydro-2H-benzo[d]imidazol-2-one

To a suspension of tert-butyl 4-(2-oxo-2,3-dihydro-1H-benzo[d]imidazol-5-yl)piperazine-1-carboxylate (65 mg) in 1,4-dioxane (1.5 ml) at room temperature was added a 4 M solution of hydrogen chloride in 1,4-dioxane (1 ml). The reaction mixture was stirred at room temperature for 3 h. LC-MS analysis indicated that the reaction was finished. The solvent was concentrated in vacuo to afford 5-(piperazin-1-yl)-1,3-dihydro-2H-benzo[d]imidazol-2-one (52 mg, 100%) as its hydrochloride salt as a white solid. MS (ISP): 219.1 ([M+H]+).

Example 59

5-[rac-(1S,5R)-3,8-diazabicyclo[3.2.1]octan-3-yl]-1,3-dihydrobenzimidazol-2-one

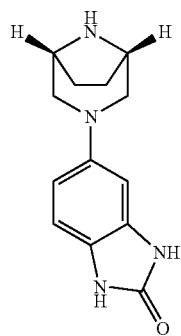 [SMILES: O=c1[nH]c2ccc(N3C[C@H]4CC[C@@H](C3)N4)cc2[nH]1]

The title compound was obtained as its hydrochloride salt in analogy to example 58 using tert-butyl rac-(1S,5R)-3,8-diazabicyclo[3.2.1]octane-8-carboxylate[119] in place of tert-butyl piperazine-1-carboxylate in step a. White solid. MS (ISP): 245.1 ([M+H]+).

Example 60

2-Isopropyl-N-methyl-2'-oxo-2',3'-dihydro-1'H-[1,5'-bibenzo[d]imidazole]-4-carboxamide

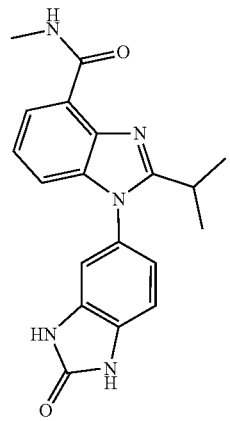 [SMILES: CNC(=O)c1cccc2c1nc(C(C)C)n2-c1ccc2[nH]c(=O)[nH]c2c1]

a) 2-Isopropyl-2'-oxo-2',3'-dihydro-1'H-[1,5'-bibenzo[d]imidazole]-4-carboxylic acid The title compound was obtained in analogy to example 18 step d using methyl 2-isopropyl-2'-oxo-2',3'-dihydro-1'H-[1,5'-bibenzo[d]imidazole]-4-carboxylate (example 47) in place of methyl 2-(2-(1-methyl-1H-imidazol-5-yl)quinolin-4-yl)-2'-oxo-2',3'-dihydro-1'H-[1,5'-bibenzo[d]imidazole]-5-carboxylate and THF in place of 1,4-dioxane. White solid. MS (ISP): 337.1 ([M+H]+).

b) 2-Isopropyl-N-methyl-2'-oxo-2',3'-dihydro-1'H-[1,5'-bibenzo[d]imidazole]-4-carboxamide The title compound was obtained in analogy to example 18 step e using 2-isopropyl-2'-oxo-2',3'-dihydro-1'H-[1,5'-bibenzo[d]imidazole]-4-carboxylic acid in place of 2-(2-(1-methyl-1H-imidazol-5-yl)quinolin-4-yl)-2'-oxo-2',3'-dihydro-1'H-[1,5'-bibenzo[d]imidazole]-5-carboxylic acid and methylamine in place of dimethylamine. White solid. MS (ISP): 350.2 ([M+H]+).

Example 61

5-[2-(Hydroxymethyl)benzimidazol-1-yl]-1,3-dihydrobenzimidazol-2-one

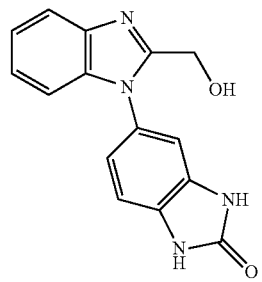 [SMILES: O=c1[nH]c2ccc(-n3c(CO)nc4ccccc43)cc2[nH]1]

a)

5-(2-Aminoanilino)-1,3-dihydrobenzimidazol-2-one

The title compound was obtained in analogy to example 1 using 1-fluoro-2-nitrobenzene[45] in place of 4-fluoro-N-methyl-3-nitrobenzamide in step a. Grey solid. MS (ISP): 241.2 ([M+H]$^+$).

b) 5-[2-(Hydroxymethyl)benzimidazol-1-yl]-1,3-dihydrobenzimidazol-2-one

A solution of 5-(2-aminoanilino)-1,3-dihydrobenzimidazol-2-one (250 mg) and glycolic acid[120] (158 mg) in a 6 M solution of HCl (8 ml) was stirred at 120° C. for 48 hours. According to LC/MS, the reaction was finished. The reaction mixture was concentrated in vacuo. The crude material was purified by preparative reversed phase HPLC to afford 5-[2-(hydroxymethyl)benzimidazol-1-yl]-1,3-dihydrobenzimidazol-2-one (170 mg, 57.9%) as a brown solid. MS (ISP): 281.2 ([M+H]$^+$).

Example 62

5-(4-Acetylpiperazin-1-yl)-1,3-dihydro-2H-benzo[d]imidazol-2-one

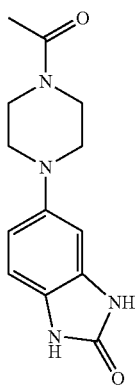 [SMILES: CC(=O)N1CCN(c2ccc3[nH]c(=O)[nH]c3c2)CC1]

To a stirred solution of 5-(piperazin-1-yl)-1,3-dihydro-2H-benzo[d]imidazol-2-one hydrochloride (50 mg, example 59) and triethylamine (82 µl) in DMF (1 ml) at room temperature was added dropwise acetic anhydride (20 mg). The reaction mixture was stirred at room temperature for 2 h. LC/MS analysis indicated that the reaction was complete. The reaction mixture was poured into water (10 ml) and extracted with 1:4 EtOAc/THF (2×30 ml). The combined organic phases were dried over Na$_2$S=4 and concentrated in vacuo. The crude material was purified by preparative HPLC followed by lyophilisation to afford 5-(4-acetylpiperazin-1-yl)-1,3-dihydro-2H-benzo[d]imidazol-2-one (23 mg, 45%) as a white solid. MS (ISP): 261.1 ([M+H]$^+$).

Example 63

5-[rac-(1S,5R)-8-Acetyl-3,8-diazabicyclo[3.2.1]octan-3-yl]-1,3-dihydrobenzimidazol-2-one

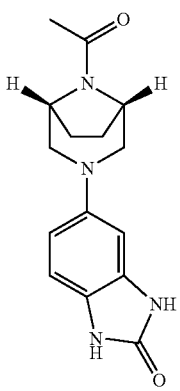 [SMILES: CC(=O)N1[C@@H]2CC[C@H]1CN(c1ccc3[nH]c(=O)[nH]c3c1)C2]

The title compound was obtained in analogy to example 62 using 5-[rac-(1S,5R)-3,8-diazabicyclo[3.2.1]octan-3-yl]-1,3-dihydrobenzimidazol-2-one hydrochloride in place of 5-(piperazin-1-yl)-1,3-dihydro-2H-benzo[d]imidazol-2-one hydrochloride. White solid. MS (ISP): 287.2 ([M+H]$^+$).

Example 64

N-Methyl-2'-oxo-2-(tetrahydro-2H-pyran-4-yl)-2',3'-dihydro-1'H-[1,5'-bibenzo[d]imidazole]-5-carboxamide

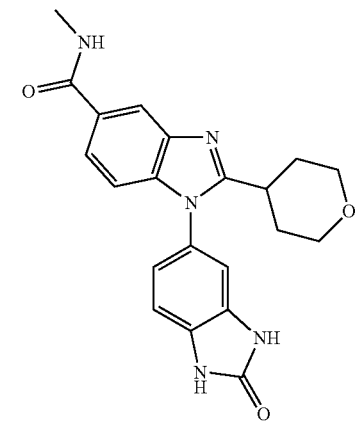 [SMILES: CNC(=O)c1ccc2c(c1)nc(C1CCOCC1)n2-c1ccc2[nH]c(=O)[nH]c2c1]

The title compound was obtained in analogy to example 2 using tetrahydro-2H-pyran-4-carbaldehyde[121] in place of 2-(3-methylimidazol-4-yl)quinoline-4-carbaldehyde. White solid. MS (ISP): 392.2 ([M+H]$^+$).

Example 65

N-Methyl-2-(1-methyl-1H-imidazol-4-yl)-2'-oxo-2',3'-dihydro-1'H-[1,5'-bibenzo[d]imidazole]-5-carboxamide

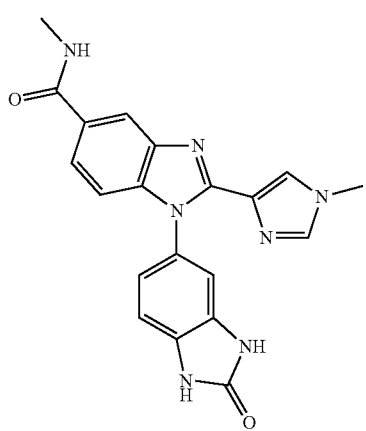 [SMILES: CNC(=O)c1ccc2c(c1)nc(-c1cn(C)cn1)n2-c1ccc2[nH]c(=O)[nH]c2c1]

The title compound was obtained in analogy to example 2 using 1-methyl-1H-imidazole-4-carbaldehyde[122] in place of 2-(3-methylimidazol-4-yl)quinoline-4-carbaldehyde. White solid. MS (ISP): 388.2 ([M+H]+).

Example 66

N-Methyl-2'-oxo-2-(1H-pyrrol-3-yl)-2',3'-dihydro-1'H-[1,5'-bibenzo[d]imidazole]-5-carboxamide

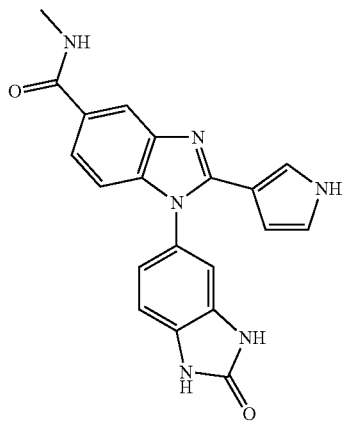 [SMILES: CNC(=O)c1ccc2c(c1)nc(-c1cc[nH]c1)n2-c1ccc2[nH]c(=O)[nH]c2c1]

The title compound was obtained in analogy to example 2 using 1H-pyrrole-3-carbaldehyde[123] in place of 2-(3-methylimidazol-4-yl)quinoline-4-carbaldehyde. White solid. MS (ISP): 373.1 ([M+H]+).

Example 67

2-Oxo-N-phenyl-2,3-dihydro-1H-imidazo[4,5-b]pyridine-6-carboxamide

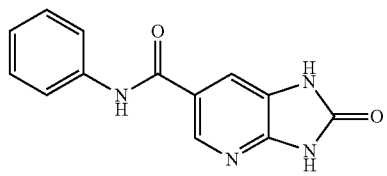 [SMILES: O=C(Nc1ccccc1)c1cnc2[nH]c(=O)[nH]c2c1]

To a mixture of aniline (50 mg) and 2-oxo-2,3-dihydro-1H-imidazo[4,5-b]pyridine-6-carboxylic acid[116] (106 mg) were added 0.36 M HATU in N,N-dimethylformamide (245 mg, 1.8 ml) and N,N-diisopropylethylamine (276 μl). The reaction mixture was shaken at 25° C. for 2 hours and was then partitioned between water and a 1:1 mixture of ethyl acetate/THF. The organic layer was washed with brine, dried over Na$_2$SO$_4$, filtered and concentrated in vacuo. The product was suspended in dichloromethane (3 ml) and stirred. The product was collected by filtration, washed with dichloromethane and dried to afford 2-oxo-N-phenyl-2,3-dihydro-1H-imidazo[4,5-b]pyridine-6-carboxamide (29.4 mg, 22%) as an off-white solid. MS (ISP): 255.3 ([M+H]+).

Example 68

N-(2-Oxo-2,3-dihydro-1H-benzo[d]imidazol-5-yl)benzofuran-3-carboxamide

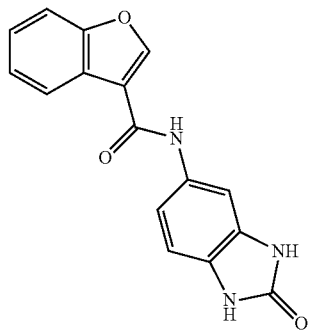 [SMILES: O=C(Nc1ccc2[nH]c(=O)[nH]c2c1)c1coc2ccccc12]

To a stirred solution of benzofuran-3-carboxylic acid[124] (40 mg), 5-amino-1,3-dihydro-2H-benzo[d]imidazol-2-one[50] (36.8 mg) and N,N-diisopropylethylamine (172 μl) in DMF (1 ml) was added HATU (141 mg). The reaction mixture was stirred at room temperature for 2 h. The reaction mixture was then poured into EtOAc/THF (1:1) and extracted with saturated brine. The organic layer was separated, dried over Na$_2$SO$_4$, and concentrated in vacuo. The crude material was purified by preparative reverse-phase HPLC (Gemini NX C18, 12 nm, 5μ, 100×30 mm, flow rate 40 ml/min, eluant: CH$_3$CN/H$_2$O containing formic acid) followed by lyophilisation to afford N-(2-oxo-2,3-dihydro-1H-benzo[d]imidazol-5-yl)benzofuran-3-carboxamide (15 mg, 21%) as an off-white solid. MS (ISP): 294.1 ([M+H]+).

Example 69

N-(2-Oxo-2,3-dihydro-1H-benzo[d]imidazol-5-yl)-2,3-dihydro-1H-indene-1-carboxamide

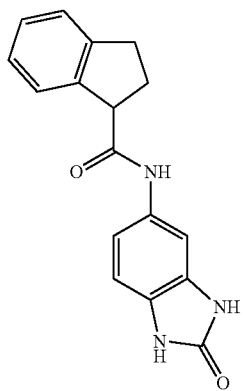 [SMILES: O=C(Nc1ccc2[nH]c(=O)[nH]c2c1)C1CCc2ccccc21]

The title compound was obtained in analogy to example 68 using 2,3-dihydro-1H-indene-1-carboxylic acid[125] in place of benzofuran-3-carboxylic acid. Off-white solid. MS (ISP): 294.1 ([M+H]$^+$).

Example 70

2-(4-Aminophenyl)-N-(2-oxo-2,3-dihydro-1H-benzo[d]imidazol-5-yl)acetamide

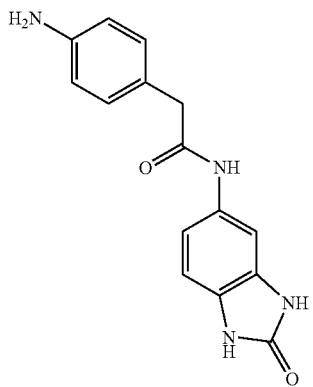 [SMILES: Nc1ccc(CC(=O)Nc2ccc3[nH]c(=O)[nH]c3c2)cc1]

The title compound was obtained in analogy to example 68 using 2-(4-aminophenyl)acetic acid[126] in place of benzofuran-3-carboxylic acid. Off-white solid. MS (ISP): 283.1 ([M+H]$^+$).

Example 71

(S)—N-(2-Oxo-2,3-dihydro-1H-benzo[d]imidazol-5-yl)-1,2,3,4-tetrahydronaphthalene-1-carboxamide

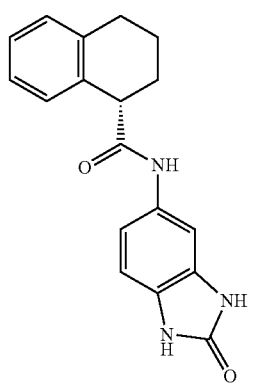 [SMILES: O=C(Nc1ccc2[nH]c(=O)[nH]c2c1)[C@H]1CCCc2ccccc21]

The title compound was obtained in analogy to example 68 using (S)-1,2,3,4-tetrahydronaphthalene-1-carboxylic acid[127] in place of benzofuran-3-carboxylic acid. White solid. MS (ISP): 308.1 ([M+H]$^+$).

Example 72

(R)—N-(2-Oxo-2,3-dihydro-1H-benzo[d]imidazol-5-yl)-1,2,3,4-tetrahydronaphthalene-1-carboxamide

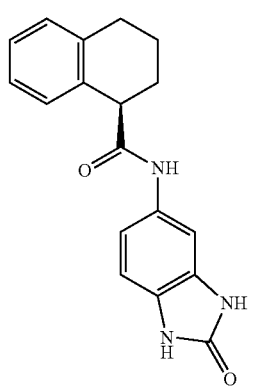 [SMILES: O=C(Nc1ccc2[nH]c(=O)[nH]c2c1)[C@@H]1CCCc2ccccc21]

The title compound was obtained in analogy to example 68 using (R)-1,2,3,4-tetrahydronaphthalene-1-carboxylic acid[128] in place of benzofuran-3-carboxylic acid. White solid. MS (ISP): 308.1 ([M+H]$^+$).

Example 73

N-(2-Oxo-2,3-dihydro-1H-benzo[d]imidazol-5-yl)benzamide

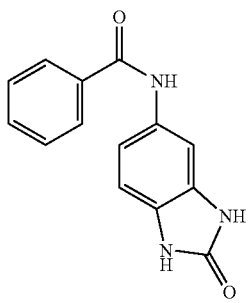 [SMILES: O=C(Nc1ccc2[nH]c(=O)[nH]c2c1)c1ccccc1]

The title compound was obtained in analogy to example 68 using benzoic acid[129] in place of benzofuran-3-carboxylic acid. White solid. MS (ISP): 254.1 ([M+H]+).

Example 74

4-Acetamido-N-(2-oxo-2,3-dihydro-1H-benzo[d]imidazol-5-yl)benzamide

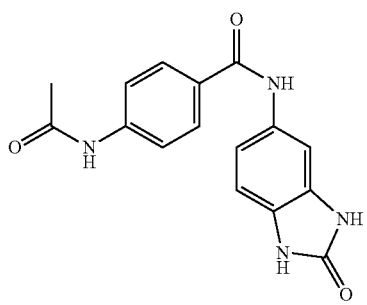 [SMILES: CC(=O)Nc1ccc(C(=O)Nc2ccc3[nH]c(=O)[nH]c3c2)cc1]

The title compound was obtained in analogy to example 68 using 4-acetamidobenzoic acid[130] in place of benzofuran-3-carboxylic acid. Off-white solid. MS (ISP): 311.1 ([M+H]+).

Example 75

3-Acetamido-N-(2-oxo-2,3-dihydro-1H-benzo[d]imidazol-5-yl)benzamide

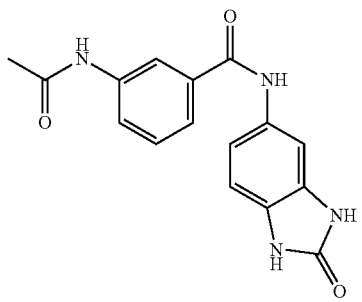 [SMILES: CC(=O)Nc1cccc(C(=O)Nc2ccc3[nH]c(=O)[nH]c3c2)c1]

The title compound was obtained in analogy to example 68 using 3-acetamidobenzoic acid[131] in place of benzofuran-3-carboxylic acid. White solid. MS (ISP): 311.1 ([M+H]+).

Example 76

N-Methyl-2-oxo-N-phenyl-2,3-dihydro-1H-imidazo[4,5-b]pyridine-6-carboxamide

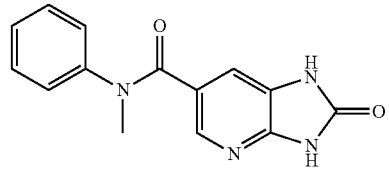 [SMILES: CN(C(=O)c1cnc2[nH]c(=O)[nH]c2c1)c1ccccc1]

The title compound was obtained in analogy to example 22 using N-methylaniline[132] in place of 1-(piperazin-1-yl)ethanone and 2-oxo-2,3-dihydro-1H-imidazo[4,5-b]pyridine-6-carboxylic acid instead of 2-oxo-2,3-dihydro-1H-benzo[d]imidazole-5-carboxylic acid. White solid. MS (ISP): 269.3 ([M+H]+).

Example 77[133]

2-Oxo-N-phenyl-2,3-dihydro-1H-benzo[d]imidazole-5-carboxamide

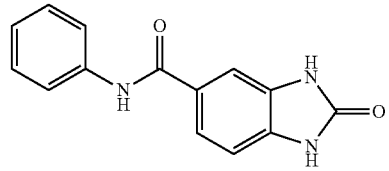 [SMILES: O=C(Nc1ccccc1)c1ccc2[nH]c(=O)[nH]c2c1]

The title compound can be purchased.

Example 78

2-(4-Acetamidophenyl)-N-(2-oxo-2,3-dihydro-1H-benzo[d]imidazol-5-yl)acetamide

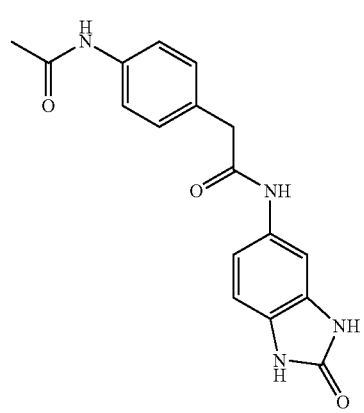 [SMILES: CC(=O)Nc1ccc(CC(=O)Nc2ccc3[nH]c(=O)[nH]c3c2)cc1]

The title compound was obtained in analogy to example 68 using 2-(4-acetamidophenyl)acetic acid[134] in place of benzofuran-3-carboxylic acid. White solid. MS (ISP): 325.1 ([M+H]+).

Example 79

2-Isopropyl-N-methyl-1-(2-oxo-1,3-dihydroimidazo[4,5-b]pyridin-6-yl)benzimidazole-5-carboxamide

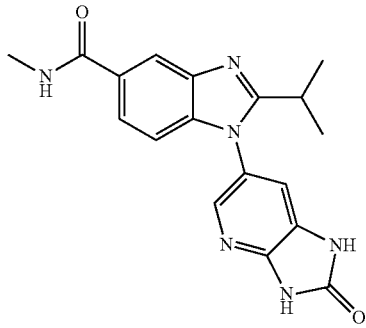 [SMILES: CNC(=O)c1ccc2c(c1)nc(C(C)C)n2-c1cnc2[nH]c(=O)[nH]c2c1]

a) N-Methyl-3-nitro-4-[(2-oxo-1,3-dihydroimidazo[4,5-b]pyridin-6-yl)amino]benzamide The title compound was obtained in analogy to example 1 using 6-amino-1, 3-dihydroimidazo[4, 5-b]pyridin-2-one[135] in place of 5-amino-1H-benzo[d]imidazol-2(3H)-one for step a. Yellow solid. MS (ISP): 297.1 ([M+H]+).

b) 2-Isopropyl-N-methyl-1-(2-oxo-1,3-dihydroimidazo[4,5-b]pyridin-6-yl)benzimidazole-5-carboxamide To a solution of N-methyl-3-nitro-4-[(2-oxo-1,3-dihydroimidazo[4,5-b]pyridin-6-yl)amino]benzamide (180 mg) in ethanol (8 ml) were added isobutyraldehyde (43.5 mg) and 1 M aqueous sodium hydrosulfite (1.64 ml). The reaction mixture was stirred at 70° C. for 12 hours. After cooling, the reaction mixture was concentrated in vacuo and the residue was dissolved in ethyl acetate (20 ml). The combined organic layer was washed with brine, dried, filtered and concentrated in vacuo. The crude material was purified by preparative reversed phase HPLC to afford 2-isopropyl-N-methyl-1-(2-oxo-1,3-dihydroimidazo[4,5-b]pyridin-6-yl)benzimidazole-5-carboxamide (16.3 mg, 8.5%) as a brown solid. MS (ISP): 351.2 ([M+H]+).

Example 80

N-[2-[1-(2-Oxo-1,3-dihydrobenzimidazol-5-yl)benzimidazol-2-yl]ethyl]acetamide

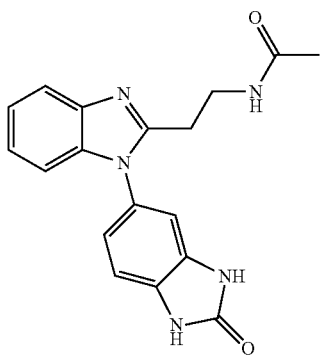 [SMILES: CC(=O)NCCc1nc2ccccc2n1-c1ccc2[nH]c(=O)[nH]c2c1]

a) 5-[2-(2-Aminoethyl)benzimidazol-1-yl]-1,3-dihydrobenzimidazol-2-one Hydrochloride Salt The title compound was obtained in analogy to example 61 using beta-alanine[136] in place of glycolic acid in step b. Grey solid. MS (ISP): 294.1 ([M+H]+).

b) N-[2-[1-(2-Oxo-1,3-dihydrobenzimidazol-5-yl)benzimidazol-2-yl]ethyl]acetamide To a stirred solution of 5-[2-(2-aminoethyl)benzimidazol-1-yl]-1,3-dihydrobenzimidazol-2-one hydrochloride (200 mg) in dichloromethane (10 ml) were added triethylamine (0.25 ml) and acetic anhydride (93 mg). The reaction mixture was stirred at room temperature for 12 hours. According to LC/MS, the reaction was finished. The reaction mixture was concentrated in vacuo. The crude material was purified by preparative reversed phase HPLC to afford N-[2-[1-(2-oxo-1,3-dihydrobenzimidazol-5-yl)benzimidazol-2-yl]ethyl]acetamide (14.6 mg, 3.6%) as a brown solid. MS (ISP): 336.1 ([M+H]+).

Example 81

N-Methyl-3-[1-(2-oxo-1,3-dihydrobenzimidazol-5-yl)benzimidazol-2-yl]propanamide

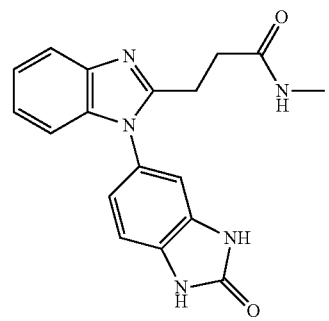 [SMILES: CNC(=O)CCc1nc2ccccc2n1-c1ccc2[nH]c(=O)[nH]c2c1]

a) 4-Oxo-4-[2-[(2-oxo-1,3-dihydrobenzimidazol-5-yl)amino]anilino]butanoic Acid

To a solution of succinic anhydride[137] (500 mg) in dichloromethane (15 ml) was added 5-(2-aminoanilino)-1,3-dihydrobenzimidazol-2-one (600 mg). The mixture was stirred at 25° C. for 12 hours. According to LC/MS, the reaction was finished. The reaction mixture was concentrated in vacuo to afford crude 4-oxo-4-[2-[(2-oxo-1,3-dihydrobenzimidazol-5-yl)amino]anilino]butanoic acid (800 mg, 94.1%), which was used in the next step without further purification. MS (ISP): 341.2 ([M+H]+).

b) 3-[1-(2-Oxo-1,3-dihydrobenzimidazol-5-yl)benzimidazol-2-yl]propanoic Acid

A solution of 4-oxo-4-[2-[(2-oxo-1,3-dihydrobenzimidazol-5-yl)amino]anilino]butanoic acid (800 mg) in a 6 M solution of HCl (15 ml) was stirred at 120° C. for 12 hours. According to LC/MS, the reaction was finished. The reaction mixture was concentrated in vacuo. The reaction mixture was concentrated in vacuo to afford crude 3-[1-(2-oxo-1,3-dihydrobenzimidazol-5-yl)benzimidazol-2-yl]

propanoic acid (550 mg, 72.6%) which was used in the next step without further purification. MS (ISP): 323.1 ([M+H]+).

c) N-Methyl-3-[1-(2-oxo-1,3-dihydrobenzimidazol-5-yl)benzimidazol-2-yl]propanamide To a solution of 3-[1-(2-oxo-1,3-dihydrobenzimidazol-5-yl)benzimidazol-2-yl]propanoic acid (500 mg) in N,N-dimethylformamide (10 ml) were added 1-(3-dimethylaminopropyl)-3-ethylcarbodiimide hydrochloride (892 mg),1-hydroxybenzotriazole (629 mg) and methylamine[94] (3.1 ml). The reaction mixture was stirred at 25° C. for 12 hours. According to LC/MS, the reaction was finished. The mixture was poured into water and extracted with ethyl acetate (3×20 ml). The combined organic layers were dried, filtered and concentrated in vacuo. The crude material was purified by preparative reversed phase HPLC to afford N-methyl-3-[1-(2-oxo-1,3-dihydrobenzimidazol-5-yl)benzimidazol-2-yl]propanamide (270 mg, 51.7%) as a yellow solid. MS (ISP): 336.1 ([M+H]+).

Example 82

Methyl 1-(2-oxo-1,3-dihydrobenzimidazol-5-yl)benzimidazole-2-carboxylate

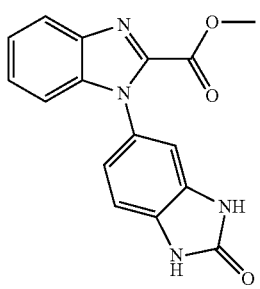 [SMILES: COC(=O)c1nc2ccccc2n1-c1ccc2[nH]c(=O)[nH]c2c1]

a) 5-[2-(Trichloromethyl)benzimidazol-1-yl]-1,3-dihydrobenzimidazol-2-one

To a solution of 5-(2-aminoanilino)-1,3-dihydrobenzimidazol-2-one (1000 mg) in acetic acid (15 ml) was added benzyl 2,2,2-trichloroacetimidate[138] (1.01 ml). The reaction mixture was stirred at 25° C. for 3 hours. According to LC/MS, the reaction was finished. The mixture was concentrated in vacuo. The residue was dissolved in ethyl acetate (30 ml) and washed with a aq. solution of sodium carbonate. The organic layer was dried, filtered and concentrated in vacuo. The crude material was purified by column chromatography (SiO2, petrol ether/ethylacetate 10:1) to afford 5-[2-(trichloromethyl)benzimidazol-1-yl]-1,3-dihydrobenzimidazol-2-one (1 g, 51.5%) as a yellow solid. MS (ISP): 368.8 ([M+H]+).

b) 5-[2-(Trimethoxymethyl)benzimidazol-1-yl]-1,3-dihydrobenzimidazol-2-one

To a solution of 5-[2-(trichloromethyl)benzimidazol-1-yl]-1,3-dihydrobenzimidazol-2-one (200 mg) in methanol (8 ml) was added sodium carbonate (86.5 mg). The reaction mixture was stirred at 80° C. for 12 hours. According to LC/MS, the reaction was finished. The reaction mixture was concentrated in vacuo to afford crude 5-[2-(trimethoxymethyl)benzimidazol-1-yl]-1,3-dihydrobenzimidazol-2-one (180 mg, 93.4%) which was used in the next step without further purification. MS (ISP): 355.2 ([M+H]+).

c) Methyl 1-(2-oxo-1,3-dihydrobenzimidazol-5-yl)benzimidazole-2-carboxylate

To a solution of 5-[2-(trimethoxymethyl)benzimidazol-1-yl]-1,3-dihydrobenzimidazol-2-one (180 mg) in methanol (8 ml) was added conc. HCl (2 ml). The reaction mixture was stirred at 25° C. for 12 hours. According to LC/MS, the reaction was finished. The reaction mixture was concentrated in vacuo. The crude material was purified by preparative reversed phase HPLC to afford methyl 1-(2-oxo-1,3-dihydrobenzimidazol-5-yl)benzimidazole-2-carboxylate (21.8 mg, 13.7%) as a yellow solid. MS (ISP): 309.1 ([M+H]+).

Example 83

5-(Benzimidazol-1-yl)-1,3-dihydrobenzimidazol-2-one

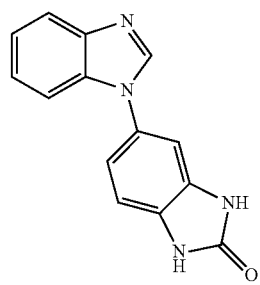 [SMILES: O=c1[nH]c2ccc(-n3cnc4ccccc43)cc2[nH]1]

The title compound was obtained in analogy to example 61 using formic acid[139] in place of glycolic acid for step b and heating for 12 hours instead of 48 hours. Grey solid. MS (ISP): 251.0 ([M+H]+).

Example 84

5-[2-(1-Hydroxyethyl)benzimidazol-1-yl]-1,3-dihydrobenzimidazol-2-one

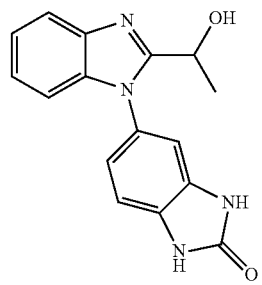

The title compound was obtained in analogy to example 61 using lactic acid[140] in place of glycolic acid for step b and heating for 12 hours instead of 48 hours. Yellow solid. MS (ISP): 295.1 ([M+H]+).

Example 85

5-[2-[Hydroxy(phenyl)methyl]benzimidazol-1-yl]-1,3-dihydrobenzimidazol-2-one

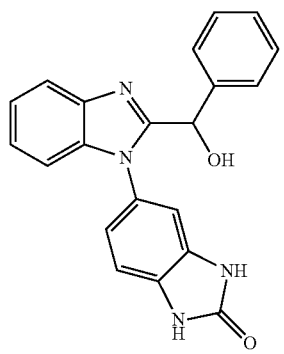 [SMILES: O=c1[nH]c2ccc(-n3c(C(O)c4ccccc4)nc4ccccc43)cc2[nH]1]

The title compound was obtained in analogy to example 61 using mandelic acid[141] in place of glycolic acid for step b and heating for 12 hours instead of 48 hours. Yellow solid. MS (ISP): 357.1 ([M+H]+).

Example 86

N-(1-Acetylpiperidin-4-yl)-N-methyl-2-oxo-2,3-dihydro-1H-benzo[d]imidazole-5-carboxamide

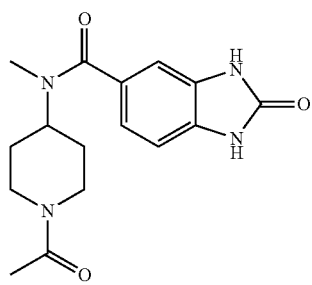 [SMILES: CC(=O)N1CCC(N(C)C(=O)c2ccc3[nH]c(=O)[nH]c3c2)CC1]

To a solution of 4-dimethylaminopyridine (165 mg) in N,N-dimethylformamide (5 ml) were added 2-oxo-2,3-dihydro-1H-benzimidazole-5-carboxylic acid[142] (200 mg), HATU (512 mg), N,N-diisopropylethylamine (0.59 ml) and 1-(4-(methylamino)piperidin-1-yl)ethanone hydrochloride[143] (216 mg), then the mixture was stirred at 25° C. for 16 hr. The reaction mixture was diluted with ethyl acetate (5 ml) and water (10 ml). The aqueous layer was extracted twice with ethyl acetate, then the combined organic layers were dried over Na2SO4 and concentrated in vacuo. The crude material was purified by preparative reversed phase HPLC to afford methyl N-(1-acetylpiperidin-4-yl)-N-methyl-2-oxo-2,3-dihydro-1H-benzo[d]imidazole-5-carboxamide (30 mg, 8.5%) as a yellow solid. MS (ISP): 317.2 ([M+H]+).

Example 87

1-(2-Oxo-2,3-dihydro-1H-benzo[d]imidazol-5-yl)-3-(4-(phenylamino)phenyl)urea

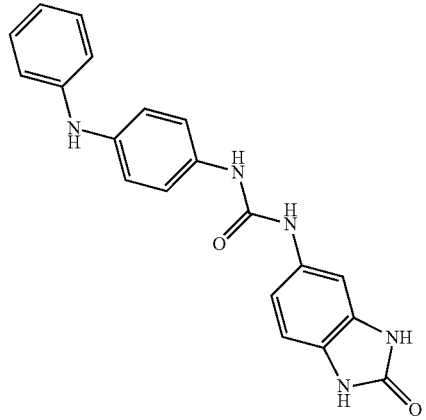 [SMILES: O=C(Nc1ccc(Nc2ccccc2)cc1)Nc1ccc2[nH]c(=O)[nH]c2c1]

To a stirred suspension of N1-phenylbenzene-1,4-diamine[144] (124 mg) and triethylamine (187 µl) in THF (2 ml) was added triphosgene (73.6 mg) at 0-5° C. The reaction mixture was stirred at room temperature for 1 h. A solution of 5-amino-1,3-dihydro-2H-benzo[d]imidazol-2-one[50] (100 mg) in DMF (1 ml) added and the reaction mixture was stirred at room temperature for 3 h. Water were added and the mixture was stirred at room temperature for 30 min. The product was collected by filtration, washing with water, and dried in vacuo in a drying oven to give 1-(2-oxo-2,3-dihydro-1H-benzo[d]imidazol-5-yl)-3-(4-(phenylamino)phenyl)urea (103 mg, 43%) as a grey solid. MS (ISP): 360.1 ([M+H]+).

Example 88

1-(2-Oxo-2,3-dihydro-1H-benzo[d]imidazol-5-yl)-3-phenylurea

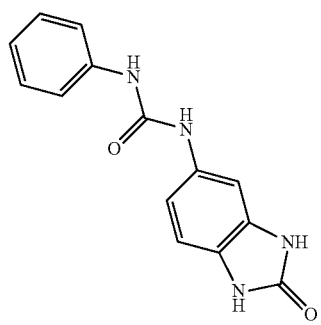 [SMILES: O=C(Nc1ccccc1)Nc1ccc2[nH]c(=O)[nH]c2c1]

The title compound was obtained in analogy to example 87 using aniline[90] in place of N1-phenylbenzene-1,4-diamine. Off-white solid. MS (ISP): 269.1 ([M+H]+).

Example 89

Methyl 1-((2-oxo-2,3-dihydro-1H-benzo[d]imidazol-5-yl)carbamoyl)indoline-4-carboxylate

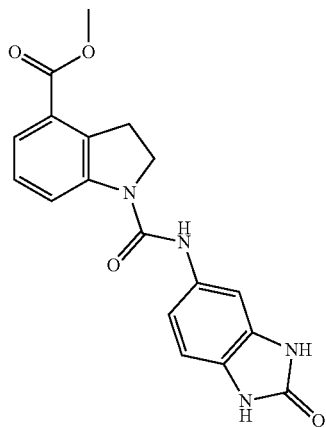 [SMILES: COC(=O)c1cccc2c1CCN2C(=O)Nc1ccc2[nH]c(=O)[nH]c2c1]

The title compound was obtained in analogy to example 87 using methyl indoline-4-carboxylate[114] in place of N1-phenylbenzene-1,4-diamine. Off-white solid. MS (ISP): 353.1 ([M+H]+).

Example 90

3-Acetamido-N-(2-oxo-2,3-dihydro-1H-benzo[d]imidazol-5-yl)propanamide

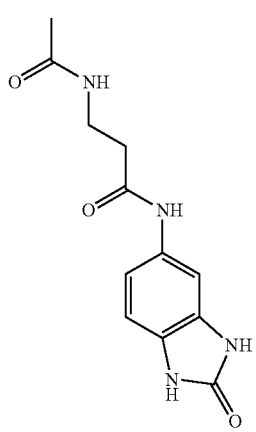 [SMILES: CC(=O)NCCC(=O)Nc1ccc2[nH]c(=O)[nH]c2c1]

The title compound was obtained in analogy to example 68 using 3-acetamidopropanoic acid[145] in place of benzofuran-3-carboxylic acid. White solid. MS (ISP): 263.1 ([M+H]+).

Example 91

1-Acetyl-N-(2-oxo-2,3-dihydro-1H-benzo[d]imidazol-5-yl)piperidine-4-carboxamide

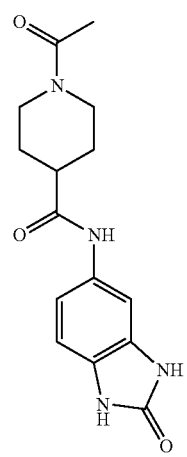 [SMILES: CC(=O)N1CCC(C(=O)Nc2ccc3[nH]c(=O)[nH]c3c2)CC1]

The title compound was obtained in analogy to example 68 using 1-acetylpiperidine-4-carboxylic acid[146] in place of benzofuran-3-carboxylic acid. White solid. MS (ISP): 303.1 ([M+H]+).

Example 92

Methyl 1-((2-oxo-2,3-dihydro-1H-benzo[d]imidazol-5-yl)carbamoyl)indoline-5-carboxylate

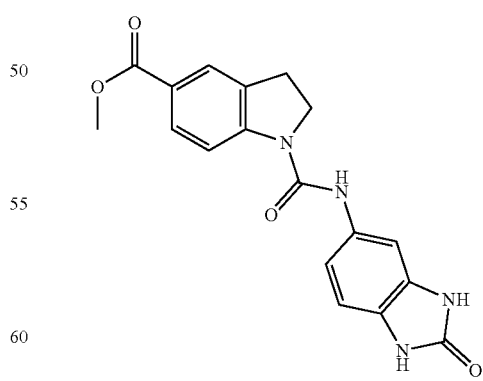

The title compound was obtained in analogy to example 87 using methyl indoline-5-carboxylate[147] in place of N1-phenylbenzene-1,4-diamine. Off-white solid. MS (ISP): 353.1 ([M+H]+).

Example 93

N4-Methyl-N1-(2-oxo-2,3-dihydro-1H-benzo[d]imidazol-5-yl)indoline-1,4-dicarboxamide

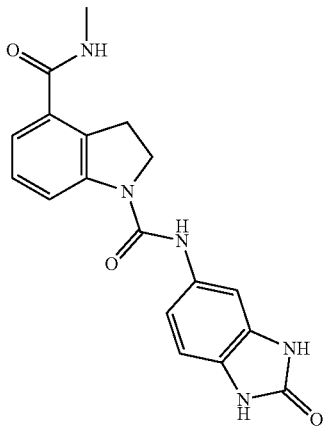 [SMILES: CNC(=O)c1cccc2c1CCN2C(=O)Nc1ccc2[nH]c(=O)[nH]c2c1]

a) 1-((2-Oxo-2,3-dihydro-1H-benzo[d]imidazol-5-yl)carbamoyl)indoline-4-carboxylic acid To a stirred suspension of methyl 1-((2-oxo-2,3-dihydro-1H-benzo[d]imidazol-5-yl)carbamoyl)indoline-4-carboxylate (120 mg, example 89) in THF (1.5 ml) and MeOH (1.5 ml) was added 1 M aq. LiOH solution (1.36 ml). The reaction mixture was stirred at room temperature overnight to afford a dark brown solution. LC-MS analysis indicated that the reaction was complete. 5 N aq. HCl was added dropwise to adjust the pH to 5 to give a light brown suspension. The reaction mixture was then filtered through a Sartorius funnel. The filter cake was dried in vacuo to afford 1-((2-oxo-2,3-dihydro-1H-benzo[d]imidazol-5-yl)carbamoyl)indoline-4-carboxylic acid (67 mg, 58%) as an off-white solid. The organic solvents of the filtrate were separated and concentrated in vacuo. Water was added to the residue and the resulting solution was lyophilised to afford a further quantity of 1-((2-oxo-2,3-dihydro-1H-benzo[d]imidazol-5-yl)carbamoyl)indoline-4-carboxylic acid as an off-white solid. The crude product was used in the next step without further purification.

b) N4-Methyl-N1-(2-oxo-2,3-dihydro-1H-benzo[d]imidazol-5-yl)indoline-1,4-dicarboxamide To a stirred suspension of 1-((2-oxo-2,3-dihydro-1H-benzo[d]imidazol-5-yl)carbamoyl)indoline-4-carboxylic acid (50 mg), N,N-diisopropylethylamine (155 μl) and methanamine (148 μl, 2 M solution in THF) in DMF (3 ml) was added HATU (112 mg). The reaction mixture was stirred at room temperature for 2 h. The reaction mixture was then poured into water and extracted with EtOAc/THF (1:2). The organic layer was separated, dried over $Na_2SO_4$, and concentrated in vacuo. The crude material was purified by preparative reverse phase HPLC (YMC-Triart C18, 12 nm, 5 μm, 100×30 mm, flow rate 40 ml/min, eluant: $CH_3CN$/$H_2O$ containing formic acid) followed by lyophilisation to afford N4-methyl-N1-(2-oxo-2,3-dihydro-1H-benzo[d]imidazol-5-yl)indoline-1,4-dicarboxamide (13 mg, 25%) as a white solid. MS (ISP): 352.1 ([M+H]$^+$).

Example 94

1-Benzyl-3-(2-oxo-2,3-dihydro-1H-benzo[d]imidazol-5-yl)urea

To a stirred suspension of (isocyanatomethyl)benzene[148] (89.3 mg) in THF (1 ml) at room temperature was added 5-amino-1,3-dihydro-2H-benzo[d]imidazol-2-one[50] (100 mg) and the reaction mixture was stirred for at room temperature for 1 h. The product was collected by filtration, washing with THF (20 ml), and dried in vacuo in a drying oven to give 1-benzyl-3-(2-oxo-2,3-dihydro-1H-benzo[d]imidazol-5-yl)urea (177 mg, 94%) as a grey solid grey solid. MS (ISP): 283.1 ([M+H]$^+$).

Example 95

6-(1,2,3,4-Tetrahydroquinoline-1-carbonyl)-1,3-dihydro-2H-imidazo[4,5-b]pyridin-2-one

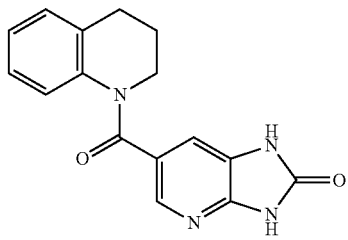 [SMILES: O=C(c1cnc2[nH]c(=O)[nH]c2c1)N1CCCc2ccccc21]

The title compound was obtained in analogy to example 22 using 1,2,3,4-tetrahydroquinoline[149] in place of 1-(piperazin-1-yl)ethanone and 2-oxo-2,3-dihydro-1H-imidazo[4,5-b]pyridine-6-carboxylic acid instead of 2-oxo-2,3-dihydro-1H-benzo[d]imidazole-5-carboxylic acid. White solid. MS (ISP): 295.3 ([M+H]$^+$).

Example 96[150]

N-Methyl-2-oxo-N-phenyl-2,3-dihydro-1H-benzo[d]imidazole-5-carboxamide

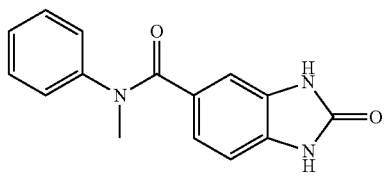 [SMILES: CN(C(=O)c1ccc2[nH]c(=O)[nH]c2c1)c1ccccc1]

The title compound can be purchased.

Example 97[151]

5-(1,2,3,4-Tetrahydroquinoline-1-carbonyl)-1,3-dihydro-2H-benzo[d]imidazol-2-one

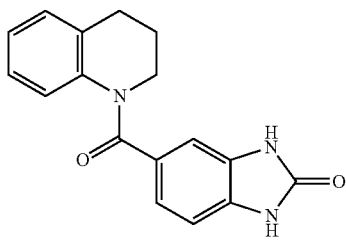 [SMILES: O=C(c1ccc2[nH]c(=O)[nH]c2c1)N1CCCc2ccccc21]

The title compound can be purchased.

Example 98

Methyl 1-((2-oxo-2,3-dihydro-1H-benzo[d]imidazol-5-yl)carbamoyl)-1,2,3,4-tetrahydroquinoline-5-carboxylate

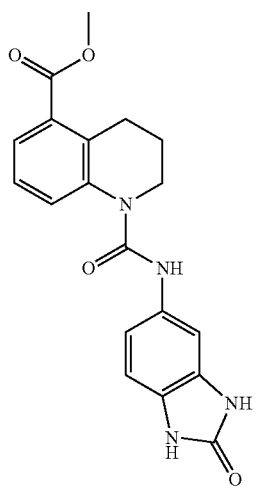 [SMILES: COC(=O)c1cccc2c1CCCN2C(=O)Nc1ccc2[nH]c(=O)[nH]c2c1]

The title compound was obtained in analogy to example 87 using methyl 1,2,3,4-tetrahydroquinoline-5-carboxylate[152] in place of N1-phenylbenzene-1,4-diamine. Grey solid. MS (ISP): 367.3 ([M+H]$^+$).

Example 99

N-(2-Oxo-2,3-dihydro-1H-benzo[d]imidazol-5-yl)-2-(4-sulfamoylphenyl)acetamide

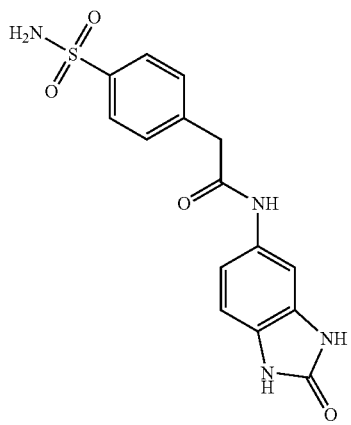 [SMILES: NS(=O)(=O)c1ccc(CC(=O)Nc2ccc3[nH]c(=O)[nH]c3c2)cc1]

The title compound was obtained in analogy to example 68 using 2-(4-sulfamoylphenyl)acetic acid[153] in place of benzofuran-3-carboxylic acid. White solid. MS (ISP): 347.1 ([M+H]$^+$).

Example 100

N-(2-Oxo-2,3-dihydro-1H-benzo[d]imidazol-5-yl)-4-sulfamoylbenzamide

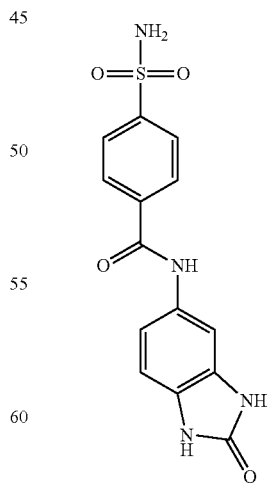

The title compound was obtained in analogy to example 68 using 4-sulfamoylbenzoic acid[154] in place of benzofuran-3-carboxylic acid. White solid. MS (ISP): 333.1 ([M+H]$^+$).

Example 101

N-(2-Oxo-2,3-dihydro-1H-benzo[d]imidazol-5-yl)-4-sulfamoylbenzamide

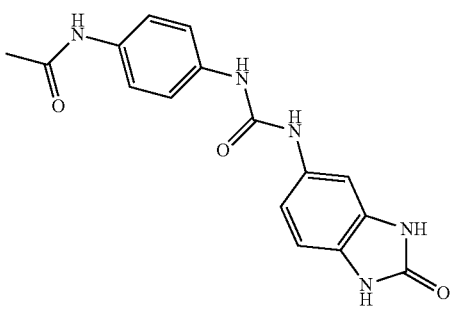 [SMILES: CC(=O)Nc1ccc(NC(=O)Nc2ccc3[nH]c(=O)[nH]c3c2)cc1]

The title compound was obtained in analogy to example 87 using N-(4-aminophenyl)acetamide[155] in place of N1-phenylbenzene-1,4-diamine. Brown solid. MS (ISP): 326.1 ([M+H]+).

Example 102

N-Methyl-1-(2-oxo-1,3-dihydrobenzimidazol-5-yl)benzimidazole-2-carboxamide

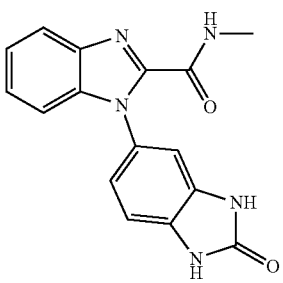 [SMILES: CNC(=O)c1nc2ccccc2n1-c1ccc2[nH]c(=O)[nH]c2c1]

a) Methyl 1-(2-oxo-1,3-dihydrobenzimidazol-5-yl)benzimidazole-2-carboxylate

To a solution of 5-[2-(trichloromethyl)benzimidazol-1-yl]-1,3-dihydrobenzimidazol-2-one (3.0 g) in methanol (40 ml) was added sodium methoxide (440 mg). The reaction mixture was stirred at 80° C. for 12 hours. According to LC/MS, the reaction was finished. The reaction mixture was concentrated in vacuo to afford crude methyl 1-(2-oxo-1,3-dihydrobenzimidazol-5-yl)benzimidazole-2-carboxylate (3 g, 67.9%) which was used in the next step without further purification. MS (ISP): 309.0 ([M+H]+).

b) N-Methyl-1-(2-oxo-1,3-dihydrobenzimidazol-5-yl)benzimidazole-2-carboxamide

To a solution of methyl 1-(2-oxo-1,3-dihydrobenzimidazol-5-yl)benzimidazole-2-carboxylate (300 mg) in methanol (10 ml) were added methylamine (0.73 ml) and triethylamine (0.27 ml The reaction mixture was stirred at 80° C. for 4 hours. According to LC/MS, the reaction was finished, the reaction mixture was concentrated in vacuo. The crude material was purified by preparative reversed phase HPLC to afford N-methyl-1-(2-oxo-1,3-dihydrobenzimidazol-5-yl)benzimidazole-2-carboxamide (85.4 mg, 27.8%) as a yellow solid. MS (ISP): 308.2 ([M+H]+).

Example 103

5-[2-(Piperidine-1-carbonyl)benzimidazol-1-yl]-1,3-dihydrobenzimidazol-2-one

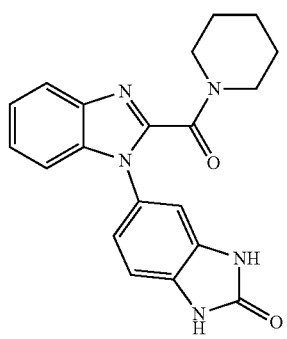 [SMILES: O=C(c1nc2ccccc2n1-c1ccc2[nH]c(=O)[nH]c2c1)N1CCCCC1]

The title compound was obtained in analogy to example 102 using piperidine[156] in place of methylamine for step b. White solid. MS (ISP): 362.6 ([M+H]+).

Example 104

6-(2-(Benzyloxy)phenyl)-1,3-dihydro-2H-imidazo[4,5-b]pyridin-2-one

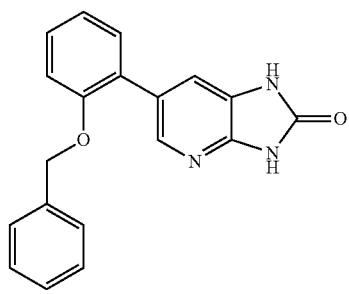 [SMILES: O=c1[nH]c2cc(-c3ccccc3OCc3ccccc3)cnc2[nH]1]

To a stirred solution of (2-(benzyloxy)phenyl)boronic acid[157] (100 mg) and 6-bromo-1,3-dihydro-2H-imidazo[4,5-b]pyridin-2-one (94 mg) in water (0.3 ml) and dioxane (1.5 ml) was added 1,1'-bis(diphenylphosphino)ferrocene-palladium(II) dichloride dichloromethane complex (35.8 mg) at room temperature. After degassing for 10 minutes with argon, Cs$_2$CO$_3$ (286 mg) was added. The suspension was stirred at 90° C. for 16 hours. The reaction mixture was partitioned between water and ethyl acetate. The organic layer was washed with brine, dried over Na$_2$SO$_4$, filtered and concentrated in vacuo. The crude material was stirred in a mixture of dichloromethane/methanol 95:5, filtered and dried to afford 6-(2-(benzyloxy)phenyl)-1,3-dihydro-2H-imidazo[4,5-b]pyridin-2-one (75.8 mg, 54.5%) as a light yellow solid MS (ISP): 318.3 ([M+H]+).

Example 105

N-(2-Oxo-2,3-dihydro-1H-benzo[d]imidazol-5-yl)indoline-1-carboxamide

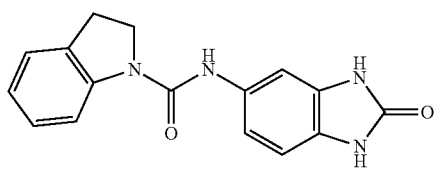 [SMILES: O=C(Nc1ccc2[nH]c(=O)[nH]c2c1)N1CCc2ccccc21]

The title compound was obtained in analogy to example 87 using 1H-indoline[86] in place of N1-phenylbenzene-1,4-diamine. Purple solid. MS (ISP): 295.1 ([M+H]$^+$).

Example 106

2-(4-(N-Methylsulfamoyl)phenyl)-N-(2-oxo-2,3-dihydro-1H-benzo[d]imidazol-5-yl)acetamide

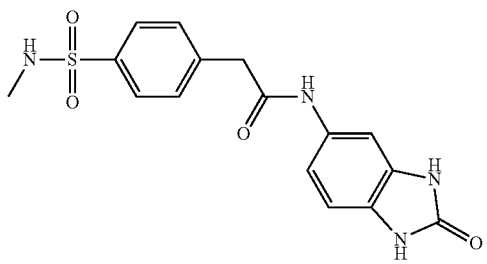 [SMILES: CNS(=O)(=O)c1ccc(CC(=O)Nc2ccc3[nH]c(=O)[nH]c3c2)cc1]

The title compound was obtained in analogy to example 68 using 2-(4-(N-methylsulfamoyl)phenyl)acetic acid[158] in place of benzofuran-3-carboxylic acid. White solid. MS (ISP): 361.1 ([M+H]$^+$).

Example 107

Methyl 2-(2-(1-methyl-1H-imidazol-5-yl)quinolin-4-yl)-2'-oxo-2',3'-dihydro-1'H-[1,5'-bibenzo[d]imidazole]-5-carboxylate

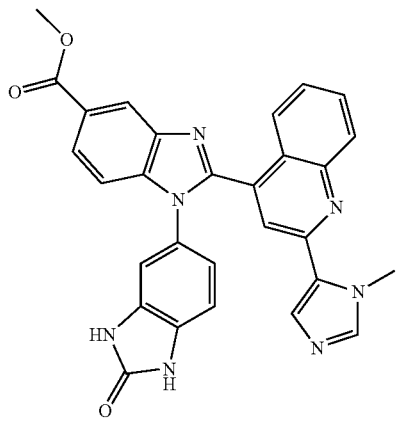 [SMILES: COC(=O)c1ccc2c(c1)nc(-c1cc(-c3cncn3C)nc3ccccc13)n2-c1ccc2[nH]c(=O)[nH]c2c1]

a) Methyl 3-amino-4-((2-oxo-2,3-dihydro-1H-benzo[d]imidazol-5-yl)amino)benzoate

The title compound was obtained in analogy to example 1 using methyl 4-fluoro-3-nitrobenzoate[48] in place of 4-fluoro-N-methyl-3-nitrobenzamide in step a. Grey solid. MS (ISP): 299.2 ([M+H]$^+$).

b) Methyl 2-(2-(1-methyl-1H-imidazol-5-yl)quinolin-4-yl)-2'-oxo-2',3'-dihydro-1'H-[1,5'-bibenzo[d]imidazole]-5-carboxylate The title compound was obtained in analogy to example 2 using methyl 3-amino-4-((2-oxo-2,3-dihydro-1H-benzo[d]imidazol-5-yl)amino)benzoate in place of 3-amino-N-methyl-4-[(2-oxo-1,3-dihydrobenzimidazol-5-yl)amino]benzamide. Light brown solid. MS (ISP): 516.2 ([M+H]$^+$).

Example 108

2-(2-Methoxypyridin-4-yl)-N-methyl-2'-oxo-2',3'-dihydro-1'H-[1,5'-bibenzo[d]imidazole]-5-carboxamide

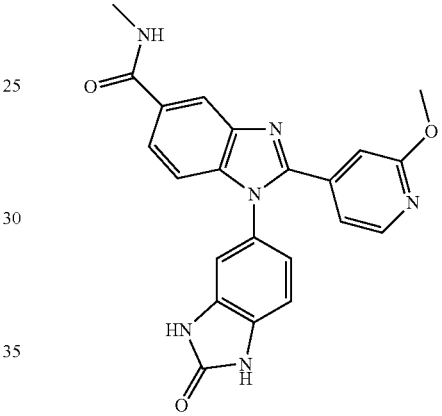

The title compound was obtained in analogy to example 2 using 2-methoxyisonicotinaldehyde[159] in place of 2-(3-methylimidazol-4-yl)quinoline-4-carbaldehyde. White solid. MS (ISP): 415.2 ([M+H]$^+$).

Example 109

N5-Methyl-N1-(2-oxo-2,3-dihydro-1H-benzo[d]imidazol-5-yl)-3,4-dihydroquinoline-1,5(2H)-dicarboxamide

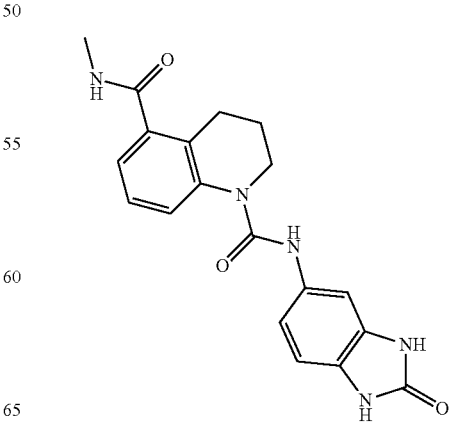

The title compound was obtained in analogy to example 93 using methyl 1-((2-oxo-2,3-dihydro-1H-benzo[d]imidazol-5-yl)carbamoyl)-1,2,3,4-tetrahydroquinoline-5-carboxylate (example 98) instead of methyl 1-((2-oxo-2,3-dihydro-1H-benzo[d]imidazol-5-yl)carbamoyl)indoline-4-carboxylate. White solid. MS (ISP): 366.2 ([M−H]−).

Example 110

5-(5-Bromo-1-oxo-isoindolin-2-yl)-1,3-dihydrobenzimidazol-2-one

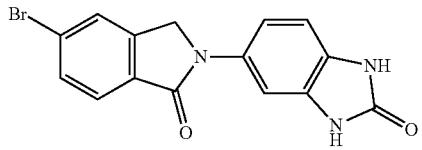 [SMILES: O=C1c2ccc(Br)cc2CN1c1ccc2[nH]c(=O)[nH]c2c1]

a) Methyl 4-bromo-2-[[(2-oxo-1,3-dihydrobenzimidazol-5-yl)amino]methyl]benzoate

To a solution of methyl 4-bromo-2-(bromomethyl)benzoate[160] (1.0 g) in methanol (10 ml) was added triethylamine (0.56 ml) and 5-amino-1,3-dihydro-2H-benzimidazol-2-one (0.4 g). The reaction mixture was stirred at 25° C. for 12 hours. The yellow suspension obtained was filtered and the solid dried in vacuo to afford crude methyl 4-bromo-2-[[(2-oxo-1,3-dihydrobenzimidazol-5-yl)amino]methyl]benzoate (1 g, 98.7%) which was used in the next step without further purification.

b) Methyl 1-oxo-2-(2-oxo-1,3-dihydrobenzimidazol-5-yl)isoindoline-5-carboxylate

To a solution of methyl 4-bromo-2-[[(2-oxo-1,3-dihydrobenzimidazol-5-yl)amino]methyl]benzoate (1.0 g) in ethanol (5 ml) was added potassium carbonate (551 mg). The reaction mixture was stirred at 80° C. for 4 hours. The resulting yellow suspension was filtered, and the filter cake was washed sequentially with water, ethyl acetate and ethanol and then dried in vacuo to afford 5-(5-bromo-1-oxo-isoindolin-2-yl)-1,3-dihydrobenzimidazol-2-one (460 mg, 50.3%). Yellow solid. MS (ISP): MS (IPS): 344.1 [M+H]+ 79Br; 346.1 [M+H]+ 81Br Example 111

Ethyl 1-oxo-2-(2-oxo-1,3-dihydrobenzimidazol-5-yl)isoindoline-5-carboxylate

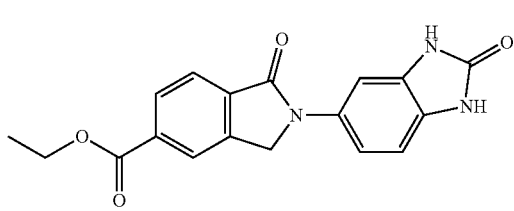 [SMILES: CCOC(=O)c1ccc2c(c1)CN(c1ccc3[nH]c(=O)[nH]c3c1)C2=O]

a) Dimethyl 2-[[(2-oxo-1,3-dihydrobenzimidazol-5-yl)amino]methyl]benzene-1,4-dicarboxylate To a solution of dimethyl 2-(bromomethyl)benzene-1,4-dicarboxylate[63] (1.7 g) in methanol (2 ml) were added triethylamine (1.24 ml) and 5-amino-1,3-dihydro-2H-benzimidazol-2-one (883 mg). The reaction mixture was stirred at 25° C. for 12 hours. The resulting suspension was filtered and the filtrate was concentrated in vacuo. The residue was diluted with water (20 ml) and ethyl acetate (30 ml). The layers were separated and the aqueous layer was extracted with ethyl acetate (2×20 ml). The combined organic layers were washed with brine, dried with $Na_2SO_4$, filtered and concentrated in vacuo to afford dimethyl 2-[[(2-oxo-1,3-dihydrobenzimidazol-5-yl)amino]methyl]benzene-1,4-dicarboxylate in a 1:1 mixture with dimethyl 2-[[[2,5-bis(methoxycarbonyl)phenyl]methyl-(2-oxo-1,3-dihydrobenzimidazol-5-yl)amino]methyl]benzene-1,4-dicarboxylate (1.47 g), which was used in the next step without further purification.

b) Ethyl 1-oxo-2-(2-oxo-1,3-dihydrobenzimidazol-5-yl)isoindoline-5-carboxylate

The title compound was obtained in analogy to example 110 using dimethyl 2-[[(2-oxo-1,3-dihydrobenzimidazol-5-yl)amino]methyl]benzene-1,4-dicarboxylate in place of methyl 4-bromo-2-[[(2-oxo-1,3-dihydrobenzimidazol-5-yl)amino]methyl]benzoate. White solid. MS (ISP): 336.3 ([M−H]−).

Example 112

Methyl 1-oxo-2-(2-oxo-1,3-dihydrobenzimidazol-5-yl)isoindoline-5-carboxylate

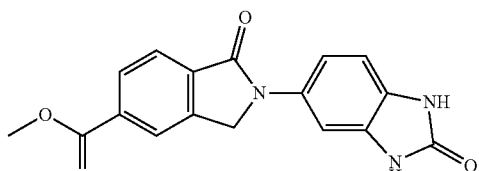

The title compound was obtained in analogy to example 111 using methanol as solvent instead of ethanol in the final step. Light yellow solid. MS (ISP): 322.3 ([M−H]−).

Example 113

2-(2-(1-Methyl-1H-imidazol-5-yl)quinolin-4-yl)-2'-oxo-2',3'-dihydro-1'H-[1,5'-bibenzo[d]imidazole]-5-carboxamide

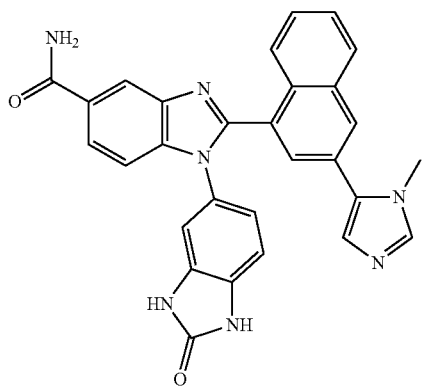 [SMILES: Cn1cncc1-c1cc(-c2nc3cc(C(N)=O)ccc3n2-c2ccc3[nH]c(=O)[nH]c3c2)c2ccccc2c1]

The title compound was obtained in analogy to example 18 step e using aqueous ammonia in place of dimethylamine. Light brown solid. MS (ISP): 501.2 ([M+H]$^+$).

Example 114

N-Methyl-2'-oxo-2-(1-phenylcyclopropyl)-2',3'-dihydro-1'H-[1,5'-bibenzo[d]imidazole]-5-carboxamide

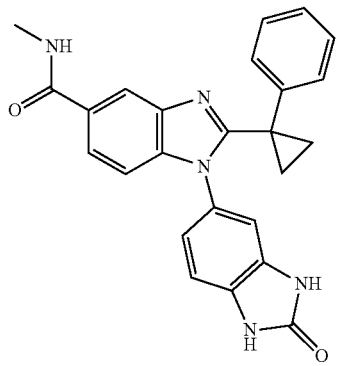 [SMILES: CNC(=O)c1ccc2c(c1)nc(C1(c3ccccc3)CC1)n2-c1ccc2[nH]c(=O)[nH]c2c1]

The title compound was obtained in analogy to example 2 using 1-phenylcyclopropane-1-carbaldehyde[161] in place of 2-(3-methylimidazol-4-yl)quinoline-4-carbaldehyde. White solid. MS (ISP): 424.2 ([M+H]$^+$).

Example 115

2-(1-(4-Methoxyphenyl)cyclopropyl)-N-methyl-2'-oxo-2',3'-dihydro-1'H-[1,5'-bibenzo[d]imidazole]-5-carboxamide

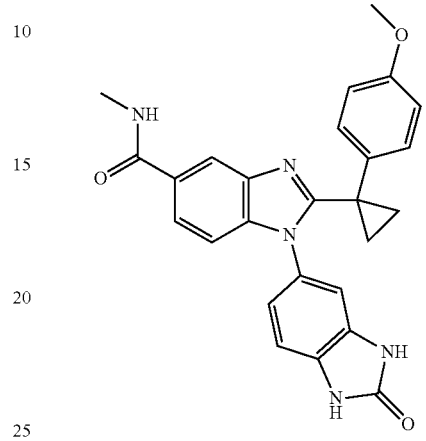

The title compound was obtained in analogy to example 2 using 1-(4-methoxyphenyl)cyclopropane-1-carbaldehyde[162] in place of 2-(3-methylimidazol-4-yl)quinoline-4-carbaldehyde. Light yellow solid. MS (ISP): 454.2 ([M+H]$^+$).

Example 116

5-(Indolin-1-ylsulfonyl)-1,3-dihydro-2H-benzo[d]imidazol-2-one

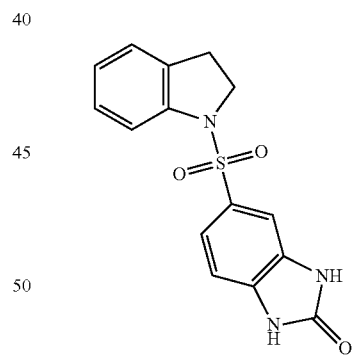

To a stirred solution of indoline[86] (25.6 mg) in pyridine (0.5 ml) was added 2-oxo-2,3-dihydro-1H-benzo[d]imidazole-5-sulfonyl chloride[59] (50 mg). The reaction mixture was stirred at room temperature overnight. LC-MS analysis indicated that the reaction was complete. The reaction mixture was poured into EtOAc/THF (1:3) and extracted sequentially with 2 M aq. HCl and with saturated brine. The organic layer was dried over Na$_2$SO$_4$ and concentrated in vacuo. The crude material was purified by flash chromatography (silica gel, 0% to 10% MeOH in dichloromethane) to afford 5-(indolin-1-ylsulfonyl)-1,3-dihydro-2H-benzo[d]imidazol-2-one (44 mg, 65%) as a white solid. MS (ISP): 314.1 ([M−H]$^-$).

Example 117

N-(1-Acetylpiperidin-4-yl)-2-oxo-2,3-dihydro-1H-benzo[d]imidazole-5-sulfonamide

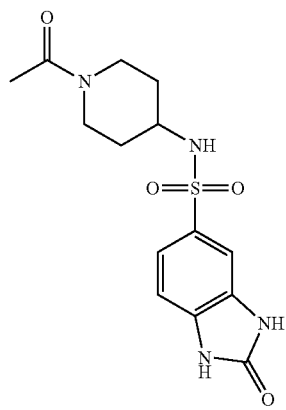 [SMILES: CC(=O)N1CCC(NS(=O)(=O)c2ccc3[nH]c(=O)[nH]c3c2)CC1]

The title compound was obtained in analogy to example 116 using 1-(4-aminopiperidin-1-yl)ethan-1-one[85] in place of indoline. White solid. MS (ISP): 339.1 ([M+H]+).

Example 118

Methyl 4-(N-(2-oxo-2,3-dihydro-1H-benzo[d]imidazol-5-yl)sulfamoyl)benzoate

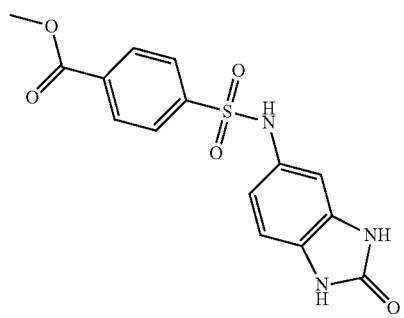 [SMILES: COC(=O)c1ccc(S(=O)(=O)Nc2ccc3[nH]c(=O)[nH]c3c2)cc1]

To a stirred solution of 5-amino-1,3-dihydro-2H-benzo[d]imidazol-2-one[50] (50 mg) in pyridine (0.5 ml) was added methyl 4-(chlorosulfonyl)benzoate[163] (78.7 mg). The reaction mixture was stirred at room temperature for 1 h. LC-MS analysis indicated that the reaction was complete. The reaction mixture was poured into EtOAc/THF (1:3) and extracted sequentially with diluted 2 M aq. HCl and with saturated brine. The organic layer was dried over $Na_2SO_4$ and concentrated in vacuo. The residue was taken up in dichloromethane and the mixture was ultrasonicated at room temperature. The mixture was then filtered through sintered glass, and the solid was dried in vacuo to afford methyl 4-(N-(2-oxo-2,3-dihydro-1H-benzo[d]imidazol-5-yl)sulfamoyl)benzoate (101 mg, 87%) as an off-white solid. MS (ISP): 348.1 ([M+H]+).

Example 119 tert-Butyl (1-((2-oxo-2,3-dihydro-1H-benzo[d]imidazol-5-yl)carbamoyl)indolin-5-yl)carbamate

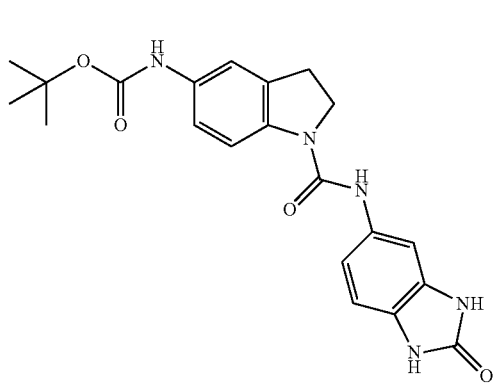 [SMILES: CC(C)(C)OC(=O)Nc1ccc2c(c1)CCN2C(=O)Nc1ccc2[nH]c(=O)[nH]c2c1]

The title compound was obtained in analogy to example 87 using tert-butyl indolin-5-ylcarbamate[164] in place of N1-phenylbenzene-1,4-diamine. Brown solid. MS (ISP): 408.2 ([M–H]−).

Example 120

5-(Benzyloxy)-2-isopropyl-1',3'-dihydro-2'H-[1,5'-bibenzo[d]imidazol]-2'-one

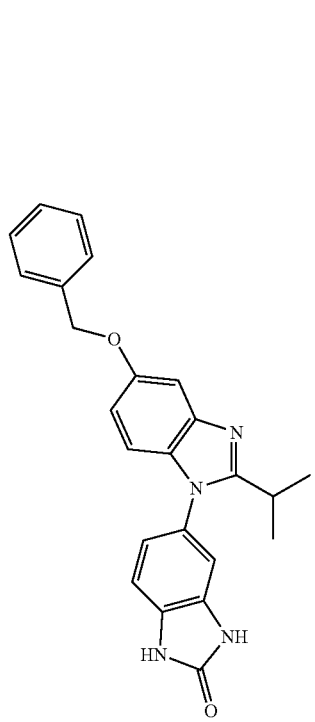 [SMILES: CC(C)c1nc2cc(OCc3ccccc3)ccc2n1-c1ccc2[nH]c(=O)[nH]c2c1]

a) 5-((4-(Benzyloxy)-2-nitrophenyl)amino)-1,3-di-hydro-2H-benzo[d]imidazol-2-one To a stirred solution of 5-amino-1,3-dihydro-2H-benzo[d]imidazol-2-one[50] (200 mg) and 4-(benzyloxy)-1-fluoro-2-nitrobenzene[165] (332 mg) in N-methyl-2-pyrrolidinone (2 ml) was added N,N-diisopropylethylamine (351 µl) at room temperature. The reaction mixture was heated at 120° C. for 15 h. LC-MS analysis indicated that the reaction was complete. The reaction mixture was partitioned between 1:1 ethyl acetate/THF (50-ml) and 1 M aqueous sodium hydroxide solution (30 ml). The layers were separated and the aqueous layer was extracted with three 30 ml portions of ethyl acetate. The combined organic layers were washed with one 25 ml portion of saturated brine, dried over anhydrous sodium sulfate, and concentrated in vacuo. The crude material was purified by flash chromatography ($SiO_2$, eluant: dichloromethane/methanol 100:0 to 95:5) to give 5-((4-(benzyloxy)-2-nitrophenyl)amino)-1,3-dihydro-2H-benzo[d]imidazol-2-one (410 mg, 81%) as a red solid. MS (ISP): 377.2 ([M+H]$^+$).

b) 5-((2-Amino-4-(benzyloxy)phenyl)amino)-1,3-dihydro-2H-benzo[d]imidazol-2-one To a stirred suspension of 5-((4-(benzyloxy)-2-nitrophenyl)amino)-1,3-dihydro-2H-benzo[d]imidazol-2-one (410 mg) and iron dust (608 mg) in 1:5 water/EtOH (2 ml) at room temperature was added acetic acid (624 µl). The reaction mixture was then heated at reflux with shaking for 2 h. LC-MS analysis indicated that the reaction was complete. The solids were removed by filtration over HiFlo Decalit and washed with ethyl acetate. The filtrate was partitioned between ethyl acetate (50 ml) and 2 M aq. sodium carbonate (30 ml). The layers were separated. The aqueous layer was extracted with two 20 ml portions of ethyl acetate. The combined organic layers were washed with one 20 ml portion of saturated brine, dried over anhydrous sodium sulfate, and concentrated in vacuo. The crude material was purified by flash chromatography ($SiO_2$, eluant: dichloromethane/methanol 100:0 to 90:10) to give 5-((2-amino-4-(benzyloxy)phenyl)amino)-1,3-dihydro-2H-benzo[d]imidazol-2-one as a red solid. MS (ISP): 347.2 ([M+H]$^+$).

c) 5-(Benzyloxy)-2-isopropyl-1',3'-dihydro-2'H-[1,5'-bibenzo[d]imidazol]-2'-one To a stirred solution of 5-((2-amino-4-(benzyloxy)phenyl)amino)-1,3-dihydro-2H-benzo[d]imidazol-2-one (95 mg,) and isobutyraldehyde (100 µl) in N,N-dimethylformamide (2 ml) at room temperature was added sodium metabisulfite (209 mg). The reaction mixture was then heated at 120° C. for 2 h. LC-MS analysis indicated that the reaction was complete. The reaction mixture was partitioned between 1:1 THF/ethyl acetate (20 ml) and water (20 ml). The layers were separated. The aqueous layer was extracted with one 15 ml portion of ethyl acetate. The combined organic layers were washed with one 10 ml portion of saturated brine, dried over anhydrous sodium sulfate, and concentrated in vacuo to afford 5-(benzyloxy)-2-isopropyl-1',3'-dihydro-2'H-[1,5'-bibenzo[d]imidazol]-2'-one ((22 mg, 20%) as a white solid. MS (ISP): 399.2 ([M+H]$^+$).

Example 121

5-Amino-N-(2-oxo-2,3-dihydro-1H-benzo[d]imidazol-5-yl)indoline-1-carboxamide

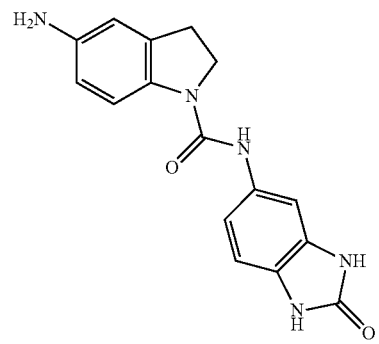 [SMILES: Nc1ccc2c(c1)CCN2C(=O)Nc1ccc2[nH]c(=O)[nH]c2c1]

To a stirred suspension of tert-butyl (1-((2-oxo-2,3-dihydro-1H-benzo[d]imidazol-5-yl)carbamoyl)indolin-5-yl)carbamate (130 mg, example 119) in 1,4-dioxane (0.5 ml) at room temperature was added 4 M hydrogen chloride solution in 1,4-dioxane (1.5 ml). The reaction mixture was stirred at room temperature overnight. LC-MS analysis indicated that the reaction was finished. The resulting solid was collected by filtration, washed with methanol and pentane and dried in vacuo to give 5-amino-N-(2-oxo-2,3-dihydro-1H-benzo[d]imidazol-5-yl)indoline-1-carboxamide (69 mg, 63%) as its hydrochloride salt as a brown solid. MS (ISP): 310.1 ([M+H]$^+$).

Example 122

2'-Methyl-N-(2-oxo-2,3-dihydro-1H-benzo[d]imidazol-5-yl)-[1,1'-biphenyl]-2-carboxamide

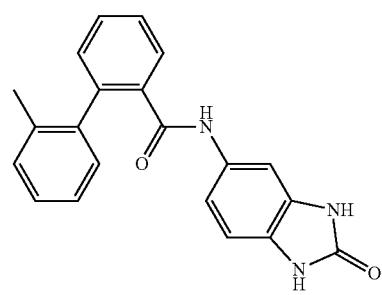 [SMILES: Cc1ccccc1-c1ccccc1C(=O)Nc1ccc2[nH]c(=O)[nH]c2c1]

The title compound was obtained in analogy to example 68 using 2'-methyl-[1,1'-biphenyl]-2-carboxylic acid[166] in place of benzofuran-3-carboxylic acid. White solid. MS (ISP): 344.1 ([M+H]$^+$).

Example 123

2-Benzyl-N-(2-oxo-2,3-dihydro-1H-benzo[d]imidazol-5-yl)benzamide

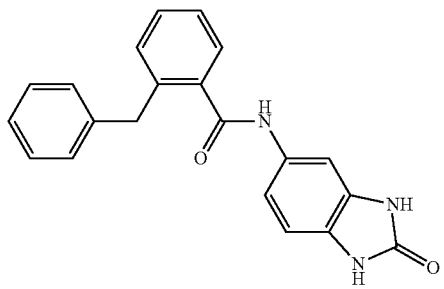 [SMILES: O=C(Nc1ccc2[nH]c(=O)[nH]c2c1)c1ccccc1Cc1ccccc1]

The title compound was obtained in analogy to example 68 using 2-benzylbenzoic acid[167] in place of benzofuran-3-carboxylic acid. White solid. MS (ISP): 344.1 ([M+H]+).

Example 124

2-Isopropyl-5-methoxy-1',3'-dihydro-2'H-[1,5'-bibenzo[d]imidazol]-2'-one

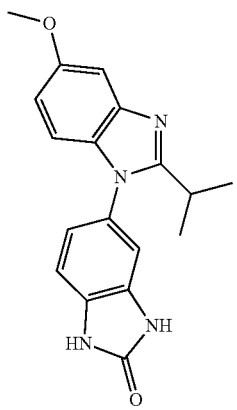 [SMILES: COc1ccc2c(c1)nc(C(C)C)n2-c1ccc2[nH]c(=O)[nH]c2c1]

The title compound was obtained in analogy to example 120 using 1-fluoro-4-methoxy-2-nitrobenzene[168] in place of 4-(benzyloxy)-1-fluoro-2-nitrobenzene in step a. Off-white solid. MS (ISP): 323.1 ([M+H]+).

Example 125 tert-Butyl 4-(N-(2-oxo-2,3-dihydro-1H-benzo[d]imidazol-5-yl)sulfamoyl)piperidine-1-carboxylate

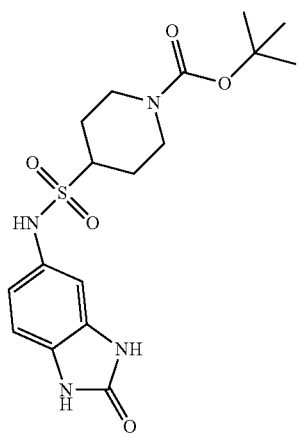 [SMILES: CC(C)(C)OC(=O)N1CCC(S(=O)(=O)Nc2ccc3[nH]c(=O)[nH]c3c2)CC1]

The title compound was obtained in analogy to example 118 using tert-butyl 4-(chlorosulfonyl)piperidine-1-carboxylate[169] in place of methyl 4-(chlorosulfonyl)benzoate. White solid. MS (ISP): 395.1 ([M−H]−).

Example 126

Ethyl 4-(3-(2-oxo-2,3-dihydro-1H-benzo[d]imidazol-5-yl)ureido)benzoate

The title compound was obtained in analogy to example 87 using ethyl 4-aminobenzoate[106] in place of N1-phenylbenzene-1,4-diamine. Off-white solid. MS (ISP): 341.1 ([M+H]+).

Example 127

1-(3-Fluorophenyl)-3-(2-oxo-2,3-dihydro-1H-benzo[d]imidazol-5-yl)urea

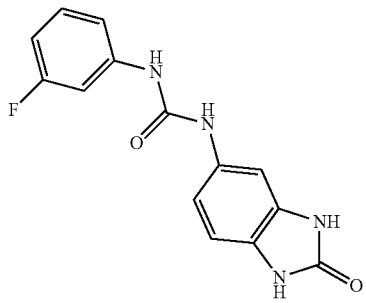 [SMILES: O=C(Nc1cccc(F)c1)Nc1ccc2[nH]c(=O)[nH]c2c1]

The title compound was obtained in analogy to example 87 using 3-fluoroaniline[170] in place of N1-phenylbenzene-1,4-diamine. Off-white solid. MS (ISP): 287.1 ([M+H]⁺).

Example 128

4-(2-Methoxyphenyl)-N-(2-oxo-2,3-dihydro-1H-benzo[d]imidazol-5-yl)piperazine-1-carboxamide

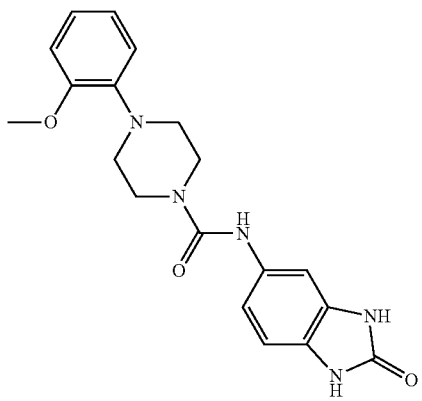 [SMILES: COc1ccccc1N1CCN(C(=O)Nc2ccc3[nH]c(=O)[nH]c3c2)CC1]

The title compound was obtained in analogy to example 87 using 1-(2-methoxyphenyl)piperazine[171] in place of N1-phenylbenzene-1,4-diamine. Off-white solid. MS (ISP): 366.1 ([M−H]⁻).

Example 129

6-Chloro-N-(2-oxo-2,3-dihydro-1H-benzo[d]imidazol-5-yl)indoline-1-carboxamide

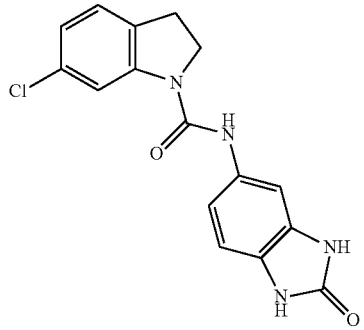 [SMILES: O=C(Nc1ccc2[nH]c(=O)[nH]c2c1)N1CCc2ccc(Cl)cc21]

The title compound was obtained in analogy to example 87 using 6-chloroindoline[172] in place of N1-phenylbenzene-1,4-diamine. Off-white solid. MS (ISP): 329.1 ([M+H]⁺) 329.1 ({³⁵Cl}[M+H]⁺), 331.1 ({³⁷Cl}) [M+H]⁺).

Example 130

N-(3-(1-Methyl-1H-pyrazol-3-yl)phenyl)-2-oxo-2,3-dihydro-1H-benzo[d]imidazole-5-carboxamide

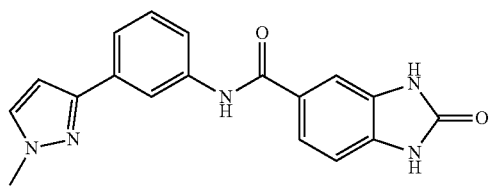 [SMILES: Cn1ccc(-c2cccc(NC(=O)c3ccc4[nH]c(=O)[nH]c4c3)c2)n1]

The title compound was obtained in analogy to example 22 using 3-(1-methyl-1H-pyrazol-3-yl)aniline[173] in place of 1-(piperazin-1-yl)ethanone. Off-white solid. MS (ISP): 334.1 ([M+H]⁺).

Example 131

2-(4-Methoxycyclohexyl)-N-methyl-2'-oxo-2',3'-dihydro-1'H-[1,5'-bibenzo[d]imidazole]-5-carboxamide

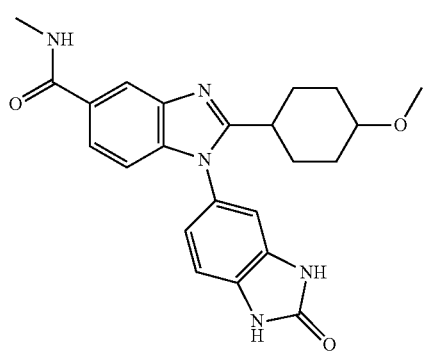 [SMILES: CNC(=O)c1ccc2c(c1)nc(C1CCC(OC)CC1)n2-c1ccc2[nH]c(=O)[nH]c2c1]

The title compound was obtained in analogy to example 2 using 4-methoxycyclohexane-1-carbaldehyde[174] in place of 2-(3-methylimidazol-4-yl)quinoline-4-carbaldehyde. Off-white solid. MS (ISP): 420.2 ([M+H]+).

Example 132

3-Methoxy-N-(2-oxo-2,3-dihydro-1H-benzo[d]imidazol-5-yl)isonicotinamide

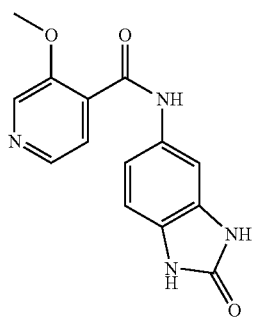 [SMILES: COc1cnccc1C(=O)Nc1ccc2[nH]c(=O)[nH]c2c1]

The title compound was obtained in analogy to example 68 using 3-methoxyisonicotinic acid[175] in place of benzofuran-3-carboxylic acid. Off-white solid. MS (ISP): 285.1 ([M+H]+).

Example 133

N2-Methyl-N5-(2-oxo-2,3-dihydro-1H-benzo[d]imidazol-5-yl)pyridine-2,5-dicarboxamide

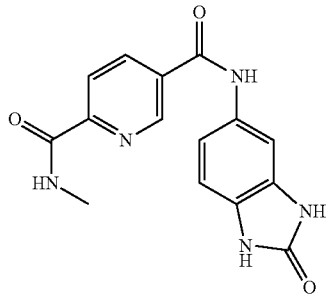 [SMILES: CNC(=O)c1ccc(C(=O)Nc2ccc3[nH]c(=O)[nH]c3c2)cn1]

The title compound was obtained in analogy to example 68 using 6-(methylcarbamoyl)nicotinic acid[176] in place of benzofuran-3-carboxylic acid. Light grey solid. MS (ISP): 312.1 ([M+H]+).

Example 134

N-(2-Oxo-2,3-dihydro-1H-benzo[d]imidazol-5-yl)piperidine-4-sulfonamide

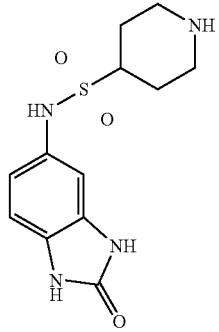

A solution of tert-butyl 4-(N-(2-oxo-2,3-dihydro-1H-benzo[d]imidazol-5-yl)sulfamoyl)piperidine-1-carboxylate (55 mg, example 125) and 4 M hydrogen chloride solution in 1,4-dioxane (1.05 g, 1 ml, 4 mmol, Eq: 28.8) in 1,4-dioxane (1 ml) was stirred at room temperature for 15 h. LC-MS analysis indicated that the reaction was finished. The solid product was collected by filtration, washing with 1,4-dioxane, to afford N-(2-oxo-2,3-dihydro-1H-benzo[d]imidazol-5-yl)piperidine-4-sulfonamide (36 mg, 78%) as its hydrochloride salt as an off-white solid. MS (ISP): 295.1 ([M−H]−).

Example 135

4-(4-Chlorobenzyl)-N-(2-oxo-2,3-dihydro-1H-benzo[d]imidazol-5-yl)piperazine-1-carboxamide

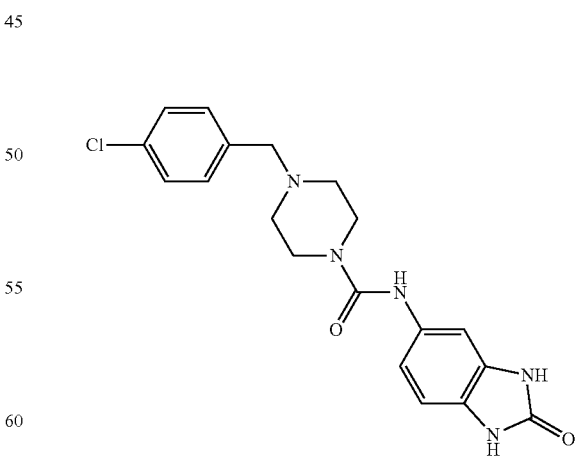

The title compound was obtained in analogy to example 87 using 1-(4-chlorobenzyl)piperazine[177] in place of N1-phenylbenzene-1,4-diamine. White solid. MS (ISP): 386.1 ({35Cl}[M+H]+), 388.1 ({37Cl}[M+H]+).

Example 136

N-(2-Oxo-2,3-dihydro-1H-benzo[d]imidazol-5-yl)-2-(pyridin-4-yl)benzamide

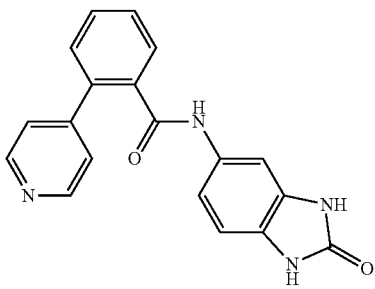 [SMILES: O=C(Nc1ccc2[nH]c(=O)[nH]c2c1)c1ccccc1-c1ccncc1]

The title compound was obtained in analogy to example 68 using 2-(pyridin-4-yl)benzoic acid[178] in place of benzofuran-3-carboxylic acid. White solid. MS (ISP): 331.1 ([M+H]+).

Example 137

N-(2-Oxo-2,3-dihydro-1H-benzo[d]imidazol-5-yl)benzofuran-3-sulfonamide

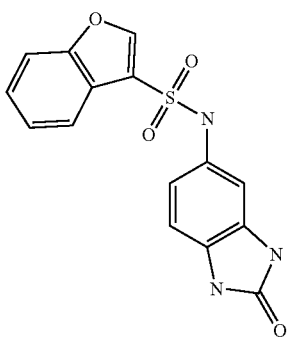 [SMILES: O=c1[nH]c2ccc(NS(=O)(=O)c3coc4ccccc34)cc2[nH]1]

The title compound was obtained in analogy to example 118 using benzofuran-3-sulfonyl chloride[179] in place of methyl 4-(chlorosulfonyl)benzoate. Off-white solid. MS (ISP): 330.1 ([M+H]+).

Example 138

2-(3-Methoxyphenyl)-N-(2-oxo-2,3-dihydro-1H-benzo[d]imidazol-5-yl)nicotinamide

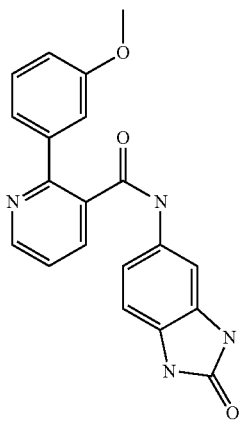 [SMILES: COc1cccc(-c2ncccc2C(=O)Nc2ccc3[nH]c(=O)[nH]c3c2)c1]

The title compound was obtained in analogy to example 68 using 2-(3-methoxyphenyl)nicotinic acid[180] in place of benzofuran-3-carboxylic acid. White solid. MS (ISP): 361.1 ([M+H]+).

Example 139

N-(1-Benzylpiperidin-4-yl)-2-oxo-2,3-dihydro-1H-benzo[d]imidazole-5-carboxamide

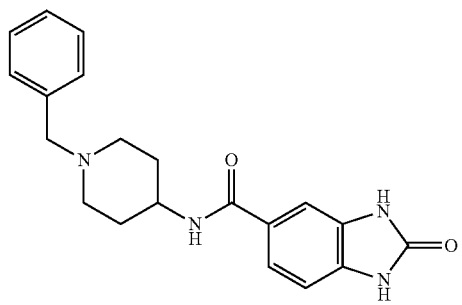 [SMILES: O=C(NC1CCN(Cc2ccccc2)CC1)c1ccc2[nH]c(=O)[nH]c2c1]

To a stirred suspension of methyl 2-oxo-2,3-dihydro-1H-benzo[d]imidazole-5-carboxylate[57] (100 mg) and 1-benzylpiperidin-4-amine[181] (119 mg) in toluene (2 ml) under argon was added dropwise trimethylaluminum (520 µl, 2 M solution in toluene) to give a brown solution. The reaction mixture was stirred at 110° C. for 2 h. LC-MS analysis indicated that the reaction was complete. The reaction mixture was quenched by dropwise addition to water (10 ml). THF (50 ml) was then added. The resulting mixture was stirred at room temperature for 1 h. The mixture was then washed twice with saturated brine. The organic layer was dried over Na2SO4 and concentrated in vacuo. The crude material was triturated in EtOAc (4 ml), then filtered through sintered glass, washing with EtOAc (2x) and then with Et2O (2x). The solid crystals were dried in vacuo to afford 124 mg of an off-white solid. The impure solid was triturated with methanol (5 ml), then filtered through sintered glass, washing with methanol (1x), and then with Et2O (2x). The crystalline product was dried in vacuo to afford N-(1-benzylpiperidin-4-yl)-2-oxo-2,3-dihydro-1H-benzo[d]imidazole-5-carboxamide (83 mg, 46%) as a white solid. MS (ISP): 351.1 ([M+H]+).

Example 140

5-(5-Aminoindolin-1-yl)-1,3-dihydro-2H-benzo[d]imidazol-2-one hydrochloride

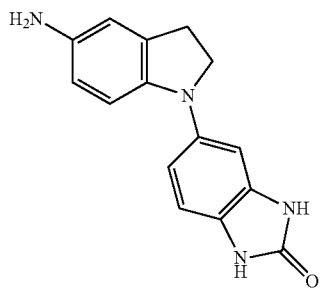 [SMILES: Nc1ccc2c(c1)CCN2c1ccc2[nH]c(=O)[nH]c2c1]

The title compound was obtained as its hydrochloride salt in analogy to example 58 using tert-butyl indolin-5-ylcarbamate[164] in place of tert-butyl piperazine-1-carboxylate in step a. Grey solid. MS (ISP): 267.1 ([M+H]+).

Example 141

N-(1-(2-Oxo-2,3-dihydro-1H-benzo[d]imidazol-5-yl)indolin-5-yl)acetamide

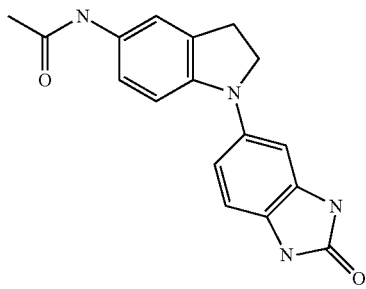 [SMILES: CC(=O)Nc1ccc2c(c1)CCN2c1ccc2[nH]c(=O)[nH]c2c1]

To a stirred suspension of 5-(5-aminoindolin-1-yl)-1,3-dihydro-2H-benzo[d]imidazol-2-one dihydrochloride (47 mg) and triethylamine (96.6 µl) in dichloromethane (3 ml) was added dropwise acetic anhydride (19.6 µl). The reaction mixture was stirred at room temperature for 2 h. LC-MS analysis indicated that the reaction was complete. The reaction mixture was poured into THF/EtOAc (3:1) and extracted sequentially with water and with saturated brine. The organic layer was dried over Na$_2$SO$_4$ and concentrated in vacuo. The crude material was purified by flash chromatography (silica gel, eluant: 0% to 10% MeOH in dichloromethane) to afford N-(1-(2-oxo-2,3-dihydro-1H-benzo[d]imidazol-5-yl)indolin-5-yl)acetamide (24 mg, 56%) as an off-white solid. MS (ISP): 309.2 ([M+H]+).

Example 142

N-(3-(Oxazol-5-yl)phenyl)-2-oxo-2,3-dihydro-1H-benzo[d]imidazole-5-carboxamide

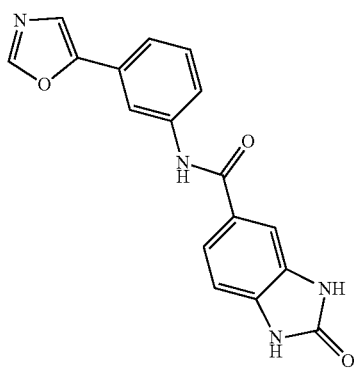 [SMILES: O=C(Nc1cccc(-c2cnco2)c1)c1ccc2[nH]c(=O)[nH]c2c1]

The title compound was obtained in analogy to example 139 using 3-(oxazol-5-yl)aniline[182] in place of 1-benzylpiperidin-4-amine. Off-white solid. MS (ISP): 321.1 ([M+H]+).

Example 143 tert-Butyl 4-((2-oxo-2,3-dihydro-1H-benzo[d]imidazol-5-yl)carbamoyl)indoline-1-carboxylate

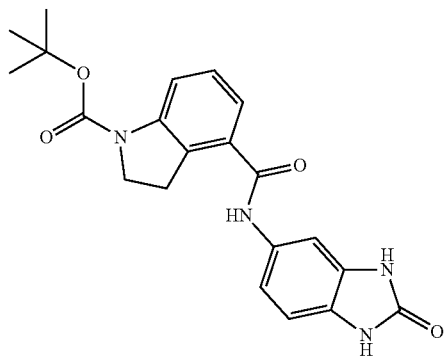 [SMILES: CC(C)(C)OC(=O)N1CCc2c(C(=O)Nc3ccc4[nH]c(=O)[nH]c4c3)cccc21]

The title compound was obtained in analogy to example 68 using 1-(tert-butoxycarbonyl)indoline-4-carboxylic acid[183] in place of benzofuran-3-carboxylic acid. Off-white solid. MS (ISP): 393.3 ([M−H]−).

Example 144

N-(2-Oxo-2,3-dihydro-1H-benzo[d]imidazol-5-yl)indoline-4-carboxamide

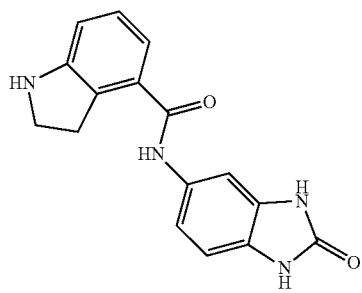 [SMILES: O=C(Nc1ccc2[nH]c(=O)[nH]c2c1)c1cccc2c1CCN2]

To a stirred suspension of tert-butyl 4-((2-oxo-2,3-dihydro-1H-benzo[d]imidazol-5-yl)carbamoyl)indoline-1-carboxylate (120 mg) in dichloromethane (5 ml) was added a solution of 4 M HCl in dioxane (1.52 ml). The reaction mixture was stirred at room temperature for 2 h. An additional aliquot of 4 M HCl in dioxane (761 µl) was added and the reaction mixture was stirred at room temperature for a further 2 h. The reaction mixture was filtered through a sintered glass funnel to afford N-(2-oxo-2,3-dihydro-1H-benzo[d]imidazol-5-yl)indoline-4-carboxamide hydrochloride (95 mg, 94% yield) as its hydrochloride salt as an off-white solid. MS (ISP): 295.2 ([M+H]+).

Example 145

1-Acetyl-N-(2-oxo-2,3-dihydro-1H-benzo[d]imidazol-5-yl)indoline-4-carboxamide

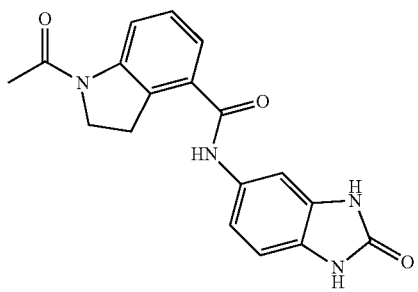 [SMILES: CC(=O)N1CCc2c(C(=O)Nc3ccc4[nH]c(=O)[nH]c4c3)cccc21]

To a stirred suspension of N-(2-oxo-2,3-dihydro-1H-benzo[d]imidazol-5-yl)indoline-4-carboxamide hydrochloride (95 mg) and triethylamine (160 µl) in dichloromethane (3 ml) was added dropwise acetic anhydride (40.6 µl). The reaction mixture was stirred at room temperature for 2 h. LC-MS analysis indicated that the reaction was complete. The reaction mixture was poured into THF/EtOAc (3:1) and extracted with water. The aqueous layer was filtered through a sintered glass funnel. The solid was collected and DMSO (2 ml) was added to give a suspension. The suspension was filtered through a sintered glass funnel and washed with water (20 ml). The solid was collected and dried in vacuo to afford 1-acetyl-N-(2-oxo-2,3-dihydro-1H-benzo[d]imidazol-5-yl)indoline-4-carboxamide (35 mg, 36.%) as a white solid. MS (ISP): 337.2 ([M+H]$^+$).

Example 146

N-(4-(((2-Oxo-2,3-dihydro-1H-benzo[d]imidazol-5-yl)methyl)amino)phenyl)acetamide

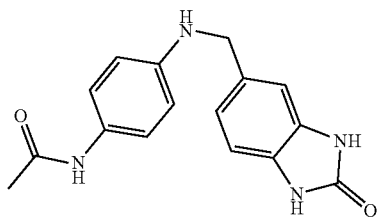 [SMILES: CC(=O)Nc1ccc(NCc2ccc3[nH]c(=O)[nH]c3c2)cc1]

To a stirred suspension of 2-oxo-2,3-dihydro-1H-benzo[d]imidazole-5-carbaldehyde[60] (100 mg) and N-(4-aminophenyl)acetamide[155] (97.5 mg) in methanol (8 ml) were added zinc chloride (336 mg) and sodium cyanoborohydride (116 mg). The reaction mixture was shaken at 60° C. for 3 h. LC-MS analysis indicated that the reaction was complete. The reaction mixture was added to water. THF was added, then 1 N aq. HCl was added to adjust the pH to 3. The reaction mixture was then stirred at room temperature for 10 min. The mixture was extracted with saturated brine. The organic layer was dried over Na$_2$SO$_4$ and concentrated in vacuo. The crude material was purified by flash chromatography (silica gel, eluant: 0% to 10% MeOH in dichloromethane) to afford N-(4-(((2-oxo-2,3-dihydro-1H-benzo[d]imidazol-5-yl)methyl)amino)phenyl)acetamide (65 mg, 36%) as a yellow solid. MS (ISP): 297.1 ([M+H]$^+$).

Example 147

N-(2-(Methylcarbamoyl)phenyl)-2-oxo-2,3-dihydro-1H-benzo[d]imidazole-5-carboxamide

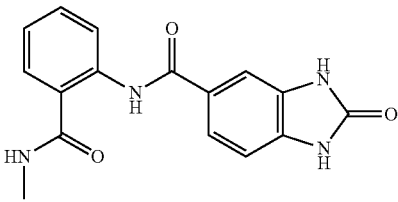 [SMILES: CNC(=O)c1ccccc1NC(=O)c1ccc2[nH]c(=O)[nH]c2c1]

The title compound was obtained in analogy to example 139 using 2-amino-N-methylbenzamide[184] in place of 1-benzylpiperidin-4-amine. White solid. MS (ISP): 311.1 ([M+H]$^+$).

Example 148 tert-Butyl (1-((2-oxo-2,3-dihydro-1H-benzo[d]imidazol-5-yl)methyl)indolin-5-yl)carbamate

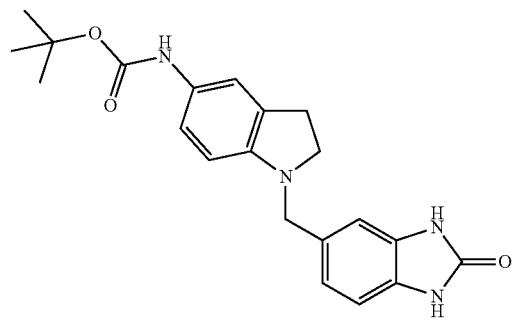 [SMILES: CC(C)(C)OC(=O)Nc1ccc2c(c1)CCN2Cc1ccc2[nH]c(=O)[nH]c2c1]

The title compound was obtained in analogy to example 146 using tert-butyl indolin-5-ylcarbamate[164] in place of N-(4-aminophenyl)acetamide. White solid. MS (ISP): 381.1 ([M+H]$^+$).

Example 149

5-((5-Aminoindolin-1-yl)methyl)-1,3-dihydro-2H-benzo[d]imidazol-2-one

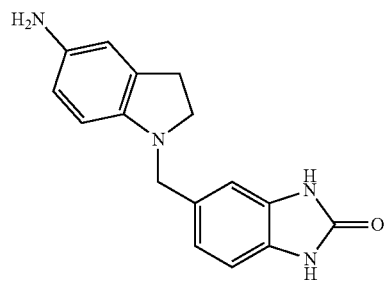 [SMILES: Nc1ccc2c(c1)CCN2Cc1ccc2[nH]c(=O)[nH]c2c1]

To a stirred suspension of tert-butyl (1-((2-oxo-2,3-dihydro-1H-benzo[d]imidazol-5-yl)methyl)indolin-5-yl)carbamate (64 mg) in dichloromethane (5 ml) at room temperature was added a solution of 4 N HCl in dioxane (841 µl). The reaction mixture was stirred at room temperature overnight. The reaction mixture was filtered through a Sartorius funnel, washing twice with diethyl ether), and the solid was dried in vacuo to afford 5-((5-aminoindolin-1-yl)methyl)-1,3-dihydro-2H-benzo[d]imidazol-2-one (74 mg, quant.) as its hydrochloride salt as a white solid. MS (ISP): 281.1 ([M+H]+).

Example 150

N-(1-((2-Oxo-2,3-dihydro-1H-benzo[d]imidazol-5-yl)methyl)indolin-5-yl)acetamide

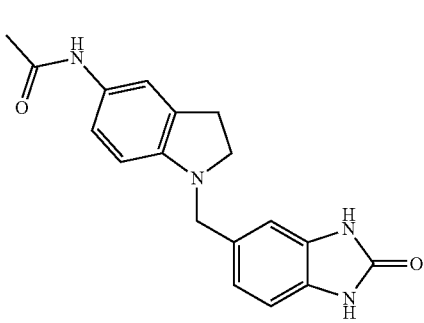 [SMILES: CC(=O)Nc1ccc2c(c1)CCN2Cc1ccc2[nH]c(=O)[nH]c2c1]

To a stirred suspension of 5-((5-aminoindolin-1-yl)methyl)-1,3-dihydro-2H-benzo[d]imidazol-2-one hydrochloride (50 mg) and triethylamine (88 µl) in dichloromethane (3 ml) at room temperature was added dropwise acetic anhydride (22.3 µl). The reaction mixture was stirred at room temperature for 2 h. LC-MS analysis indicated that the reaction was complete. The reaction mixture was poured into THF/EtOAc (4:1) and extracted with saturated brine. The organic layer was dried over $Na_2SO_4$ and concentrated in vacuo. The crude material was purified by flash chromatography (silica gel, eluant: 0% to 10% MeOH in dichloromethane) to afford N-(1-((2-oxo-2,3-dihydro-1H-benzo[d]imidazol-5-yl)methyl)indolin-5-yl)acetamide (10 mg, 20%) as an off-white solid. MS (ISP): 323.2 ([M+H]+).

Example 151

Methyl 2-((2-oxo-2,3-dihydro-1H-benzo[d]imidazol-5-yl)carbamoyl)benzoate

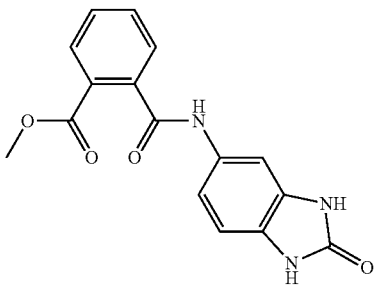 [SMILES: COC(=O)c1ccccc1C(=O)Nc1ccc2[nH]c(=O)[nH]c2c1]

The title compound was obtained in analogy to example 68 using 2-(methoxycarbonyl)benzoic acid[185] in place of benzofuran-3-carboxylic acid. White solid. MS (ISP): 312.1 ([M+H]+).

Example 152

5-((1-Benzylpiperidin-4-yl)amino)-1,3-dihydro-2H-benzo[d]imidazol-2-one

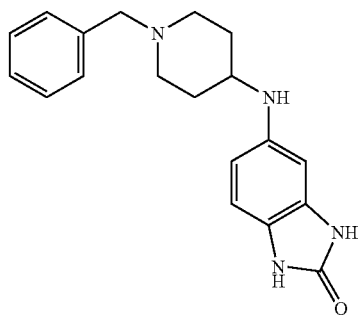 [SMILES: O=c1[nH]c2ccc(NC3CCN(Cc4ccccc4)CC3)cc2[nH]1]

The title compound was obtained in analogy to example 58 steps a-c using 1-benzylpiperidin-4-amine[181] in place of tert-butyl piperazine-1-carboxylate in step a. Purple solid. MS (ISP): 323.1 ([M+H]+).

Example 153

Methyl 6-((2-oxo-2,3-dihydro-1H-benzo[d]imidazol-5-yl)amino)nicotinate

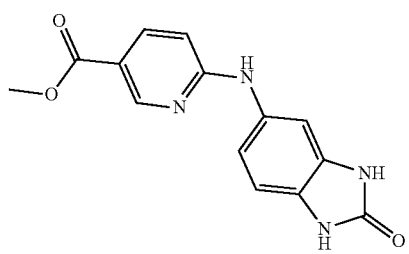 [SMILES: COC(=O)c1ccc(Nc2ccc3[nH]c(=O)[nH]c3c2)nc1]

The title compound was obtained in analogy to example 58 steps a-c using methyl 6-aminonicotinate[186] in place of tert-butyl piperazine-1-carboxylate, potassium tert-butoxide in place of N,N-diisopropylethylamine, and DMSO in place of acetonitrile in step a. Light yellow solid. MS (ISP): 285.1 ([M+H]+).

Example 154

5-(Benzyloxy)-1,3-dihydro-2H-benzo[d]imidazol-2-one

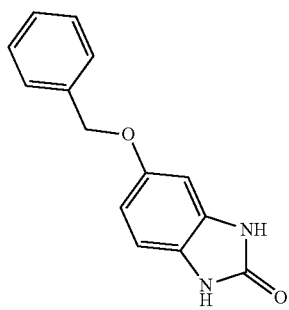 [SMILES: O=c1[nH]c2ccc(OCc3ccccc3)cc2[nH]1]

a) 4-(Benzyloxy)-1,2-dinitro-benzene

To a stirred suspension of benzyl alcohol (1 ml) and potassium hydroxide (49.7 mg) at room temperature was added 4-fluoro-1,2-dinitrobenzene[62] (150 mg) and tris[2-(2-methoxyethoxy)ethyl]amine (25.8 µl). The reaction mixture was stirred at room temperature for 15 h. LC-MS analysis indicated that the reaction was complete. The reaction mixture was partitioned between ethyl acetate (75 ml) and water (40 ml). The layers were separated and the aqueous layer was extracted with two 30 ml portions of ethyl acetate. The combined organic layers were washed sequentially with one 40 ml portion of water and one 40 ml portion of saturated brine, then dried over anhydrous sodium sulfate and concentrated in vacuo. The crude material was purified by flash chromatography (SiO2, eluant: n-heptane/ethyl acetate: 100:0 to 75:25) to give, after concentration under high vacuum, 4-(benzyloxy)-1,2-dinitro-benzene (242 mg, 93%) as a light yellow oil which was used in the next step without further purification.

b) 4-(Benzyloxy)benzene-1,2-diamine

To a solution of 4-(benzyloxy)-1,2-dinitrobenzene (247 mg) and 37% aq. HCl (2 ml) in ethanol (2 ml) at room temperature was added tin (II) chloride dihydrate (711 mg). The reaction mixture was stirred at 60° C. for 5 h. LC-MS analysis indicated that the reaction was finished. The reaction mixture was quenched at 0-5° C. with 2 M aqueous sodium hydroxide solution and then stirred for 10 min. The reaction mixture was partitioned between 1:1 ethyl acetate/THF (50 ml) and 1 M aqueous sodium hydroxide solution (30 ml). The layers were separated. The aqueous layer was extracted once with ethyl acetate (40 ml). The combined organic layers were washed once with saturated brine (30 ml), dried over anhydrous sodium sulfate, and concentrated in vacuo to afford 4-(benzyloxy)benzene-1,2-diamine (148 mg, 77%) as a yellow solid which was used in the next step without further purification. MS (ISP): 215.0 ([M+H]$^+$).

c) 5-(Benzyloxy)-1,3-dihydro-2H-benzo[d]imidazol-2-one

To a stirred suspension of 4-(benzyloxy)benzene-1,2-diamine (148 mg) in tetrahydrofuran (3 ml) at room temperature was added CDI (168 mg). The reaction mixture was stirred at room temperature for 30 min. LC-MS analysis indicated that the reaction was finished. The reaction mixture was partitioned between 1:1 ethyl acetate/THF (50 ml) and saturated brine (30 ml). The layers were separated and the organic layer was washed with once with saturated brine (20 ml), dried over anhydrous sodium sulfate, and concentrated in vacuo. Preparative reverse-phase HPLC (Gemini NX 3 um, 50 mm×4.6 mm column) afforded 5-(benzyloxy)-1,3-dihydro-2H-benzo[d]imidazol-2-one (32 mg, 19%) as a white solid. MS (ISP): 241.1 ([M+H]$^+$).

Example 155

Methyl 2-((2-oxo-2,3-dihydro-1H-benzo[d]imidazol-5-yl)methyl)isoindoline-5-carboxylate

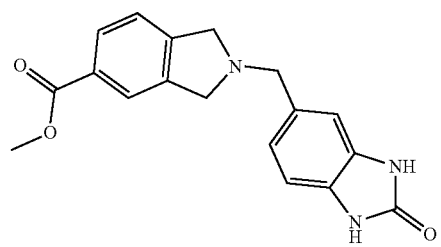 [SMILES: COC(=O)c1ccc2c(c1)CN(Cc1ccc3[nH]c(=O)[nH]c3c1)C2]

The title compound was obtained in analogy to example 146 using methyl isoindoline-5-carboxylate[187] in place of N-(4-aminophenyl)acetamide. Grey solid. MS (ISP): 324.1 ([M+H]$^+$).

Example 156

N-Methyl-4-((2-oxo-2,3-dihydro-1H-benzo[d]imidazol-5-yl)oxy)benzamide

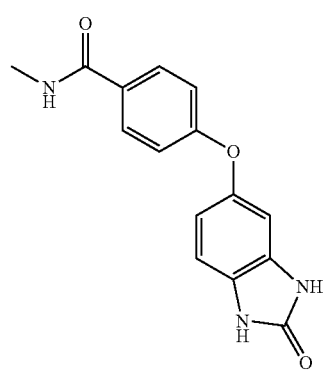 [SMILES: CNC(=O)c1ccc(Oc2ccc3[nH]c(=O)[nH]c3c2)cc1]

The title compound was obtained in analogy to example 154 using 4-hydroxy-N-methylbenzamide[188] in place of benzyl alcohol in step a. Off-white solid. MS (ISP): 284.1 ([M+H]$^+$).

Example A

N-(5-(2-((6S)-4-(4-chlorophenyl)-2,3,9-trimethyl-6H-thieno[3,2-f][1,2,4]triazolo[4,3-a][1,4]diazepin-6-yl)acetamido)pentyl)-2-ethyl-2'-oxo-2',3'-dihydro-1'H-[1,5'-bibenzo[d]imidazole]-5-carboxamide

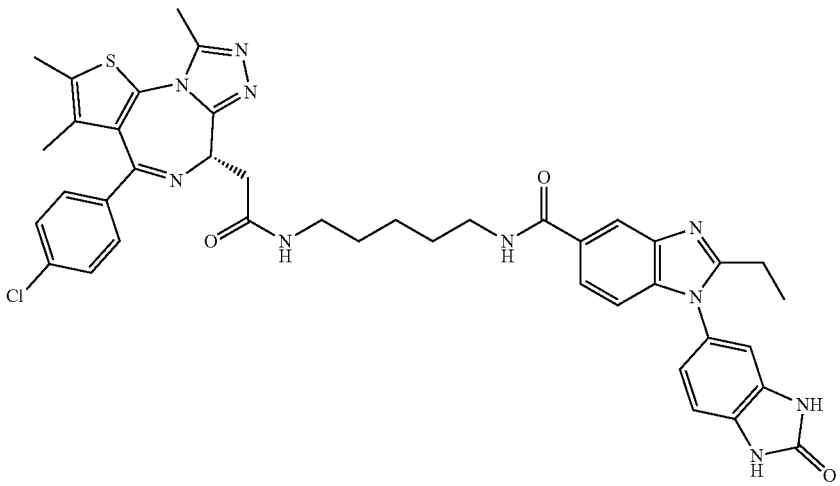 [SMILES: CCc1nc2cc(C(=O)NCCCCCNC(=O)C[C@@H]3N=C(c4ccc(Cl)cc4)c4c(sc(C)c4C)-n4c(C)nnc43)ccc2n1-c1ccc2[nH]c(=O)[nH]c2c1]

a) tert-Butyl (5-(2-((6S)-4-(4-chlorophenyl)-2,3,9-trimethyl-6H-thieno[3,2-f][1,2,4]triazolo[4,3-a][1,4]diazepin-6-yl)acetamido)pentyl)carbamate To a solution of 2-((6S)-4-(4-chlorophenyl)-2,3,9-trimethyl-6H-thieno[3,2-f][1,2,4]triazolo[4,3-a][1,4]diazepin-6-yl)acetic acid (150 mg) in dichloromethane (15 ml) was added 1-ethyl-3-(3-dimethylaminopropyl)carbodiimide[189] (108 mg) and DMAP (54.9 mg). After stirring at room temperature for 10 minutes, tert-butyl (5-aminopentyl)carbamate[190] (75.7 mg) was added and the resulting solution was stirred at room temperature for 48 h. The reaction mixture was partitioned between water and dichloromethane, 1 M aq. HCl was added and the mixture was separated. The organic layer was dried over MgSO$_4$, filtered and concentrated in vacuo. The crude material was purified by flash chromatography (silica gel, eluent: 0 to 5% of methanol in dichloromethane) to afford tert-butyl (5-(2-((6S)-4-(4-chlorophenyl)-2,3,9-trimethyl-6H-thieno[3,2-f][1,2,4]triazolo[4,3-a][1,4]diazepin-6-yl)acetamido)pentyl)carbamate (124 mg, 57%) as a light brown oil. MS (ISP): 585.2 ([M+H]$^+$).

b) (S)—N-(5-Aminopentyl)-2-(4-(4-chlorophenyl)-2,3,9-trimethyl-6H-thieno[3,2-f][1,2,4]triazolo[4,3-a][1,4]diazepin-6-yl)acetamide Hydrochloride To a solution of tert-butyl (5-(2-((6S)-4-(4-chlorophenyl)-2,3,9-trimethyl-6H-thieno[3,2-f][1,2,4]triazolo[4,3-a][1,4]diazepin-6-yl)acetamido)pentyl)carbamate (124 mg) in dioxane (2 ml) was added a 4 M solution of HCl in dioxane (795 µl). The reaction mixture was stirred at room temperature for 1 h. The solid was filtered to afford (S)—N-(5-aminopentyl)-2-(4-(4-chlorophenyl)-2,3,9-trimethyl-6H-thieno[3,2-f][1,2,4]triazolo[4,3-a][1,4]diazepin-6-yl)acetamide hydrochloride (98 mg, 89%) which was used in the next step without further purification. MS (ISP): 485.1 ([M+H]$^+$).

c) Methyl 2-ethyl-2'-oxo-2',3'-dihydro-1'H-[1,5'-bibenzo[d]imidazole]-5-carboxylate The title compound was obtained in analogy to example 1 starting from methyl 3-amino-4-((2-oxo-2,3-dihydro-1H-benzo[d]imidazol-5-yl)amino)benzoate (example 9).

d) 2-Ethyl-2'-oxo-2',3'-dihydro-1'H-[1,5'-bibenzo[d]imidazole]-5-carboxylic Acid To a solution of methyl 2-ethyl-2'-oxo-2',3'-dihydro-1'H-[1,5'-bibenzo[d]imidazole]-5-carboxylate (155 mg) in MeOH (1 ml) and THF (2 ml) was added 1 M aq. LiOH (1.38 ml). The reaction mixture was stirred at room temperature for 20 h. LC-MS analysis showed that the reaction was not complete. 1 M aq. LiOH (1 mL) was added and the reaction mixture was stirred overnight. The volatiles were evaporated and a solution of 2 M aq. HCl was added to the remaining aqueous phase until pH=0. The resulting light yellow suspension was stirred at 0° C. for 15 min and was filtered to give 2-ethyl-2'-oxo-2',3'-dihydro-1'H-[1,5'-bibenzo[d]imidazole]-5-carboxylic acid (125 mg, 84%) which was used in the next step without further purification. MS (ISP): 323.1 ([M+H]$^+$).

e) N-(5-(2-((6S)-4-(4-Chlorophenyl)-2,3,9-trimethyl-6H-thieno[3,2-f][1,2,4]triazolo[4,3-a][1,4]diazepin-6-yl)acetamido)pentyl)-2-ethyl-2'-oxo-2'3'-dihydro-1'H-[1,5'-bibenzo[d]imidazole]-5-carboxamide To 2-ethyl-2'-oxo-2',3'-dihydro-1'H-[1,5'-bibenzo[d]imidazole]-5-carboxylic acid (50 mg) was added a solution of HATU in DMF (692 µl, 0.944 g/ml). N,N-Diisopropylethylamine (108 µl) and N-(5-aminopentyl)-2-((6S)-4-(4-chlorophenyl)-2,3,9-trimethyl-6H-thieno[3,2-f][1,2,4]triazolo[4,3-a][1,4]diazepin-6-yl)acetamide (75.2 mg) were added. The reaction mixture was shaken at room temperature for 4 hours and then transferred to a separating funnel. Water and ethyl acetate were added to give a sticky solid. After removal of the aqueous and organic layer, the sticky solid was recovered by dissolving in CH$_2$Cl$_2$/MeOH (90:10). The organic layer was dried over MgSO$_4$, filtered and concentrated in vacuo. The crude material was purified by flash chromatography (silica gel, eluent: 0 to 20% of methanol in dichloromethane) to afford N-(5-(2-(((6S)-4-(4-chlorophenyl)-2,3,9-trimethyl-6H-thieno[3,2-f][1,2,4]triazolo[4,3-a][1,4]diazepin-6-yl)acetamido)pentyl)-2-ethyl-2'-oxo-2',3'-dihydro-1'H-[1,5'-bibenzo[d]imidazole]-5-carboxamide (30 mg, 25%) as a white solid. MS (ISP): 789.29 ([M+H]$^+$).

Example B (S)—N-(2-(2-(2-(2-(4-(4-Chlorophenyl)-2,3,9-trimethyl-6H-thieno[3,2-f][1,2,4]triazolo[4,3-a][1,4]diazepin-6-yl)acetamido)ethoxy)ethoxy)ethyl)-2-ethyl-2'-oxo-2',3'-dihydro-1'H-[1,5'-bibenzo[d]imidazole]-5-carboxamide

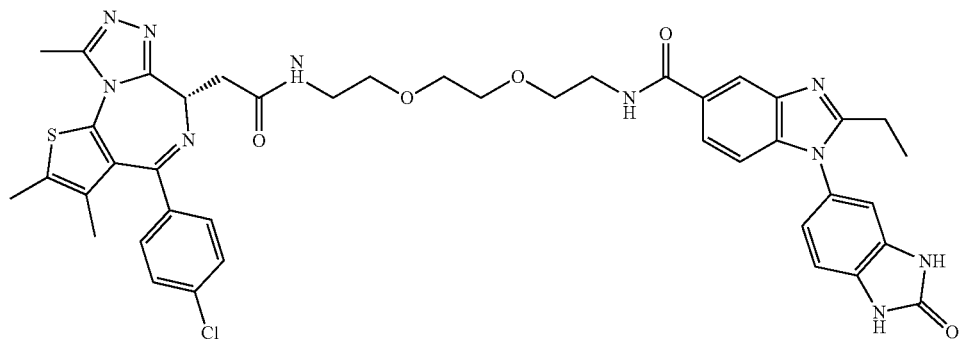 [SMILES: CCc1nc2cc(C(=O)NCCOCCOCCNC(=O)C[C@@H]3N=C(c4ccc(Cl)cc4)c4c(sc(C)c4C)-n4c(C)nnc43)ccc2n1-c1ccc2[nH]c(=O)[nH]c2c1]

a) tert-Butyl (2-(2-(2-(2-(((6S)-4-(4-chlorophenyl)-2,3,9-trimethyl-6H-thieno[3,2-f][1,2,4]triazolo[4,3-a][1,4]diazepin-6-yl)acetamido)ethoxy)ethoxy)ethyl)carbamate To a solution of 2-((6S)-4-(4-chlorophenyl)-2,3,9-trimethyl-6H-thieno[3,2-f][1,2,4]triazolo[4,3-a][1,4]diazepin-6-yl)acetic acid (150 mg) in dichloromethane (15 ml) were added 1-ethyl-3-(3-dimethylaminopropyl)carbodiimide (108 mg) and DMAP (54.9 mg). After stirring at room temperature for 10 minutes, tert-butyl (5-aminopentyl)carbamate[191] (75.7 mg) was added and the resulting solution was stirred at room temperature for 48 h. The reaction mixture was partitioned between water and dichloromethane, then 1 M aq. HCl was added and the mixture was separated. The organic layer was dried over MgSO$_4$, filtered and concentrated in vacuo. The crude material was purified by flash chromatography (silica gel, eluent: 0 to 5% of methanol in dichloromethane) to afford tert-butyl (2-(2-(2-(2-(((6S)-4-(4-chlorophenyl)-2,3,9-trimethyl-6H-thieno[3,2-f][1,2,4]triazolo[4,3-a][1,4]diazepin-6-yl)acetamido)ethoxy)ethoxy)ethyl)carbamate (213 mg, 90%) as a colorless oil. MS (ISP): 631.4 ([M+H]$^+$).

b) N-(2-(2-(2-Aminoethoxy)ethoxy)ethyl)-2-((6S)-4-(4-chlorophenyl)-2,3,9-trimethyl-6H-thieno[3,2-f][1,2,4]triazolo[4,3-a][1,4]diazepin-6-yl)acetamide Hydrochloride To a solution of tert-butyl (2-(2-(2-(2-(((6S)-4-(4-chlorophenyl)-2,3,9-trimethyl-6H-thieno[3,2-f][1,2,4]triazolo[4,3-a][1,4]diazepin-6-yl)acetamido)ethoxy)ethoxy)ethyl)carbamate (213 mg) in dioxane (2 ml) was added a solution of 4 M HCl in dioxane (1.27 ml). The reaction was stirred at room temperature for 1 h. The solvent was evaporated and the residue was dissolved in a minimum of ethanol, then diethyl ether was added dropwise. The solid obtained was filtered to afford N-(2-(2-(2-aminoethoxy)ethoxy)ethyl)-2-((6S)-4-(4-chlorophenyl)-2,3,9-trimethyl-6H-thieno[3,2-f][1,2,4]triazolo[4,3-a][1,4]diazepin-6-yl)acetamide hydrochloride (105 mg, 55%) which was used in the next step without further purification. MS (ISP): 531.3 ([M+H]$^+$).

c) (S)—N-(2-(2-(2-(2-(4-(4-Chlorophenyl)-2,3,9-trimethyl-6H-thieno[3,2-f][1,2,4]triazolo[4,3-a][1,4]diazepin-6-yl)acetamido)ethoxy)ethoxy)ethyl)-2-ethyl-2'-oxo-2'3'-dihydro-1'H-[1,5'-bibenzo[d]imidazole]-5-carboxamide To 2-ethyl-2'-oxo-2',3'-dihydro-1'H-[1,5'-bibenzo[d]imidazole]-5-carboxylic acid (30 mg) in DMF (1 ml) were added (S)—N-(2-(2-(2-aminoethoxy)ethoxy)ethyl)-2-(4-(4-chlorophenyl)-2,3,9-trimethyl-6H-thieno[3,2-f][1,2,4]triazolo[4,3-a][1,4]diazepin-6-yl)acetamide hydrochloride (52.8 mg), HATU (42.5 mg) and N,N-diisopropylethylamine (65 µl). The reaction mixture was shaken at room temperature for 4 hours then transferred to a separating funnel. LC/MS analysis indicated that the reaction was finished. Water and ethyl acetate were added to give a sticky solid. After removal of the aqueous and organic layer, the sticky solid was recovered by dissolving in CH$_2$Cl$_2$/MeOH (90:10). The organic layer was dried over MgSO$_4$, filtered and concentrated in vacuo. The crude material was purified by flash chromatography (silica gel, eluent: 0 to 20% of methanol in dichloromethane) to afford (S)—N-(2-(2-(2-(2-(4-(4-chlorophenyl)-2,3,9-trimethyl-6H-thieno[3,2-f][1,2,4]triazolo[4,3-a][1,4]diazepin-6-yl)acetamido)ethoxy)ethoxy)ethyl)-2-ethyl-2'-oxo-2',3'-dihydro-1'H-[1,5'-bibenzo[d]imidazole]-5-carboxamide (23.6 mg, 30%) as a white solid. MS (ISP): 835.29 ([M+H]$^+$).

Example C (S)—N-(2-(2-(2-(2-(4-(4-Chlorophenyl)-2,3,9-trimethyl-6H-thieno[3,2-f][1,2,4]triazolo[4,3-a][1,4]diazepin-6-yl)acetamido)ethoxy)ethoxy)ethyl)-2'-oxo-2-(quinolin-4-yl)-2',3'-dihydro-1'H-[1,5'-bibenzo[d]imidazole]-5-carboxamide

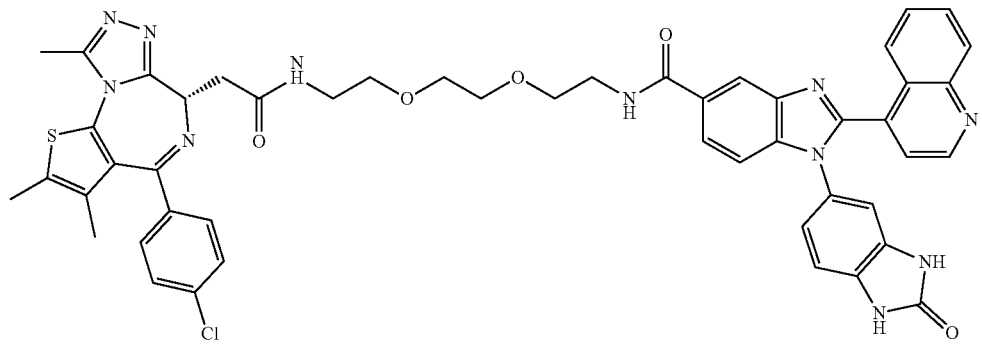 [SMILES: Cc1sc2c(c1C)C(c1ccc(Cl)cc1)=N[C@@H](CC(=O)NCCOCCOCCNC(=O)c1ccc3c(c1)nc(-c1ccnc4ccccc14)n3-c1ccc3[nH]c(=O)[nH]c3c1)c1nnc(C)n1-2]

a) Methyl 2'-oxo-2-(quinolin-4-yl)-2',3'-dihydro-1'H-[1,5'-bibenzo[d]imidazole]-5-carboxylate The title compound was obtained in analogy to example 1 starting from methyl 3-amino-4-((2-oxo-2,3-dihydro-1H-benzo[d]imidazol-5-yl)amino)benzoate (example 9).

b) 2'-Oxo-2-(quinolin-4-yl)-2',3'-dihydro-1'H-[1,5'-bibenzo[d]imidazole]-5-carboxylic Acid To a solution of methyl 2'-oxo-2-(quinolin-4-yl)-2',3'-dihydro-1'H-[1,5'-bibenzo[d]imidazole]-5-carboxylate (90 mg) in MeOH (1 ml) and THF (2 ml) was added 1 M aq. LiOH (1.41 ml). The reaction mixture was stirred at room temperature for 20 h. The reaction mixture was partitioned between ethyl acetate and water. The organic layer was discarded and the aqueous layer was acidified by addition of a solution of 2 M aq. HCl until pH=0. The aqueous phase was extracted with a 1:1 mixture of ethyl acetate and THF. The organic layer was dried over MgSO$_4$, filtered and concentrated in vacuo to give 2'-oxo-2-(quinolin-4-yl)-2',3'-dihydro-1'H-[1,5'-bibenzo[d]imidazole]-5-carboxylic acid (90 mg, 46%) which was used in the next step without further purification. MS (ISP): 422.2 ([M+H]$^+$).

c) (S)—N-(2-(2-(2-(2-(4-(4-Chlorophenyl)-2,3,9-trimethyl-6H-thieno[3,2-f][1,2,4]triazolo[4,3-a][1,4]diazepin-6-yl)acetamido)ethoxy)ethoxy)ethyl)-2'-oxo-2-(quinolin-4-yl)-2',3'-dihydro-1'H-[1,5'-bibenzo[d]imidazole]-5-carboxamide To a solution of 2'-oxo-2-(quinolin-4-yl)-2',3'-dihydro-1'H-[1,5'-bibenzo[d]imidazole]-5-carboxylic acid (33.7 mg) in DMF (1 ml) were added (S)—N-(2-(2-(2-aminoethoxy)ethoxy)ethyl)-2-(4-(4-chlorophenyl)-2,3,9-trimethyl-6H-thieno[3,2-f][1,2,4]triazolo[4,3-a][1,4]diazepin-6-yl)acetamide hydrochloride (50 mg), HATU (36.5 mg) and N,N-diisopropylethylamine (56 µl). The reaction mixture was shaken at room temperature for 4 hours and then transferred to a separating funnel. LC/MS analysis indicated that the reaction was finished. Water and ethyl acetate were added to give a sticky solid. After removal of the aqueous and organic layer, the sticky solid was recovered by dissolving in CH$_2$Cl$_2$/MeOH (90:10). The organic layer was dried over MgSO$_4$, filtered and concentrated in vacuo. The crude material was purified by flash chromatography (silica gel, eluent: 0 to 20% of methanol in dichloromethane) to afford (S)—N-(2-(2-(2-(2-(4-(4-chlorophenyl)-2,3,9-trimethyl-6H-thieno[3,2-f][1,2,4]triazolo[4,3-a][1,4]diazepin-6-yl)acetamido)ethoxy)ethoxy)ethyl)-2'-oxo-2-(quinolin-4-yl)-2',3'-dihydro-1'H-[1,5'-bibenzo[d]imidazole]-5-carboxamide (37.6 mg, 50.3%) as a white solid. MS (ISP): 934.30 ([M+H]$^+$).

Example D

N4-[5-[[2-[(9S)-7-(4-Chlorophenyl)-4,5,13-trimethyl-3-thia-1,8,11,12-tetrazatricyclo[8.3.0.02,6]trideca-2(6),4,7,10,12-pentaen-9-yl]acetyl]amino]pentyl]-N1-(2-oxo-1,3-dihydrobenzimidazol-5-yl)indoline-1,4-dicarboxamide

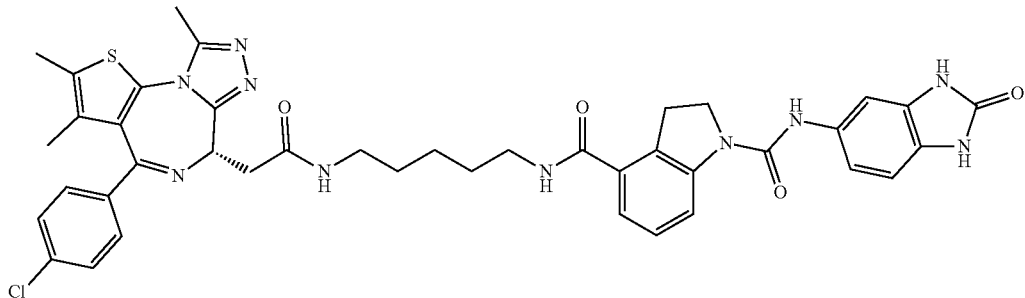 [SMILES: Cc1sc2c(c1C)C(c1ccc(Cl)cc1)=N[C@@H](CC(=O)NCCCCCNC(=O)c1cccc3c1CCN3C(=O)Nc1ccc3[nH]c(=O)[nH]c3c1)c1nnc(C)n1-2]

a) Methyl 1-((2-oxo-2,3-dihydro-1H-benzo[d]imidazol-5-yl)carbamoyl)indoline-4-carboxylate To a stirred solution of methyl indoline-4-carboxylate (119 mg) and triethylamine (178 µl) in THF (2 ml) was added triphosgene (73.6 mg) at 0-5° C. The reaction mixture was stirred at 25° C. for 1 hour then a solution of 5-amino-1,3-dihydrobenzimidazol-2-one (100 mg) in N,N-dimethylformamide (1 ml) was added. The reaction mixture was stirred at 25° C. for 1 hour According to LC/MS, the reaction was finished. The reaction was quenched by addition of water (10 ml) and the suspension was stirred for 10 min. The solid was collected by filtration and was suspended in a 1:1 mixture of DMSO/THF. After stirring, the suspension was filtered and the filtercake was washed with water, dried in vacuo to afford methyl 1-((2-oxo-2,3-dihydro-1H-benzo[d]imidazol-5-yl)carbamoyl)indoline-4-carboxylate (236 mg, 86%). Off-white solid. MS (ISP): 353.1 ([M+H]$^+$).

b) 1-((2-Oxo-2,3-dihydro-1H-benzo[d]imidazol-5-yl)carbamoyl)indoline-4-carboxylic Acid To a suspension of methyl 1-((2-oxo-2,3-dihydro-1H-benzo[d]imidazol-5-yl)carbamoyl)indoline-4-carboxylate (120 mg) in a 1:1 mixture of THF/methanol (3 ml) was added a 1 m solution of LiOH (1.36 ml). The reaction mixture was stirred at 25° C. overnight. A solution of 5N HCl was slowly added to the dark brown solution until precipitation. The solid was filtered and the solid was dried in vacuo. The filtrate was evaporated, the residue was dissolved and the solution was submit lyophilisation. The solids were mixed together to afford 1-((2-oxo-2,3-dihydro-1H-benzo[d]imidazol-5-yl)carbamoyl)indoline-4-carboxylic acid (67 mg, 58.1%). Off-white solid. MS (ISP): 339.1 ([M+H]$^+$).

c) N4-[5-[[2-[(9S)-7-(4-Chlorophenyl)-4,5,13-trimethyl-3-thia-1,8,11,12-tetrazatricyclo[8.3.0.02,6]trideca-2(6),4,7,10,12-pentaen-9-yl]acetyl]amino]pentyl]-N1-(2-oxo-1,3-dihydrobenzimidazol-5-yl)indoline-1,4-dicarboxamide The title compound was obtained in analogy to example A using 1-((2-oxo-2,3-dihydro-1H-benzo[d]imidazol-5-yl)carbamoyl)indoline-4-carboxylic acid in place of 2-ethyl-2'-oxo-2',3'-dihydro-1'H-[1,5'-bibenzo[d]imidazole]-5-carboxylic acid for step e. White foam. MS (ISP): 805.3 ([M+H]$^+$).

Although the foregoing invention has been described in some detail by way of illustration and example for purposes of clarity and understanding, it will be readily apparent to one of ordinary skill in the art in light of the teachings of this invention that certain changes and modifications may be made thereto without departing from the spirit or scope of their invention as defined in the appended claims.

[1] Collins et al., *Biochem J.* 2017, 474(7), 1127-47
[2] WO2013020557
[3] WO2013063560
[4] WO 2013106643
[5] WO2015160845
[6] WO2016011906
[7] WO2016105518
[8] WO2017007612
[9] WO2017024318
[10] WO2017117473
[11] WO2011035124
[12] WO02072576
[13] WO2010085684
[14] WO2014134240
[15] WO2011130628
[16] WO2007065518
[17] WO2016176460
[18] WO2009135651
[19] WO2011156245
[20] WO2017046318
[21] WO2010130794
[22] WO2012021382
[23] WO2005060967
[24] WO2012174199
[25] EP385850
[26] WO2016176449
[27] WO2016040508
[28] WO00020358
[29] EP1256578
[30] WO2006058338
[31] WO2004108133
[32] WO2010108187
[33] WO2005113489
[34] WO2012061708

[35] WO2010023161
[36] WO2007041598
[37] WO2009050232
[38] Terefenko et al., *Bioorganic & Med Chem Lett.*, 2005, 15(15), 3600-03
[39] Smolyar et al., *Russian Journal of Organic Chemistry* 2011, 47(8), 119-3
[40] Jun Yon Choi et al., *J Med Chem*, 2012, 55(13), 852-70
[41] Hyeju Choi et al., *J. Materials Chem. A*, 2014, 2, 12931-9
[42] Mitsuaki et al., *Chem. Pharm. Bull.* 1996, 44(9), 1717-22
[43] Yu et al., *Chemistry of Heterocyclic Compounds* 1968, 4(4), 698-701
[44] Vincent et al., *Tetrahedron Lett.* 1994, 35(16), 2601-2
[45] CAS 1493-27-2
[46] CAS 475216-25-2
[47] CAS 658700-20-0
[48] CAS 329-59-9
[49] CAS 185629-31-6
[50] CAS 95-23-8
[51] CAS 54732-89-7
[52] CAS 73778-92-4
[53] CAS 53439-88-6
[54] CAS 39513-26-3
[55] CAS 40644-14-2
[56] CAS 23814-14-4
[57] CAS 106429-57-6
[58] CAS 634602-84-9
[59] CAS 53439-87-5
[60] CAS 500295-27-2
[61] CAS 2369-11-1
[62] CAS 364-53-4
[63] CAS 57834-13-6
[64] CAS 1268524-70-4
[65] Filippakopoulos, P. et al. *Nature* 2010, 468, 1067-1073
[66] CAS 202592-23-2
[67] Sigma-Aldrich Cat. No. A7089
[68] Yen, H.-C. S., Xu, Q., Chou, D. M., Zhao, Z. & Elledge, S. J. Global Protein Stability Profiling in Mammalian Cells. *Science* 2008, 322, 918-923, doi:10.1126/science.1160489
[69] Birdsall, B., King, R. W., Wheeler, M. R., Lewis, C. A. Jr, Goode, S. R., Dunlap, R. B. & Roberts, G. C. *Anal. Biochem.* 1983, 132, 353-361
[70] Eftink *Methods Enzymol.* 1997, 278, 221-257
[71] CAS 432517-57-2
[72] CAS 4363-93-3
[73] CAS 123-38-6
[74] CAS 75-07-0
[75] CAS 100-52-7
[76] CAS 872-85-5
[77] CAS 123-72-8
[78] CAS 3034-50-2
[79] CAS 78-84-2
[80] CAS 39513-26-3
[81] CAS 1692-25-7
[82] CAS 458532-96-2
[83] CAS 1218791-01-5
[84] CAS 13889-98-0
[85] CAS 160357-94-8
[86] CAS 496-15-1
[87] CAS 838891-16-0
[88] CAS 33259-72-2
[89] CAS 122-78-1
[90] CAS 62-53-3
[91] CAS 1553181-04-6
[92] CAS 65292-99-1
[93] CAS 5810-56-0
[94] CAS 74-89-5
[95] CAS 36947-68-9
[96] CAS 616-45-5
[97] CAS 879658-18-1
[98] CAS 1013914-22-1
[99] CAS 335255-72-6
[100] CAS 335255-70-4
[101] CAS 238765-06-5
[102] CAS 1521702-21-5
[103] CAS 1258867-72-9
[104] CAS 39513-26-3
[105] CAS 355386-94-6
[106] CAS 94-09-7
[107] CAS 98-80-6
[108] CAS 40852-06-0
[109] CAS 33567-59-8
[110] CAS 630-19-3
[111] CAS 1214353-57-7
[112] CAS 87120-72-7
[113] CAS 20870-91-1
[114] CAS 155135-61-8
[115] CAS 3945-69-5
[116] CAS 1388048-97-2
[117] CAS 591-31-1
[118] CAS 57260-71-6
[119] CAS 149771-44-8
[120] CAS 79-14-1
[121] CAS 50675-18-8
[122] CAS 17289-26-8
[123] CAS 7126-39-8
[124] CAS 26537-68-8
[125] CAS 14381-42-1
[126] CAS 1197-55-3
[127] CAS 85977-52-2
[128] CAS 23357-47-3
[129] CAS 65-85-0
[130] CAS 556-08-1
[131] CAS 587-48-4
[132] CAS 100-61-8
[133] CAS 1790471-53-2
[134] CAS 18699-02-0
[135] CAS 1781710-76-6
[136] CAS 107-95-9
[137] CAS 108-30-5
[138] CAS 81927-55-1
[139] CAS 64-18-6
[140] CAS 50-21-5
[141] CAS 611-72-3
[142] CAS 291289-41-3
[143] CAS 71879-46-4
[144] CAS 101-54-2
[145] CAS 3025-95-4
[146] CAS 25503-90-6
[147] CAS 141452-01-9
[148] CAS 3173-56-6
[149] CAS 635-46-1
[150] CAS 1788023-93-7
[151] CAS 1790760-29-0
[152] CAS 939758-71-1
[153] CAS 22958-64-1
[154] CAS 138-41-0
[155] CAS 122-80-5
[156] CAS 110-89-4
[157] CAS 190661-29-1
[158] CAS 261524-34-9
[159] CAS 72716-87-1
[160] CAS 78471-43-9

[161] CAS 21744-88-7
[162] CAS 34603-55-9
[163] CAS 69812-51-7
[164] CAS 885270-06-4
[165] CAS 941867-91-0
[166] CAS 7111-77-5
[167] CAS 612-35-1
[168] CAS 61324-93-4
[169] CAS 782501-25-1
[170] CAS 372-19-0
[171] CAS 35386-24-4
[172] CAS 52537-00-5
[173] CAS 175202-37-6
[174] CAS 120552-57-0
[175] CAS 654663-32-8
[176] CAS 170464-32-1
[177] CAS 23145-88-2
[178] CAS 133362-99-9
[179] CAS 1051942-46-1
[180] CAS 912773-03-6
[181] CAS 50541-93-0
[182] CAS 157837-31-5
[183] CAS 208774-11-2
[184] CAS 4141-08-6
[185] CAS 4376-18-5
[186] CAS 36052-24-1
[187] CAS 742666-57-5
[188] CAS 27642-27-9
[189] CAS 1892-57-5
[190] CAS 51644-96-3
[191] CAS 153086-78-3
We claim:
1. A compound selected from
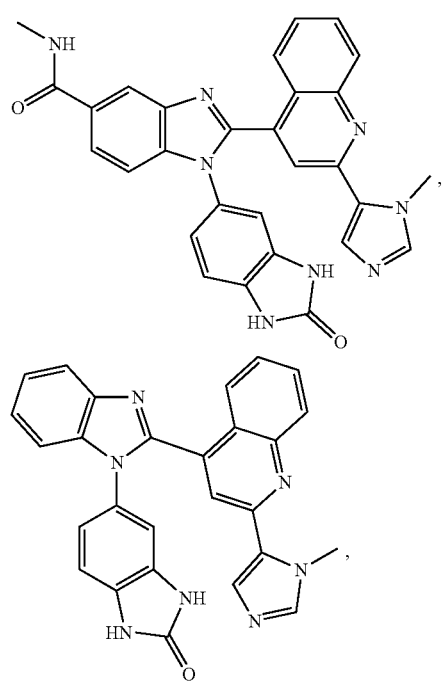
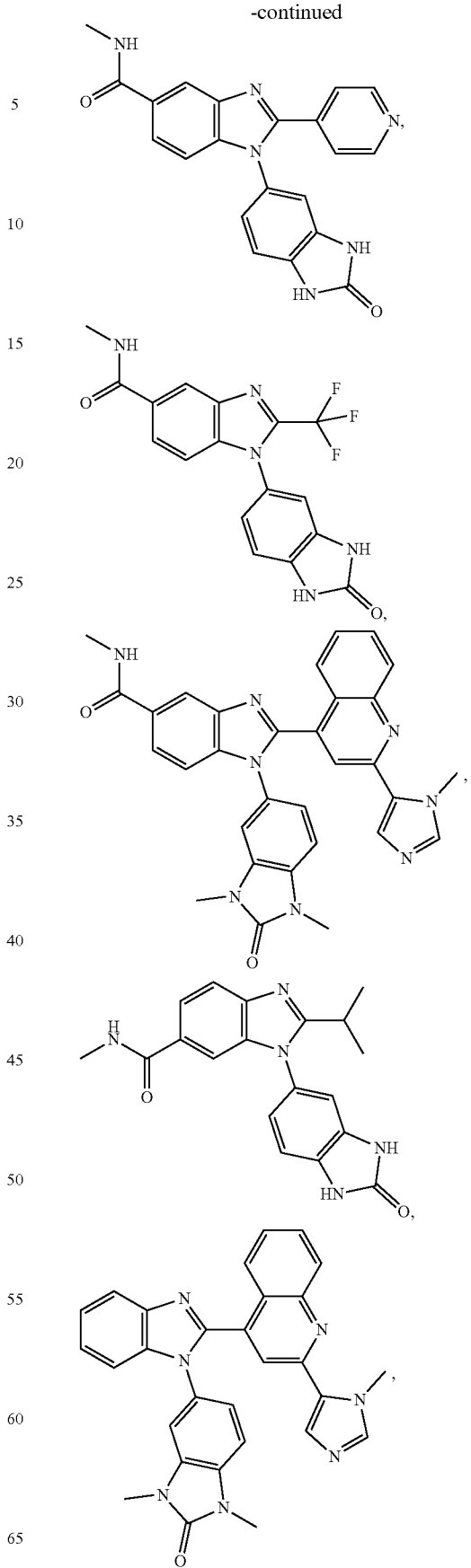

153
-continued
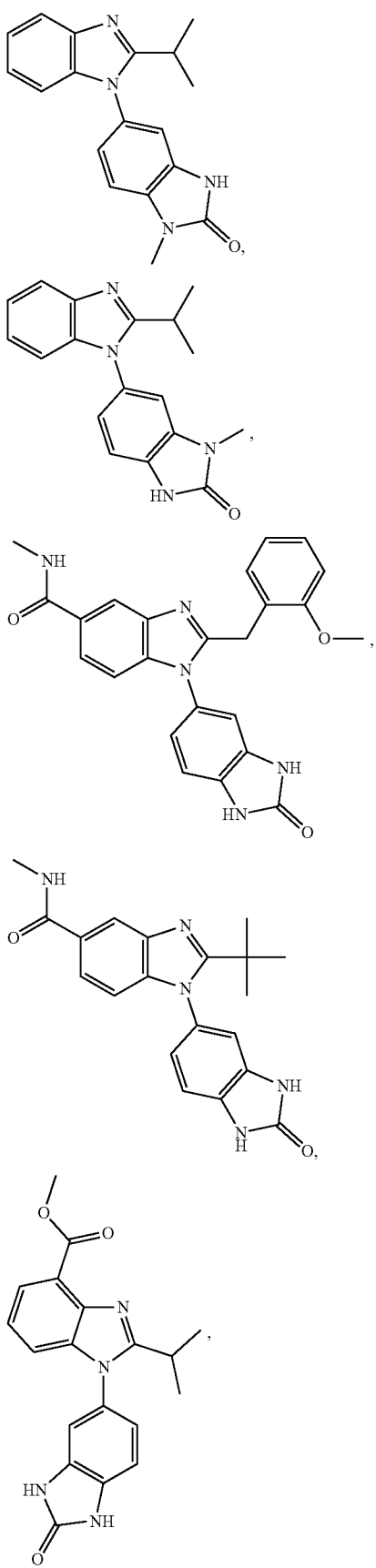
154
-continued
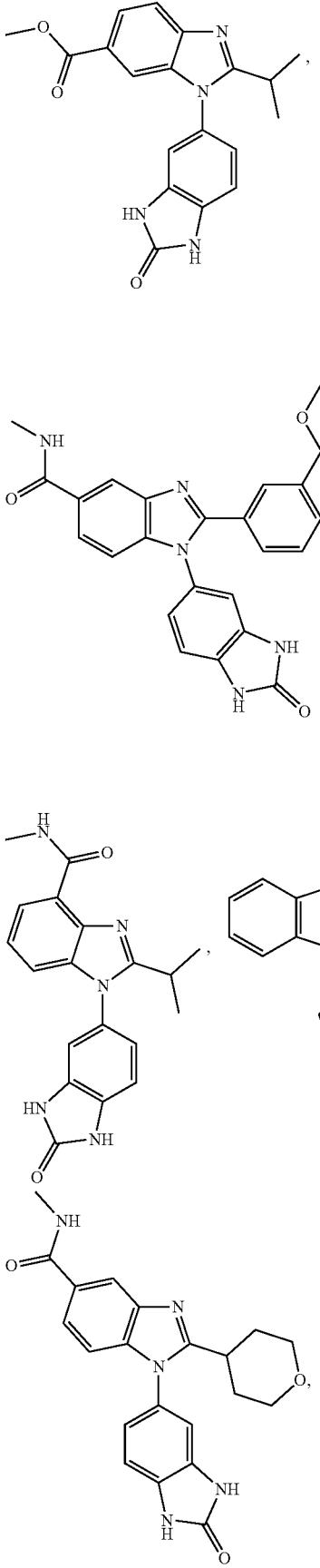

155
-continued
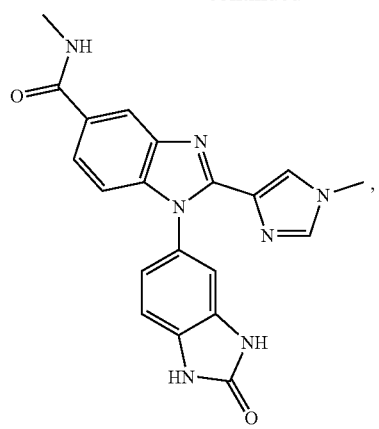
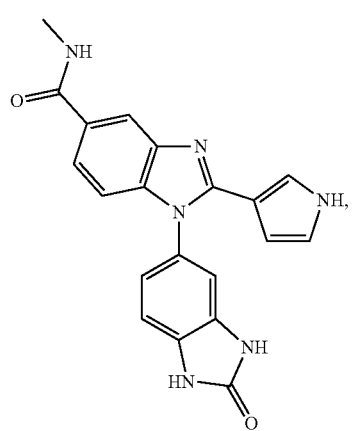
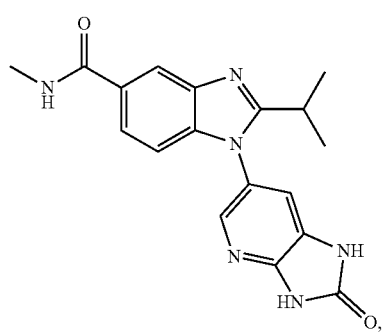
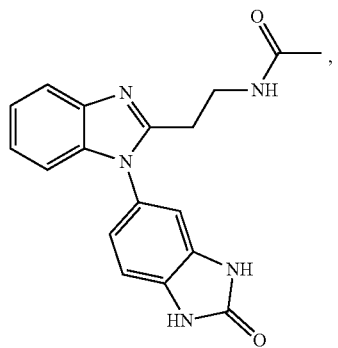
156
-continued
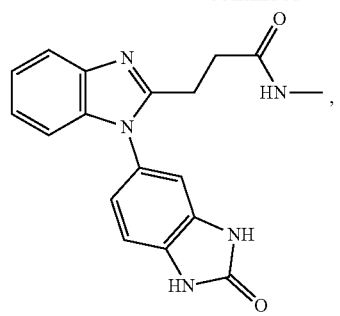
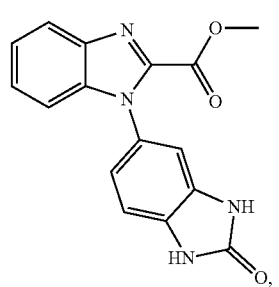
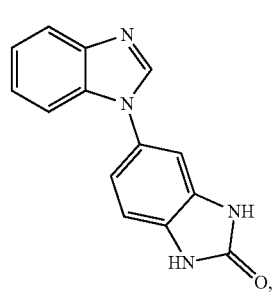
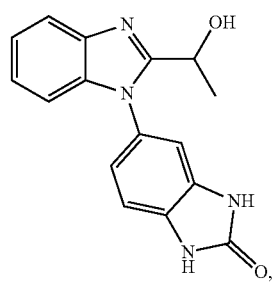
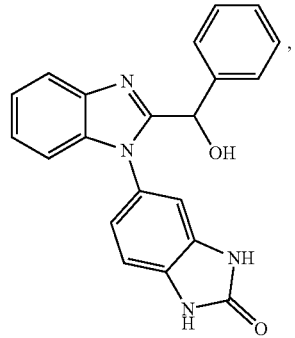

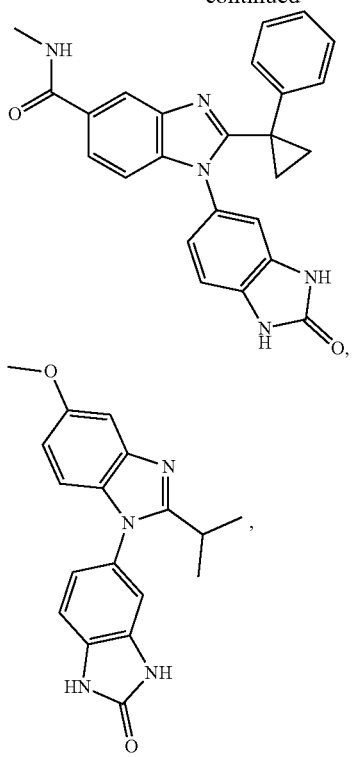
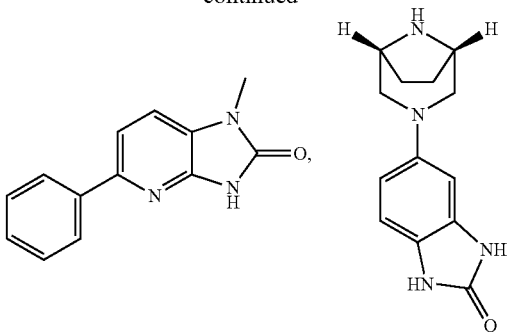
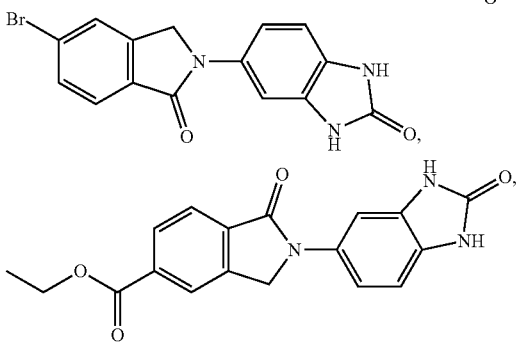
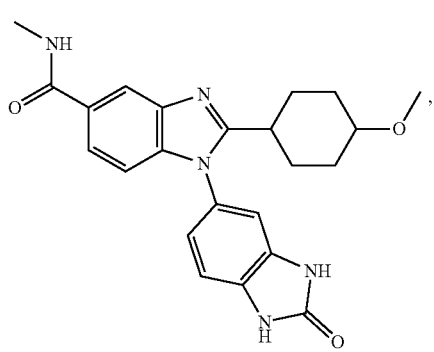
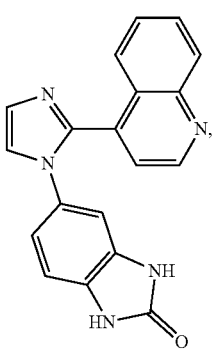
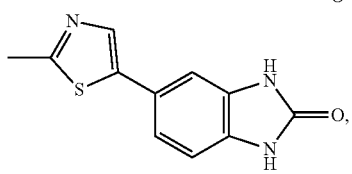
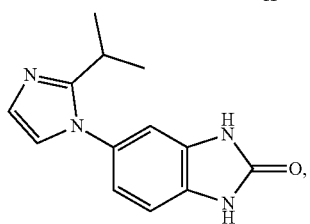
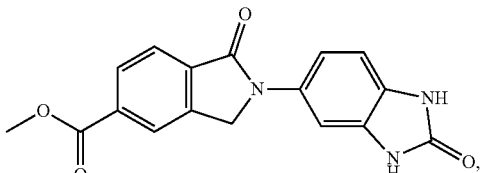
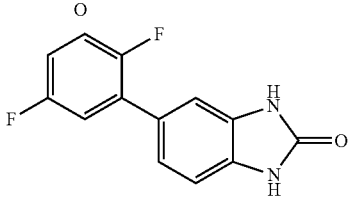
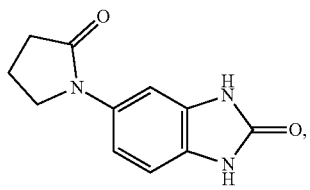
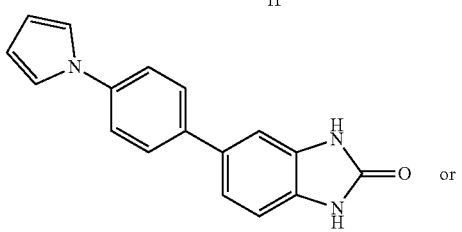 or 159
-continued
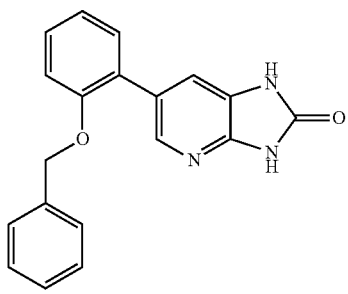
or a pharmaceutically acceptable salt thereof.
2. The compound of claim 1 of the formula
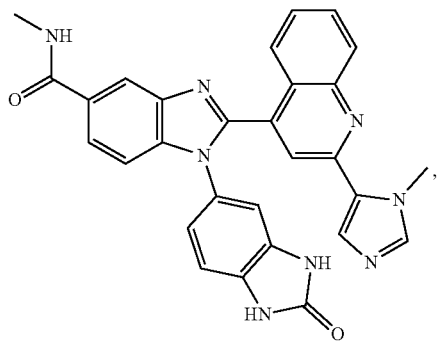
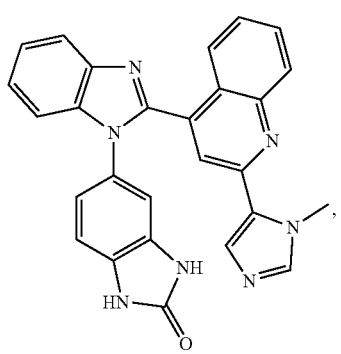
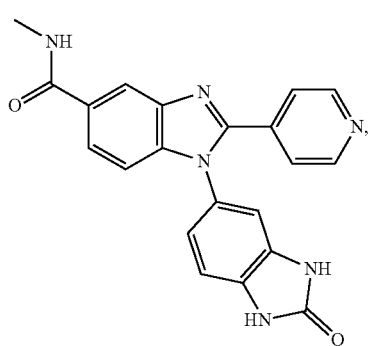
160
-continued
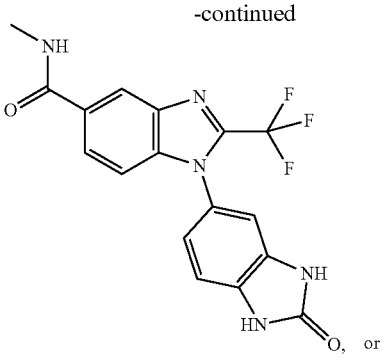
O, or
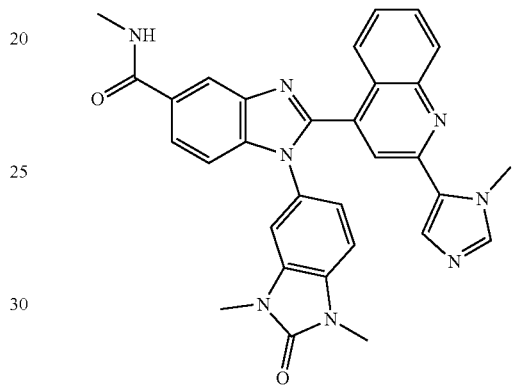
or a pharmaceutically acceptable salt thereof.
3. The compound of claim 1 of the formula
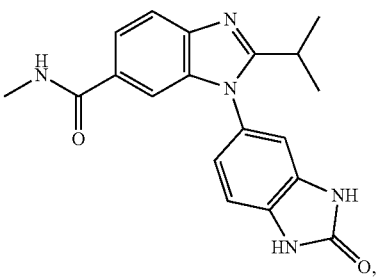
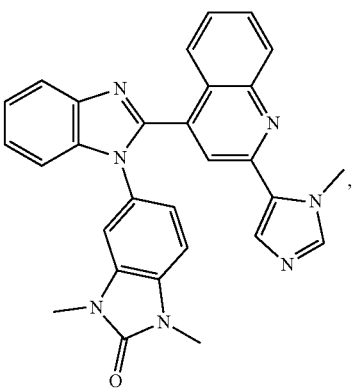

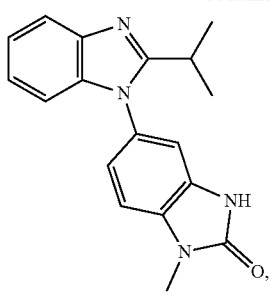
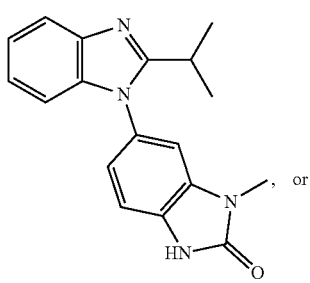, or
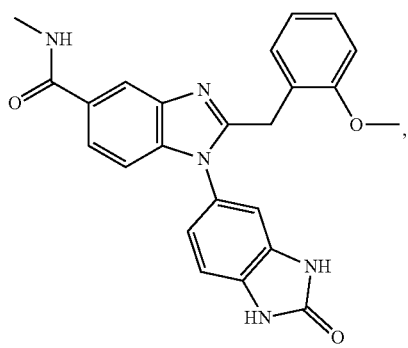
or a pharmaceutically acceptable salt thereof.
4. The compound of claim 1 of the formula
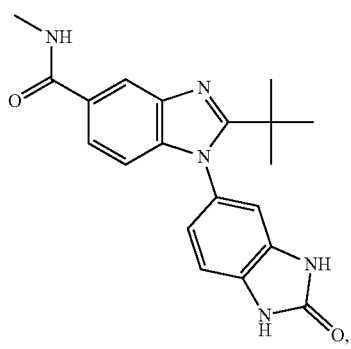
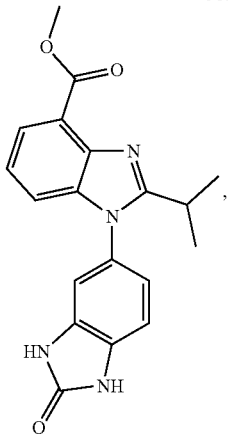,
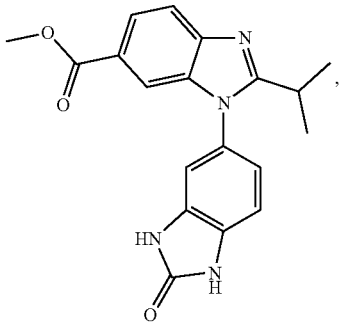,
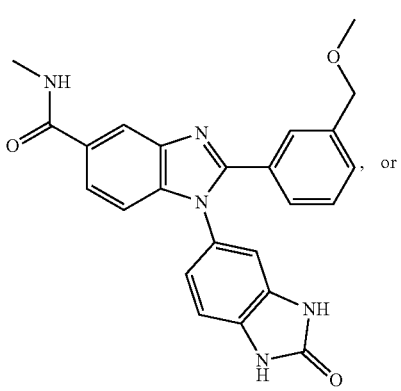, or
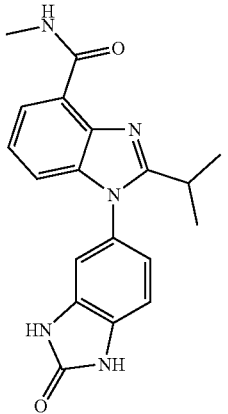 [SMILES: CNC(=O)c1cccc2c1nc(C(C)C)n2-c1ccc2[nH]c(=O)[nH]c2c1]
or a pharmaceutically acceptable salt thereof.

5. The compound of claim 1 of the formula
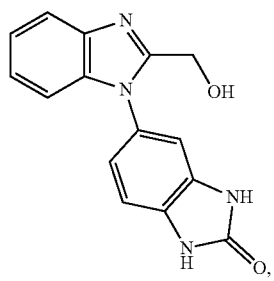
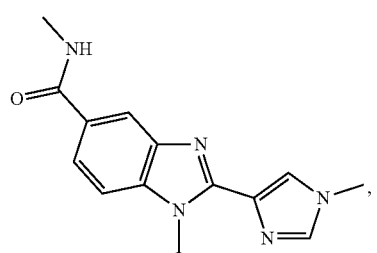
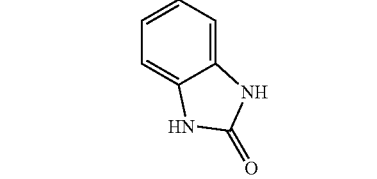
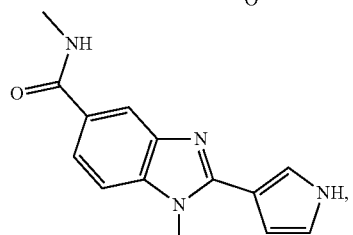
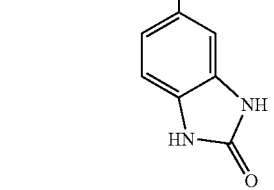
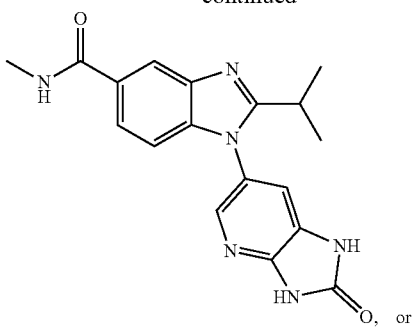
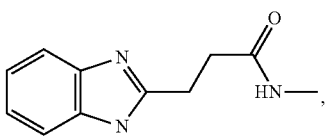
or a pharmaceutically acceptable salt thereof.
6. The compound of claim 1 of the formula
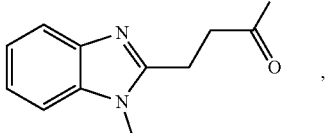
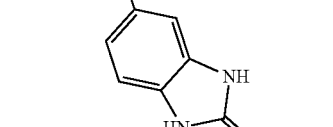
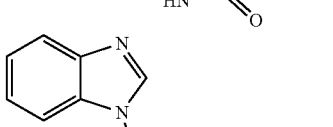
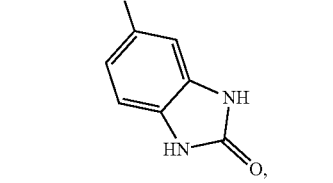

-continued
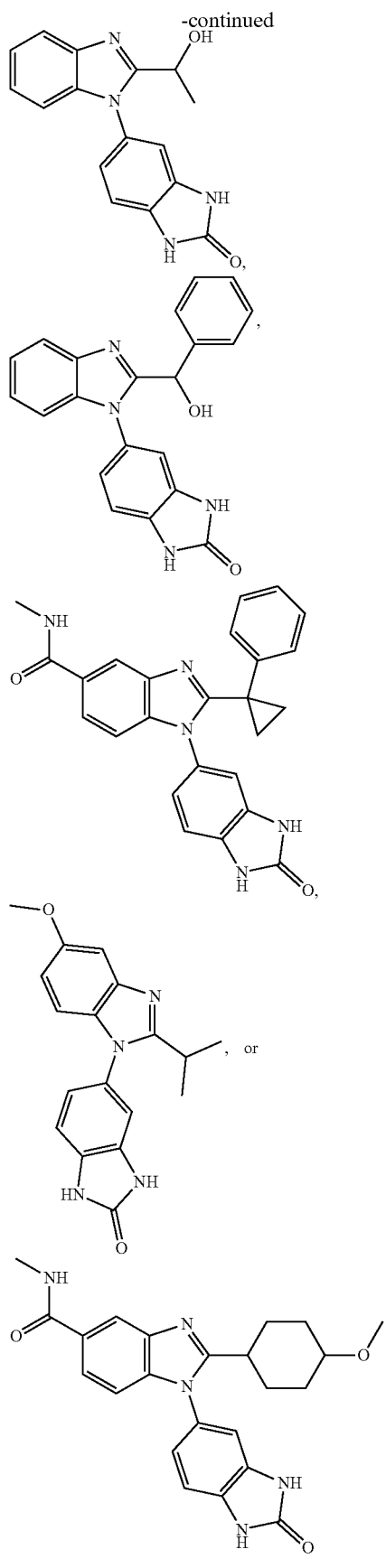
or a pharmaceutically acceptable salt thereof.
7. The compound of claim 1 of the formula
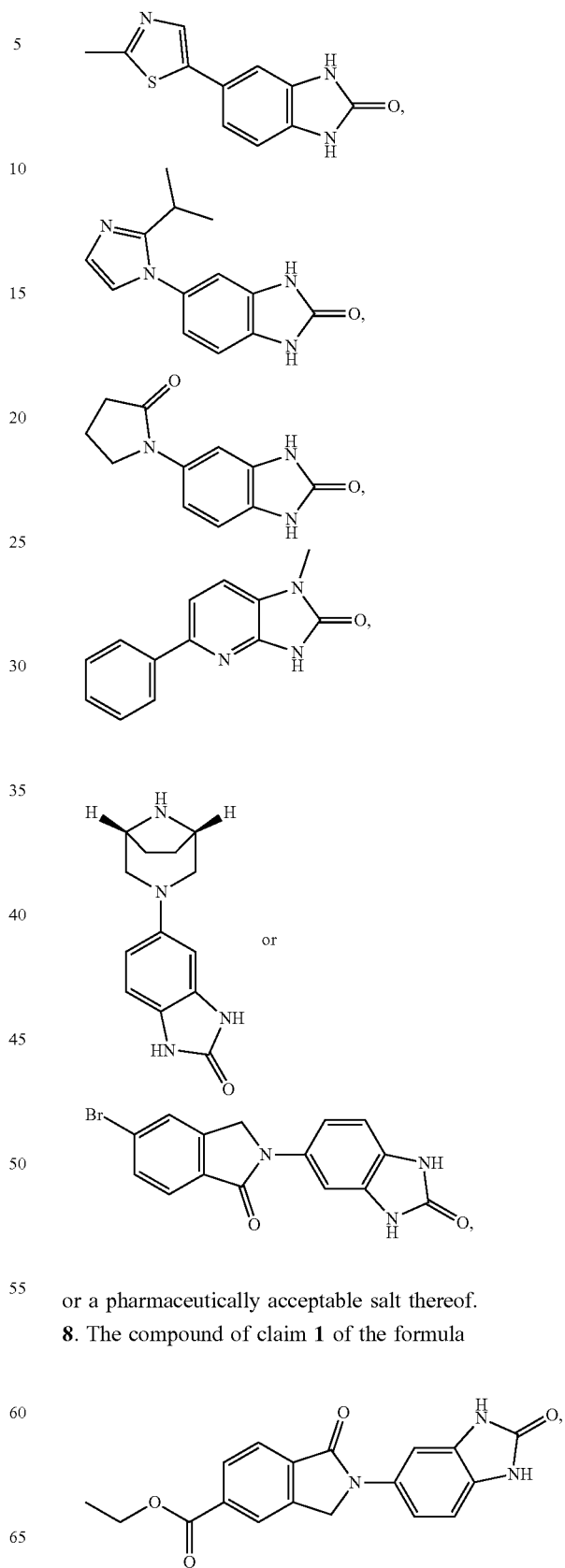
or a pharmaceutically acceptable salt thereof.
8. The compound of claim 1 of the formula

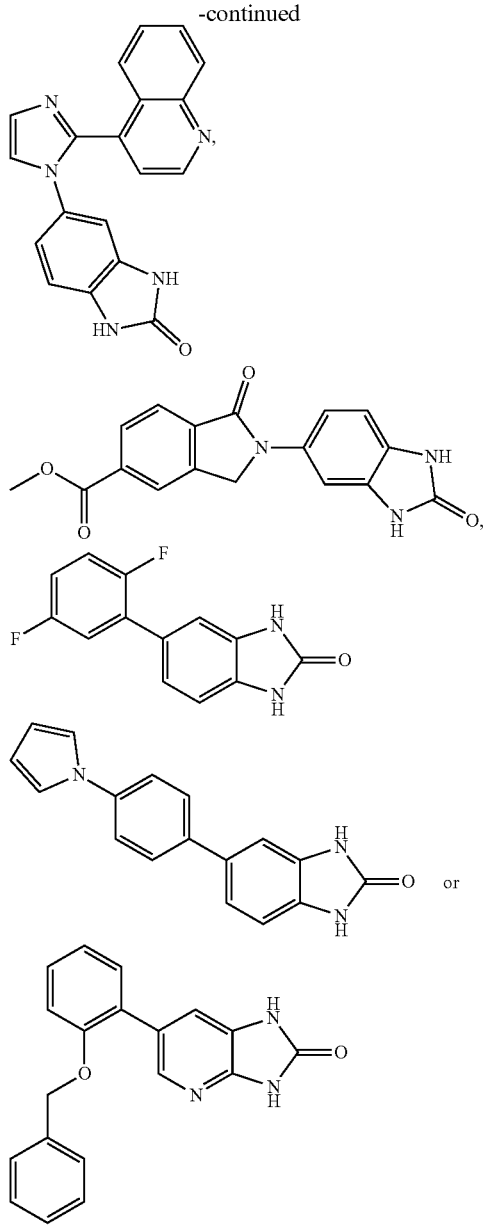
or a pharmaceutically acceptable salt thereof.
9. A compound selected from
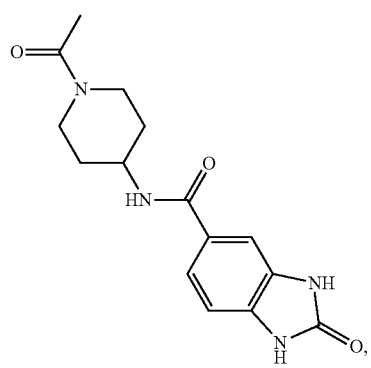
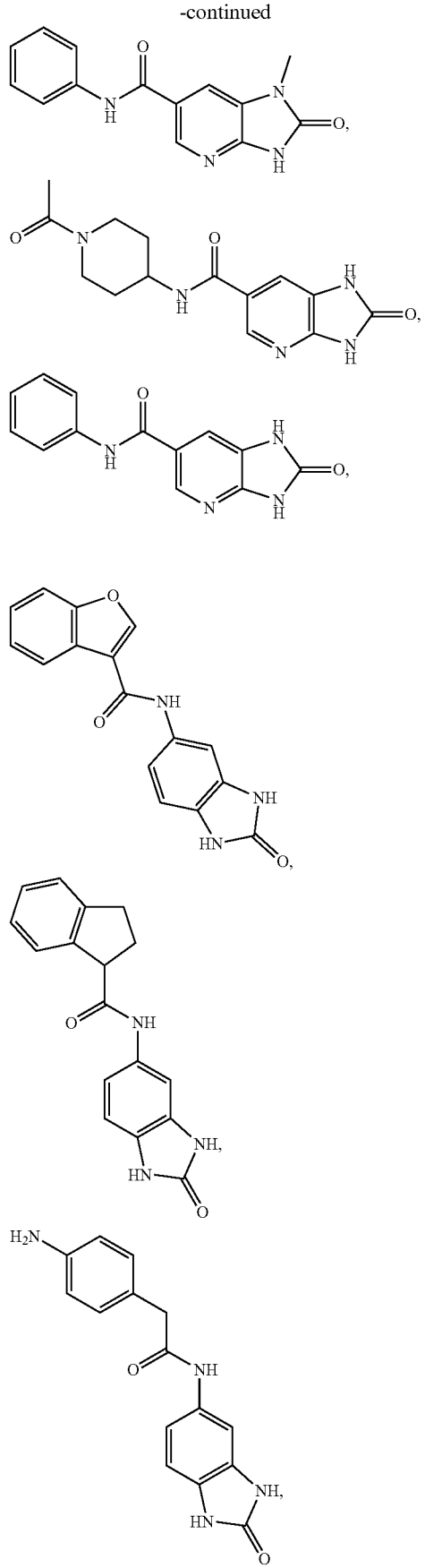

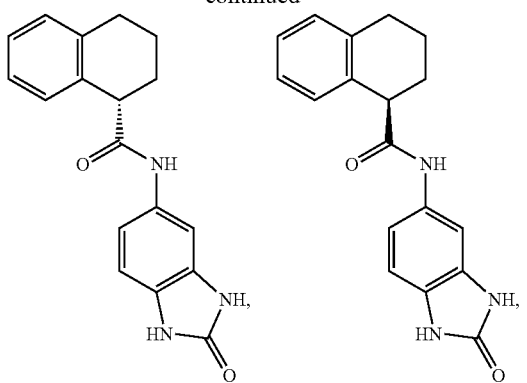
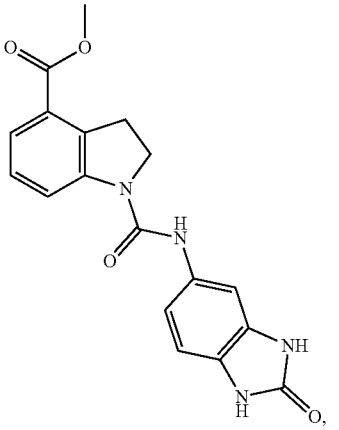
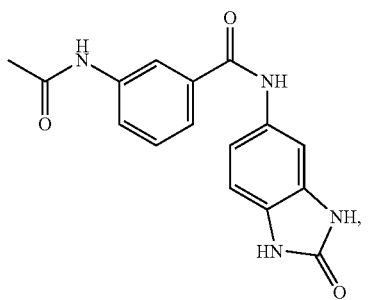
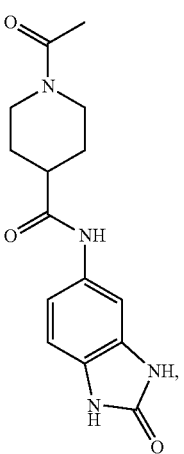
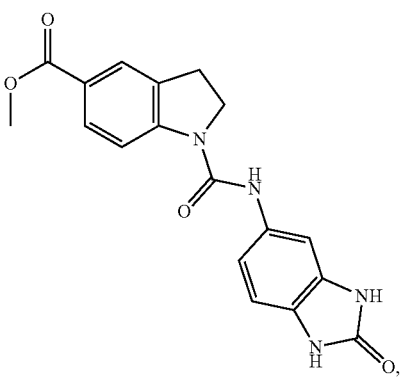
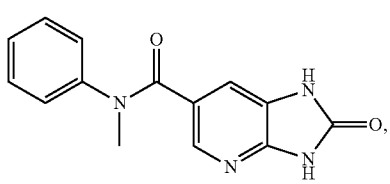
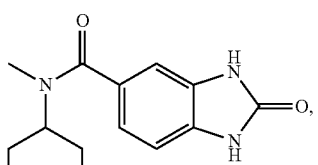
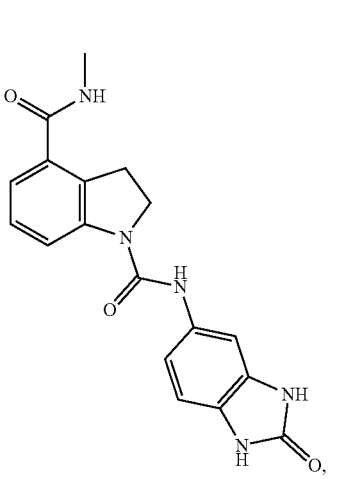

-continued
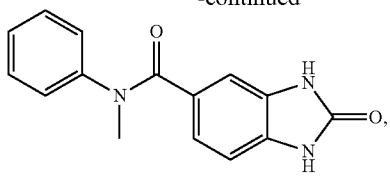
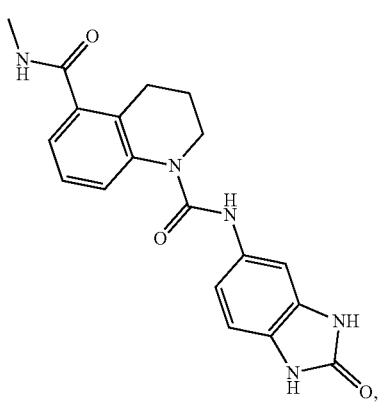
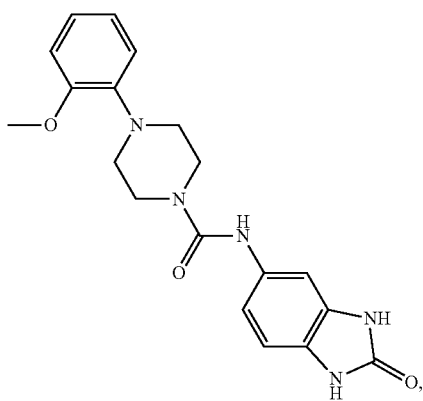
-continued
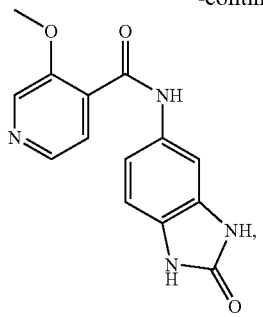
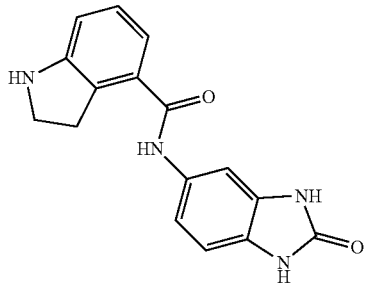 [SMILES: O=C(Nc1ccc2[nH]c(=O)[nH]c2c1)c1cccc2c1CCN2]
or a pharmaceutically acceptable salt thereof.
10. The compound of claim 9 of the formula
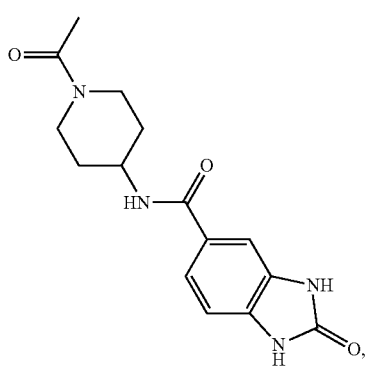
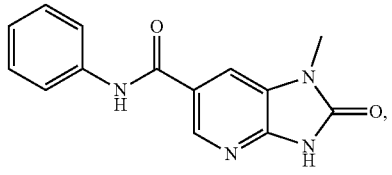

-continued
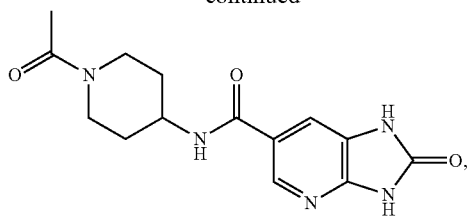
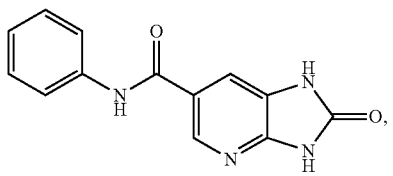
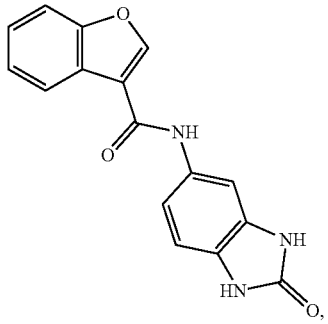
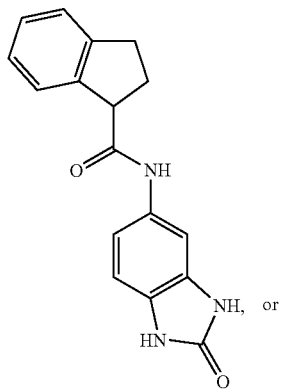
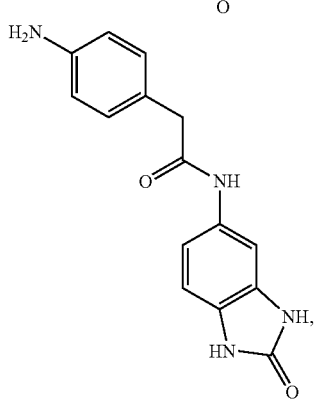
or a pharmaceutically acceptable salt thereof.
11. The compound of claim 9 of the formula
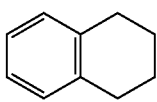 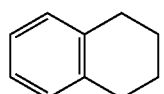
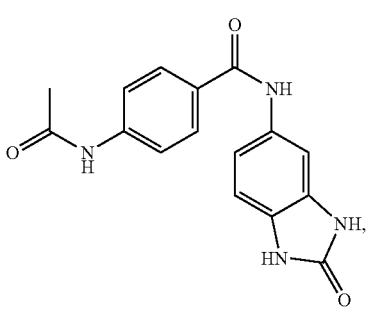
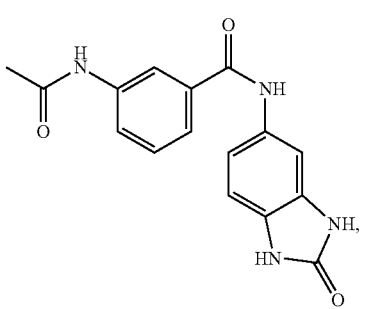
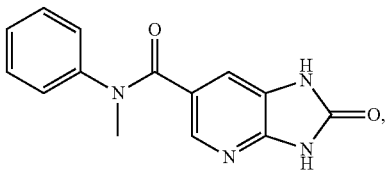
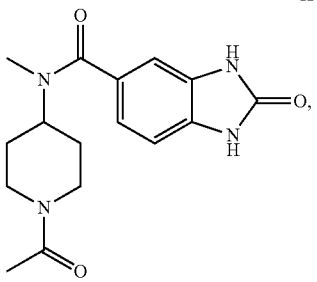

175
-continued
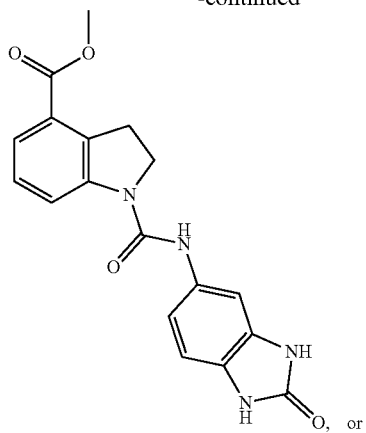
O, or
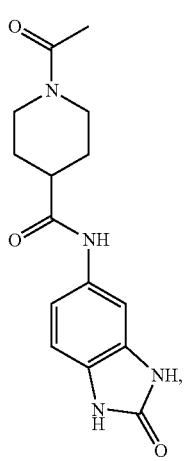
or a pharmaceutically acceptable salt thereof.
12. The compound of claim 9 of the formula
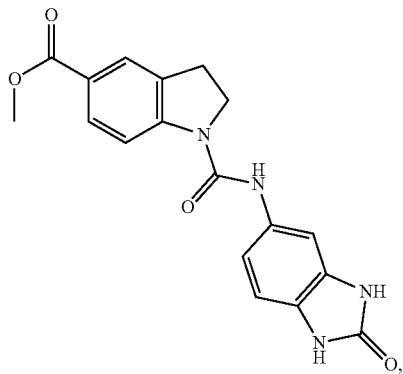
176
-continued
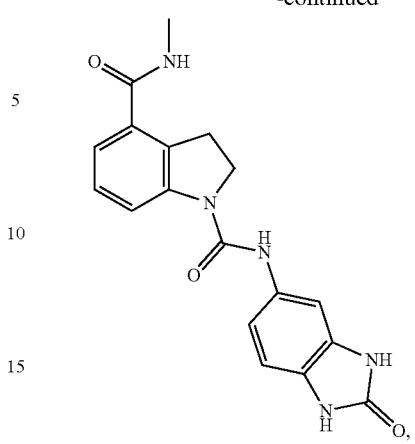
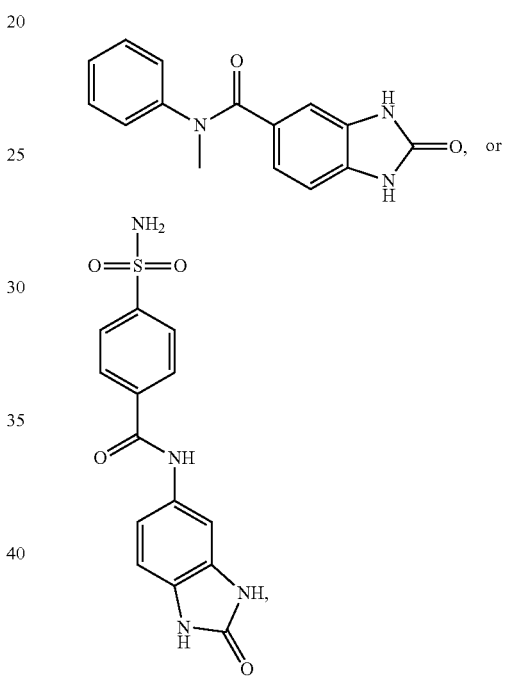
or a pharmaceutically acceptable salt thereof.
13. The compound of claim 9 of the formula
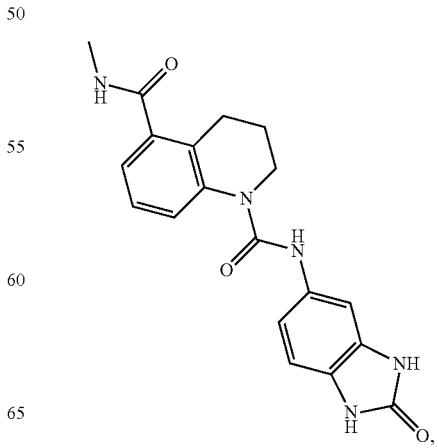

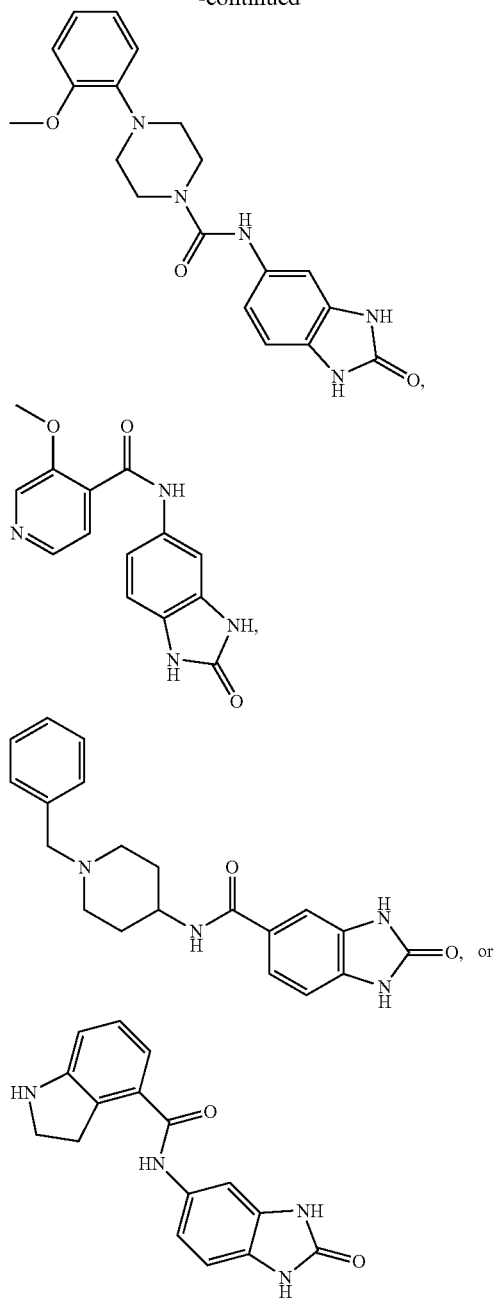
or a pharmaceutically acceptable salt thereof.
14. A compound selected from
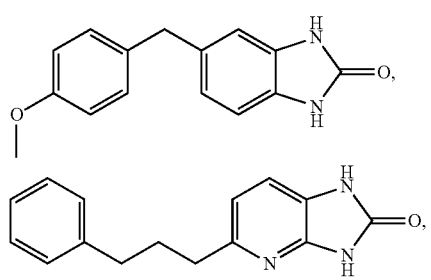
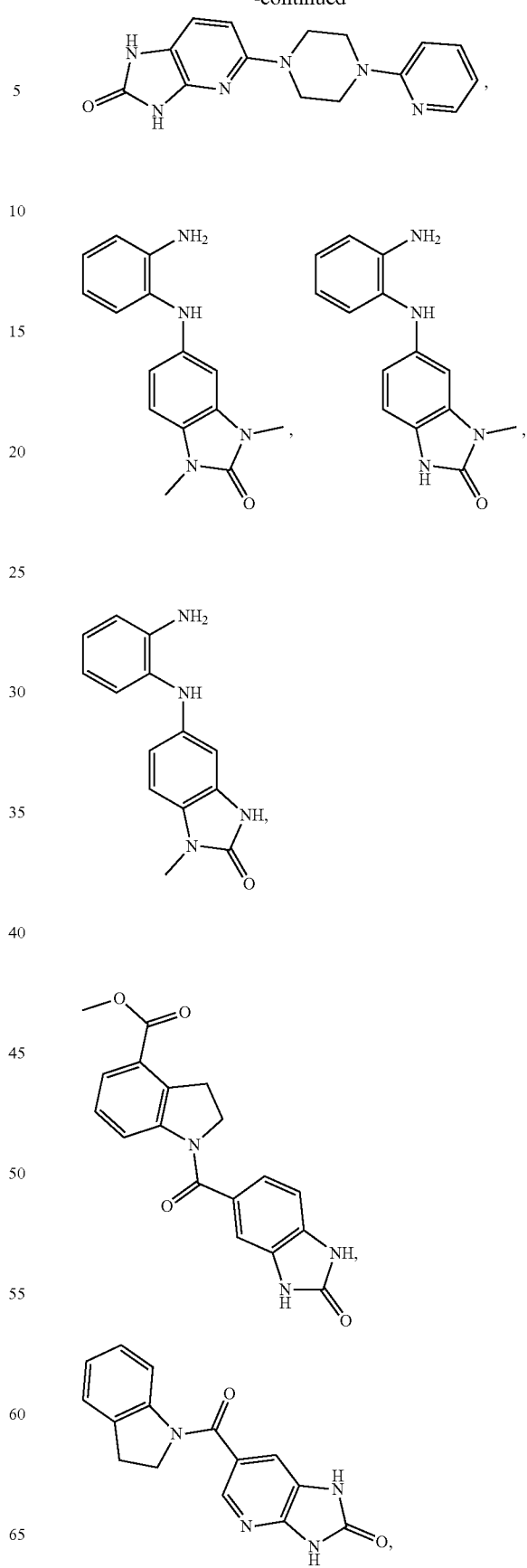

-continued
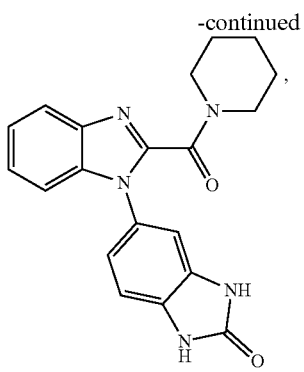
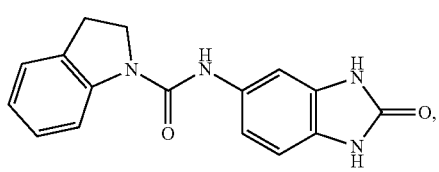
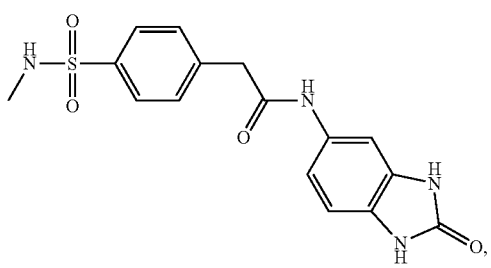
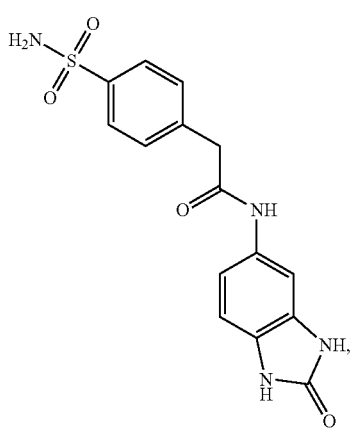
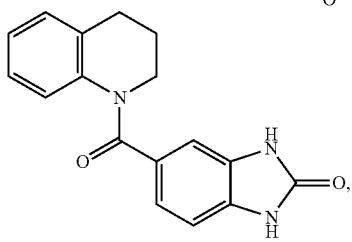
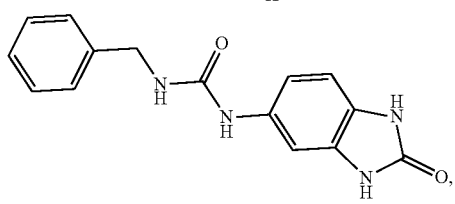
-continued
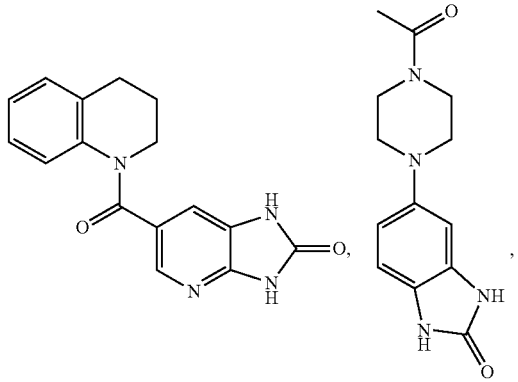
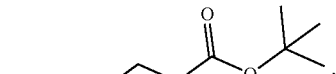
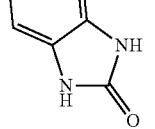
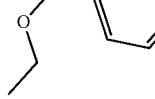
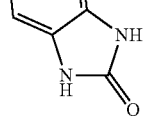

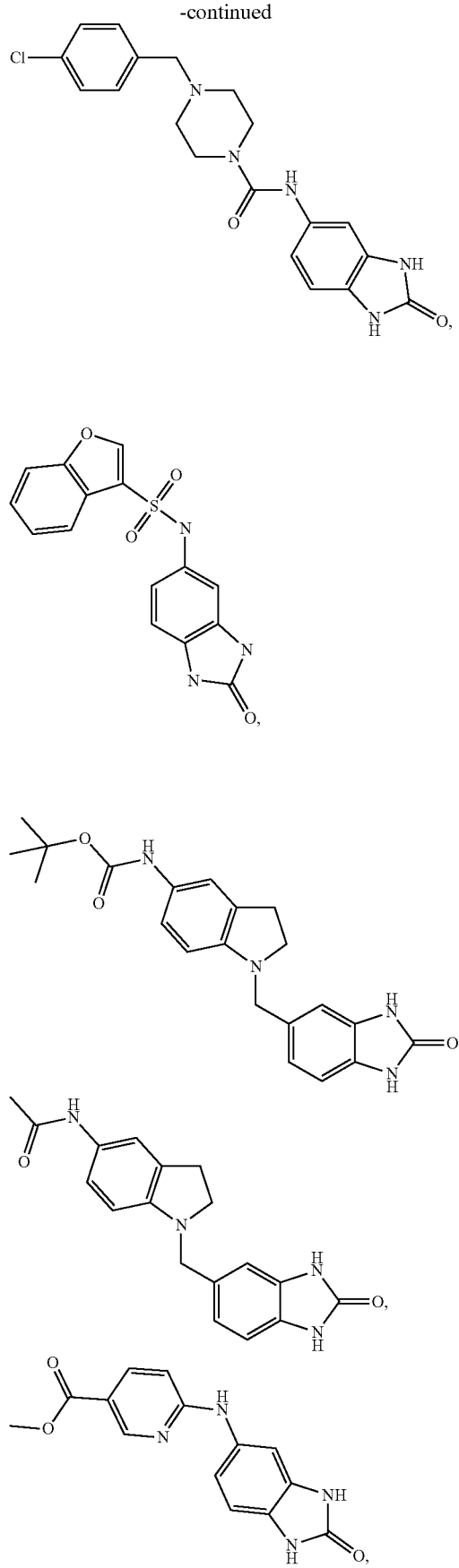
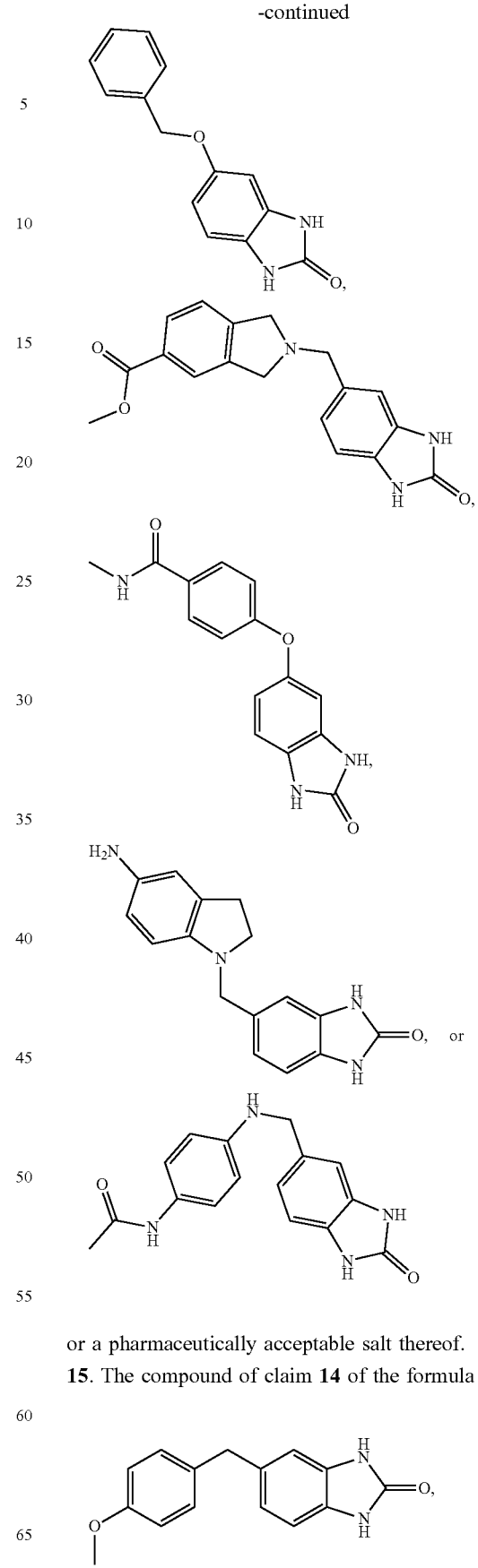
or a pharmaceutically acceptable salt thereof.
15. The compound of claim 14 of the formula -continued
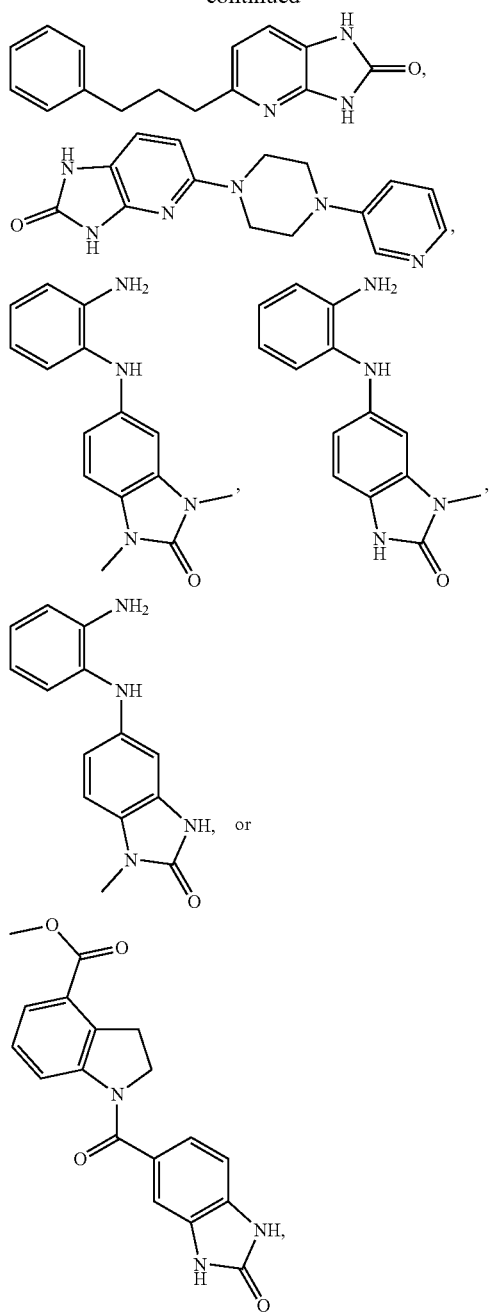
or a pharmaceutically acceptable salt thereof.
16. The compound of claim 14 of the formula
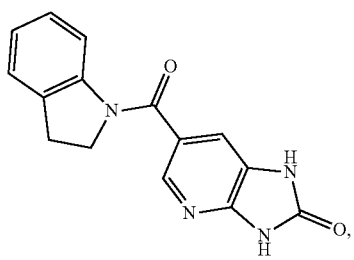
-continued
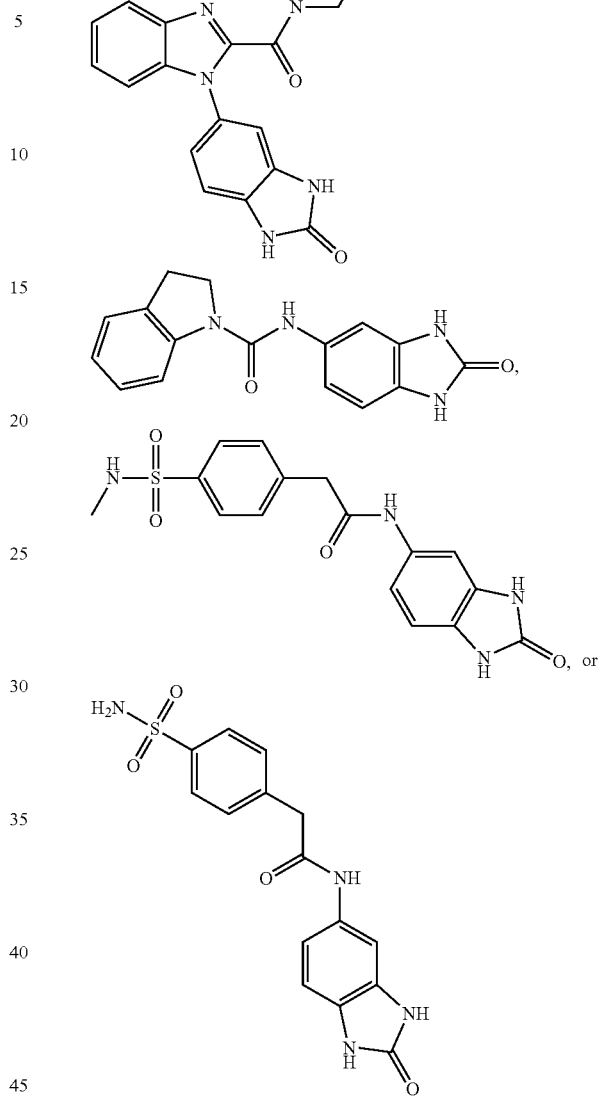
or a pharmaceutically acceptable salt thereof.
17. The compound of claim 14 of the formula
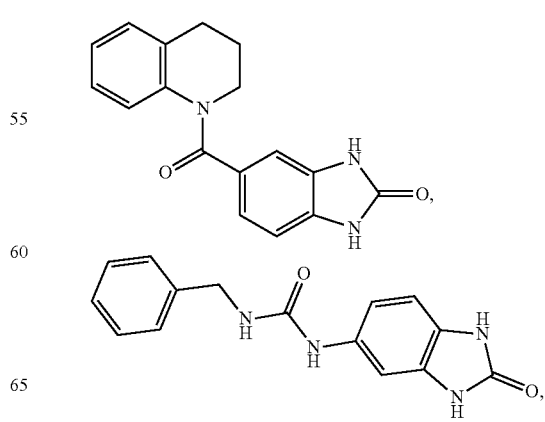

-continued
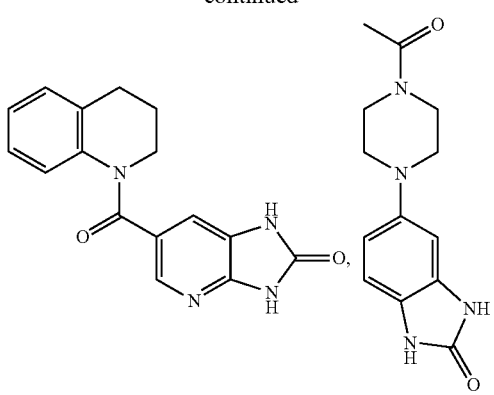, or
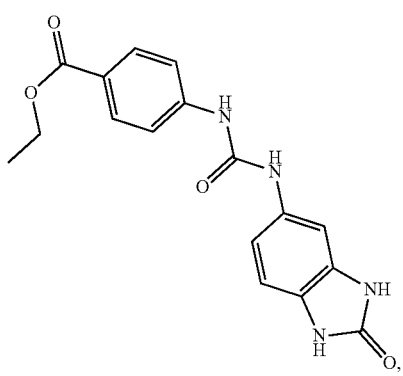
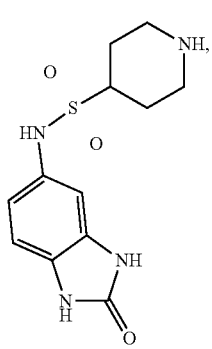
or a pharmaceutically acceptable salt thereof.
18. The compound of claim 14 of the formula
-continued
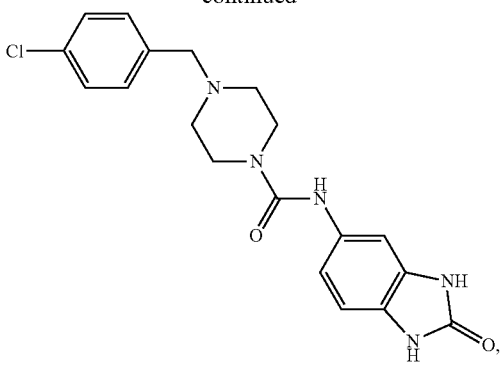
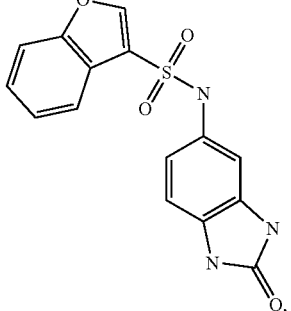
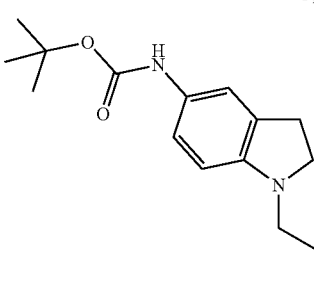
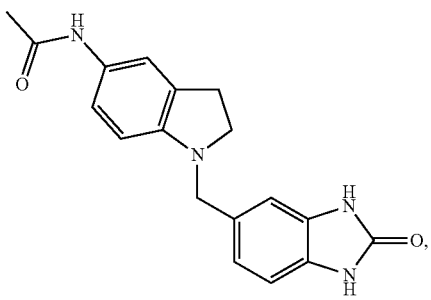
or a pharmaceutically acceptable salt thereof.
19. The compound of claim 14 of the formula 187
-continued

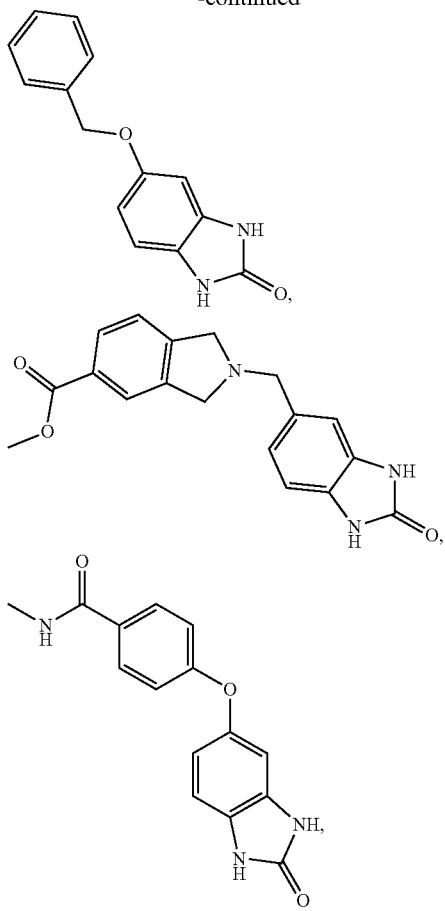

188
-continued

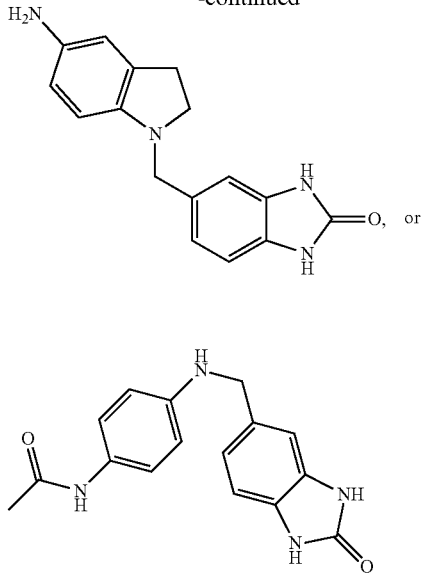

or a pharmaceutically acceptable salt thereof.

20. A pharmaceutical composition comprising a compound or pharmaceutically acceptable salt thereof of claim 1 optionally in a pharmaceutically acceptable carrier.

21. A pharmaceutical composition comprising a compound or pharmaceutically acceptable salt thereof of claim 9 optionally in a pharmaceutically acceptable carrier.

22. A pharmaceutical composition comprising a compound or pharmaceutically acceptable salt thereof of claim 14 optionally in a pharmaceutically acceptable carrier.

* * * * *